US011229698B2

(12) United States Patent
Cook et al.

(10) Patent No.: US 11,229,698 B2
(45) Date of Patent: Jan. 25, 2022

(54) RECOMBINANT NON-PATHOGENIC MAREK'S DISEASE VIRUS CONSTRUCTS ENCODING MULTIPLE HETEROLOGOUS ANTIGENS

(71) Applicant: Intervet Inc., Madison, NJ (US)

(72) Inventors: Stephanie M. Cook, Omaha, NE (US); Mohamad Morsey, Omaha, NE (US); Ian Tarpey, St. Ives (GB)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 16/753,133

(22) PCT Filed: Oct. 11, 2018

(86) PCT No.: PCT/EP2018/077725
§ 371 (c)(1),
(2) Date: Apr. 2, 2020

(87) PCT Pub. No.: WO2019/072964
PCT Pub. Date: Apr. 18, 2019

(65) Prior Publication Data
US 2020/0323978 A1 Oct. 15, 2020

Related U.S. Application Data

(60) Provisional application No. 62/571,524, filed on Oct. 12, 2017, provisional application No. 62/729,673, filed on Sep. 11, 2018.

(51) Int. Cl.
*A61K 39/255* (2006.01)
*A61P 31/20* (2006.01)
(Continued)

(52) U.S. Cl.
CPC ............ *A61K 39/255* (2013.01); *A61K 39/17* (2013.01); *A61P 31/20* (2018.01); *C12N 15/86* (2013.01);
(Continued)

(58) Field of Classification Search
None
See application file for complete search history.

(56) References Cited

U.S. PATENT DOCUMENTS 5,187,087 A    2/1993   Sondermeijer et al.
5,733,554 A    3/1998   Audonnet et al.
(Continued)

FOREIGN PATENT DOCUMENTS

EP    728842 A2    8/1996
EP    1298139 B1   5/2007
(Continued)

OTHER PUBLICATIONS

Afonso, et al., The Genome of Turkey Herpesvirus, Journal of Virology, 2001, 971-978, 75-2.
(Continued)

*Primary Examiner* — Michelle S Horning
(74) *Attorney, Agent, or Firm* — Michael D. Davis

(57) ABSTRACT

The present invention discloses novel recombinant multivalent non-pathogenic Marek's Disease virus constructs that encode and express foreign antigens from three or more avian viruses, along with methods of the use of the multivalent poultry virus vaccines.

20 Claims, 3 Drawing Sheets

Specification includes a Sequence Listing.

(51) Int. Cl.
*A61K 39/17* (2006.01)
*C12N 15/86* (2006.01)
*A61K 39/00* (2006.01)

(52) U.S. Cl.
CPC ........... *A61K 2039/5254* (2013.01); *A61K 2039/5256* (2013.01); *A61K 2039/552* (2013.01); *A61K 2039/70* (2013.01)

(56) References Cited

U.S. PATENT DOCUMENTS

| | | | |
|---|---|---|---|
| 5,830,745 | A | 11/1998 | Hock et al. |
| 5,834,305 | A | 11/1998 | Cochran et al. |
| 5,853,733 | A | 12/1998 | Cochran et al. |
| 5,928,648 | A | 7/1999 | Cochran |
| 5,961,982 | A | 10/1999 | Cochran |
| 5,965,138 | A | 10/1999 | Cochran et al. |
| 5,980,906 | A | 11/1999 | Audonnet et al. |
| 6,121,043 | A | 9/2000 | Cochran et al. |
| 6,183,753 | B1 | 2/2001 | Cochran et al. |
| 6,299,882 | B1 | 10/2001 | Junker |
| 6,875,856 | B2 | 4/2005 | Wild et al. |
| 6,913,751 | B2 | 7/2005 | Cochran et al. |
| 8,932,604 | B2 * | 1/2015 | Cook ............... A61P 31/22 424/199.1 |
| 9,114,108 | B2 | 8/2015 | Bublot et al. |
| 9,409,954 | B2 * | 8/2016 | Cook ............... C07K 14/005 |
| 9,555,016 | B2 | 1/2017 | Makridakis |
| 9,555,096 | B2 | 1/2017 | Bublot et al. |
| 9,770,502 | B2 | 9/2017 | Bublot et al. |
| 10,188,720 | B2 | 1/2019 | Esaki et al. |
| 10,308,956 | B2 | 6/2019 | Verstegen et al. |
| 10,323,257 | B2 | 6/2019 | Bublot et al. |
| 2008/0233146 | A1 | 9/2008 | Sato |
| 2018/0163230 | A1 | 6/2018 | Bublot et al. |

FOREIGN PATENT DOCUMENTS

| | | | |
|---|---|---|---|
| EP | 2644702 A1 | 10/2013 | |
| EP | 3041939 B1 | 3/2019 | |
| WO | 198704463 A1 | 7/1987 | |
| WO | 199203554 A1 | 3/1992 | |
| WO | 1996005291 A1 | 2/1996 | |
| WO | 1998037216 A1 | 8/1998 | |
| WO | 2000061736 A2 | 10/2000 | |
| WO | WO 2013/082317 * | 11/2012 | ............ A61K 39/12 |
| WO | 2013057235 A1 | 4/2013 | |
| WO | 2013057236 A1 | 4/2013 | |
| WO | 2013082327 A1 | 6/2013 | |
| WO | 2016102647 A1 | 6/2016 | |
| WO | 2017216287 A1 | 12/2017 | |
| WO | 2018112051 A1 | 6/2018 | |

OTHER PUBLICATIONS

Dartiel, et al., Herpesvirus of Turkey Recombinant Viruses Expressing Infectious Bursal Disease Virus (IBDV) VP2 Immunogen Induce Protection Against an IBDV Virulent Challenge in Chickens, Virology, 1995, 481-490, 211.
Fuchs, et al., Molecular Biology of Avian Infectious Laryngotracheitis Virus, Veterinary Research, 2007, 261-279, 38.
International Search report for PCT/EP2018/077725 dated Nov. 28, 2018, 18 pages.
Johnson, et al., Protection Against Infectious Laryngotracheitis by In Ovo Vaccination with Commercially Available Viral Vector Recombinant Vaccines, Avian Diseases, 2010, 1251-1259, 54.
Kingham, et al., The Genome of Herpesvirus of Turkeys: Comparative Analysis with Marek's Disease Viruses, Journal of General Virology, 2001, 1123-1135, 82.
Murthy, et al., Pathogenesis of Marek's Disease: Effect of Immunization with Inactivated Viral and Tumor-Associated Antigens, Infection and Immunity, 1979, pp. 547-533, 26-2.
Petherbridge, et al., Cloning of Gallid Herpesvirus 3 (Marek's Disease Virus Serotype-2), Journal of Virological Methods, 2009, 11-17, 158.
Sondermeijer, et al., Avian Herpesvirus as a Live Viral Vector for the Expression of Heterologous Antigens, Vaccine, 1993, 349-358, 11.
Sun, et al., Protection of Chickens from Newcastle Disease and Infectious Laryngotracheitis with A Recombinant Fowlpox Virus Co-Expressing the F, HN Genes of Newcastle Disease Virus and gB Gene of Infectious Laryngotracheitis Virus, Avian Diseases, 2008 ,111-117, 52.
Tsukamoto, et al., Complete, Long-Lasting Protection Against Lethal Infectious Bursal Disease Virus Challenge by a Single Vaccination with an Avian Herepesvirus Vector Expressing VP2 Antigens, Journal of Virology, 2002, 5637-5645, 76-11.
Van Zijl, et al., Regeneration of Herpesviruses from Molecularly Cloned Subgenomic Fragments, Journal of Virology, 1988, 2191-2195, 62-6.
Wild, et al., A Genomic map of Infectious Laryngotracheitis Virus and the Sequence and Organization of Genes Present in the Unique Short and Flanking Regions, Virus Genes, 1996, 107-116, 12-2.
Wu, et al., Molecular Detection and Differentiation of Infectious Bursal Disease Virus, Avian Diseases, 2007, 515-526, 51.

* cited by examiner

RECOMBINANT NON-PATHOGENIC MAREK'S DISEASE VIRUS CONSTRUCTS ENCODING MULTIPLE HETEROLOGOUS ANTIGENS

CROSS-REFERENCE TO RELATED APPLICATIONS

This application is a national stage entry under 35 U.S.C. § 371 of PCT/EP2018/077725, filed on Oct. 11, 2018, which claims priority to U.S. Ser. No. 62/571,524, filed on Oct. 12, 2017 and U.S. Ser. No. 62/729,673, filed on Sep. 11, 2018, the content of PCT/EP2018/077725 is hereby incorporated by reference in its entirety.

FIELD OF THE INVENTION

The present invention relates to novel recombinant multivalent recombinant non-pathogenic Marek's Disease virus constructs encoding and expressing foreign antigens from three or more avian viruses and methods of employing these multivalent recombinant non-pathogenic Marek's Disease virus constructs in poultry vaccines.

BACKGROUND OF THE INVENTION

Pathogenic poultry viruses are not only debilitating to chickens, but they also are costly to chicken breeders because most of the resulting diseases are contagious and the poultry industry relies heavily on confined, large-scale breeding facilities. Vaccinating young chicks is often the only viable means to combat these viruses. Although attenuated or killed poultry viral vaccines remain important in the market place, in recent years significant resources have been expended on developing vaccines containing recombinant viral constructs which express pathogenic viral protein antigens. Furthermore, substantial efforts have been made to construct stable and efficacious multivalent recombinant non-pathogenic Marek's Disease virus (abbreviated as $rMDV_{np}$) vectors that express foreign genes from multiple viral pathogens. Such multivalent vaccines would serve to minimize the number of injections given to the chicks and thereby, reduce discomfort and stress on the vaccinated chick, as well as significantly reduce costs in labor and materials. Vaccinating with such single multivalent constructs also would be preferable to alternative multivalent $rMDV_{np}$ vaccines that contain multiple recombinant monovalent $rMDV_{np}$ constructs, because these alternative vaccines have, at least to date, resulted in protection against only a single viral pathogen. The failure of such alternative vaccines is presumably due to one of the monovalent $rMDV_{np}$ constructs overgrowing the other monovalent $rMDV_{np}$ constructs thereby, preventing these other monovalent $rMDV_{np}$ constructs from inducing a significant immune response. In any case, despite substantial efforts in the past to construct stable and efficacious multivalent $rMDV_{np}$ vectors that express foreign genes from multiple viral pathogens indeed, such vaccines had been suggested more than twenty years ago [see e.g., U.S. Pat. No. 5,965,138], it has been only recently that a multivalent vaccine that comprises a recombinant herpesvirus of turkeys (abbreviated as rHVT) encoding antigens from more than one other pathogen has been shown to be both stable and efficacious.

One poultry virus disease that can be controlled through vaccination is Marek's disease. Marek's disease is a pathogenic disease that adversely affects chickens worldwide. Marek's disease occurs predominantly in young chickens between 2 and 5 months of age. Clinical signs include: progressive paralysis of one or more of the extremities, incoordination due to paralysis of legs, drooping of the limb due to wing involvement, and a lowered head position due to involvement of the neck muscles. In acute cases, severe depression may result. Bursal and thymic atrophy may also develop.

The etiological agent for Marek's disease is Marek's disease virus serotype 1 (abbreviated as MDV1), a cell-associated virus having a double-stranded DNA genome. MDV1 is a lymphotropic avian alphaherpesvirus that both: (i) infects B cells, which can result in cytolysis, and (ii) latently infects T cells, which can induce T-cell lymphoma. Closely related to the virulent MDV1 strain, Marek's disease virus serotype 2 (abbreviated as MDV2), previously known as Gallid herpes virus 3, is a naturally attenuated MDV strain that has been shown to have little to no pathogenicity in chickens [Petherbridge et al., *J. Virological Methods* 158:11-17 (2009)]. SB-1 is a specific MDV2 strain that has been shown to be useful in vaccines against MDV1 [see e.g., Murthy and Calnek, Infection and Immunity 26(2) 547-553 (1979)].

Another closely related alphaherpesvirus, Marek's disease virus serotype 3 (abbreviated as MDV3), more widely known as herpesvirus of turkeys (abbreviated as HVT), is a nonpathogenic virus of domestic turkeys [see e.g., Kingham et al., *J. of General Virology* 82:1123-1135 (2001)]. Two commonly used strains of HVT are the PB1 strain and the FC126 strain. Whereas, HVT is also nonpathogenic in chickens, it does induce a long-lasting protective immune response in chickens against MDV1. Accordingly, HVT has been used in poultry vaccines against virulent MDV1 for many years, generally in combination with SB-1, which is more viraemic than HVT, but considered less safe. Alternatively, when flocks are challenged with particularly virulent MDV1 strains, HVT can be combined with the Rispen's vaccine. The Rispen's vaccine is an isolate that originated from a mildly virulent MDV1 strain that was subsequently further weakened by cell passaging. The Rispen's strain however, retains some virulence towards highly susceptible lines of chickens.

The sequence of the complete genome of HVT has been disclosed [Afonso et al., *J. Virology* 75(2):971-978 (2001)], and as most alphaherpesviruses, HVT possesses a significant number of potential nonessential insertion sites [see e.g., U.S. Pat. Nos. 5,187,087; 5,830,745; 5,834,305; 5,853,733; 5,928,648; 5,961,982; 6,121,043; 6,299,882 B1]. HVT also has been shown to be amenable to genetic modification and thus, has been used as a recombinant vector for many years [WO 87/04463]. Accordingly, recombinant HVT vectors have been reported to express foreign genes that encode antigens from e.g., Newcastle Disease Virus (NDV), [Sondermeijer et al., *Vaccine*, 11:349-358 (1993); Reddy et al., *Vaccine*, 14:469-477 (1996)], Infectious Bursal Disease Virus (IBDV), [Darteil et al., *Virology*, 211:481-490 (1995); Tsukamoto et al., *J. of Virology* 76(11):5637-5645 (2002)], and Infectious Laryngotracheitis Virus (ILTV) [Johnson et al., *Avian Disease*, 54(4):1251-1259 (2010); WO 92/03554; U.S. Pat. No. 6,875,856]. The entire genomic sequence of MDV2 is also known [see, GenBank acc. nr: AB049735.1, and Petherbridge et al., supra]. The genomic organization of the MDV2 is very similar to that of HVT, with the US region in particular, being identical to that of HVT [see, Kingham et al., supra].

In addition a recombinant chimeric virus, known as the novel avian herpesvirus (NAHV), has been constructed in which specific regions of the HVT genome have been replaced by the corresponding regions of the MDV1 genome. The NAHV also has been used to express foreign genes that encode antigens from other poultry viruses [U.S. Pat. Nos. 5,965,138; 6,913,751].

Like MDV, infectious laryngotracheitis virus (abbreviated as ILTV or ILT) is an alphaherpesvirus that adversely affects chickens, worldwide [Fuchs et al., *Veterinary Research* 38:261-279 (2007)]. ILTV causes acute respiratory disease in chickens, which is characterized by respiratory depression, gasping, and expectoration of bloody exudate. Viral replication is limited to cells of the respiratory tract, where in the trachea the infection gives rise to tissue erosion and hemorrhage.

Newcastle disease is another highly contagious and debilitating disease of chickens. The etiological agent for Newcastle disease is the Newcastle disease virus (NDV). NDV belongs to the order of the Mononegavirales and is in the family of Paramyxoviridae. Newcastle disease viruses have a non-segmented, negative sense, single-stranded RNA genome. NDV has been grouped into three distinct pathotypes according to their virulence. Infection of poultry by the non-pathogenic lentogenic strains of NDV is essentially asymptomatic. In direct contrast, the mesogenic (medium pathogenic) and velogenic (highly pathogenic) NDV strains cause extensive disease that can be fatal. Most types of NDV infect the respiratory system and/or the nervous system, and can result in gasping and torticollis.

Infectious bursal disease virus (abbreviated as IBDV or IBD), also called Gumboro disease virus, is the causative agent of infectious bursal disease. IBDV causes an acute, highly-contagious, viral infection of a chicken's lymphoid tissue, with its primary target being the bird's essential immunological organ: the bursa of Fabricius. The morbidity rate in susceptible flocks is high, with rapid weight loss and moderate to high mortality rates. Chicks that recover from the disease may have immune deficiencies because of destruction of (or parts of) the bursa of Fabricius. This makes them particularly vulnerable to secondary infections.

IBDV is a member of the Birnaviridae family. The viruses in this family have a genome consisting of two segments (A and B) of double-stranded RNA. Two serotypes of IBDV exist, serotype 1 and 2, which can be differentiated by virus neutralization (VN) tests. Serotype 1 viruses have been shown to be pathogenic to chickens, while serotype 2 viruses cause only sub-acute disease in turkeys. Historically, IBDV serotype 1 viruses consisted of only one type that is now known as "classic" IBD virus. More recently, so-called "variant" IBDV strains have emerged. Classic and variant strains of IBDV can be identified and distinguished by a virus neutralization test using a panel of monoclonal antibodies, or by RT-PCR [Wu et al., *Avian Diseases*, 51:515-526(2007)]. Well-known classic IBDV strains include, D78, Faragher 52/70, and STC, whereas 89/03 is a well-known variant strain. Many live or inactivated IBDV vaccines are commercially available, e.g. a live vaccine such as NOBILIS$^R$ Gumboro D78 (MSD Animal Health).

As indicated above, because HVT can act as both an antigen that provides significant protection against Marek's Disease and as a recombinant vector, it is presently used as a platform vector for such multivalent vaccines as Innovax®-ILT (sold by Merck Animal Health), which protects against ILTV; Innovax®-ND-SB (sold by Merck Animal Health) Vectormune® HVT-NDV (sold by Ceva), both of which protect against NDV; and Vaxxitek® HVT+IBD (Merial; previously named: Gallivac™ HVT-IBD), and Vectormune™ HVT-IBD (Ceva) both of which protect against IBDV. Notably, Innovax®-ILT comprises two foreign genes, i.e., ILTV gD and ILTV gI, which has proved to be safe, effective, and stable. However, these two foreign genes are from the same pathogen and moreover, they naturally overlap and need to be co-expressed in order to allow proper immunization against ILTV. More recently, a recombinant safe, effective, and stable multivalent vaccine comprising HVT-ILTV-NDV has been disclosed [U.S. Pat. No. 8,932, 604 B2 and U.S. Pat. No. 9,409,954 B2, the contents of which are hereby incorporated by reference in their entireties]. An early HVT-NDV-IBDV also has been disclosed, though upon prolonged testing during the development of the corresponding product one of the main constructs, HVP309, was found neither to display adequate genetic stability nor sustained expression of the heterologous inserts [WO 2013/057,235]. Subsequently, a more stable and efficatious construct was developed [WO 2016/102647]. Other recombinant HVT constructs also have been described [see e.g., U.S. Pat. Nos. 9,114,108, 9,555,016, 9,555,096, and US 2018/0163230 A1].

However, despite the clear advantages of stable, multivalent, recombinant $MDV_{np}$ constructs that can efficaciously express heterologous antigens from three or more different pathogens, and the substantial efforts to design them, heretofore, none have been forthcoming. Indeed, prior unsuccessful attempts to construct such recombinant $MDV_{np}$ constructs has led to the general consensus in the field that the insertion of foreign antigens from three or more different viral pathogens into an $MDV_{np}$ construct overtaxes that construct, leading to the observed lack of stability. Accordingly, the suitability of any given multivalent recombinant $MDV_{np}$ as a vaccine remains at best, unpredictable when the recombinant $MDV_{np}$ comprises a combination of heterologous antigens that are obtained from a unique set of three or more poultry viruses. Therefore, there is a clear need to overcome the collective industry failures, by constructing novel, stable, recombinant $MDV_{np}$ vectors that can be used in multivalent vaccines as the sole active to protect against three or more different non-MDV1 poultry virus pathogens.

The citation of any reference herein should not be construed as an admission that such reference is available as "prior art" to the instant application.

SUMMARY OF THE INVENTION

Accordingly, the present invention provides a novel, multivalent recombinant nonpathogenic Marek's Disease virus ($rMDV_{np}$) for use as a vector to express foreign genes from multiple viral pathogens. In particular embodiments, the $rMDV_{np}$ is a recombinant herpesvirus of turkeys (rHVT). In alternative embodiments, the $rMDV_{np}$ is a recombinant Marek's disease virus serotype 2 (rMDV2). An $rMDV_{np}$, e.g., an rHVT or an rMDV2, of the present invention can be used in safe and efficacious multivalent vaccines against pathogenic poultry viruses. The present invention thus provides recombinant nonpathogenic Marek's Disease virus ($rMDV_{np}$) vectors (including HVT vectors) that encode and express antigens from three or more foreign chicken virus pathogens. In specific embodiments the $rMDV_{np}$ encodes one or more antigens from Laryngotracheitis Virus (ILTV), one or more antigens from Infectious Bursal Disease Virus (IBDV), and one or more antigens from Newcastle Disease Virus (NDV). In more specific embodiments such $rMDV_{np}$ vectors aid in the protection of the chicken vaccinate from clinical signs arising from an infection from pathogenic MDV, pathogenic IBDV, pathogenic NDV, and/or pathogenic ILTV. The vaccines are preferably effective for the vaccination of healthy animals at 18-19 day of embryonation, and for day old chicks and older.

In particular embodiments, the recombinant nonpathogenic Marek's Disease Virus (rMDV$_{np}$) comprises in one or more nonessential sites of its genome a first heterologous nucleotide sequence encoding one or more antigens from a first chicken pathogen, a second heterologous nucleotide sequence encoding one or more antigens from a second chicken pathogen, and a third heterologous nucleotide sequence encoding one or more antigens from a third chicken pathogen. In specific embodiments the first chicken pathogen, the second chicken pathogen, and the third chicken pathogen are all avian viruses. In more specific embodiments the first chicken pathogen, the second chicken pathogen, and the third chicken pathogen are all different viral species from each other and are a different viral species than Marek's Disease Virus. In certain embodiments of this type, the first chicken pathogen is Infectious Bursal Disease Virus (IBDV), the second chicken pathogen is Infectious Laryngotracheitis Virus (ILTV), and the third chicken pathogen is Newcastle Disease Virus (NDV).

In specific rMDV$_{np}$ embodiments, the first heterologous nucleotide sequence encodes an Infectious Bursal Disease Virus viral protein 2 (IBDV VP2); and/or the second heterologous nucleotide sequence encodes an Infectious Laryngotracheitis Virus glycoprotein D (ILTV gD), an Infectious Laryngotracheitis Virus glycoprotein I (ILTV gI), or both an ILTV gI and an ILTV gD; and/or the third heterologous nucleotide sequence encodes a Newcastle Disease Virus fusion protein (NDV F). In more specific rMDV$_{np}$ embodiments, the first heterologous nucleotide sequence encodes an Infectious Bursal Disease Virus viral protein 2 (IBDV VP2), the second heterologous nucleotide sequence encodes both an Infectious Laryngotracheitis Virus glycoprotein D (ILTV gD) and an Infectious Laryngotracheitis Virus glycoprotein I (ILTV gI), and the third heterologous nucleotide sequence encodes a Newcastle Disease Virus fusion protein (NDV F).

Accordingly, in particular rMDV$_{np}$ embodiments of the present invention, the first heterologous nucleotide sequence, the second heterologous nucleotide sequence and the third heterologous nucleotide sequence are located in three different nonessential sites in the rMDV$_{np}$ genome. In particular embodiments the three different sites are individually selected from the group consisting of the US2 site, the UL54.5 site, the UL7/8 site, the UL40 site, the UL43 site, the UL45/46 site, the UL55 site, the US10 site, the region between US10 and SORF3, the region between US2 and SORF3, the IG1 site, the IG2 site, and the IG3 site. In a specific embodiment of this type the first nonessential site is the US2 site, the second nonessential site is the UL54.5 site, and the third nonessential site is the UL45/46 site.

In alternative embodiments, the first heterologous nucleotide sequence, the second heterologous nucleotide sequence, and the third heterologous nucleotide sequence are located in a first nonessential site in the rMDV$_{np}$ genome or in a second nonessential site in the rMDV$_{np}$ genome. In specific embodiments of this type, the first nonessential site and the second nonessential site are the same (i.e., there is a lone nonessential insertion site). In particular embodiments of this type, the lone nonessential insertion site is the US2 site. In other embodiments of this type, the lone nonessential insertion site is the UL54.5 site. In still other embodiments of this type, the lone nonessential insertion site is the UL7/8 site. In yet other embodiments of this type, the lone nonessential insertion site is the UL40 site. In still other embodiments of this type, the lone nonessential insertion site is the UL45/46 site. In yet other embodiments of this type, the lone nonessential insertion site is the UL55 site. In still other embodiments of this type, the lone nonessential insertion site is the US10 site. In yet other embodiments of this type, lone nonessential insertion site is the region between US10 and SORF3. In still other embodiments of this type, the lone nonessential insertion site is the region between US2 and SORF3. In yet other embodiments of this type the lone nonessential insertion site is the IG1 site. In still other embodiments of this type, the lone nonessential insertion site is the IG2 site. In yet other embodiments of this type the lone nonessential insertion site is the IG3 site. In still other embodiments of this type, the lone nonessential insertion site is the UL43 site.

In yet other types of embodiments, the first nonessential site, and the second nonessential site are different. The two different sites are individually selected from the group consisting of the US2 site, the UL54.5 site, the UL7/8 site, the UL40 site, the UL43 site, the UL45/46 site, the UL55 site, the US10 site, the region between US10 and SORF3, the region between US2 and SORF3, the IG1 site, the IG2 site, and the IG3 site. In particular embodiments, the first heterologous nucleotide sequence and the second heterologous nucleotide sequence are located in a first nonessential site and the third heterologous nucleotide sequence is located in a second nonessential site. In other embodiments, the first heterologous nucleotide sequence and the third heterologous nucleotide sequence are located in a first nonessential site and the second heterologous nucleotide sequence is located in a second nonessential site. In still other embodiments, the second heterologous nucleotide sequence and the third heterologous nucleotide sequence are located in a first nonessential site and the first heterologous nucleotide sequence is located in a second nonessential site. In preferred embodiments of this type, the first heterologous nucleotide sequence encodes an Infectious Bursal Disease Virus viral protein 2 (IBDV VP2), the second heterologous nucleotide sequence encodes an Infectious Laryngotracheitis Virus glycoprotein D (ILTV gD), an Infectious Laryngotracheitis Virus glycoprotein I (ILTV gI), or both an ILTV gI and an ILTV gD, and the third heterologous nucleotide sequence encodes a Newcastle Disease Virus fusion protein (NDV F).

In certain embodiments of this type, an rMDV$_{np}$ comprising heterologous nucleotide sequences encoding an ILTV gD protein, an ILTV gI protein, and an IBDV VP2 protein in the first nonessential site, and a heterologous nucleotide sequence that encodes a NDV F protein in the second nonessential site is constructed so that the heterologous nucleotide sequence encoding the IBDV VP2 protein is 5' to the heterologous nucleotide sequence encoding the ILTV gD protein and the ILTV gI protein. In other embodiments of this type, the rMDV$_{np}$ is constructed so that the heterologous nucleotide sequence encoding the ILTV gD protein and the ILTV gI protein are 5' to the heterologous nucleotide sequence encoding the IBDV VP2 protein.

In alternative embodiments, an rMDV$_{np}$ comprising heterologous nucleotide sequences encoding a NDV F protein and an IBDV VP2 protein in the first nonessential site and a heterologous nucleotide sequence that encodes an ILTV gD protein and an ILTV gI protein in the second nonessential site is constructed so that the heterologous nucleotide sequence encoding the NDV F protein is 5' to the heterologous nucleotide sequence encoding the IBDV VP2 protein. In other embodiments of this type, the rMDV$_{np}$ is constructed so that the heterologous nucleotide sequence encoding the IBDV VP2 protein is 5' to the heterologous nucleotide sequence encoding the NDV F protein.

In yet other alternative embodiments, an rMDV$_{np}$ comprising heterologous nucleotide sequences encoding a NDV F protein, an ILTV gD protein and an ILTV gI protein in the first nonessential site and a heterologous nucleotide sequence encoding an IBDV VP2 protein in the second nonessential site is constructed so that the heterologous nucleotide sequence encoding the NDV F protein is 5' to the heterologous nucleotide sequence encoding the ILTV gD protein and the ILTV gI protein. In alternative embodiments of this type, the rMDV$_{np}$ is constructed so that the heterologous nucleotide sequence encoding the ILTV gD protein and the ILTV gI protein is 5' to the heterologous nucleotide sequence encoding the NDV F protein.

In specific embodiments of this type, the first nonessential site is the US2 site and the second nonessential site is the UL54.5 site. In alternative embodiments, the first nonessential site is the UL54.5 site and the second nonessential site is the US2 site. In yet another embodiment of this type, the first nonessential site is the US2 site and the second nonessential site is the UL45/46 site. In still another embodiment of this type, the first nonessential site is the UL45/46 site and the second nonessential site is the US2 site. In yet another embodiment of this type, the first nonessential site is the UL54.5 site and the second nonessential site is the UL45/46 site. In still another embodiment of this type, the first nonessential site is the UL45/46 site and the second nonessential site is the UL54.5 site. In yet another embodiment of this type, the first nonessential site is the US2 site and the second nonessential site is the UL55 site. In still another embodiment of this type, the first nonessential site is the UL55 site and the second nonessential site is the US2 site.

Accordingly, the rMDV$_{np}$ vectors of the present invention can comprise heterologous nucleotide sequences that encode any combination of these foreign protein antigens. In specific embodiments, the ILTV gD protein comprises the amino acid sequence of SEQ ID NO: 2. In other embodiments, the ILTV gI protein comprises the amino acid sequence of SEQ ID NO: 4. In still other embodiments, the IBDV VP2 protein comprises the amino acid sequence of SEQ ID NO: 6. In yet other embodiments the NDV F protein comprises the amino acid sequence of SEQ ID NO: 8. In still other embodiments, the NDV F protein comprises the amino acid sequence of SEQ ID NO: 10. Moreover, the present invention also provides rMDV$_{np}$ vectors that comprise any combination of nucleotide sequences that encode one or more of these amino acid sequences, including specific embodiments that encode all of them.

In yet other embodiments of the rMDV$_{np}$, the ILTV gD protein comprises the amino acid sequence of SEQ ID NO: 2 and the ILTV gI protein comprises the amino acid sequence of SEQ ID NO: 4. In certain embodiments of this type, the ILTV gD protein comprises the amino acid sequence of SEQ ID NO: 2, the ILTV gI protein comprises the amino acid sequence of SEQ ID NO: 4, and the IBDV VP2 protein comprises the amino acid sequence of SEQ ID NO: 6. In related embodiments the ILTV gD protein comprises the amino acid sequence of SEQ ID NO: 2, the ILTV gI protein comprises the amino acid sequence of SEQ ID NO: 4, and the NDV F protein comprises the amino acid sequence of SEQ ID NO: 8. In similar embodiments the ILTV gD protein comprises the amino acid sequence of SEQ ID NO: 2, the ILTV gI protein comprises the amino acid sequence of SEQ ID NO: 4, and the NDV F protein comprises the amino acid sequence of SEQ ID NO: 10. In more specific embodiments the ILTV gD protein comprises the amino acid sequence of SEQ ID NO: 2, the ILTV gI protein comprises the amino acid sequence of SEQ ID NO: 4, the IBDV VP2 protein comprises the amino acid sequence of SEQ ID NO: 6, and the NDV F protein either comprises the amino acid sequence of SEQ ID NO: 8 or the amino acid sequence of SEQ ID NO: 10. In specific embodiments, the rMDV$_{np}$ is an rHVT. In alternative embodiments, the rMDV$_{np}$ is an rMDV2.

In related embodiments, the ILTV gD protein is encoded by the nucleotide sequence of SEQ ID NO: 1. In other embodiments, the ILTV gI protein is encoded by the nucleotide sequence of SEQ ID NO: 3. In still other embodiments, the IBDV VP2 protein is encoded by the nucleotide sequence of SEQ ID NO: 5. In yet other embodiments, the NDV F protein is encoded by the nucleotide sequence of SEQ ID NO: 7. In still other embodiments, the NDV F protein is encoded by the nucleotide sequence of SEQ ID NO: 9.

Similarly, the rMDV$_{np}$ vectors of the present invention can comprise heterologous nucleic acids that comprise any combination of such heterologous nucleotide sequences. In certain embodiments, the rMDV$_{np}$ comprises a first heterologous nucleic acid located in the first nonessential site in the rMDV$_{np}$ genome and a second heterologous nucleic acid located in the second nonessential site in the rMDV$_{np}$ genome, with the first heterologous nucleic acid comprising both the first heterologous nucleotide sequence and the second heterologous nucleotide sequence, whereas the second heterologous nucleic acid comprises the third heterologous nucleotide sequence.

In certain embodiments of this type, the first heterologous nucleic acid comprises heterologous nucleotide sequences encoding an Infectious Laryngotracheitis Virus (ILTV) glycoprotein D (gD) protein, an Infectious Laryngotracheitis Virus (ILTV) glycoprotein I (gI) protein, and an Infectious Bursal Disease Virus (IBDV) viral protein 2 (VP2), whereas the second heterologous nucleic acid comprises a heterologous nucleotide sequence that encodes a Newcastle Disease Virus (NDV) F protein. In certain embodiments of this type, the first heterologous nucleic acid is constructed and/or inserted into the rMDV$_{np}$ genome so that the heterologous nucleotide sequence encoding the IBDV VP2 protein is 5' to the heterologous nucleotide sequence encoding the ILTV gD protein and the ILTV gI protein. In other embodiments of this type, the first heterologous nucleic acid is constructed and/or inserted into the rMDV$_{np}$ genome so that the heterologous nucleotide sequence encoding the ILTV gD protein and the ILTV gI protein is 5' to the heterologous nucleotide sequence encoding the IBDV VP2 protein.

In alternative embodiments, the first heterologous nucleic acid comprises heterologous nucleotide sequences that encode a NDV F protein and an IBDV VP2 protein, whereas the second heterologous nucleic acid comprises a heterologous nucleotide sequence encoding an ILTV gD protein and an ILTV gI protein. In certain embodiments of this type, the first heterologous nucleic acid is constructed and/or inserted into the rMDV$_{np}$ genome so that the heterologous nucleotide sequence encoding the NDV F protein is 5' to the heterologous nucleotide sequence encoding the IBDV VP2 protein. In alternative embodiments of this type, the first heterologous nucleic acid is constructed and/or inserted into the rMDV$_{np}$ genome so that the heterologous nucleotide sequence encoding the IBDV VP2 protein is 5' to the heterologous nucleotide sequence encoding the NDV F protein.

In yet other alternative embodiments, the first heterologous nucleic acid comprises heterologous nucleotide sequences that encode a NDV F protein, an ILTV gD protein, and an ILTV gI protein, whereas the second heterologous nucleic acid comprises a heterologous nucleotide sequence encoding an IBDV VP2 protein. In certain embodiments of this type, the first heterologous nucleic acid is constructed and/or inserted into the rMDV$_{np}$ genome so that the heterologous nucleotide sequence encoding the NDV F protein is 5' to the heterologous nucleotide sequence encoding the ILTV gD protein and the ILTV gI protein. In alternative embodiments of this type, the first heterologous nucleic acid is constructed and/or inserted into the rMDV$_{np}$ genome so that the heterologous nucleotide sequence encoding the ILTV gD protein and the ILTV gI protein is 5' to the heterologous nucleotide sequence encoding the NDV F protein.

Moreover, the present invention also provides rMDV$_{np}$ vectors that encode any combination of these nucleotide sequences, including specific embodiments wherein a first heterologous nucleic acid encodes the nucleotide sequence of SEQ ID NOs: 1, 3, and 5, and the second heterologous nucleic acid comprises the nucleotide sequence of SEQ ID NO: 7. In alternative embodiments, the first heterologous nucleic acid encodes the nucleotide sequence of SEQ ID NOs: 1, 3, and 5, and the second heterologous nucleic acid comprises the nucleotide sequence of SEQ ID NO: 9. In specific embodiments, the rMDV$_{np}$ is an rHVT. In alternative embodiments, the rMDV$_{np}$ is an rMDV2.

In particular embodiments the two different nonessential sites of the rMDV$_{np}$ are individually selected from the group consisting of the US2 site, the UL54.5 site, the UL7/8 site, the UL40 site, the UL 43 site, the UL45/46 site, the UL55 site, the US10 site, the region between US10 and SORF3, the region between US2 and SORF3, intergenic region 1 (IG 1) site, intergenic region 2 (IG2) site and intergenic region (IG3).

In certain embodiments, the first nonessential site of the rMDV$_{np}$ is the US2 site, while the second nonessential site of the rMDV$_{np}$ is a nonessential site other than the US2 site. In other embodiments, the first nonessential site of the rMDV$_{np}$ is the UL 54.5 site, while the second nonessential site of the rMDV$_{np}$ is a nonessential site other than the UL 54.5 site. In specific embodiments of this type, the first nonessential site is the US2 site and the second nonessential site is the UL54.5 site. In alternative embodiments, the first nonessential site is the UL54.5 site and the second nonessential site is the US2 site. In yet another embodiment of this type, the first nonessential site is the US2 site and the second nonessential site is the UL45/46 site. In still another embodiment of this type, the first nonessential site is the UL45/46 site and the second nonessential site is the US2 site. In yet another embodiment of this type, the first nonessential site is the UL54.5 site and the second nonessential site is the UL45/46 site. In still another embodiment of this type, the first nonessential site is the UL45/46 site and the second nonessential site is the UL54.5 site. In yet another embodiment of this type, the first nonessential site is the US2 site and the second nonessential site is the UL55 site. In still another embodiment of this type, the first nonessential site is the UL55 site and the second nonessential site is the US2 site. In related embodiments, the first nonessential site of the rMDV$_{np}$ is the UL 54.5 and the second nonessential site of the rMDV$_{np}$ is the UL7/8 site. In yet other embodiments, the first nonessential site of the rMDV$_{np}$ is the UL 54.5 and the second nonessential site of the rMDV$_{np}$ is the US10 site. In related embodiments, the second nonessential site of the rMDV$_{np}$ is the US2 site and the first nonessential site of the rMDV$_{np}$ is the UL7/8 site. In yet other embodiments, the second nonessential site of the rMDV$_{np}$ is the US2 site and the first nonessential site of the rMDV$_{np}$ is the US10 site. In specific embodiments, the rMDV$_{np}$ is an rHVT. In alternative embodiments, the rMDV$_{np}$ is an rMDV2.

In specific embodiments of this type, the first nonessential site and the second nonessential site are the same (i.e., there is a lone nonessential insertion site). In particular embodiments of this type, the lone nonessential insertion site is the US2 site. In other embodiments of this type, the lone nonessential insertion site is the UL54.5 site. In still other embodiments of this type, the lone nonessential insertion site is the UL7/8 site. In yet other embodiments of this type, the lone nonessential insertion site is the UL40 site. In still other embodiments of this type, the lone nonessential insertion site is the UL45/46 site. In yet other embodiments of this type, the lone nonessential insertion site is the UL55 site. In still other embodiments of this type, the lone nonessential insertion site is the US10 site. In yet other embodiments of this type, lone nonessential insertion site is the region between US10 and SORF3. In still other embodiments of this type, the lone nonessential insertion site is the region between US2 and SORF3. In yet other embodiments of this type the lone nonessential insertion site is the IG1 site. In still other embodiments of this type, the lone nonessential insertion site is the IG2 site. In yet other embodiments of this type the lone nonessential insertion site is the IG3 site. In still other embodiments of this type, the lone nonessential insertion site is the UL43 site. In specific embodiments, the rMDV$_{np}$ is an rHVT. In alternative embodiments, the rMDV$_{np}$ is an rMDV2.

The nucleotide sequences encoding the ILTV gD protein, the ILTV gI protein, and the IBDV VP2 protein can be operatively under the control of exogenous promoters, i.e., promoters that are not naturally found in the MDV$_{np}$. In certain embodiments, these three nucleotide sequences are operatively under the control of different promoters, i.e., the nucleotide sequence encoding the ILTV gD protein is operatively under the control of a first promoter, the nucleotide sequence encoding the ILTV gI protein is operatively under the control of a second promoter, and the nucleotide sequence encoding the IBDV VP2 protein is operatively under the control of a third promoter, with the first promoter, the second promoter, and the third promoter all being different. In particular embodiments, the promoter for the nucleotide sequence encoding the ILTV gD protein is the endogenous ILTV gD promoter (i.e., endogenous for ILTV). In certain embodiments, the promoter for the nucleotide sequence encoding the ILTV gI protein is the endogenous ILTV gI promoter. In particular embodiments of this type, the promoter for the nucleotide sequence encoding the ILTV gD protein is the endogenous ILTV gD promoter and the promoter for the nucleotide sequence encoding the ILTV gI protein is the endogenous ILTV gI promoter. In specific embodiments, the rMDV$_{np}$ is an rHVT. In alternative embodiments, the rMDV$_{np}$ is an rMDV2.

In certain embodiments, at least one of the promoters operably linked to a nucleotide sequence encoding the NDV F protein, the ILTV gD protein, the ILTV gI protein, or the IBDV VP2 protein is the murine cytomegalovirus immediate early (mCMV IE) promoter. In related embodiments, at least one of the promoters operably linked to a nucleotide sequence encoding the NDV F protein, the ILTV gD protein, the ILTV gI protein, or the IBDV VP2 protein is the human cytomegalovirus immediate early (hCMV IE) promoter or a derivative thereof (e.g., from strain AD169). In other embodiments, at least one of the promoters operably linked to a nucleotide sequence encoding the NDV F protein, the ILTV gD protein, the ILTV gI protein, or the IBDV VP2 protein is the guinea pig cytomegalovirus immediate early promoter. In other embodiments, at least one of the promoters operably linked to a nucleotide sequence encoding the NDV F protein, the ILTV gD protein, the ILTV gI protein, or the IBDV VP2 protein is the chicken β-actin promoter. In still other embodiments, at least one of the promoters operably linked to a nucleotide sequence encoding the NDV F protein, the ILTV gD protein, the ILTV gI protein or the IBDV VP2 protein is the pseudorabies virus (PRV) gpX promoter.

In particular embodiments, the promoter for the nucleotide sequence encoding the IBDV VP2 protein is the mCMV IE promoter. In related embodiments, the promoter for the nucleotide sequence encoding the IBDV VP2 protein is the human cytomegalovirus immediate early (hCMV IE) promoter or a derivative thereof (e.g., from strain AD169). In other embodiments, the promoter for the nucleotide sequence encoding the IBDV VP2 protein is the guinea pig cytomegalovirus immediate early promoter. In yet other embodiments, the promoter for the nucleotide sequence encoding the IBDV VP2 protein is the chicken beta-actin gene promoter.

In certain embodiments, the promoter operably linked to a nucleotide sequence encoding the NDV F protein is the human cytomegalovirus immediate early (hCMV IE) promoter. In other embodiments, the promoter operably linked to a nucleotide sequence encoding the NDV F protein is the pseudorabies virus (PRV) gpX promoter. In related embodiments, the promoter operably linked to a nucleotide sequence encoding the NDV F protein is the chicken beta-actin gene promoter. In still other embodiments, the promoter operably linked to a nucleotide sequence encoding the NDV F protein is the Simian virus 40 (SV40) promoter.

In more specific embodiments, the promoter for the nucleotide sequence encoding the IBDV VP2 protein is the mCMV IE promoter, the promoter for the nucleotide sequence encoding the ILTV gD protein is the endogenous ILTV gD promoter, the promoter for the nucleotide sequence encoding the ILTV gI protein is the endogenous ILTV gI promoter, and the promoter for the nucleotide sequence encoding the NDV F protein is the hCMV IE promoter. In other specific embodiments, the promoter for the nucleotide sequence encoding the IBDV VP2 protein is the hCMV IE promoter (or a derivative thereof), the promoter for the nucleotide sequence encoding the ILTV gD protein is the endogenous ILTV gD promoter, the promoter for the nucleotide sequence encoding the ILTV gI protein is the endogenous ILTV gI promoter, and the promoter for the nucleotide sequence encoding the NDV F protein is the hCMV IE promoter. In yet other specific embodiments, the promoter for the nucleotide sequence encoding the IBDV VP2 protein is the chicken β-actin promoter, the promoter for the nucleotide sequence encoding the ILTV gD protein is the endogenous ILTV gD promoter, the promoter for the nucleotide sequence encoding the ILTV gI protein is the endogenous ILTV gI promoter, and the promoter for the nucleotide sequence encoding the NDV F protein is the hCMV IE promoter.

In certain embodiments, an rMDV$_{np}$ of the present invention that includes insertions of nucleotide sequences encoding the ILTV gD protein, the ILTV gI protein, and the IBDV VP2 protein also includes one or more exogenous transcription terminator sequences. In specific embodiments of this type, a transcription terminator sequence is downstream from the nucleotide sequence encoding the IBDV VP2 protein. In particular embodiments, the nucleotide sequences encoding the ILTV gD protein and the ILTV gI protein share one transcription terminator sequence and the nucleotide sequence encoding the IBDV VP2 protein has another. In more particular embodiments, at least one of the transcription terminator sequences comprises a feline herpesvirus US-9 (FHV US-9) polyadenylation sequence. In even more particular embodiments, at least one of the transcription terminator sequences comprises a Simian virus 40 (SV40) polyadenylation sequence.

In certain embodiments, the NDV F protein also includes one or more exogenous transcription terminator sequences. In specific embodiments of this type, a transcription terminator sequence is downstream from the nucleotide sequence encoding the NDV F protein. In related embodiments at least one of the transcription terminator sequences comprises a Herpes Simplex Virus thymidine kinase (HSV TK) polyadenylation sequence. In alternative embodiments at least one of the transcription terminator sequences comprises a human cytomegalovirus immediate early (hCMV IE) polyadenylation sequence. In specific embodiments, the rMDV$_{np}$ is an rHVT. In alternative embodiments, the rMDV$_{np}$ is an rMDV2.

The present invention also provides an rMDV$_{np}$ that comprises (i) an mCMV IE promoter, a chicken beta-actin gene promoter, or an hCMV promoter (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein in the UL54.5 site of the rMDV$_{np}$ genome. In particular embodiments of this type, the nucleotide sequence of SEQ ID NO: 21 is comprised within the UL54.5 site of the rMDV$_{np}$ genome. In specific embodiments, the rMDV$_{np}$ further comprises (i) an hCMV IE promoter, (ii) a coding sequence for the NDV F protein and (iii) a hCMV IE transcription terminator sequence in the US2 site of its genome. In particular embodiments of this type, the nucleotide sequence of SEQ ID NO: 22 is comprised within the US2 site of the rMDV$_{np}$ genome.

The present invention further provides an rMDV$_{np}$ comprising (i) an mCMV IE promoter, a chicken beta-actin gene promoter, or an hCMV promoter (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein in the US2 site of the rMDV$_{np}$, genome. In certain embodiments of this type, the nucleotide sequence of SEQ ID NO: 24 is comprised within the US2 site of the rMDV$_{np}$ genome. In yet other embodiments of this type, the nucleotide sequence of SEQ ID NO: 25 is comprised within the US2 site of the rMDV$_{np}$ genome. In more particular embodiments of this type, the nucleotide sequence of SEQ ID NO: 23 is comprised within the US2 site of the rMDV$_{np}$ genome. In specific embodiments, the rMDV$_{np}$ further comprises (i) an hCMV IE promoter, (ii) a coding sequence for the NDV F protein and (iii) a hCMV IE transcription terminator sequence in the UL54.5 site of its genome. In particular embodiments of this type, the nucleotide sequence of SEQ ID NO: 26 is comprised within the UL54.5 site of the rMDV$_{np}$ genome.

In addition, the present invention also provides an rMDV$_{np}$ comprising (i) an ILTV gD promoter, (ii) a coding sequence for the ILTV gD protein, (iii) an ILTV gI promoter, (iv) a coding sequence for the ILTV gI protein (v) an hCMV IE promoter, (vi) a coding sequence for the NDV F protein and (vii) a hCMV IE transcription terminator sequence in the UL54.5 site of the rMDV$_{np}$ genome. In particular embodiments of this type, the nucleotide sequence of SEQ ID NO: 31 is comprised within the UL54.5 site of the rMDV$_{np}$ genome. In specific embodiments, the rMDV$_{np}$ further comprises (i) a mCMV IE promoter (ii) a coding sequence for the IBDV VP2 protein, and (iii) a transcription terminator sequence within the US2 site of the rMDV$_{np}$ genome. In particular embodiments of this type, the nucleotide sequence of SEQ ID NO: 32 is comprised within the US2 site of the rMDV$_{np}$ genome.

The present invention also provides an rMDV$_{np}$ comprising (i) an ILTV gD promoter, (ii) a coding sequence for the ILTV gD protein, (iii) an ILTV gI promoter, (iv) a coding sequence for the ILTV gI protein (v) an hCMV IE promoter, (vi) a coding sequence for the NDV F protein and (vii) a hCMV IE transcription terminator sequence in the US2 site of the rMDV$_{np}$ genome. In particular embodiments of this type, the nucleotide sequence of SEQ ID NO: 28 is comprised within the US2 site of the rMDV$_{np}$ genome. In specific embodiments, the rMDV$_{np}$ further comprises (i) a mCMV IE promoter (ii) a coding sequence for the IBDV VP2 protein, and (iii) a transcription terminator sequence within the UL54.5 site of the rMDV$_{np}$ genome. In particular embodiments of this type, the nucleotide sequence of SEQ ID NO: 27 is comprised within the UL54.5 site of the rMDV$_{np}$ genome.

The present invention further provides an rMDV$_{np}$ comprising (i) an mCMV IE promoter (ii) a coding sequence for the IBDV VP2 protein, (iii) a transcription terminator sequence (iv) an hCMV IE promoter, (v) a coding sequence for the NDV F protein and (vi) a hCMV IE transcription terminator sequence in in the US2 site of the rMDV$_{np}$ genome. In particular embodiments of this type, the nucleotide sequence of SEQ ID NO: 30 is comprised within the US2 site of the rMDV$_{np}$ genome. In specific embodiments, the rMDV$_{np}$ further comprises (i) an ILTV gD promoter, (ii) a coding sequence for the ILTV gD protein, (iii) an ILTV gI promoter, and (iv) a coding sequence for the ILTV gI protein is comprised within the UL54.5 site of its genome. In particular embodiments of this type, the nucleotide sequence of SEQ ID NO: 29 is comprised within the UL54.5 site of the rMDV$_{np}$ genome.

The present invention also provides an rMDV$_{np}$ comprising (i) an mCMV IE promoter (ii) a coding sequence for the IBDV VP2 protein, (iii) a transcription terminator sequence (iv) an hCMV IE promoter, (v) a coding sequence for the NDV F protein and (vi) a hCMV IE transcription terminator sequence in in the UL54.5 site of the rMDV$_{np}$ genome. In specific embodiments, the rMDV$_{np}$ further comprises (i) an ILTV gD promoter, (ii) a coding sequence for the ILTV gD protein, (iii) an ILTV gI promoter, and (iv) a coding sequence for the ILTV gI protein is comprised within the US2 site of its genome.

The present invention also provides an rMDV$_{np}$ comprising (i) an mCMV IE promoter (ii) a coding sequence for the IBDV VP2 protein, (iii) a transcription terminator sequence (iv) an hCMV IE promoter, (v) a coding sequence for the NDV F protein and (vi) a hCMV IE transcription terminator sequence in the US2 site of the rMDV$_{np}$ genome and (i) an ILTV gD promoter, (ii) a coding sequence for the ILTV gD protein, (iii) an ILTV gI promoter, and (iv) a coding sequence for the ILTV gI protein comprised within the UL7/8 site of its genome.

In more specific embodiments, the present invention provides an rHVT that comprises a first heterologous nucleic acid and a second heterologous nucleic acid. The first heterologous nucleic acid comprising (i) a murine cytomegalovirus immediate early (mCMV IE) promoter, (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein. In particular embodiments of this type, the specific 5' to 3' order for the nucleotide sequences of this recombinant nucleic acid is (i) (vii). In a more specific embodiment the transcription terminator sequence comprises an SV40 polyadenylation sequence. In an even more specific embodiment of this type, the first heterologous nucleic is located in the US2 site of the rHVT genome. The second heterologous nucleic acid comprises a recombinant nucleic acid that comprises in 5' to 3' direction in the following order (i) a human cytomegalovirus immediate early (hCMV IE) promoter, (ii) a coding sequence for the NDV F protein, and (iii) a transcription terminator sequence. In a more specific embodiment the transcription terminator sequence comprises a human cytomegalovirus immediate early (hCMV IE) polyadenylation sequence. In more specific embodiments of this type, the second heterologous nucleic acid is located in the UL54.5 site of the rHVT genome.

Accordingly the present invention includes recombinant HVTs (rHVTs) that comprises two heterologous nucleic acids, each inserted in separate nonessential sites of the HVT genome. In certain embodiments the first heterologous nucleic acid comprises (i) a murine cytomegalovirus immediate early (mCMV IE) promoter, (ii) a coding sequence for the IBDV VP2 protein, (iii) a transcription terminator sequence (iv) an ILTV gD promoter, (v) a coding sequence for the ILTV gD protein, (vi) an ILTV gI promoter, and (vii) a coding sequence for the ILTV gI protein. In particular embodiments of this type, the specific 5' to 3' order for the nucleotide sequences of this recombinant nucleic acid is (i) (vii). The second heterologous nucleic acid comprises the following 5' to 3' order (i) a human cytomegalovirus immediate early (hCMV IE) promoter, (ii) a coding sequence for the NDV F protein, and (iii) a transcription terminator sequence. In particular embodiments the first heterologous nucleic acid is inserted into the US2 site and the second heterologous nucleic acid is inserted into the UL54.5 site. In particular embodiments of this type, the first heterologous nucleic acid comprises the nucleotide sequence of SEQ ID NO: 23 and the second heterologous nucleic acid comprises the nucleotide sequence of SEQ ID NO: 26. In alternative embodiments the second heterologous nucleic acid is inserted into the US2 site and the first heterologous nucleic acid is inserted into the UL54.5 site. In certain embodiments of this type, the first heterologous nucleic acid comprises the nucleotide sequence of SEQ ID NO: 21 and the second heterologous nucleic acid comprises the nucleotide sequence of SEQ ID NO: 22.

In other embodiments, the first heterologous nucleic acid comprises (i) a murine cytomegalovirus immediate early (mCMV IE) promoter, (ii) a coding sequence for the IBDV VP2 protein, (iii) a transcription terminator sequence (iv) a human cytomegalovirus immediate early (hCMV IE) promoter, (v) a coding sequence for the NDV F protein, and (vi) a transcription terminator sequence. In particular embodiments of this type, the specific 5' to 3' order for the nucleotide sequences of this recombinant nucleic acid is (i) (vi). The second heterologous nucleic acid comprises the following 5' to 3' order (i) an ILTV gD promoter, (ii) a coding sequence for the ILTV gD protein, (iii) an ILTV gI promoter, and (iv) a coding sequence for the ILTV gI protein. In particular embodiments the first heterologous nucleic acid is inserted into the US2 site and the second heterologous nucleic acid is inserted into the UL54.5 site. In particular embodiments, the first heterologous nucleic acid comprises the nucleotide sequence of SEQ ID NO: 30 and the second heterologous nucleic acid comprises the nucleotide sequence of SEQ ID NO: 29. In alternative embodiments the second heterologous nucleic acid is inserted into the US2 site and the first heterologous nucleic acid is inserted into the UL54.5 site.

In still other embodiments, the first heterologous nucleic acid comprises (i) an ILTV gD promoter, (ii) a coding sequence for the ILTV gD protein, (iii) an ILTV gI promoter, (iv) a coding sequence for the ILTV gI protein (v) a human cytomegalovirus immediate early (hCMV IE) promoter, (vi) a coding sequence for the NDV F protein, and (vii) a transcription terminator sequence. In particular embodiments of this type, the specific 5' to 3' order for the nucleotide sequences of this recombinant nucleic acid is (i) (vii). The second heterologous nucleic acid comprises the following 5' to 3' order (i) a murine cytomegalovirus immediate early (mCMV IE) promoter, (ii) a coding sequence for the IBDV VP2 protein, (iii) a transcription terminator sequence. In particular embodiments the first heterologous nucleic acid is inserted into the US2 site and the second heterologous nucleic acid is inserted into the UL54.5 site. In particular embodiments of this type the first heterologous nucleic acid comprises the nucleotide sequence of SEQ ID NO: 28 and the second heterologous nucleic acid comprises the nucleotide sequence of SEQ ID NO: 27. In alternative embodiments the second heterologous nucleic acid is inserted into the US2 site and the first heterologous nucleic acid is inserted into the UL54.5 site. In particular embodiments of this type the first heterologous nucleic acid comprises the nucleotide sequence of SEQ ID NO: 31 and the second heterologous nucleic acid comprises the nucleotide sequence of SEQ ID NO: 32.

The present invention further provides methods for making any $rMDV_{np}$ of the present invention (e.g., a rHVT). In certain embodiments, a first heterologous nucleic acid is constructed to comprise a nucleotide sequence that encodes an ILTV gD protein, a nucleotide sequence that encodes an ILTV gI protein, and a nucleotide sequence that encodes an IBDV VP2 protein. In particular embodiments of this type, the promoters for the nucleotide sequences that encode the ILTV gD protein and the ILTV gI protein respectively, are their respective endogenous promoters. In related embodiments, the promoter for the nucleotide sequence that encodes an IBDV VP2 protein is the mCMV IE promoter, the chicken beta-actin gene promoter, or the hCMV promoter.

The first heterologous nucleic acid is then inserted into a nonessential site of an $rMDV_{np}$ of the present invention. In certain embodiments, the first heterologous nucleic acid is an expression cassette. In particular embodiments of this type, the expression cassette comprises the nucleotide sequence of SEQ ID NO: 21.

The process can further comprises a second heterologous nucleic acid being constructed that is also inserted into a nonessential site of the $rMDV_{np}$. In particular embodiments, the second heterologous nucleic acid comprises a human cytomegalovirus immediate early (hCMV IE) promoter, a coding sequence for the NDV F protein, and a transcription terminator sequence. In certain embodiments, the second heterologous nucleic acid is an expression cassette. In particular embodiments of this type, the expression cassette comprises the nucleotide sequence of SEQ ID NO: 22. In specific embodiments the first heterologous nucleic acid is inserted into a first nonessential site of the $rMDV_{np}$, and the second heterologous nucleic acid is inserted into second nonessential site of the $rMDV_{np}$. In certain embodiments, the first nonessential site of the $rMDV_{np}$ is the UL 54.5 site.

In related embodiments, the second nonessential site of the $rMDV_{np}$ is the US2 site. In alternative embodiments, the first nonessential site of the $rMDV_{np}$ is the US2 site and the second nonessential site of the $rMDV_{np}$ is the UL 54.5 site. In specific embodiments of this type, the first heterologous nucleic acid comprises the nucleotide sequence of SEQ ID NO: 23 and the second heterologous nucleic acid comprises the nucleotide sequence of SEQ ID NO: 26. In other embodiments of this type, the first heterologous nucleic acid comprises the nucleotide sequence of SEQ ID NO: 24 and the second heterologous nucleic acid comprises the nucleotide sequence of SEQ ID NO: 26. In still other embodiments of this type the the first heterologous nucleic acid comprises the nucleotide sequence of SEQ ID NO: 25 and the second heterologous nucleic acid comprises the nucleotide sequence of SEQ ID NO: 26. In certain embodiments, the method of making an $rMDV_{np}$ is a method of making an rHVT. In alternative embodiments, the method of making an $rMDV_{np}$ is a method of making an rMDV2.

Accordingly in one aspect, the present invention provides immunogenic compositions and/or vaccines that comprise an $rMDV_{np}$ of the present invention (e.g., a rHVT). In particular embodiments these immunogenic compositions and/or vaccines are stable, safe, and have relatively strong antigen expression and/or efficacy. Alternatively, or in addition, the immunogenic compositions and/or vaccines that comprise an $rMDV_{np}$ of the present invention aid in the protection of a chicken against a disease caused by ILTV and/or IBDV and/or NDV and/or MDV1, following the administration of the immunogenic compositions and/or vaccines to the chicken.

The present invention further provides immunogenic compositions and/or vaccines that comprise any $rMDV_{np}$ of the present invention (e.g., a rHVT) that are further combined with an additional IBDV, ILTV, NDV, and/or MDV antigen(s) to improve and expand the immunogenicity provided. In a particular embodiment of this type, the antigen is an attenuated or mild live variant IBDV (e.g., IBDV 89/03). In another particular embodiment of this type, the antigen is an attenuated (or mild live) Newcastle Disease Virus (NDV), e.g., NDV C2. In yet another particular embodiment of this type, the antigen is an attenuated Marek's disease virus e.g., SB1. In addition, the present invention also provides immunogenic compositions and/or vaccines that comprise any $rMDV_{np}$ of the present invention that is further encodes an antigen for a pathogen other than MDV, ILTV, or NDV.

The present invention also provides methods for aiding in the protection of poultry against a disease caused by ILTV and/or IBDV and/or NDV and/or MDV1 by administering such vaccines and/or immunogenic compositions to a poultry subject (e.g., to a chicken). In particular embodiments of this type, a vaccine of the present invention is administered subcutaneously. In other embodiments, a vaccine of the present invention is administered in ovo.

These and other aspects of the present invention will be better appreciated by reference to the following Figures and the Detailed Description.

Figure 1:
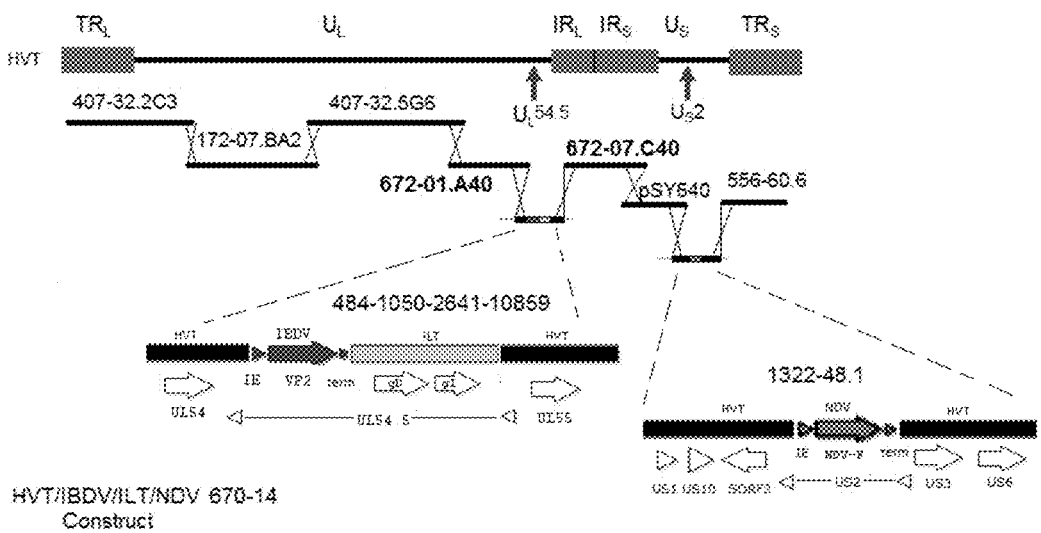
FIG. 1 is a schematic drawing of insertion fragments for generating HVT/IBDV/ILTV/NDV constructs as described in Example 2, below. In short, this is a schematic view of the HVT genome, consisting of two unique regions, each flanked by repeat regions, and the cloned fragments required to reconstruct the HVT/IBDV/ILTV/NDV 670-14 virus. The orientation of the inserted gene cassettes (mIE-IBDV-vp2 and ILTV-gD/gI or hIE-NDV-F), relative to the interrupted genes (UL54.5 or US2), and the flanking genes are shown in the blow-up regions. Legend: TRL: Terminal Repeat Long region, UL: Unique Long region; IRL: Internal Repeat Long region, IRS: Internal Repeat Short region; US: Unique Short region; TRS: Terminal Repeat Short region.
Figure 2:
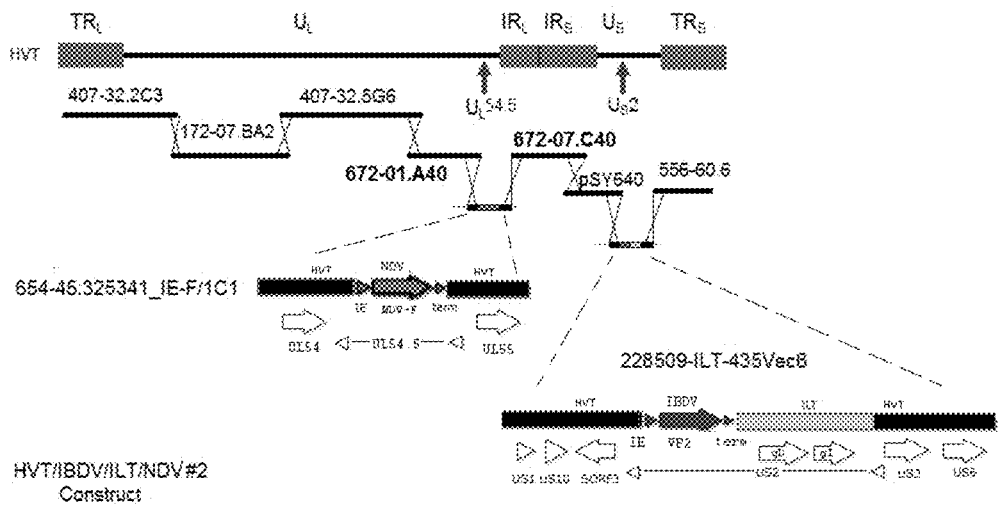

FIG. 2 is a schematic drawing of insertion fragments for generating HVT/IBDV/ILT/NDV construct #2. The two HVT insertion sites are UL54.5 and US2. [See also description for FIG. 1 above].

Figures 3, 4:
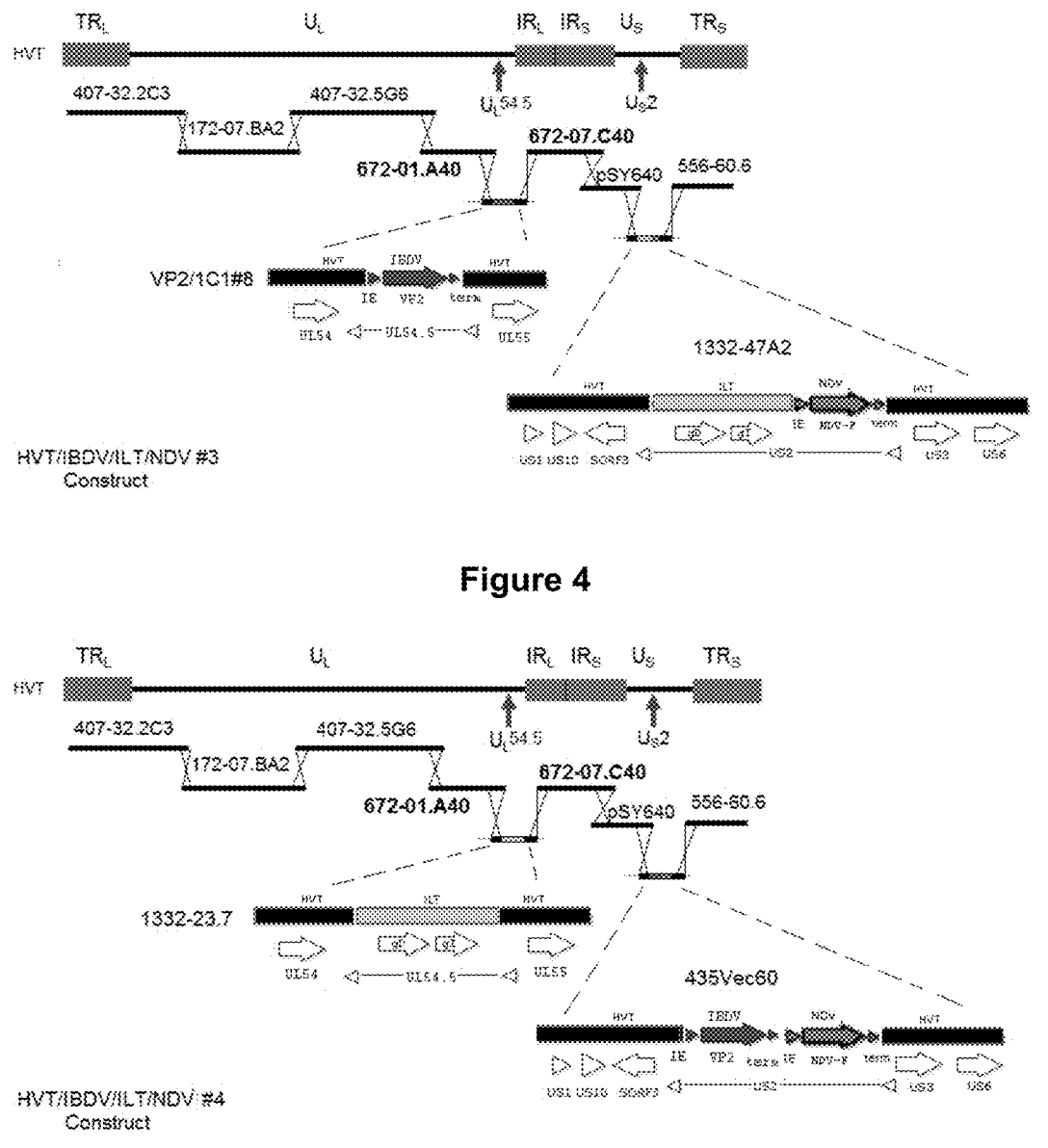

FIG. 3 is a schematic drawing of insertion fragments for generating HVT/IBDV/ILT/NDV construct #3. The two HVT insertion sites are UL54.5 and US2. [See also description for FIG. 1 above].

FIG. 4 is a schematic drawing of insertion fragments for generating HVT/IBDV/ILT/NDV construct: #4. The two HVT insertion sites are UL54.5 and US2. [See also description for FIG. 1 above].

Figure 5:
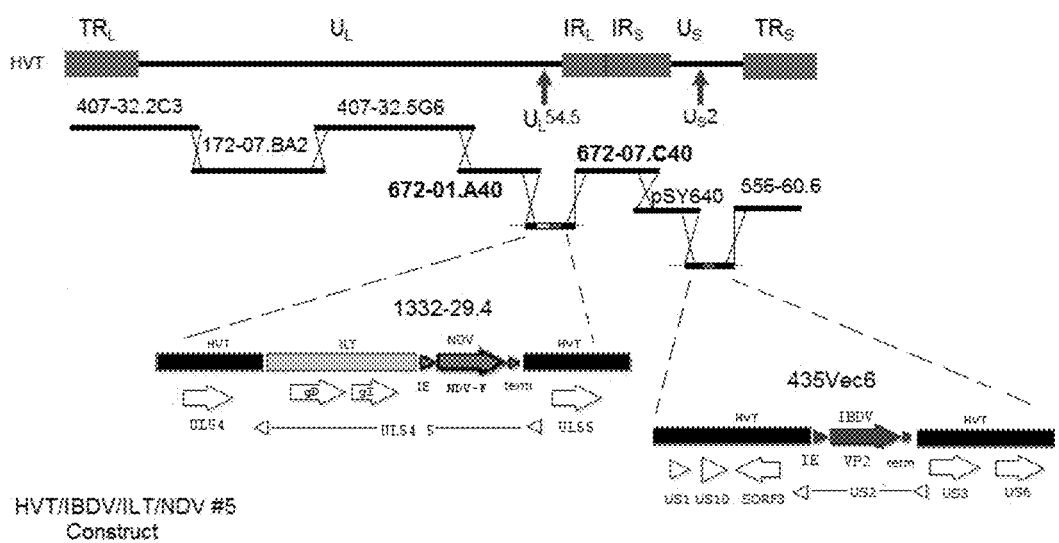

FIG. 5 is a schematic drawing of insertion fragments for generating HVT/IBDV/ILT/NDV construct #5. The two HVT insertion sites are UL54.5 and US2. [See also description for FIG. 1 above].

DETAILED DESCRIPTION OF THE INVENTION

The present invention overcomes the prior failure to be able to construct a single $rMDV_{np}$ vector that encodes and expresses antigens from three or more foreign pathogenic chicken viruses. In particular embodiments, an $rMDV_{np}$ of the present invention encodes and expresses foreign antigen proteins from three or more of the avian viruses. In particular embodiments the avian viruses are Newcastle Disease Virus (NDV), Infectious Laryngotraceitis virus (ILTV), and Infectious Bursal Disease (IBDV). Such $rMDV_{np}$ vectors can be employed in vaccines and/or immunogenic compositions that aid in the protection against Marek's disease, Infectious Bursal Disease (Gumboro disease), Infectious Laryngotraceitis virus, and/or Newcastle Disease Virus. In specific embodiments, the $rMDV_{np}$ is an rHVT. In alternative embodiments, the $rMDV_{np}$ is an rMDV2. The present invention further provides immunogenic compositions and/or vaccines that comprise any $rMDV_{np}$ of the present invention combined with an additional IBDV, ILTV, NDV, and/or MDV antigen, and/or one or more antigens from a chicken pathogen other than MDV, ILTV, NDV, or IBDV. In a completely different aspect, the recombinant vector that encodes and expresses the foreign antigens from NDV, ILTV, IBDV is not an $rMDV_{np}$, but rather a chimeric Marek's Disease virus that contains specified genomic sequences from MDV1 replacing their counterparts in an HVT vector, e.g., the novel avian herpes virus (NAHV) [see e.g., U.S. Pat. No. 6,913,751].

Prior to the present invention, an HVT vector already had been constructed containing an NDV gene inserted into the US10 region. This HVT-NDV vector was shown to be stable and to express sufficient levels of the corresponding NDV gene product, the NDV F protein, to protect vaccinated chickens against a virulent NDV challenge. In addition, an HVT vector already had been constructed containing a pair of ILTV genes inserted in the HVT UL54.5 region. This HVT-ILTV vector was shown to be stable and to express sufficient levels of the corresponding ILTV gene products, the ILTV gI and gD proteins, to protect vaccinated chickens against a virulent ILTV challenge virus. More recently, other multivalent constructs also have been reported.

More particularly, a multivalent HVT construct to protect against both NDV and ILTV was designed based on the successful constructs comprising the insertion of the NDV-F gene in the US10 site and the insertion of the ILTV gD and gI genes in UL54.5 site in individual constructs [see, U.S. Pat. No. 8,932,604 B2]. Unexpectedly however, following the passaging of this multivalent construct in tissue culture the recombinant virus lost its ability to express the ILTVgD, ILTVgI, and NDV F proteins. This proved to be true with a number of duplicate recombinant HVT constructs. Indeed, these recombinant viruses were unstable and unsuitable for further development as vaccines. These findings demonstrate that the design of a single multivalent rHVT vector that can stably express both the NDV F protein and the ILTVgD and ILTVgI proteins was not a simple process that can be extrapolated from existing information. Indeed, if such stable and efficacious multivalent rHVT vectors were possible at all, their design needed to be premised on an unpredictable set of complex interactions minimally involving the relationship between the insertion sites used and the foreign nucleotide sequences to be inserted. Accordingly, the design of rHVT constructs remains unpredictable from the known art. This would appear to be even a bigger issue for an $rMDV_{np}$ that encodes heterologous antigens from three or more avian virus pathogens.

Despite the clear difficulties outlined above, and the general consensus in the field that the insertion of foreign antigens from three or more different viral pathogens into an $MDV_{np}$ construct overtaxes that construct, leading to a lack of stability, the present invention surprisingly provides stable recombinant $MDV_{np}$ vectors in which two genes from ILTV, one gene from IBDV, and one gene from NDV have been inserted into a single $MDV_{np}$. Accordingly, such a single $rMDV_{np}$ construct can be employed as the sole active in a vaccine that aids in the protection against four major pathogenic poultry viruses.

In particular embodiments of the present invention nucleotide sequences encoding four foreign antigens are inserted into one or more nonessential regions of the genome of a single HVT. Accordingly, such a recombinant HVT vector should be capable of being used to provide protection against MDV, NDV, IBDV, and ILTV infections. Previously, multiple different rHVT vectors were necessary to protect against these four viruses, which can interfere with the antigenicity of each other.

The present invention therefore, is advantageous over current methods because it should be able to provide simultaneous protection against MDV, NDV, IBDV, and ILTV infections by inoculation of poultry and/or poultry eggs with only a single recombinant $MDV_{np}$. In particular, this allows for additional vaccines to be administered via the in ovo route, because there is a limit on how much volume can be injected into an egg, and further saves on manufacturing costs because only one rather than two vectors is needed.

Furthermore, the present invention includes embodiments that comprise different $rMDV_{np}$ constructs in the same vaccine and/or immunogenic compositions. In certain embodiments of this type, the vaccine and/or immunogenic composition comprise both an rMDV2 and an rHVT, each of which encode one or more foreign antigens. Indeed, unlike the combination of two rHVTs, which inevitably lead to one construct significantly overgrowing the other, combining an rHVT with an rMDV2 has been reported not to lead to significant overgrowth.

Therefore, in specific embodiments, a vaccine of the present invention comprises an rHVT that encodes an ILTV gD protein, an ILTV gI protein, an IBDV VP2 protein, and an NDV F protein, with an rMDV2 that encodes yet another poultry viral antigen. Heretofore, no rMDV$_{np}$ had been shown to encode and express foreign antigens from three different poultry viruses, and still remain stable, as well as capable of expressing sufficient levels of the corresponding antigens for protecting vaccinated chickens against a virulent challenge with the corresponding three viruses, as well as against virulent MDV.

Accordingly, the present invention provides immunogenic compositions and/or vaccines that comprise any rMDV$_{np}$ of the present invention. In specific embodiments, the rMDV$_{np}$ is an rHVT. In alternative embodiments, the rMDV$_{np}$ is an rMDV2. In addition, the present invention provides methods for aiding in the protection of poultry (and in certain embodiments protects) against a disease caused by ILTV and/or IBDV and/or NDV and/or MDV1 by administering such a vaccine and/or immunogenic composition of the present invention. In specific embodiments, the poultry subject is a chicken. In particular embodiments of this type, a vaccine of the present invention is administered subcutaneously. In other embodiments, a vaccine of the present invention is administered in ovo. In preferred embodiments, the rMDV$_{np}$ vaccine of the present invention is both safe, stable, and efficacious.

In order to more fully appreciate the instant invention, the following definitions are provided.

The use of singular terms for convenience in description is in no way intended to be so limiting. Thus, for example, reference to a composition comprising "a polypeptide" includes reference to one or more of such polypeptides.

As used herein a "nonpathogenic Marek's Disease Virus" or "MDV$_{np}$" or "npMDV" is a virus in the MDV family that shows little to no pathogenicity in poultry. The term "MDV$_{np}$" includes naturally occurring MDVs that have been passaged or otherwise similarly manipulated, but does not include viral constructs in which a specific region of the genome of one MDV serotype is replaced by the corresponding region of a different MDV serotype to form a chimeric virus, such as the novel avian herpesvirus (NAHV). In certain embodiments, the MDV$_{np}$ is an HVT. In other embodiments, the MDV$_{np}$ is an MDV2. In particular embodiments of this type, the MDV2 is SB1.

As used herein, an MDV$_{np}$ that has been genetically modified to encode a heterologous nucleotide sequence (e.g., a foreign gene) is defined as a "recombinant MDV$_{np}$" or "rMDV$_{np}$". The term "rMDV$_{np}$" includes naturally occurring MDV$_{np}$'s that have been genetically modified to encode a heterologous nucleotide sequence, but does not include viral constructs in which a specific region of the genome of one MDV serotype is replaced by the corresponding region of a different MDV serotype to form a chimeric virus, such as the novel avian herpesvirus (NAHV).

As used herein a "novel avian herpesvirus" ("NAHV") is a recombinant chimeric virus comprising a unique long viral genomic region which naturally occurs in herpesvirus of turkeys virus (HVT) and a unique short viral genomic region which naturally occurs in Marek's disease 1 (MDV1) [see, U.S. Pat. Nos. 5,965,138, 6,183,753, 6,913,751 B2]. In a preferred embodiment the NAHV comprises a unique long viral genomic region which naturally occurs in herpesvirus of turkeys virus (HVT), a unique short viral genomic region which naturally occurs in Marek's disease 1 (MDV1), and the repeat viral regions of the HVT [see, U.S. Pat. No. 6,913,751 B2].

As used herein, a "nonessential site" is a site in the MDV$_{np}$ genome (or alternatively in the NAVH genome) in which an insertion of a heterologous nucleotide sequence into that site does not prevent the MDV$_{np}$ (or NAVH) from replicating in a host cell. Nonessential sites are generally identified by the open reading frame in which they reside, e.g., the US2 site, or a region between two open reading frames, e.g., the UL7/8 site. The use of the term "nonessential site" is in no way intended to even suggest that there is only a single unique nucleotide position in the nucleotide sequence of a given open reading frames (or in the region between two open reading frames) where an insertion of a heterologous nucleic acid must be made in order for the MDV$_{np}$ (or NAVH) to maintain its ability to replicate in a host cell.

As used herein, when an rMDV$_{np}$ (or NAHV) is said to comprise a given nucleic acid "inserted" in a nonessential site in the rMDV$_{np}$ genome (or NAHV genome), it means that the given nucleic acid is a heterologous nucleic acid that is located in that nonessential site of the MDV$_{np}$ (or NAHV). Accordingly, an rMDV$_{np}$ comprising a first nucleic acid inserted in a first nonessential site in the rMDV$_{np}$ genome and a second nucleic acid inserted in a second nonessential site in the rMDV$_{np}$ genome is equivalent to an rMDV$_{np}$ comprising a first heterologous nucleic acid located in a first nonessential site in the rMDV$_{np}$ genome and a second heterologous nucleic acid located in a second nonessential site in the rMDV$_{np}$ genome, and vice versa.

As used herein the term "poultry" can include chickens, turkeys, ducks, geese, quail, and pheasants.

As used herein, a "vaccine" is a composition that is suitable for application to an animal (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a disease arising from an infection with a wild-type micro-organism, i.e., strong enough for aiding in the prevention of the disease, and/or preventing, ameliorating or curing the disease.

As used herein, the term "aids in the protection" does not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

The vaccines of the present invention comprise at least one stable rMDV$_{np}$ of the present invention. A rMDV$_{np}$ is considered phenotypically stable when at least 90% of the viral plaques examined are positive for expression of the inserted foreign antigen, as demonstrated by binding of antibodies specific for the expressed protein in an immunofluorescent assay, following at least 10 tissue culture passages from the original stock, or following reisolation of the virus from vaccinated birds.

The vaccines of the present invention also are efficacious and preferably minimally provide at least 70% protection against NDV, and/or at least 70% protection against IBDV, and/or at least 70% protection against ILTV, and/or at least 60% protection against MDV from clinical signs or lesions associated with the disease. More preferably, the vaccine minimally provides at least 80% protection against NDV, at least 80% protection against IBDV, at least 80% protection against ILTV, and at least 70% protection against MDV from clinical signs or lesions associated with the disease. Even more preferably the vaccines follow the guidelines established by the USDA and codified in the Title 9 Code of Federal Regulations, part 113 (9CFR 113) «Standard requirements for Animal Products» live virus vaccines must provide at least 90% protection, in the case of NDV, IBDV and ILTV, and at least 80% in the case of MDV, from clinical signs or lesions associated with the disease to obtain a license.

As used herein, a "multivalent vaccine" is a vaccine that comprises two or more different antigens. In a particular embodiment of this type, the multivalent vaccine stimulates the immune system of the recipient against two or more different pathogens.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal or transdermal), underneath the skin (subcutaneous), underneath the mucosa (submucosal), in the veins (intravenous) etc.

As used herein the term "parenteral administration" includes subcutaneous injections, submucosal injections, intravenous injections, intramuscular injections, intradermal injections, and infusion.

The term "approximately" is used interchangeably with the term "about" and signifies that a value is within twenty-five percent of the indicated value i.e., a peptide containing "approximately" 100 amino acid residues can contain between 75 and 125 amino acid residues.

As used herein, the term, "polypeptide" is used interchangeably with the terms "protein" and "peptide" and denotes a polymer comprising two or more amino acids connected by peptide bonds. The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 155, 154, 153, etc., in all practical combinations.

Optionally, a polypeptide may lack certain amino acid residues that are encoded by a gene or by an mRNA. For example, a gene or mRNA molecule may encode a sequence of amino acid residues on the N-terminus of a polypeptide (i.e., a signal sequence) that is cleaved from, and therefore, may not be part of the final protein.

As used herein the term "antigenic fragment" in regard to a particular protein (e.g., a protein antigen) is a fragment of that protein (including large fragments that are missing as little as a single amino acid from the full-length protein) that is antigenic, i.e., capable of specifically interacting with an antigen recognition molecule of the immune system, such as an immunoglobulin (antibody) or T cell antigen receptor. For example, an antigenic fragment of an IBDV VP2 protein is a fragment of the VP2 protein that is antigenic. Preferably, an antigenic fragment of the present invention is immunodominant for antibody and/or T cell receptor recognition. In particular embodiments, an antigenic fragment with respect to a given protein antigen is a fragment of that protein that retains at least 25% of the antigenicity of the full length protein. In preferred embodiments an antigenic fragment retains at least 50% of the antigenicity of the full length protein. More preferred embodiments it retains at least 75% of the antigenicity of the full length protein. Antigenic fragments can be as small as 5-10 amino acids or at the other extreme, be large fragments that are missing as little as a single amino acid from the full-length protein. In particular embodiments the antigenic fragment comprises 25 to 100 amino acid residues.

As used herein an amino acid sequence is 100% "homologous" to a second amino acid sequence if the two amino acid sequences are identical, and/or differ only by neutral or conservative substitutions as defined below. Accordingly, an amino acid sequence is about 80% "homologous" to a second amino acid sequence if about 80% of the two amino acid sequences are identical, and/or differ only by neutral or conservative substitutions.

Functionally equivalent amino acid residues often can be substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred conservative substitutions are: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained. The amino acids also can be placed in the following similarity groups: (1) proline, alanine, glycine, serine, and threonine; (2) glutamine, asparagine, glutamic acid, and aspartic acid; (3) histidine, lysine, and arginine; (4) cysteine; (5) valine, leucine, isoleucine, methionine; and (6) phenylalanine, tyrosine, and tryptophan.

In a related embodiment, two highly homologous DNA sequences can be identified by their own homology, or the homology of the amino acids they encode. Such comparison of the sequences can be performed using standard software available in sequence data banks. In a particular embodiment two highly homologous DNA sequences encode amino acid sequences having about 80% identity, more preferably about 90% identity and even more preferably about 95% identity. More particularly, two highly homologous amino acid sequences have about 80% identity, even more preferably about 90% identity and even more preferably about 95% identity.

As used herein, protein and DNA sequence percent identity can be determined using software such as MacVector v9, commercially available from Accelrys (Burlington, Mass.) and the Clustal W algorithm with the alignment default parameters, and default parameters for identity. See, e.g., Thompson, et al., 1994. *Nucleic Acids Res.* 22:4673-4680. ClustalW is freely downloadable for Dos, Macintosh and Unix platforms from, e.g., EMBLI, the European Bioinformatics Institute. The present download link is found at www dot ebi dot ac dot uk/clustalw/. These and other available programs can also be used to determine sequence similarity using the same or analogous default parameters.

As used herein the terms "polynucleotide", or a "nucleic acid" or a "nucleic acid molecule" are used interchangeably and denote a molecule comprising nucleotides including, but is not limited to, RNA, cDNA, genomic DNA and even synthetic DNA sequences. The terms are also contemplated to encompass nucleic acid molecules that include any of the art-known base analogs of DNA and RNA.

A nucleic acid "coding sequence" or a "sequence encoding" a particular protein or peptide, is a nucleotide sequence which is transcribed and translated into a polypeptide in vitro or in vivo when placed under the control of appropriate regulatory elements.

The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., avian) DNA, and even synthetic DNA sequences. A transcription termination sequence can be located 3' to the coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

As used herein, the term "transcription terminator sequence" is used interchangeably with the term "polyadenylation regulatory element" and is a sequence that is generally downstream from a DNA coding region and that may be required for the complete termination of the transcription of that DNA coding sequence. A transcription terminator is a regulatory DNA element involved in the termination of the transcription of a coding region into RNA. Generally, such an element encodes a section, e.g. a hairpin structure, which has a secondary structure that can cause the RNA polymerase complex to stop transcription. A transcription terminator is therefore always situated downstream of the stop codon from the region to be translated, the 3' untranslated region.

As used herein an "expression cassette" is a recombinant nucleic acid that minimally comprises a promoter and a heterologous coding sequence operably linked to that promoter. In many such embodiments, the expression cassette further comprises a transcription terminator sequence. Accordingly, the insertion of an expression cassette into a nonessential site of the $rMDV_{np}$ genome can lead to the expression of the heterologous coding sequence by the $rMDV_{np}$. In specific embodiments, the $rMDV_{np}$ is an rHVT. In alternative embodiments, the $rMDV_{np}$ is an rMDV2.

A "heterologous nucleotide sequence" as used herein is a nucleotide sequence that is added to a nucleotide sequence of the present invention by recombinant methods to form a nucleic acid that is not naturally formed in nature. In specific embodiments, a "heterologous nucleotide sequence" of the present invention can encode a protein antigen, (e.g., encoded by a "foreign gene" relative to the $rMDV_{np}$, vectors of the present invention) such as an IBDV VP2 protein, an ILTV gI protein, an ILTV gD protein, and/or an NDV F protein. In this case, such protein antigens can be termed "foreign antigens" or more specifically "foreign protein antigens".

Heterologous nucleotide sequences can also encode fusion (e.g., chimeric) proteins. In addition, a heterologous nucleotide sequence can encode peptides and/or proteins that contain regulatory and/or structural properties. In other such embodiments, a heterologous nucleotide sequence can encode a protein or peptide that functions as a means of detecting the protein or peptide encoded by the nucleotide sequence of the present invention after the recombinant nucleic acid is expressed. In still another embodiment, the heterologous nucleotide sequence can function as a means of detecting a nucleotide sequence of the present invention. A heterologous nucleotide sequence can comprise non-coding sequences including restriction sites, regulatory sites, promoters and the like. A "heterologous nucleic acid" comprises a heterologous nucleotide sequence.

Insertion of a nucleic acid encoding an antigen of the present invention into an $rMDV_{np}$ vector is easily accomplished when the termini of both the nucleic acid and the vector comprise compatible restriction sites. If this cannot be done, it may be necessary to modify the termini of the nucleotide sequence and/or vector by digesting back single-stranded nucleic acid overhangs (e.g., DNA overhangs) generated by restriction endonuclease cleavage to produce blunt ends, or to achieve the same result by filling in the single-stranded termini with an appropriate polymerase. Alternatively, desired sites may be produced, e.g., by ligating nucleotide sequences (linkers) onto the termini. Such linkers may comprise specific oligonucleotide sequences that define desired restriction sites. Restriction sites can also be generated through the use of the polymerase chain reaction (PCR). [See, e.g., Saiki et al., *Science* 239:487-491 (1988)]. The cleaved vector and the DNA fragments may also be modified, if required, by homopolymeric tailing. Alternatively, a recombinant nucleotide sequence can be synthesized de novo.

Protein Antigens and Nucleic Acids Encoding the Protein Antigens

The ILTV gD gene appears to encode a glycoprotein of 434 amino acids in length having a molecular weight of 48,477 daltons, although others have suggested that a downstream start codon, which leads to an ILTV gD protein comprising only 377 amino acid residues, is the actual start codon [Wild et al., *Virus Genes* 12:104-116 (1996)]. The ILTV gI gene encodes a glycoprotein of 362 amino acids in length having a molecular weight of 39,753 daltons [U.S. Pat. No. 6,875,856, hereby incorporated by reference]. Nucleic acids encoding natural and/or laboratory derived variants of the ILTV gD and ILTV gI may be substituted for those presently exemplified.

In particular embodiments of the present invention, an rMDV$_{np}$ comprises a recombinant nucleic acid (e.g., an expression cassette) that encodes an ILTV gD protein comprising the amino acid sequence of SEQ ID NO: 2 or an antigenic fragment thereof. In related embodiments the rMDV$_{np}$ comprises a recombinant nucleic acid that encodes an ILTV gD protein comprising an amino acid sequence that has greater than 90%, and/or greater than 95%, and/or greater than 98%, and/or greater than 99% identity to the amino acid sequence of SEQ ID NO: 2. In particular embodiments, the ILTV gD protein is encoded by the nucleotide sequence of SEQ ID NO: 1. In specific embodiments, the rMDV$_{np}$ is an rHVT. In alternative embodiments, the rMDV$_{np}$ is an rMDV2.

In certain embodiments of the present invention, an rMDV$_{np}$ comprises a recombinant nucleic acid (e.g., an expression cassette) that encodes an ILTV gI protein comprising the amino acid sequence of SEQ ID NO: 4 or an antigenic fragment thereof. In related embodiments, the rMDV$_{np}$ comprises a recombinant nucleic acid that encodes an ILTV gI protein comprising an amino acid sequence that has greater than 90%, and/or greater than 95%, and/or greater than 98%, and/or greater than 99% identity to the amino acid sequence of SEQ ID NO: 4. In particular embodiments, the ILTV gI protein is encoded by the nucleotide sequence of SEQ ID NO: 3. In specific embodiments, the rMDV$_{np}$ is an rHVT. In alternative embodiments, the rMDV$_{np}$ is an rMDV2.

As mentioned earlier, IBDV is a member of the Birnaviridae family, which has a genome consisting of two segments (A and B) of double-stranded RNA. The larger segment A encodes a polyprotein of 110 kDa, which is subsequently cleaved by autoproteolysis to form mature viral proteins VP2, VP3 and VP4. Of these, VP2 and VP3 are the structural capsid proteins for the virion, with VP2 protein being the major host-protective immunogen. In the case of IBDV, two serotypes exist, serotype 1 and 2 which can be distinguished by virus neutralization (VN) tests. Serotype 1 viruses have been shown to be pathogenic to chickens, while serotype 2 IBDV only causes sub-acute disease in turkeys. Historically, IBDV serotype 1 viruses consisted of only one type that is known as "classic" IBD virus, but subsequently, so-called "variant" IBDV strains have emerged. In particular embodiments of the present invention the IBDV VP2 gene encodes a VP2 protein from an IBDV that is of the classic type. Such genes are well known and their sequence information is readily available, [see e.g., GenBank acc.nr: D00869 (F52/70), D00499 (STC), or AF499929 (D78)]. Alternatively, this gene can be obtained from the genome of a classic IBDV isolated from nature, using routine techniques for manipulating a Birnavirus. Classic type IBDV's can be readily identified using serology, or molecular biology.

In particular embodiments of the present invention, an rMDV$_{np}$ comprises a recombinant nucleic acid (e.g., an expression cassette) that encodes an IBDV VP2 protein comprising the amino acid sequence of SEQ ID NO: 6 or an antigenic fragment thereof. In related embodiments, the rMDV$_{np}$ comprises a recombinant nucleic acid that encodes an IBDV VP2 protein comprising an amino acid sequence that has greater than 90%, and/or greater than 95%, and/or greater than 98%, and/or greater than 99% identity to the amino acid sequence of SEQ ID NO: 6. In specific embodiments, the IBDV VP2 protein is encoded by the nucleotide sequence of SEQ ID NO: 5. In specific embodiments, the rMDV$_{np}$ is an rHVT. In alternative embodiments, the rMDV$_{np}$ is an rMDV2.

Routine vaccinations against IBDV are performed as early as possible in the life of poultry using attenuated IBDV strains, but these can only be applied when the level of MDA against IBDV has decreased enough, which commonly is somewhere between 15 and 20 days post hatch. Many 'live' or inactivated IBDV vaccines are commercially available, e.g., a 'live' vaccine such as Nobilis™ Gumboro D78 (Merck Animal Health).

NDV has a non-segmented, negative sense, single stranded RNA genome, which is about 15 kb in size, and contains six genes, amongst which is the NDV F protein gene which encodes the so-called "fusion" glycoprotein (F protein). The F protein is involved in NDV's attachment of and entry into host cells, and as the immunodominant protein it can be the basis of an effective immune response against NDV. The NDV F protein is expressed as a native F0 protein, which is activated upon cleavage by extra-cellular peptidases.

An NDV F protein gene, for example, can be derived from NDV Clone 30, a common lentogenic NDV vaccine strain. In certain embodiments of the present invention, an rMDV$_{np}$ comprises a recombinant nucleic acid (e.g., an expression cassette) that encodes an NDV F protein comprising the amino acid sequence of SEQ ID NO: 8 or an antigenic fragment thereof. In related embodiments, the rMDV$_{np}$ comprises a recombinant nucleic acid that encodes an NDV F protein comprising an amino acid sequence that has greater than 90%, and/or greater than 95%, and/or greater than 98%, and/or greater than 99% identity to the amino acid sequence of SEQ ID NO: 8. In particular embodiments, the NDV F protein is encoded by the nucleotide sequence of SEQ ID NO: 7. In specific embodiments, the rMDV$_{np}$ is an rHVT. In alternative embodiments, the rMDV$_{np}$ is an rMDV2.

In related embodiments of the present invention, an rMDV$_{np}$ comprises a recombinant nucleic acid (e.g., an expression cassette) that encodes an NDV F protein comprising the amino acid sequence of SEQ ID NO: 10 or an antigenic fragment thereof. In other embodiments, the rMDV$_{np}$ comprises a recombinant nucleic acid that encodes an NDV F protein comprising an amino acid sequence that has greater than 90%, and/or greater than 95%, and/or greater than 98%, and/or greater than 99% identity to the amino acid sequence of SEQ ID NO: 10. In particular embodiments, the NDV F protein is encoded by the nucleotide sequence of SEQ ID NO: 9. In specific embodiments, the rMDV$_{np}$ is an rHVT. In alternative embodiments, the rMDV$_{np}$ is an rMDV2.

Nucleic acids encoding natural and/or laboratory derived variants of the F protein gene would equally be applicable, either from lentogenic, mesogenic or velogenic NDV, as the F protein gene sequence itself is highly conserved in these different NDV pathotypes.

Nucleotide and/or protein sequences for the chicken pathogen protein antigens encoded by the rMDV$_{np}$'s of the present invention also can be found in publically available databases such as GenBank or the Protein Information Resource.

Promoters and Polyadenylation Regulatory Elements

A promoter is a functional region on the genome of an organism that directs the transcription of a downstream coding region. A promoter is therefore situated upstream of the coding region of a gene. The mRNA synthesis directed by the promoter starts from the 'transcription start site' (TSS). The mRNA produced is in turn translated into protein starting from the gene's start codon, which is the first ATG sequence in the open reading frame (the first AUG in the mRNA). Typically the TSS is located at 30-40 nucleotides upstream of the start codon. A TSS can be determined by sequencing the 5' end of the mRNA of a gene, e.g. by the RACE technique. In general promoters are comprised within about 1000 nucleotides upstream of the position of the A of the start codon, which is generally denoted as A+1, and most promoters are situated between nucleotides −500 and A+1.

The nomenclature for a promoter is commonly based on the name of gene that it controls the expression of. For example, the murine cytomegalovirus immediate early 1 gene (mCMV-IE1) promoter "mCMV-IE1 gene promoter", refers to the promoter that naturally drives the expression of the early 1 gene (IE1 gene) for mCMV and accordingly, is situated immediately upstream of that gene. Because the IE1—gene is such a well-documented and clearly recognizable gene, and because the genomes of several mCMVs have been sequenced (in whole or in part), such a promoter readily can be identified by routine techniques. For example, in a basic protocol a promoter can be obtained by roughly sub-cloning the region in between two consecutive genes, e.g. from the poly A signal of an upstream gene to the TSS of a downstream gene. The promoter then can be identified by standard tests, e.g., by the expression of a marker gene by progressively smaller sections of a suspected promoter.

Generally, promoters contain a number of recognizable regulatory regions, such as an enhancer region, which is involved in binding regulatory factors that influence the time, the duration, the conditions, and the level of transcription. Whereas the enhancer region is normally situated upstream, a promoter also contains a region more downstream that is involved in the binding of transcription factors and directing RNA polymerase itself. This downstream region generally contains a number of conserved promoter sequence elements such as the TATA box, the CAAT box, and the GC box.

A promoter comprising both the enhancer- and the downstream region is termed a "complete" promoter, whereas a promoter comprising only the downstream region, is termed a "core" promoter.

A promoter for the expression of a (heterologous) gene in a (virus) vector needs to be able to effectively drive the transcription of that downstream coding sequence. This is generally referred to as the promoter being "operatively linked" to the coding sequence, such that the gene is 'under the control' of the promoter, or is 'driven by' the promoter. This generally means that in an expression cassette the promoter and the coding sequence of the gene are found on the same nucleic acid, in effective proximity, and with no signals or sequences between them that would intervene with effective transcription of the coding sequence.

The mCMV-IE1 gene promoter is well known in the art, and can be readily obtained from a variety of commercial sources, such as from suppliers of commercial plasmids for cloning and expression. The IE1 gene is also called the 'major IE gene'. The mCMV-IE1 protein has also been referred to as pp89. Dörsch-Häsler et al. [*Proc. Nat. Acad. Sci.*, 82:8325-8329 (1985)] described the mCMV IE1 gene promoter in 1985, and the use of this promoter in heterologous expression is also described in WO 87/03.905 and EP 728,842. The nucleotide sequence of the complete mCMV IE locus is available from GenBank under acc. nr. L06816.1 (from March 2004). The mCMV itself is available from the ATCC: initially under acc. nr. VR-194, and more recently this has been continued under acc. nr. VR-1399.

In one embodiment of the invention, the mCMV-IE1 gene promoter is a complete promoter, comprising both the core promoter region, as well as the enhancer region for the mCMV-IE1 gene. The complete mCMV-IE1 gene promoter is about 1.4 kb in size. However, the present invention also allows for some variance in length of not only the mCMV IE1-gene promoter, but also of the other elements that make up the recombinant DNA expression cassette employed in the present invention. This can result from differences in the exact conditions that are used for cloning and construction. For example, this variance may arise from using different restriction enzyme sites, PCR cloning primers, or different conditions for adapting the ends of the cloning molecules used. Consequently, some variation in length—smaller or larger—of the constituting elements may occur, without affecting the stability, and relatively strong antigen expression and/or efficacy of the overall expression cassette. In that case these length differences are immaterial, and are within the scope of the invention. Therefore, an mCMV-IE1 gene promoter of "about 1.4 kb" is: 1.4 kb±about 25%. In particular embodiments the promoter is 1.4 kb±about 20%. In still other embodiments the variance can be 1.4 kb±about 15%, 1.4 kb±about 12%, 1.4 kb±about 10%, 1.4 kb±about 8%, 1.4 kb±about 6%, 1.4 kb±about 5%, 1.4 kb±about 4%, 1.4 kb±about 3%, 1.4 kb±about 2%, or even 1.4 kb±about 1%.

Similarly, homologs or variants of the promoter element may be used that are equally effective and stable. Therefore, in certain embodiments the mCMV-IE1 gene promoter of the present invention can be a DNA molecule of about 1.4 kb that comprises a nucleotide sequence with at least 95%, 96%, 97%, 98%, or even 99% nucleotide sequence identity to the nucleotide sequence of SEQ ID NO: 13. In a particular embodiment the mCMV-IE1 gene promoter consists of nucleotide sequence of SEQ ID NO: 13.

Many alternative promoters can be used to drive the expression of a heterologous gene encoding a protein antigen or antigenic fragment thereof in an $rMDV_{np}$ of the present invention. Examples include the pseudorabies virus (PRV) gpX promoter [see, WO 87/04463], the Rous sarcoma virus LTR promoter, the SV40 early gene promoter, the chicken beta-actin gene promoter comprising the nucleotide sequence of SEQ ID NO: 17, the Towne Strain hCMV IE promoter SEQ ID NO: 16, a derivative of the hCMV IE promoter (from strain AD169) comprising the nucleotide sequence of SEQ ID NO: 14, an ILTV gD promoter comprising the nucleotide sequence of SEQ ID NO: 11, and an ILTV gI promoter comprising the nucleotide sequence of SEQ ID NO: 12, [see e.g., U.S. Pat. No. 6,183,753 B1], the human cytomegalovirus immediate earlyl (hCMV IE1) gene promoter [U.S. Pat. Nos. 5,830,745; 5,980,906], and the chicken beta-actin gene promoter [EP 1 298 139 B1]. A particular heterologous promoter for the IBDV VP2 gene is the murine (mCMV IE1) cytomegalovirus promoter. In a particular embodiment of this type the mCMV IE1 comprises the nucleotide sequence of SEQ ID NO: 13 [see e.g., EP 728,842; PCT/EP2015/081121].

The inclusion of a polyadenylation regulatory element downstream from a DNA coding region is oftentimes required to terminate the transcription of the coding DNA sequence. Accordingly, many genes comprise a polyadenylation regulatory element at the downstream end of their coding sequence. Many such regulatory elements have been identified and can be used in an $rMDV_{np}$ of the present invention. Specific examples of polyadenylation regulatory elements as exemplified herein, include a Feline Herpesvirus (FHV) US-9 polyadenylation signal comprising the nucleotide sequence of SEQ ID NO: 18, and the human Herpes Simplex Virus (HSV) thymidine kinase polyadenylation signal comprising the nucleotide sequence of SEQ ID NO: 19. The terminator and polyadenylation sequence also may come from the glycoprotein B (gB) gene of Feline Herpesvirus (FHV), from the immediate early (IE) gene of human cytomegalovirus (hCMV), strain AD 169, or from simian virus 40 (SV40).

Vaccines and Immunogenic Compositions

The present invention relates to the use of the recombinant $MDV_{np}$, the nucleic acid molecules used to construct the $MDV_{np}$, or the host cells to grow them, or any combination thereof, all according to the present invention for the manufacture of a vaccine for poultry. Accordingly, the present invention provides vaccines and/or immunogenic compositions that include a multivalent recombinant $MDV_{np}$ of the present invention. Such vaccines can be used to aid in the prevention and/or prevent Infectious Bursal Disease (Gumboro disease), and/or Marek's disease, and/or maladies associated with ILTV infections and/or maladies associated with NDV infections. A vaccine according to the present invention can be used for prophylactic and/or for therapeutic treatment, and thus can interfere with the establishment and/or with the progression of an infection and/or its clinical signs of disease.

A recombinant $MDV_{np}$ of the present invention can be grown by any number of means currently practiced in the field. For example, a recombinant $MDV_{np}$ of the present invention can be grown through the use of in vitro cultures of primary chicken cells, see e.g., the Examples below where chicken embryo fibroblast cells (CEFs) were used. The CEFs can be prepared by trypsinization of chicken embryos. The CEFs also can be plated in monolayers and then infected with the $MDV_{np}$. This particular process can be readily scaled up to industrial-sized production.

Therefore, a further aspect of the invention relates to a method for the preparation of the vaccine according to the invention comprising the steps of infecting host cells with a recombinant $MDV_{np}$ of the present invention, harvesting the infected host cells, and then mixing the harvested infected host cells with a pharmaceutically acceptable carrier. Suitable methods for infection, culture and harvesting are well known in the art and are described and exemplified herein.

Typically, the infected host cells are harvested while still intact to obtain the recombinant $MDV_{np}$ in its cell-associated form. These cells can be taken up in an appropriate carrier composition to provide stabilization for storage and freezing. The infected cells can be filled into glass ampoules, which are sealed, frozen and stored in liquid nitrogen. Accordingly, in certain embodiments of the present invention, the vaccines and/or immunogenic compositions of the present invention are stored frozen and accordingly, comprise a cryopreservative, such as dimethyl sulfoxide (DMSO), to preserve the frozen infected cells.

Alternatively, when the recombinant $MDV_{np}$ is a recombinant HVT, it can be isolated from its host cell, for instance through sonication at the end of culturing, and then taken up into a stabilizer, and freeze-dried (lyophilized) for stable storage or otherwise reduced in liquid volume, for storage, and then reconstituted in a liquid diluent before or at the time of administration. Such reconstitution may be achieved using, for example, vaccine-grade water. In certain embodiments, a lyophilized portion of a multivalent vaccine can comprise one or more antigens and the diluent can comprise one or more other antigens.

In particular embodiments a vaccine of the present invention (or a portion thereof) can be in a freeze-dried form, e.g., as tablets and/or spheres that are produced by a method described in WO 2010/125084, hereby incorporated by reference in its entirety. In particular, reference is made to the examples, from page 15, line 28 to page 27, line 9 of WO 2010/125084, describing a method to produce such fast disintegrating tablets/spheres. Such freeze-dried forms can be readily dissolved in a diluent, to enable systemic administration of the vaccine.

Vaccines and immunogenic compositions can, but do not necessarily include, physiologically compatible buffers and saline and the like, as well as pharmaceutically acceptable adjuvants. Adjuvants can be useful for improving the immune response and/or increasing the stability of vaccine preparations. Adjuvants are typically described as non-specific stimulators of the immune system, but also can be useful for targeting specific arms of the immune system. One or more compounds which have this activity may be added to the vaccine. Therefore, particular vaccines of the present invention can further comprise an adjuvant. Examples of chemical compounds that can be used as adjuvants include, but are not limited to aluminum compounds (e.g., aluminum hydroxide), metabolizable and non-metabolizable oils, mineral oils including mannide oleate derivatives in mineral oil solution (e.g., MONTANIDE ISA 70 from Seppic SA, France), and light mineral oils such as DRAKEOL 6VR, block polymers, ISCOM's (immune stimulating complexes), vitamins and minerals (including but not limited to: vitamin E, vitamin A, selenium, and vitamin B12) and CARBOPOL®.

Other suitable adjuvants, which sometimes have been referred to as immune stimulants, include, but are not limited to: cytokines, growth factors, chemokines, supernatants from cell cultures of lymphocytes, monocytes, cells from lymphoid organs, cell preparations and/or extracts from plants, bacteria or parasites (*Staphylococcus aureus* or lipopolysaccharide preparations) or mitogens. Generally, an adjuvant is administered at the same time as an antigen of the present invention. However, adjuvants can also or alternatively be administered within a two-week period prior to the vaccination, and/or for a period of time after vaccination, i.e., so long as the antigen, e.g., a recombinant $MDV_{np}$ of the present invention persists in the tissues.

The vaccines and/or immunogenic compositions of the present invention may be administered by any route such as in ovo, by parenteral administration, including intramuscular injection, subcutaneous injection, intravenous injection, intradermal injection, by scarification, by oral administration, or by any combination thereof.

Furthermore, the multivalent recombinant $MDV_{np}$ of the present invention can be used and/or combined with additional IBDV, ILTV, NDV, and/or MDV antigens to improve and expand the immunogenicity provided, and/or antigens for other pathogens in order to provide immune protection against such other pathogens. These additional antigens can be either live or killed whole microorganisms, other recombinant vectors, cell homogenates, extracts, proteins, or any other such derivative, provided that they do not negatively interfere with the safety, and stability with relatively strong antigen expression and/or efficacy of the vaccine according to the present invention.

The combination of a multivalent recombinant $MDV_{np}$ of the present invention with an additional MDV, IBDV, NDV, and/or ILTV antigen can be advantageous in those cases in which very virulent field strains of MDV, IBDV, NDV, or ILTV are prevalent, e.g., in a particular geographic region. In this regard, the combination of a multivalent recombinant $MDV_{np}$ of the present invention with an MDV1, MDV2, or HVT includes the Rispens (MDV1) strain, the SB1 (MDV2) strain, the FC-126 (HVT) strain and/or PB1 (HVT) strain. To improve the response against IBDV, multivalent recombinant $MDV_{np}$ may be combined with an IBDV vaccine strain, such as a mild live IBDV vaccine strain, e.g., D78 (cloned intermediate strain), PBG98, Cu-1, ST-12 (an intermediate strain), or 89/03 (a live Delaware variant strain) in a multivalent vaccine.

Examples of other microorganisms that can be used as antigens together with the multivalent recombinant $MDV_{np}$ of the present invention include: (i) viruses such as infectious bronchitis virus, avian influenza virus, adenovirus, egg drop syndrome virus, infectious bursal disease virus, chicken anaemia virus, avian encephalo-myelitis virus, fowl pox virus, turkey rhinotracheitis virus, duck plague virus (duck viral enteritis), pigeon pox virus, avian leucosis virus, avian pneumovirus, and reovirus, (ii) bacteria, such as *Escherichia coli*, *Salmonella* spec., *Ornitobacterium rhinotracheale*, *Haemophilis paragallinarum*, *Pasteurella multocida*, *Erysipelothrix rhusiopathiae*, *Erysipelas* spec., *Mycoplasma* spec., and *Clostridium* spec., (iii) parasites such as *Eimeria* spec., and (iv) fungi, such as *Aspergillus* spec. In particular embodiments of the present invention, a recombinant $MDV_{np}$ of the present invention can be combined with a mild live NDV vaccine strain such as vaccine strain C2. Many of such strains are used in commercial vaccines.

The combination vaccine can be made in a variety of ways including by combining the recombinant $MDV_{np}$ of the present invention with preparations of virus, or bacteria, or fungi, or parasites, or host cells, or a mixture of any and/or all of these. In particular embodiments, the components for such a combination vaccine are conveniently produced separately and then combined and filled into the same vaccine container.

As described above, a vaccine according to the invention can be used advantageously to provide safe and effective immune protection to a chicken, for example, from one or more poultry diseases by a single inoculation at very young age or in ovo. Alternatively, as would be apparent to anyone skilled in the art of poultry vaccines, the combinations described above also could include vaccination schedules in which the multivalent recombinant $MDV_{np}$ of the present invention and an additional antigen are not applied simultaneously; e.g., the recombinant $MDV_{np}$ may be applied in ovo, and the NDV C2 and/or the IBDV strain (e.g., 89/03) could be applied at a subsequent time/date.

Accordingly, the vaccines of the present invention can be administered to the avian subject in a single dose or in multiple doses. For example, a vaccine of the present invention may be applied at the day of hatch and/or in ovo at day 16-18 (Embryonation Day) ED. When multiple doses are administered, they may be given either at the same time or sequentially, in a manner and time compatible with the formulation of the vaccine, and in such an amount as will be immunologically effective. Therefore, a vaccine of the present invention may effectively serve as a priming vaccination, which later can be followed and amplified by a booster vaccination of the identical vaccine, or with a different vaccine preparation e.g., a classical inactivated, adjuvanted whole-virus vaccine. Alternatively, a vaccine of the present invention can be administered to the avian subject solely as a booster vaccination.

The volume per dose of a vaccine of the present invention can be optimized according to the intended route of application: in ovo inoculation is commonly applied with a volume between 0.05 and 0.5 ml/egg, and parenteral injection is commonly done with a volume between 0.1 and 1 ml/avian. In any case, optimization of the vaccine dose volume is well within the capabilities of the skilled artisan.

SEQUENCE TABLE

| SEQ ID NO: | Description | Type |
|---|---|---|
| 1 | ILTV gD Glycoprotein | nucleic acid |
| 2 | ILTV gD Glycoprotein | amino acid |
| 3 | ILTV gI Glycoprotein | nucleic acid |
| 4 | ILTV gI Glycoprotein | amino acid |
| 5 | IBDV VP2 | nucleic acid |
| 6 | IBDV VP2 | amino acid |
| 7 | NDV F Protein (Clone 30) | nucleic acid |
| 8 | NDV F Protein (Clone 30) | amino acid |
| 9 | NDV F Protein (B1 Hitchner) | nucleic acid |
| 10 | NDV F Protein (B1 Hitchner) | amino acid |
| 11 | ILTV gD promoter | nucleic acid |
| 12 | ILTV gI promoter | nucleic acid |
| 13 | mCMV IE promoter | nucleic acid |
| 14 | hCMV IE promoter (from strain AD169) | nucleic acid |
| 15 | hCMV IE promoter (Truncated) | nucleic acid |
| 16 | hCMV IE promoter (Towne Strain) | nucleic acid |
| 17 | chicken β-actin promoter | nucleic acid |
| 18 | FHV US-9 polyadenylation signal | nucleic acid |
| 19 | HSV TK polyadenylation signal | nucleic acid |
| 20 | SV40 polyadenylation signal | nucleic acid |
| 21 | 484-1050-2641-10859 (HVT/IBDV/ILTV/NDV 670-14) mCMV IEpro-VP2-SV40pA/ILTV/HVT UL54.5 | nucleic acid |
| 22 | (HVT/IBDV/ILTV/NDV 670-14) hCMV IEpro-F-IE(term)/HVT US2 1322-48.1 | nucleic acid |
| 23 | (HVT/IBDV/ILTV/NDV #2) 228509-ILT-435Vec6 (mCMV IEpro-VP2-SV40pA/ILTV/HVT) | nucleic acid |
| 24 | 1333-85.B6 (ILTV/Chicken β-actin pro-VP2-FHV US9pA/HVT) | nucleic acid |
| 25 | 1386-04.4#1 (ILTV/hCMV IEpro-VP2-HSV TKpA/HVT) | nucleic acid |
| 26 | 654-45:325341_IE-F/1C1 (HVT/IBDV/ILT/NDV #2) hCMV IEpro-F-IE(term)/HVT UL54.5 | nucleic acid |
| 27 | VP2/1C1#8 (HVT/IBDV/ILT/NDV #3) mCMV IEpro-VP2-SV40pA/HVT UL54.5 | nucleic acid |
| 28 | 1332-47.A2 (HVT/IBDV/ILT/NDV #3) ILT/hCMV IEpro-F-IE(term)/HVT US2 | nucleic acid |
| 29 | 1332-23.7 (HVT/IBDV/ILT/NDV # 4) ILT/HVT UL54.5 | nucleic acid |
| 30 | 435Vec60 (HVT/IBDV/ILT/NDV #4) mCMV IEpro-VP2-SV40pA/ hCMV IEpro-F-IE(term)/HVT US2 | nucleic acid |
| 31 | 1332-29.4 (HVT/IBDV/ILT/NDV #5) ILT/hCMV IEpro-F-IE(term)/HVT UL54.5 | nucleic acid |
| 32 | 435Vec6 (HVT/IBDV/ILT/NDV #5) mCMV IEpro-VP2-SV40pA/HVT US2 | nucleic acid |

The present invention may be better understood by reference to the following non-limiting examples, which are provided as exemplary of the invention. The following examples are presented in order to more fully illustrate embodiments of the invention and should in no way be construed as limiting the broad scope of the invention.

EXAMPLES

Example 1

Construction of Recombinant HVT/ILTV/IBDV/NDV Viral Vectors

Recombinant multivalent non-pathogenic Marek's Disease virus constructs were prepared that encode and express (i) two Infectious Laryngotracheitis Virus protein antigens, (ii) an Infectious Bursal Disease Virus protein antigen, and (iii) a Newcastle Disease Virus protein antigen. The present invention overcomes the problem of vaccine interference encountered when two recombinant HVT vaccines, such as Innovax®-ILT (sold by Merck Animal Health) and Vaxxitek® (sold by Merial) are given to the same animal. Moreover, the present invention uniquely provides the first recombinant nonpathogenic Marek's Disease Virus (rMDV$_{np}$) that encodes antigens from three different viral pathogens other than MDV.

Recombinant Herpesvirus of Turkey (HVT) constructs were created in which antigenic donor material from three poultry pathogens, Infectious Laryngotracheitis Virus (ILTV), Newcastle Disease Virus (NDV) and Infectious Bursal Disease virus (IBDV) were inserted into the HVT vector [see also, U.S. Pat. No. 8,932,604 B2, WO 2013/057, 235, WO 2016/102647, and U.S. Ser. No. 62/351,471 filed Jun. 17, 2016, the contents of all of which are hereby incorporated by reference in its entireties]. The donor materials include a 3.563 kb SalI-HindIII fragment from ILTV, NVSL Challenge Strain, Lot #83-2 [nucleotide positions 10532-14094; Wild et al., Virus Genes 12:104-116 (1996): Acc. # U28832], encoding the full length genes for glycoprotein D (gD) and glycoprotein I (gI), plus partial coding regions from glycoprotein E (amino acids 1-101), and ORF5 (amino acids 734-985); an expression cassette consisting of the coding region for NDV, Clone 30 strain, fusion protein (F) gene (nucleotide positions 4544-6205; Romer-Oberdorfer et al., (1999); Acc. # Y18898), driven by a viral promoter and followed by a terminator sequence; and an expression cassette consisting of the coding region for IBDV, Faragher, type F52/70 strain, viral protein 2 (vp2) gene, driven by a viral promoter and followed by a terminator sequence. In the exemplified embodiment, the promoter driving IBDV VP2 expression comes from the immediate early (IE) of mouse cytomegalovirus (mCMV) strain ATCC VR-194, whereas that for NDV F expression comes from the immediate early (IE) gene of human cytomegalovirus (hCMV), strain AD 169. The terminator and polyadenylation sequence for IBDV VP2 comes from Simian virus 40 (SV40), whereas the terminator and polyadenylation sequence for NDV F comes from the immediate early (IE) gene of human cytomegalovirus (hCMV). The donor material for the first heterologous nucleic acid was inserted into the UL54.5 site (pos. 111240/111241, Afonso et al., J. Virology 75(2):971-978 (2001); Acc. # AF291866, between amino acids residues 21 and 22), whereas the donor material for the second heterologous nucleic acid was inserted into the US2 site (position 140540/140541, Afonso et al., (2001)supra; Acc. # AF291866, between amino acids residues 124 and 125) [see, FIG. 1].

Genetic and phenotypic stability is a major component of the safety and relatively strong antigen expression and/or efficacy profile of any new recombinant viral vaccine candidate. The IBDV/ILTV and NDV expression cassettes inserted into the HVT backbone are not intrinsically required for viral replication and therefore may be lost due to mutation during amplification of the virus stock in tissue culture passages. A satisfactory vaccine candidate must not easily mutate to lose expression of the foreign gene insert. A vaccine candidate is considered stable if it can be demonstrated that at least 90% of the viral plaques express the inserted foreign antigenic protein following greater than or equal to 10 passages in tissue culture.

The ability to generate herpesviruses by the cosmid reconstruction method previously had been demonstrated for pseudorabies virus [van Zijl et al., J. Virology 62:2191-2195 (1988)]. This procedure subsequently was employed to construct recombinant HVT vectors [see, U.S. Pat. No. 5,853,733, hereby incorporated by references with respect to the methodology disclosed regarding the construction of recombinant HVT vectors] and was used to construct the recombinant HVT/IBDV/ILTV/NDV vectors of the present invention. In this method, the entire HVT genome is cloned into bacterial vectors as several large overlapping subgenomic fragments constructed utilizing standard recombinant DNA techniques [Maniatis et al., Molecular Cloning, Cold Spring Harbor Laboratory press, Cold Spring Harbor, N.Y. (1982); and Sambrook et al., Molecular Cloning, Cold Spring Harbor Laboratory press, Cold Spring Harbor, N.Y. (1989)]. An HVT strain FC126 cosmid library was derived from sheared viral DNA cloned into the cosmid vector pWE15 (Stratagene, now Agilent Technologies of Santa Clara, Calif.). In addition, several large genomic DNA fragments were isolated by restriction digestion with the enzyme, BamHI, and cloned into either pWE15 or the plasmid vector pSP64 (Promega, Madison Wis.). As described in U.S. Pat. No. 5,853,733, cotransfection of these fragments into chicken embryo fibroblast (CEF) cells results in the regeneration of the HVT genome mediated by homologous recombination across the overlapping regions of the fragments. If an insertion is engineered directly into one or more of the subgenomic fragments prior to the cotransfection, this procedure results in a high frequency of viruses containing the insertion. Five overlapping subgenomic clones are required to generate the complete genome of FC126 HVT, and served as the basis for creating all HVT/IBDV/ILTV/NDV recombinant viruses.

Construction of HVT/IBDV/ILTV/NDV 670-14.1-1A1 or A2

The triple recombinant HVT vector virus, HVT/IBDV/ILTV/NDV 670-14.1-1 contains an IBDV/ILTV expression cassette inserted into the HVT UL54.5 site, and an NDV expression cassette inserted into the HVT US2 site. The cosmid regeneration of HVT/IBDV/ILTV/NDV 670-14.1-1 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-31.1C1 in U.S. Pat. No. 5,853,733, was now provided from three smaller plasmids: 672-01.A40 and 672-07.C40, and one transfer plasmid (484-1050-2641-10859), overlapping these two, and containing the IBDV/ILTV expression cassettes in the UL54.5 gene locus. To allow integration into the US region of the FC126 HVT genome, the region covered by the cosmid nr. 378-50 in U.S. Pat. No. 5,853,733, was now provided from three smaller plasmids: pSY640 and 556-

60.6, and one transfer plasmid (1322-48.1), overlapping these two, and containing the NDV expression cassettes in the US2 gene locus.

The set of nine linearized constructs: 2 cosmids and 7 plasmids are transfected all together into chicken embryo fibroblasts (CEFs), using a standard $CaCl_2$ transfection protocol and the resulting virus stock was plaque purified two times.

Description of Subgenomic Fragments for Generating FC126 HVT

Subgenomic Clone 407-32.2C3

Cosmid 407-32.2C3 contains an approximately 40,170 base pair region of genomic HVT DNA [Left terminus pos. 39,754; Afonso et al., (2001), supra; Acc. # AF291866]. This region includes HVT BamHI fragments F', L, P, N1, E, D, and 2,092 base pairs of fragment B.

Subgenomic Clone 172-07.BA2

Plasmid 172-07.BA2 contains a 25,931 base pair region of genomic HVT DNA. It was constructed by cloning the HVT BamHI B fragment [pos. 37,663 to 63,593; Afonso et al., 2001, supra; Acc. # AF291866], into the plasmid pSP64 (Promega, Madison Wis.).

Subgenomic Clone 407-32.5G6

Cosmid 407-32.5G6 contains a 39,404 base pair region of genomic HVT DNA [pos. 61,852-101,255; Afonso et al., (2001), supra; Acc. # AF291866]. This region includes HVT BamHI fragments H, C, Q, K1, M, K2, plus 1,742 base pairs of fragment B, and 3,880 base pairs of fragment J.

Subgenomic Clone 407-31.1C1

Cosmid 407-31.1C1 contains a 37,444 base pair region of genomic HVT DNA [pos. 96,095-133,538; Afonso et al., (2001), supra; Acc. # AF291866]. This region includes HVT BamHI fragments J, G, I, F, O, plus 1,281 base pairs of fragment K2, and 6,691 base pairs of fragment A.

Subgenomic Clone 378-50

Cosmid 378-50 contains a 28,897 base pair region of genomic HVT DNA [see, FIG. 8 of U.S. Pat. No. 5,853,733]. This region includes the HVT BamHI fragment A. It was constructed by cloning the HVT BamHI A fragment [position 126,848-155,744; Afonso et al., (2001), supra; Acc. # AF291866] into cosmid pWE15.

Additional Insertion Fragments for Generating HVT/IBDV/ILTV/NDV 670-14.1-1A1 or A2 (see, FIG. 1)

Subgenomic Clone 484-1050-2641-10859

The insertion plasmid 484-1050-2641-10859 contains an 8636 base pair region of genomic HVT unique long region [pos. 109489-118124; Afonso et al., 2001, supra; Acc. # AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. # AF291866, between amino acid residues 21 and 22] are 2 elements: an expression cassette consisting of the MCMV IE promoter, the IBDV classic type F52/70, Faragher strain, virus protein 2 gene (VP2), and the SV40 polyadenylation signal, followed by a 3563 base pair SalI-HindIII fragment from ILTV, NVSL Challenge Strain, Lot #83-2 [pos. 10532-14094; Wild et al., Virus Genes 12:104-116 (1996); Acc. # U28832], encoding the full length genes for glycoprotein D (gD) and glycoprotein I (gI), plus partial coding regions from glycoprotein E (amino acids 1-101), and ORF5 (amino acids 734-985). The IBDV VP2, ILTV gD and ILTV gI genes are transcribed in the opposite direction relative to the HVT UL54.5 gene.

Subgenomic Clone 672-01.A40

Plasmid 672-01.A40 contains a 14,731 base pair region of genomic HVT DNA derived from the unique long region [pos. 96095-110825; Afonso et al., 2001, supra; Acc. # AF291866], cloned into a derivative of plasmid pNEB193. This region includes HVT BamHI fragments G, J and 1281 base pairs of K2.

Subgenomic Clone 672-07. C40

Plasmid 672-07.C40 contains a 12,520 base pair region of genomic HVT DNA derived from the unique long region [pos. 116948-129467; Afonso et al., 2001, supra; Acc. # AF291866], cloned into a derivative of plasmid pNEB193. This region includes HVT BamHI fragments F, O and 2620 base pairs of A.

Subgenomic Clone 1322-48.1

The insertion plasmid 1322-48.1 contains a 7311 base pair EcoRI fragment of the HVT unique short regions [pos. 126880-144190; Afonso et al., 2001, supra; Acc. # AF291866], cloned into the plasmid pSP64 (Promega, Madison, Wis.). Inserted into a unique StuI site within the HVT US2 gene [pos. 140540/140541; Afonso et al., 2001, supra; Acc. # AF291866, between amino acid residues 124 and 125] is an expression cassette consisting of the HCMV IE promoter, the NDV, Clone 30 strain, fusion gene (F), and the transcription terminator from the HCMV IE gene. The NDV F gene is transcribed in the opposite direction relative to the HVT US2 gene.

Subgenomic Clone pSY640

Plasmid pSY640 contains an approximately 13,600 base pair region of genomic HVT DNA (pos. 126848-140540; Afonso et al., 2001, supra; Acc. # AF291866] derived from BamHI fragment A. To generate this plasmid the region of DNA located upstream of the US2 gene, beginning at the StuI site located in the US2 gene and continuing to the end of the BamHI A fragment, was cloned into the plasmid pSP64 (Promega, Madison Wis.).

Subgenomic Clone 556-60.6

Plasmid 556-60.6 contains an approximately 12,500 base pair region of genomic HVT DNA derived from BamHI fragment A (approximate pos. 143300-155744; Afonso et al., 2001, supra; Acc. # AF291866]. To generate this plasmid, the region of DNA located downstream of the US2 gene (beginning at the StuI site located in the US2 gene and continuing to the end of the BamHI A fragment) was cloned into pSP64 (Promega, Madison Wis.), and then treated with exonuclease to "chewed back" from StuI site 150 bp, and re-cloned into pBR322 plasmid vector.

Standard $CaCl_2$ Transfection Protocol

Secondary CEF's are seeded on 6 well culture plates and incubated at 38° C. with 5% $CO_2$ for 24 hours and confluent monolayers form. For each well a total amount of 0.5 µg DNA of cosmids and plasmids were mixed in Hepes buffer and 125 mM $CaCl_2$ was added dropwise until precipitation was imminent. This mixture was added to the CEF cell monolayer, and incubated for 2 to 3 hours. The supernatant was removed and an overlay of 15% glycerol was added, and kept on the cells for one minute. Then this was removed, washed with phosphate buffered saline (PBS), and fresh culture medium was added and the cells were incubated for two days. Next, the infection was expanded twice by harvesting cells by trypsinization and seeding onto larger plates, 6 cm plates first, then 10 cm plates 3 days later, until 50-90% CPE was achieved. Next, the amplified transfected cells were harvested by trypsinization, and dilutions of $10^{-3}$ to $10^{-4}$ were plated on 6 cm plates with CEF monolayers and incubated. The following day, the plates were covered with agar, and a number of individual plaques of HVT/IBDV/ILTV/NDV were isolated and amplified on CEFs. Each virus stock was plaque purified a second time by infecting confluent monolayers of CEFs on 6 cm plates with first round purified stocks diluted to $10^{-4}$ to $10^{-5}$ and incubating cells. The following day, the plates were covered with agar, and a number of individual plaques of HVT/IBDV/ILTV/NDV were isolated and amplified on CEFs.

Example 2

Recombinant HVT/IBDV/ILTV/NDV Virus Stocks are Phenotypically Stable for Expression of the IBDV, ILTV, and NDV Proteins Following Serial Passage in Tissue Culture Two plaque purified isolates of HVT/IBDV/ILTV/NDV, each from a separate cotransfection stock were serial passaged 15 times on secondary CEF cells and evaluated for expression of the inserted ILTV, NDV and IBDV genes in an Immunofluorescence Assay.

Generation of Tissue Culture Passage Stocks

For each tissue culture passage, confluent secondary CEF monolayers were inoculated with 50-100 μL of virus stock, and incubated at 38° C., 5% $CO_2$ for 2-5 days until CPE was evident. Next, cells were harvested by trypsinization, passage 1 (P1). The process was repeated to prepare further passage stocks (P2 P15).

Phenotypic Stability Analysis

Six well plates were planted with secondary CEF monolayers. The cells were inoculated with virus stocks harvested at various passage levels: P0-P15, or diluent alone. The plates were inoculated at multiple dilutions to achieve a countable number of plaques per well, and incubated at 38° C., 5% $CO_2$. After a five-day incubation, the supernatant was decanted and CEF monolayers were fixed with 70% acetone for approximately 20 minutes at 15-30° C. The acetone solution was decanted and the cells were allowed to air dry prior to staining with ILTV gD (polyclonal Rabbit anti-ILTV gD), ILTV gI (polyclonal rabbit anti-ILTV gI), NDV F (Mab #57), and IBDV VP2 (MCA GDV-R63) primary antibodies. Following an approximately 1.5 hour blocking step, 5% goat sera in PBS+0.5% Triton-X 100, 2 mL per well, is added to the dishes, and then incubated at 36°–39° C. in a humidified incubator. The primary antibodies were diluted as appropriate, added at 2 mL per well, and then incubated at 36°–39° C. for 1.3 hours in a humidified incubator.

Following the antibody incubation, the plates were washed three times with PBS+0.5% Triton-X 100. The FITC-labeled secondary antibody solution (rabbit anti-mouse or goat anti-rabbit) was prepared at 1:50 and 2 mL was added to each well. Following incubation, plates were washed three times with PBS+0.5% Triton-X 100, and examined under a fluorescent scope, and the plaques were scored as positive or negative for fluorescent staining. Plates were then examined under a white light microscope and the plaques were re-counted. The percentage of fluorescing plaques at each passage level is described in the Table 1 below. Both isolates maintain an acceptable expression level for all four antigens (greater than 90%) at passage level 15.

TABLE 1

STABILITY OF EXPRESSION FOLLOWING PASSAGE IN TISSUE CULTURE

| Virus Number | Passage Level | Percent Expression | | | |
|---|---|---|---|---|---|
| | | ILT-gD | ILT-gI | IBDV-VP2 | NDV-F |
| 640-14.1-1A1 | P0 | 100% | 100% | 100% | 100% |
| | P5 | 100% | 100% | 100% | 100% |
| | P10 | 100% | 100% | 100% | 100% |
| | P15 | 100% | 100% | 93% | 99% |
| 640-14.1-1A2 | P0 | 100% | 100% | 100% | 100% |
| | P5 | 100% | 100% | 100% | 100% |
| | P10 | 100% | 100% | 100% | 100% |
| | P15 | 100% | 100% | 96% | 100% |

Example 3

Recombinant HVT/IBDV/ILTV/NDV Virus Stocks are Phenotypically Stable for Expression of the ILTV, NDV, and IBDV Proteins Following Vaccination and Recovery from Birds Vaccines were prepared from the two isolates of HVT/IBDV/ILTV/NDV 670-14.1-1, isolate A1 and isolate A2, and used to inoculate two groups of twenty-one (21) day-of-age chickens by the subcutaneous route. A third group of birds were vaccinated with diluent alone to serve as a negative control group. Pooled spleen samples from three birds were collected twice weekly for four weeks post vaccination, and processed for virus isolation on chicken embryo fibroblast cells (CEFs). When a cytopathic effect was clearly visible, monolayers were fixed, and the plaques were analyzed for the expression of the IBDV VP2, ILTV gD, and ILTV gI, and NDV F proteins by immunofluorescence assay (IFA), with antibodies that are specific for each protein.

Phenotypic Stability Analysis

Six well plates were planted with secondary CEF monolayers. The cells were inoculated with $5 \times 10^6$ spleen cells, and incubated at 38° C., 5% $CO_2$. After five days of incubation, the supernatant was decanted and the CEF monolayers were fixed with 70% acetone for approximately 20 minutes at 15-30° C. The acetone solution was decanted and the cells were allowed to air dry prior to staining with ILTV gD (polyclonal rabbit anti-ILTV gD), ILTV gI (polyclonal rabbit anti-ILTV gI), NDV F (Mab #57) and IBDV VP2 (MCA GDV-R63) primary antibodies. Following an approximately 0.5 hour blocking step, 5% goat sera in PBS+0.5% Triton-X 100, 2 mL per well, is added to the dishes, and then incubated at 36°–39° C. in a humidified incubator. The primary antibodies were diluted as appropriate, added at 2 mL per well, and then incubated at 36°–39° C. for 1 hour in a humidified incubator. After the antibody incubation, the plates were washed three times with PBS+0.5% Triton-X 100. The FITC-labeled secondary antibody solution (rabbit anti-mouse or goat anti-rabbit) was prepared at 1:50, and 2 mL was added to each well. The plates were incubated for 1 hour at 36°–39° C. in a humidified incubator.

Following incubation, the plates were washed three times with PBS+0.5% Triton-X 100, and examined under a fluorescent scope and the plaques were scored for positive (+) or negative (−) fluorescence staining. The plates were then examined under a white light microscope and the plaques were re-counted. The percentage of fluorescing plaques at each passage level is provided in Table 2 below.

TABLE 2

STABILITY OF EXPRESSION FOLLOWING PASSAGE IN BIRDS (D18)

| Vaccine | Vaccine Dose (PFU) | Percent Expressing | | | |
|---|---|---|---|---|---|
| | | NDVF | ILTVgI | ILTV gD | IBDV VP2 |
| HVT/IBDV/ILTV/NDV 670-14.1-1A1 (p10) | 1660 | 100% | 100% | 100% | 100% |
| HVT/IBDV/ILTV/NDV 670-14.1-1A2 (p10) | 4800 | 100% | 100% | 100% | 100% |
| Diluent | NA | 0 | 0 | 0 | 0 |

Example 4

HVT/IBDV/ILTV/NDV

Efficacy Data for Two Isolates of a Particular Construct

The following four studies were conducted to demonstrate the effectiveness of a single construct HVT/IBDV/ILTV/NDV 670-14 as a vaccine candidate for protecting against a challenge with virulent Infectious Laryngotracheitis virus (ILTV), or virulent Infectious Bursal Disease Virus (IBDV), or virulent Marek's disease virus (MDV).

In the first study, one-day-old specific pathogen free (SPF) chicks were vaccinated with an HVT/IBDV/ILTV/NDV 670-14.1-1A2 vaccine candidate. Controls included a second group that remained unvaccinated. At 28 days post-vaccination, the vaccinated chicks and the non-vaccinated control chicks were challenged with virulent ILTV/USDA lot LT 96-3 via the intracheal (IT) route. Birds were then observed for clinical signs of disease for 10 days. In Table 3, the results show the 670-14.1-1A2 vaccine provided partial protection from challenge. A second study was conducted using a second clone of the vaccine, 670-14.1-1A1. In Table 4, the results show a marked improvement in protection. Accordingly, the next two studies were performed with the 670-14.1-1A1 vaccine candidate. These results provide evidence that an HVT/IBDV/ILTV/NDV can be both stable and efficacious.

TABLE 3

ILTV Challenge Following Vaccination with Isolate 670-14.1-1A2

| | | Vaccination | | | Challenge at 4 weeks | | |
|---|---|---|---|---|---|---|---|
| Group | Vaccine Identification | Age | Actual Dose | Route | # Affected/Total | % Affected | % Protected |
| 5 | Challenged controls | 1 day | NA | SC | 15/15 | 100% | 0% |
| 6 | Non-challenged controls | 1 day | NA | SC | 0/10 | 0% | NA |
| 7 | HVT/IBDV/ILTV/NDV | 1 day | 2394 | SC | 14/22 | 64% | 36% |

TABLE 4

ILTV CHALLENGE FOLLOWING VACCINATION WITH ISOLATE 670-14.1-1A1

| | | Vaccination | | | Challenge at 4 weeks | | |
|---|---|---|---|---|---|---|---|
| Group | Vaccine Identification | Age | Actual Dose | Route | # Affected/Total | % Affected | % Protected |
| 5 | HVT/IBDV/ILTV/NDV | 1 day | 1359 | SC | 9/20 | 45% | 55% |
| 6 | Challenged controls | 1 day | NA | SC | 10/10 | 100% | NA |
| 7 | Non-challenged controls | 1 day | NA | SC | 0/10 | 0% | NA |

In the third study, one-day-old specific pathogen free (SPF) chicks were vaccinated with the HVT/IBDV/ILTV/NDV 670-14.1-1A1 vaccine. Controls included a second unvaccinated group. At 28 days post-vaccination, vaccinated chicks and non-vaccinated control chicks were challenged with virulent IBDV/CS89 strain via the intraocular (IO) route. Birds were then observed for clinical signs of disease for 10 days, and bursa collected and examined histologically for gross lesions consistent with IBDV and scored as per the European Pharmacopoeia 9.0 (04/2013:0587). The results, in Table 5, show the 670-14.1-1A1 vaccine provided 100% protection from challenge.

TABLE 5

IBDV CHALLENGE FOLLOWING VACCINATION WITH ISOLATE 670-14.1-1A1[#]

| Group | Vaccine Identification | Vaccination Age | Route | Dose (0.2 mL) | Virulent CS89 IBDV Challenge at 4 weeks # Affected/Total | % Protection |
|---|---|---|---|---|---|---|
| 3 | Placebo (Marek's Diluent) | 1 day | SC | N/A | 0/15 | 0 |
| 4 | Negative Controls (Non-Challenged) | 1 day | N/A | N/A | 10/10 | NA |
| 5 | HVT/IBD/ILTV/NDV | 1 day | SC | 1,810 | 21/21 | 100 |

[#]P10

In a fourth study, one-day-old specific pathogen free (SPF) chicks were vaccinated with the HVT/IBD/ILTV/NDV 670-14.1-1A1 vaccine. Controls included a second group of unvaccinated chicks. At 5 days post-vaccination, the vaccinated chicks and the non-vaccinated control chicks were challenged with virulent MDV/GA strain via the intra-abdominal (IA) route. Birds were then observed for clinical signs of disease for 50 days, and following death or euthanasia examined for gross lesions consistent with MDV. The results, in Table 6, show that the 670-14.1-1A1 vaccine provided 95% protection from challenge. In sum, these results indicate that an HVT/IBD/ILTV/NDV vaccine can be both stable and efficacious. It also leads credence for the upper limit of foreign antigens encoded in a multivalent HVT construct has not been reached for stable and efficacious multivalent HVT vaccines.

TABLE 6

MDV CHALLENGE FOLLOWING VACCINATION WITH ISOLATE 670-14.1-1A1

| Group | Vaccine Identification | Vaccination SC Age | Dose | Challenge MDV GA5 Age at Challenge | Results Day 50 Necropsy # Affected/Total | % Affected | % Protection |
|---|---|---|---|---|---|---|---|
| 3 | HVT/IBDV/ILTV/NDV | 1 day | 3328 | Day 5 | 1/22 | 5% | 95% |
| 4 | HVT | 1 day | 2372 | Day 5 | 0/22 | 0% | 100% |
| 5 | Diluent | 1 day | NA | Day 5 | 15/22 | 68% | NA |
| 6 | Diluent | 1 day | NA | — | 0/12 | 0% | NA |

Example 5

Additional HVT/IBDV/ILTV/NDV Constructs

Construction of HVT/IBDV/ILTV/NDV #2

The triple recombinant HVT vector virus, HVT/IBDV/ILTV/NDV #2 contains an NDV expression cassette inserted into the HVT UL54.5 site, and an IBDV/ILTV expression cassette inserted into the HVT US2 site. The cosmid regeneration of HVT/IBDV/ILTV/NDV #2 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-32.1C1 in U.S. Pat. No. 5,853,733, was now provided from three smaller plasmids: 672-01.A40 and 672-07.C40, and one transfer plasmid (654-45:325341_IE-F/1C1), overlapping these two, and containing the NDV expression cassette in the UL54.5 gene locus. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (228509-ILT-435Vec6), overlapping these two, and containing the IBDV/ILTV expression cassettes in the US2 gene locus.

The set of nine linearized constructs: 2 cosmids and 7 plasmids are transfected all together into chicken embryo fibroblasts (CEFs), using a standard CaCl$_2$ transfection protocol and the resulting virus stock was plaque purified two times.

Construction of HVT/IBDV/ILTV/NDV #3

The triple recombinant HVT vector virus, HVT/IBDV/ILTV/NDV #3 contains an IBDV expression cassette inserted into the HVT UL54.5 site, and an ILTV/NDV expression cassette inserted into the HVT US2 site. The cosmid regeneration of HVT/IBDV/ILTV/NDV #3 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-32.1C1 in U.S. Pat. No. 5,853,733, was now provided from three smaller plasmids: 672-01.A40 and 672-07.C40, and one transfer plasmid (VP2/1C1#8), overlapping these two, and containing the IBDV expression cassette in the UL54.5 gene locus. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (1332-47.A2), overlapping these two, and containing the ILTV/NDV expression cassettes in the US2 gene locus.

The set of nine linearized constructs: 2 cosmids and 7 plasmids are transfected all together into chicken embryo fibroblasts (CEFs), using a standard $CaCl_2$ transfection protocol and the resulting virus stock was plaque purified two times.

Construction of HVT/IBDV/ILTV/NDV #4

The triple recombinant HVT vector virus, HVT/IBDV/ILTV/NDV #4 contains an ILTV expression cassette inserted into the HVT UL54.5 site, and an IBDV/NDV expression cassette inserted into the HVT US2 site. The cosmid regeneration of HVT/IBDV/ILTV/NDV #4 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-32.1C1 in U.S. Pat. No. 5,853,733, was now provided from three smaller plasmids: 672-01.A40 and 672-07.C40, and one transfer plasmid (1332-23.7), overlapping these two, and containing the ILTV expression cassette in the UL54.5 gene locus. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (435Vec60), overlapping these two, and containing the IBDV/NDV expression cassettes in the US2 gene locus. The set of nine linearized constructs: 2 cosmids and 7 plasmids are transfected all together into chicken embryo fibroblasts (CEFs), using a standard $CaCl_2$ transfection protocol and the resulting virus stock was plaque purified two times.

Construction of HVT/IBDV/ILTV/NDV #5

The triple recombinant HVT vector virus, HVT/IBDV/ILTV/NDV #5 contains an ILTV/NDV expression cassettes inserted into the HVT UL54.5 site, and an IBDV expression cassette inserted into the HVT US2 site. The cosmid regeneration of HVT/IBDV/ILTV/NDV #5 was performed essentially as described in U.S. Pat. No. 5,853,733 [e.g., FIG. 8 of U.S. Pat. No. 5,853,733]. To allow integration into the UL54.5 region of the FC126 HVT genome, the region covered by the cosmid nr. 407-32.1C1 in U.S. Pat. No. 5,853,733, was now provided from three smaller plasmids: 672-01.A40 and 672-07.C40, and one transfer plasmid (1332-29.4), overlapping these two, and containing the ILTV/NDV expression cassettes in the UL54.5 gene locus. To allow integration into the US region of the FC126 HVT genome, the region covered by the cosmid nr. 378-50 in U.S. Pat. No. 5,853,733, was now provided from three smaller plasmids: pSY640 and 556-60.6, and one transfer plasmid (435Vec6), overlapping these two, and containing the IBDV expression cassette in the US2 gene locus.

The set of nine linearized constructs: 2 cosmids and 7 plasmids are transfected all together into chicken embryo fibroblasts (CEFs), using a standard $CaCl_2$ transfection protocol and the resulting virus stock was plaque purified two times.

Additional Insertion Fragments for Generating HVT/IBDV/ILTV/NDV #2 (see, FIG. 2)

Subgenomic Clone 654-45:325341_IE-F/1C1 The insertion plasmid 654-45:325341_IE-F/1C1 contains an 8636 base pair region of genomic HVT unique long region [pos. 109489-118124; Afonso et al., 2001, supra; Acc. # AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. # AF291866, between amino acid residues 21 and 22] is an expression cassette consisting of the HCMV IE promoter, the NDV, Clone 30 strain, fusion gene (F), and the transcription terminator from the HCMV IE gene. The NDV F gene is transcribed in the opposite direction relative to the HVT UL54.5 gene.

Subgenomic Clone 228509-ILT-435Vec6 [see, International Application PCT/EP2017/064662]

The insertion plasmid 228509-ILT-435Vec6 contains a 7311 base pair EcoRI fragment of the HVT unique short regions [pos. 126880-144190; Afonso et al., 2001, supra; Acc. # AF291866], cloned into the plasmid pSP64 (Promega, Madison, Wis.). Inserted into a unique StuI site within the HVT US2 gene [pos. 140540/140541; Afonso et al., 2001, supra; Acc. # AF291866, between amino acid residues 124 and 125] are two elements: an expression cassette consisting of the MCMV IE promoter, the IBDV classic type F52/70, Faragher strain, virus protein 2 gene (VP2), and the SV40 polyadenylation signal; followed by a 3563 base pair SalI-HindIII fragment from ILTV, NVSL Challenge Strain, Lot #83-2 [pos. 10532-14094; Wild et al., *Virus Genes* 12:104-116 (1996); Acc. # U28832], encoding the full length genes for glycoprotein D (gD) and glycoprotein I (gI), plus partial coding regions from glycoprotein E (amino acids 1-101), and ORF5 (amino acids 734-985). The IBDV VP2, ILTV gD and ILTV gI genes are transcribed in the opposite direction relative to the HVT US2 gene.

Additional Insertion Fragments for Generating HVT/IBDV/ILTV/NDV #3 (see, FIG. 3)

Subgenomic Clone VP2/1C1#8

The insertion plasmid VP2/1C1#8 contains an 8636 base pair region of genomic HVT unique long region [pos. 109489-118124; Afonso et al., 2001, supra; Acc. # AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. # AF291866, between amino acid residues 21 and 22] is an expression cassette consisting of the MCMV IE promoter, the IBDV classic type F52/70, Faragher strain, virus protein 2 gene (VP2), and the SV40 polyadenylation signal. The IBDV VP2 gene is transcribed in the opposite direction relative to the HVT UL54.5 gene.

Subgenomic Clone 1332-47.A2

The insertion plasmid 1332-47.A2 contains a 7311 base pair EcoRI fragment of the HVT unique short regions [pos. 126880-144190; Afonso et al., 2001, supra; Acc. # AF291866], cloned into the plasmid pSP64 (Promega, Madison, Wis.). Inserted into a unique StuI site within the HVT US2 gene [pos. 140540/140541; Afonso et al., 2001, supra; Acc. # AF291866, between amino acid residues 124 and 125] are two elements: a 3563 base pair SalI-HindIII fragment from ILTV, NVSL Challenge Strain, Lot #83-2 [pos. 10532-14094; Wild et al., *Virus Genes* 12:104-116 (1996); Acc. # U28832], encoding the full length genes for glycoprotein D (gD) and glycoprotein I (gI), plus partial coding regions from glycoprotein E (amino acids 1-101), and ORF5 (amino acids 734-985); followed by an expression cassette consisting of the HCMV IE promoter, the NDV, Clone 30 strain, fusion gene (F), and the transcription terminator from the HCMV IE gene. The ILTV gD, the ILTV gI, and the NDV F genes are transcribed in the opposite direction relative to the HVT US2 gene.

Additional Insertion Fragments for Generating HVT/IBDV/ILTV/NDV #4 (see, FIG. 4)

Subgenomic Clone 1332-23.7

The insertion plasmid 1332-23.7 contains an 8636 base pair region of genomic HVT unique long region [pos. 109489-118124; Afonso et al., 2001, supra; Acc. # AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. # AF291866, between amino acid residues 21 and 22] is a 3563 base pair SalI-HindIII fragment from ILTV, NVSL Challenge Strain, Lot #83-2 [pos. 10532-14094; Wild et al., *Virus Genes* 12:104-116 (1996); Acc. # U28832], encoding the full length genes for glycoprotein D (gD) and glycoprotein I (gI), plus partial coding regions from glycoprotein E (amino acids 1-101), and ORF5 (amino acids 734-985). The ILTV gD and the ILTV gI genes are transcribed in the opposite direction relative to the HVT UL54.5 gene.

Subgenomic Clone 435Vec60

The insertion plasmid 435Vec60 contains a 7311 base pair EcoRI fragment of the HVT unique short regions [pos. 126880-144190; Afonso et al., 2001, supra; Acc. # AF291866], cloned into the plasmid pSP64 (Promega, Madison, Wis.). Inserted into a unique StuI site within the HVT US2 gene [pos. 140540/140541; Afonso et al., 2001, supra; Acc. # AF291866, between amino acid residues 124 and 125] are two elements: an expression cassette consisting of the MCMV IE promoter, the IBDV classic type F52/70, Faragher strain, virus protein 2 gene (VP2), and the SV40 polyadenylation signal; followed by an expression cassette consisting of the HCMV IE promoter, the NDV, Clone 30 strain, fusion gene (F), and the transcription terminator from the HCMV IE gene. Both the IBDV VP2 and NDV F genes are transcribed in in the opposite direction relative to the HVT US2 gene.

Additional Insertion Fragments for Generating HVT/IBDV/ILTV/NDV #5 (see, FIG. 5)

Subgenomic Clone 1332-29.4 [see, U.S. Pat. No. 9,409,954 B2] The insertion plasmid 1332-29.4 contains an 8636 base pair region of genomic HVT unique long region [pos. 109489-118124; Afonso et al., 2001, supra; Acc. # AF291866], cloned into a derivative of plasmid pNEB193 (deleted AatII-PvuII). It is flanked by AscI sites and includes HVT BamHI fragments I, S, plus 1337 base pairs of fragment G and 1177 base pairs of fragment F. Inserted into an XhoI site within the HVT UL54.5 open reading frame [pos. 111240/111241; Afonso et al., 2001, supra; Acc. # AF291866, between amino acid residues 21 and 22] are two elements: a 3563 base pair SalI-HindIII fragment from ILTV, NVSL Challenge Strain, Lot #83-2 [pos. 10532-14094; Wild et al., *Virus Genes* 12:104-116 (1996); Acc. # U28832], encoding the full length genes for glycoprotein D (gD) and glycoprotein I (gI), plus partial coding regions from glycoprotein E (amino acids 1-101), and ORF5 (amino acids 734-985); followed by an expression cassette consisting of the HCMV IE promoter, the NDV, Clone 30 strain, fusion gene (F), and the transcription terminator from the HCMV IE gene. The ILTV gD, the ILTV gI, and the NDV F genes are transcribed in the opposite direction relative to the HVT UL54.5 gene.

Subgenomic Clone 435Vec6

The insertion plasmid 435Vec6 contains a 7311 base pair EcoRI fragment of the HVT unique short regions [pos. 126880-144190; Afonso et al., 2001, supra; Acc. # AF291866], cloned into the plasmid pSP64 (Promega, Madison, Wis.). Inserted into a unique StuI site within the HVT US2 gene [pos. 140540/140541; Afonso et al., 2001, supra; Acc. # AF291866, between amino acid residues 124 and 125] is an expression cassette consisting of the MCMV IE promoter, the IBDV classic type F52/70, Faragher strain, virus protein 2 gene (VP2), and the SV40 polyadenylation signal. The IBDV VP2 gene is transcribed in in the opposite direction relative to the HVT US2 gene.

The sequences used in the HVT/ILTV/IBDV/NDV viral vectors disclosed in this example are provided in Example 7 below as SEQ ID NOs: 23 and 26-32.

Example 6

Unsuccessful Constructs

The recombinant vector vaccine viruses, by definition are engineered to carry and express foreign genes. Should transcription and expression of these foreign genes provide a growth disadvantage to the recombinant virus relative to the parental virus, it is possible for these genes to be lost during production of the vaccine. For this reason, vaccine candidates must be tested for both genetic and phenotypic stability.

In addition, the protection criteria used is that which has been established by the USDA and codified in the Title 9 Code of Federal Regulations, part 113 (9CFR 113) «Standard requirements for Animal Products». Live virus vaccines must provide at least 90% protection, in the case of NDV, IBDV and ILTV, and at least 80% in the case of MDV, from clinical signs or lesions associated with the disease to obtain a license.

Genetic stability of the viral constructs was determined by Southern blot analysis after a defined number of passages in tissue culture, the highest anticipated vaccine production level, and compared with DNA from the original isolate. DNA extracted from viral stocks would be digested with restriction enzymes, transferred to a membrane and hybridized with probes designed to detect the presence of the inserted foreign genes. Genetic stability may also be determined by PCR analysis. PCR primers designed to anneal to DNA within or flanking the foreign DNA could be used to amplify fragments of a known size from the viral DNA templates both before and after passage in tissue culture.

Phenotypic stability of the viral constructs was determined by immunological staining of individual viral plaques with antibodies directed against the protein products of these inserted foreign genes. Protection provided by these recombinant vaccines relies on expression of these protein products in order to stimulate the animals immune system. In most cases, if the percent of viruses staining positive for the foreign protein expression dropped below 90%, it was likely detrimental to the viruses ability to be grown in tissue culture, and therefore unsuitable as a vaccine candidate.

As is readily apparent from Tables 7A and 7B below, most rMDVnp constructs do not meet these two criteria, namely stability with relatively strong antigen expression and/or efficacy. Table 7A provides a series of recombinant HVT constructs with multiple heterologous inserts in which one of the heterologous inserts encodes an IBDV antigen. As the results show, all of the constructs in Table 7A failed to meet the stability with relatively strong antigen expression and/or efficacy criteria.

TABLE 7A

DOUBLE RECOMBINANT HVT AND IBDV VIRUS CONSTRUCTS:

| Name/ Designation | Insertion site | Insert | IBDV Promoter | IBDV Expression | Stability |
|---|---|---|---|---|---|
| HVT 003 | UL43 | [IBDV] polyprotein [Ecoli] Bgal | PRV gX | Poor | stable |
| HVT 016 | UL43 | [IBDV] VP2 [Ecoli] Bgal | hCMV IE | Strong | unstable |
| HVT 056 | US2 | [MDV] gA, gB [IBDV] VP2 | hCMV IE | Strong | Unstable |
| HVT 060 | US2 | [MDV] gA, gB [IBDV] VP2, 16kD ORF | IE-VP2, gX-16dk ORF | Strong | unstable |
| HVT 137 | US2 UL54.5 | [MDV] gA, gB, gC [IBDV] VP2 | [BHV] VP8 (tegument) | Poor | stable |
| HVT 143 | US2 US2 UL54.5 | [MDV] gA, gB, gD [NDV] HN, F [IBDV] VP2 | [BHV] VP8 (tegument) | Poor | Unstable |
| HVT/NDV/IBDV 1312-92 | US2 UL7/UL8 | [IBDV] VP2 [NDV] F | hCMV IE | Strong | Unstable |
| HVT/NDV/IBDV 1312-94 | US2 UL7/UL8 | [IBDV] VP2 [NDV] F | hCMV IE | Strong | Unstable |
| HVT/NDV/IBDV 1312-95 | US2 UL7/UL8 | [IBDV] VP2 [NDV] F | hCMV IE | Strong | Unstable |
| HVT/NDV/IBDV 1329-54 | US2 | [IBDV] VP2 [NDV] F | FHV gB | Strong | Unstable |

Table 7B below, provides a series of eleven recombinant HVT constructs and one lone NAHV construct each of which comprise multiple heterologous inserts in which at least one of the heterologous inserts encodes either an NDV or an ILTV antigen.[1] As the results show, all of the constructs in Table 7B failed to meet the stability with relatively strong antigen expression and/or efficacy criteria.

[1] The data in Table 7B was submitted to the U.S. Patent Office during the prosecution of U.S. Pat. No. 8,932,604 B2 in a Declaration signed by one of the co-Inventors of the present application.

Example 7

Sequences

The following sequences have been used in the exemplary rHVT constructs. The coding sequences provided below include individual stop codons, which can be readily replaced with alternative stop codons without modifying the properties of the protein antigens that the coding sequences encode.

TABLE 7B

DOUBLE RECOMBINANT HVT AND NAHV VIRUS CONSTRUCTS:

| Name | Insertion site | Insert | Stability | NDV Protection | MDV Protection | ILTV Protection |
|---|---|---|---|---|---|---|
| HVT 048 | US2 | [MDV] gA, gB [NDV] F | Stable | Good | *Protective | — |
| HVT 049 | US2 | [MDV] gA, gB [NDV] HN | Stable | Poor (<20%) | Not tested | — |
| HVT 050 | US2 | [MDV] gA, gB [NDV] F, HN | Stable | Good | *Protective | — |
| HVT 053 | US2 | [MDV] gA, gB [ILTV] gB, gD | Unstable | — | Not tested | None |
| HVT 078 | US2 | [MDV] gA, gB, gD [NDV] HN, F | Unstable | Not tested | Not tested | — |
| HVT 079 | US2 | [MDV] gA, gB, gD [ILTV] gB, gD | Unstable | — | Not tested | (71-100%) |
| HVT 106 | US2 | [MDV] gA, gB, gD [NDV] HN, F | Stable | **Unknown | Not tested | — |
| HVT 123 | UL54.5 + US2 | [ILTV] gD, gB/UL54.5 [MDV] gA, gD, gB/US2 | Unstable | — | Not tested | Not tested |
| HVT 125 | UL54.5 + US2 | [ILTV] gDgI, gB/UL54.5 [MDV] gA, gD, gB/US2 | Unstable | — | Not tested | Not tested |
| HVT 128 | UL54.5 + US2 | [NDV] HN, F/UL54.5 [MDV] gA, gD, gB/US2 | Unstable | Not tested | Not tested | — |
| HVT 139 | UL54.5 + US2 | [ILTV] gDgI/UL54.5 [MDV] gA, gD, gB/US2 | Unstable | — | Not tested | Not tested |
| HVY-198 (NAHV) | US2* | [NDV] F + (MDV) [ILTV] gD, gI | Unstable | | | |

*Protective, but subsequently failed in field studies
**Only 75% birds seroconverted to NDV F SEQ ID NO 1: ILTV gD Glycoprotein (1134 bp)
atggaccgccatttattttgaggaatgcttttggactatcgtactgctttcttccttcgctagcca
gagcaccgccgccgtcacgtacgactacattttaggccgtcgcgcgctcgacgcgctaaccataccgg
cggttggcccgtataacagatacctcactagggtatcaagaggctgcgacgttgtcgagctcaaccg
atttctaacgtggacgacatgatatcggcggccaaagaaaaagaagggggcccttcgaggcctc
cgtcgtctggttctacgtgattaagggcgacgacggcgaggacaagtactgtccaatctatagaaaag
agtacagggaatgtggcgacgtacaactgctatctgaatgcgccgttcaatctgcacagatgtgggca
gtggactatgttcctagcacccttgtatcgcgaaatggcgcgggactgactatattctccccactgc
tgcgctctctggccaatacttgctgaccctgaaaatcgggagatttgcgcaaacagctctcgtaactc
tagaagttaacgatcgctgtttaaagatcgggtcgcagcttactttttaccgtcgaaatgctggaca
acagaacagtatcagactggatttcaaggcgaacacctttatccgatcgcagacaccaatacacgaca
cgcggacgacgtatcggggatacgaagatattctgcagcgctggaataatttgctgaggaaaaaga
atcctagcgcgccagaccctcgtccagatagcgtcccgcaagaaattcccgctgtaaccaagaaagcg
gaagggcgcaccccggacgcagaaagcagcgaaaagaaggcccctccagaagactcggaggacgacat
gcaggcagaggcttctggagaaaatcctgccgccctccccgaagacgacgaagtccccgaggacaccg
agcacgatgatccaaactcggatcctgactattacaatgacatgcccgccgtgatcccggtggaggag
actactaaaagttctaatgccgtctccatgcccatattcgcggcgttcgtagcctgcgcggtcgcgct
cgtggggctactggtttggagcatcgtaaaatgcgcgcgtagctaa SEQ ID NO 2: ILTV gD Glycoprotein (377 amino acids)
MDRHLFLRNAFWTIVLLSSFASQSTAAVTYDYILGRRALDALTIPAVGPYNRYLTRVSRGCDVVELNP
ISNVDDMISAAKEKEGGPFEASVVWFYVIKGDDGEDKYCPIYRKEYRECGDVQLLSECAVQSAQMWA
VDYVPSTLVSRNGAGLTIFSPTAALSGQYLLTLKIGRFAQTALVTLEVNDRCLKIGSQLNFLPSKCWT
TEQYQTGFQGEHLYPIADTNTRHADDVYRGYEDILQRWNNLLRKKNPSAPDPRPDSVPQEIPAVTKKA
EGRTPDAESSEKKAPPEDSEDDMQAEASGENPAALPEDDEVPEDTEHDDPNSDPDYYNDMPAVIPVEE
TTKSSNAVSMPIFAAFVACAVALVGLLVWSIVKCARS SEQ ID NO 3: ILTV gI Glycoprotein (1089 bp)
atggcatcgctacttggaactctggctctccttgccgcgacgctcgcacccttcggcgcgatgggaat
cgtgatcactggaaatcacgtctccgccaggattgacgacgatcacatcgtgatcgtcgcgcctcgcc
ccgaagctacaattcaactgcagctatttttcatgcctggccagagaccccacaaaccctactcagga
accgtccgcgtcgcgtttcggtctgatataacaaaccagtgctaccaggaacttagcgaggagcgctt
tgaaaattgcactcatcgatcgtcttctgtttttgtcggctgtaaagtgaccgagtacacgttctccg
cctcgaacagactaaccggacctccacacccgtttaagctcactatacgaaatcctcgtccgaacgac
agcgggatgttctacgtaattgttcggctagacgacaccaaagaacccattgacgtcttcgcgatcca
actatcggtgtatcaattcgcgaacaccgccgcgactcgcggactctattccaaggcttcgtgtcgca
ccttcggattacctaccgtccaacttgaggcctatctcaggaccgaggaaagttggcgcaactggcaa
gcgtacgttgccacggaggccacgacgaccagcgccgaggcgacaaccccgacgcccgtcactgcaac
cagcgcctccgaacttgaagcggaacacttttaccttttccctgcctagaaaatggcgtggatcattacg
aaccgacacccgcaaacgaaaattcaaacgttactgtccgtctcgggacaatgagccctacgctaatt
ggggtaaccgtggctgccgtcgtgagcgcaacgatcggcctcgtcattgtaatttccatcgtcaccag
aaacatgtgcacccgcaccgaaaattagacacggtctcgcaagacgacgaagaacgttcccaaacta
gaagggaatcgcgaaaatttggacccatggttgcgtgcgaaataaacaaggggggctgaccaggatagt
gaacttgtggaacttggttgcgattgttaacccgtctgcgctaagctcgcccgactcaataaaaatgtg
a SEQ ID NO 4: ILTV gI Glycoprotein (362 amino acids)
MASLLGTLALLAATLAPFGAMGIVITGNHVSARIDDDHIVIVAPRPEATIQLQLFFMPGQRPHKPYSG
TVRVAFRSDITNQCYQELSEERFENCTHRSSSVFVGCKVTEYTFSASNRLTGPPHPFKLTIRNPRPND
SGMFYVIVRLDDTKEPIDVFAIQLSVYQFANTAATRGLYSKASCRTFGLPTVQLEAYLRTEESWRNWQ
AYVATEATTTSAEATTPTPVTATSASELEAEHFTFPWLENGVDHYEPTPANENSNVTVRLGTMSPTLI
GVTVAAVVSATIGLVIVISIVTRNMCTPHRKLDTVSQDDEERSQTRRESRKFGPMVACEINKGADQDS
ELVELVAIVNPSALSSPDSIKM SEQ ID NO 5: IBDV VP2 (1362 bp)
atgacaaacctgcaagatcaaacccaacagattgttccgttcatacggagccttctgatgccaacaac
cggaccggcgtccattccggacgacacctggagaagcacactctcaggtcagagacctcgacctaca
atttgactgtggggggacacagggtcagggctaattgtcttttttccctggattccctggctcaattgtg
ggtgctcactacacactgcagagcaatgggaactacaagttcgatcagatgctcctgactgcccagaa
cctaccggccagctacaactactgcagactagtgagtcggagtctcacagtgaggtcaagcacactcc
ctggtggcgtttatgcactaaacggcaccataaacgccgtgacctccaaggaagcctgagtgaactg
acagatgttagctacaatgggttgatgtctgcaacagccaacataaacgacaaaattgggaatgtcct
ggtaggggaaggggtcactgtcctcagcctacccacatcatatgatcttgggtatgtgaggcttggtg
accccattcccgctataggctgacccaaaaatggtagctacatgcgacagcagtgacaggccgaga
gtctacaccataactgcagccgatgattaccaattctcatcacagtaccaaccaggtggggtaacaat
cacactgttctcagccaacattgatgctatcacaagcctcagcattggggagagctcgtgtttcaaa
caagcgtccaaggccttgtactgggcgccaccatctacctatagcctttgatgggactgcggtaatc
accagagctgtggccgcagataatgtctgacggccggcaccgacaatctttatgccattcaatcttgt
cattccaaccaatgagataacccagccaatcacatccatcaaactggagatagtgacctccaaagtg
gtggtcaggcagggggatcagatgtcatggtcggcaagtgggagcctagcagtgacgatccatggtggc
aactatccaggggcctccgtcccgtcacactagtagcctacgaaagagtggcaacaggatccgtcgt
tacggtcgctggggtgagtaactcgactgattccaaatcctgactagcaaagaacctggttacag
aatacgccgatttgacccaggagccatgaactacacaaaattgatactgagtgagagggaccgtctt
ggcatcaagaccgtctggccaacaagggagtacactgattttcgtgagtacttcatggaggtggccga
cctcaactctcccctgaagattgcaggagcatttggcttcaaagacataatccgggctataaggaggt
aa SEQ ID NO 6: IBDV VP2 (453 amino acids)
MTNLQDTQQIVPFIRSLLMPTTGPASIPDDTLEKHTLRSETSTYNLTVGDTSGLIVFFPGFPGSIV
GAHYTLQSNGNYKFDQMLLTAQNLPASYNYCRLVSRSLTVRSSTLPGGVYALNGTINAVTFQGSLSEL
TDVSYNGLMSATANINDKIGNVLVGEGVTVLSLPTSYDLGYVRLGDPIPAIGLDPKMVATCDSSDRPR -continued VYTITAADDYQFSSQYQPGGVTITLFSANIDAITSLSIGGELVFQTSVQGLVLGATIYLIGFDGTAVI
TRAVAADNGLTAGTDNLMPFNLVIPTNEITQPITSIKLEIVTSKSGGQAGDQMSWSASGSLAVTIHGG
NYPGALRPVTLVAYERVATGSVVTVAGVSNFELIPNPELAKNLVTEYGRFDPGAMNYTKLILSERDRL
GIKTVWPTREYTDFREYFMEVADLNSPLKIAGAFGFKDIIRAIRR SEQ ID NO: 7: NDV F Protein, coding sequence (Clone 30; 1662 bp)
atgggccccagaccttctaccaagaacccagtacctatgatgctgactgtccgagtcgcgctggtact
gagttgcatctgtccggcaaactccattgatggcaggcctcttgcggctgcaggaattgtggttacag
gagacaaagccgtcaacatatacacctcatcccagacaggatcaatcatagttaagctcctcccgaat
ctgcccaaggataaggaggcatgtgcgaaagccccccttggatgcatacaacaggacattgaccacttt
gctcaccccccttggtgactctatccgtaggatacaagagtctgtgactacatctggaggggggagac
aggggcgccttataggcgccattattggcggtgtggctcttggggttgcaactgccgcacaaataaca
gcggccgcagctctgatacaagccaaacaaaatgctgccaacatcctccgacttaaagagagcattgc
cgcaaccaatgaggctgtgcatgaggtcactgacggattatcgcaactagcagtggcagttgggaaga
tgcagcagtttgttaatgaccaatttaataaaacagctcaggaattagactgcatcaaaattgcacag
caagttggtgtagagctcaacctgtacctaaccgaattgactacagtattcggaccacaaatcacttc
acctgctttaaacaagctgactattcaggcactttacaatctagctggtggaaatatggattacttat
tgactaagttaggtgtagggaacaatcaactcagctcattaatcggtagcggcttaatcaccggtaac
cctattctatacgactcacagactcaactcttgggtatacaggtaactctaccttcagtcgggaagct
aaataatatgcgtgccacctacttggaaaccttatccgtaagcacaaccaggggatttgcctcggcac
ttgtcccaaaagtggtgacacaggtcggttctgtgatagaagaacttgacacctcatactgtatagaa
actgacttacatttatattgtacaagaatagtaacgttccctatgtcccctggtatttattcctgctt
gagcggcaatacgtcggcctgtatgtactcaaagaccgaaggcgcacttactacaccatacatgacta
tcaaaggttcagtcatcgccaactgcaagatgacaacatgtagatgtgtaaaccccccgggtatcata
tcgcaaaactatggagaagccgtgtctctaatagataaacaatcatgcaatgttttatccttaggcgg
gataactttaaggctcagtggggaattcgatgtaacttatcagaagaatatctcaatacaagattctc
aagtaataataacaggcaatcttgatatctcaactgagcttgggaatgtcaacaactcgatcagtaat
gctttgaataagttagaggaaagcaacagaaaactagacaaagtcaatgtcaaactgactagcacatc
tgctctcattacctatatcgtgttgactatcatatctcttgtttttggtatacttagcctgattctag
catgctacctaatgtacaagcaaaaggcgcaacaaaagaccttattatggcttgggaataatactcta
gatcagatgagagccactacaaaaatgtga SEQ ID NO: 8: NDV F Protein (Clone 30; 553 amino acids)
MGPRPSTKNPVPMMLTVRVALVLSCICPANSIDGRPLAAAGIVVTGDKAVNIYTSSQTGSIIVKLLPN
LPKDKEACAKAPLDAYNRTLTTLLTPLGDSIRRIQESVTTSGGGRQGRLIGAIIGGVALGVATAAQIT
AAAALIQAKQNAANILRLKESIAATNEAVHEVTDGLSQLAVAVGKMQQFVNDQFNKTAQELDCIKIAQ
QVGVELNLYLTELTTVFGPQITSPALNKLTIQALYNLAGGNMDYLLTKLGVGNNQLSSLIGSGLITGN
PILYDSQTQLLGIQVTLPSVGKLNNMRATYLETLSVSTTRGFASALVPKVVTQVGSVIEELDTSYCIE
TDLHLYCTRIVTFPMSPGIYSCLSGNTSACMYSKTEGALTTPYMTIKGSVIANCKMTTCRCVNPPGII
SQNYGEAVSLIDKQSCNVLSLGGITLRLSGEFDVTYQKNISIQDSQVIITGNLDISTELGNVNNSISN
ALNKLEESNRKLDKVNVKLTSTSALITYIVLTIISLVFGILSLILACYLMYKQKAQQKTLLWLGNNTL
DQMRATTKM SEQ ID NO: 9: NDV F Protein, coding sequence: (B1 Hitchner; 1698 bp)
atggatcgatcccggttggcgccctccaggtgcaggatgggctccagaccttctaccaagaacccagc
acctatgatgctgactatccgggtcgcgctggtactgagttgcatctgtccggcaaactccattgatg
gcaggcctcttgcagctgcaggaattgtggttacaggagacaaagcagtcaacatatacacctcatcc
cagacaggatcaatcatagttaagctcctcccgaatctgcccaaggataaggaggcatgtgcgaaagc
cccccttggatgcatacaacaggacattgaccactttgctcaccccccttggtgactctatccgtagga
tacaagagtctgtgactacatctggaggggggagacaggggcgccttataggcgccattattggcggt
gtggctcttggggttgcaactgccgcacaaataacagcggccgcagctctgatacaagccaaacaaaa
tgctgccaacatcctccgacttaaagagagcattgccgcaaccaatgaggctgtgcatgaggtcactg
acggattatcgcaactagcagtggcagttgggaagatgcagcagttcgttaatgaccaatttaataaa
acagctcaggaattagactgcatcaaaattgcacagcaagttggtgtagagctcaacctgtacctaac
cgaatcgactacagtattcggaccacaaatcacttcacctgccttaaacaagctgactattcaggcac
tttacaatctagctggtgggaatatggattacttattgactaagttaggtatagggaacaatcaactc
agctcattaatcggtagcggcttaatcaccggtaaccctattctatacgactcacagactcaactctt
gggtatacaggtaactctaccttcagtcgggaacctaaataatatgcgtgccacctacttggaaacct
tatccgtaagcacaaccaggggatttgcctcggcacttgtcccaaaagtggtgacacgggtcggttct
gtgatagaagaacttgacacctcatactgtatagaaactgacttagatttatattgtacaagaatagt
aacgttccctatgtcccctggtatttactcctgcttgagcggcaatacatcggcctgtatgtactcaa
agaccgaaggcgcacttactacaccatatatgactatcaaaggctcagtcatcgctaactgcaagatg
acaacatgtagatgtgtaaaccccccgggtatcatatcgcaaaactatggagaagccgtgtctctaat
agataaacaatcatgcaatgttttatccttaggcgggataactttaaggctcagtggggaattcgatg
taacttatcagaagaatatctcaatacaagattctcaagtaataataacaggcaatcttgatatctca
actgagcttgggaatgtcaacaactcgatcagtaatgccttgaataagttagaggaaagcaacagaaa
actagacaaagtcaatgtcaaactgaccagcacatctgctctcattacctatatcgttttgactatca
tatctcttgtttttggtatacttagcctgattctagcatgctacctaatgtacaagcaaaaggcgcaa
caaaagaccttattatggcttgggaataataccctagatcagatgagagccactacaaaaatgtga SEQ ID NO: 10: NDV F Protein (B1 Hitchner; 565 amino acids)
MDRSRLAPSRCRMGSRPSTKNPAPMMLTIRVALVLSCICPANSIDGRPLAAAGIVVTGDKAVNIYTSS
QTGSIIVKLLPNLPKDKEACAKAPLDAYNRTLTTLLTPLGDSIRRIQESVTTSGGGRQGRLIGAIIGG
VALGVATAAQITAAAALIQAKQNAANILRLKESIAATNEAVHEVTDGLSQLAVAVGKMQQFVNDQFNK
TAQELDCIKIAQQVGVELNLYLTESTTVFGPQITSPALNKLTIQALYNLAGGNMDYLLTKLGIGNNQL
SSLIGSGLITGNPILYDSQTQLLGIQVTLPSVGNLNNMRATYLETLSVSTTRGFASALVPKVVTRVGS -continued VIEELDTSYCIETDLDLYCTRIVTFPMSPGIYSCLSGNTSACMYSKTEGALTTPYMTIKGSVIANCKM
TTCRCVNPPGIISQNYGEAVSLIDKQSCNVLSLGGITLRLSGEFDVTYQKNISIQDSQVIITGNLDIS
TELGNVNNSISNALNKLEESNRKLDKVNVKLTSTSALITYIVLTIISLVFGILSLILACYLMYKQKAQ
QKTLLWLGNNTLDQMRATTKM SEQ ID NO 11: ILTV gD promoter (527 bp)
aaacagctgtactacagagtaaccgatggaagaacatcggtccagctaatgtgcctgtcgtgcacgag
ccattctccggaaccttactgtcttttcgacacgtctcttatagcgagggaaaaagatatcgcgccag
agttatactttacctctgatccgcaaacggcatactgcacaataactctgccgtccggcgttgttccg
agattcgaatggagccttaataatgtttcactgccggaatatttgacggccacgaccgttgtttcgca
taccgctggccaaagtacagtgtggaagagcagcgcgagagcaggcgaggcgtggatttctggccggg
gaggcaatatatacgaatgcaccgtcctcatctcagacggcactcgcgttactacgcgaaaggagagg
tgcttaacaaacacatggattgcggtggaaaacggtgctgctcaggcgcagctgtattcactcttttc
tggacttgtgtcaggattatgcgggagcatatctgctttgtacgcaacgct SEQ ID NO 12: ILTV gI promoter (264 bp)
tgactattacaatgacatgcccgccgtgatcccggtggaggagactactaaaagttctaatgccgtct
ccatgcccatattcgcggcgttcgtagcctgcgcggtcgcgctcgtggggctactggtttggagcatc
gtaaaatgcgcgcgtagctaatcgagcctagaataggtggtttcttcctacatgccacgcctcacgct
cataatataaatcacatggaatagcataccaatgcctattcattgggacgttcgaaaagc SEQ ID NO 13: mCMV IE promoter (1391 bp)
aactccgcccgttttatgactagaaccaatagtttttaatgccaaatgcactgaaatcccctaatttg
caaagccaaacgcccccctatgtgagtaatacggggactttttacccaatttcccacgcggaaagcccc
ctaatacactcatatggcatatgaatcagcacggtcatgcactctaatggcggcccatagggactttc
cacataggggggcgttcaccatttcccagcataggggtggtgactcaatggcctttacccaagtacatt
gggtcaatgggaggtaagccaatgggtttttcccattactggcaagcacactgagtcaaatgggactt
tccactgggttttgcccaagtacattgggtcaatgggaggtgagccaatgggaaaaacccattgctgc
caagtacactgactcaatagggactttccaatgggtttttccattgttggcaagcatataaggtcaat
gtgggtgagtcaatagggactttccattgtattctgcccagtacataaggtcaataggggtgaatca
acaggaaagtcccattggagccaagtacactgcgtcaatagggactttccattgggttttgcccagta
cataaggtcaataggggatgagtcaatgggaaaaacccattggagccaagtacactgactcaataggg
actttccattgggttttgcccagtacataaggtcaataggggtgagtcaacaggaaagttccattgg
agccaagtacattgagtcaatagggactttccaatgggttttgcccagtacataaggtcaatgggagg
taagccaatgggtttttcccattactggcacgtatactgagtcattagggactttccaatgggttttg
cccagtacataaggtcaataggggtgaatcaacaggaaagtcccattggagccaagtacactgagtca
atagggactttccattgggttttgcccagtacaaaaggtcaataggggggtgagtcaatgggtttttcc
cattattggcacgtacataaggtcaataggggtgagtcattgggtttttccagccaatttaattaaaa
cgccatgtactttcccaccattgacgtcaatgggctattgaaactaatgcaacgtgacctttaaacgg
tactttcccatagctgattaatgggaaagtaccgttctcgagccaatacacgtcaatgggaagtgaaa
gggcagccaaaacgtaacaccgccccggtttcccctggaaattccatattggcacgcattctattgg
ctgagctgcgttctacgtgggtataagaggcgcgaccagcgtcggtaccgtcgcagtcttcggtctga
ccaccgtagaacgcagagctcctcgctgcag SEQ ID NO 14: hCMV IE promoter, from strain AD169 (301 bp)
ggcagtacatctacgtattagtcatcgctattaccatggtgatgcggttttggcagtacatcaatggg
cgtggatagcggtttgactcacggggatttccaagtctccaccccattgacgtcaatgggagtttgtt
ttggcaccaaaatcaacgggactttccaaaatgtcgtaacaactccgccccattgacgcaaatgggcg
gtaggcgtgtacggtgggaggtctatataagcagagctcgtttagtgaaccgtcagatcgcctggaga
cgccatccacgctgttttgacctccatag SEQ ID NO: 15: hCMV IE Promoter (Truncated; 360 bp)
cgcgccaggtcaattccctggcattatgcccagtacatgaccttatgggactttcctacttggcagta
catctacgtattagtcatcgctattaccatggtgatgcggttttggcagtacatcaatgggcgtggat
agcggtttgactcacggggatttccaagtctccaccccattgacgtcaatgggagtttgttttggcac
caaaatcaacgggactttccaaaatgtcgtaacaactccgccccattgacgcaaatgggcggtagcgt
gtacggtgggaggtctatataagcagagctcgtttagtgaaccgtcagatcgcctggagacgccatcc
acgctgttttgacctccata SEQ ID NO: 16: hCMV IE Promoter (Towne Strain; 1191 bp)
gtgaataataaaatgtgtgtttgtccgaaatacgcgtttgagatttctgtcccgactaaattcatgtc
gcgcgatagtggtgtttatcgccgatagagatggcgatattggaaaaatcgatatttgaaaatatggc
atattgaaaatgtcgccgatgtgagtttctgtgtaactgatatcgccatttttccaaaagttgatttt
tgggcatacgcgatatctggcgatacgcttatatcgtttacgggggatggcgatagacgcctttggtg
acttgggcgattctgtgtgtcgcaaatatcgcagtttcgatataggtgacagacgatatgaggctata
tcgccgatagaggcgacatcaagctggcacatggccaatgcatatcgatctatacattgaatcaatat
tggccattagccatattattcattggttatatagcataaatcaatattggctattggccattgcatac
gttgtatccatatcataatatgtacatttatattggctcatgtccaacattaccgccatgttgacatt
gattattgactagttattaatagtaatcaattacggggtcattagttcatagcccatatatggagttc
cgcgttacataacttacggtaaatggcccgcctggctgaccgcccaacgacccccgcccattgacgtc
aataatgacgtatgttcccatagtaacgccaatagggactttccattgacgtcaatgggtggagtatt
tacggtaaactgcccacttggcagtacatcaagtgtatcatatgccaagtacgccccctattgacgtc
aatgacggtaaatggcccgcctggcattatgcccagtacatgaccttatgggactttcctacttggca
gtacatctacgtattagtcatcgctattaccatggtgatgcggttttggcagtacatcaatgggcgtg
gatagcggtttgactcacggggatttccaagtctccaccccattgacgtcaatgggagtttgttttgg
caccaaaatcaacgggactttccaaaatgtcgtaacaactccgccccattgacgcaaatgggcggtag
gcgtgtacggtgggaggtctatataagcagagctcgtttagtgaaccgtcagatcgcctggagacgcc
atccacgctgttttgacctccatagaagacaccgg -continued SEQ ID NO 17: chicken β-actin promoter (692 bp)
(Note: "nnn" denotes an ambiguous sequence in highly GC-rich region.
Could be 3-5 "g's")
cgcgccggatcagatctccatggtcgaggtgagccccacgttctgcttcactctccccatctcccccc
cctccccacccccaattttgtatttatttattttttaattattttgtgcagcgatgggggcgggggggg
ggggnnncgcgcgccaggcggggcggggcggggcgaggggcggggcggggcgaggcggagaggtgcgg
cggcagccaatcagagcggcgcgctccgaaagtttccttttatggcgaggcggcggcggcggcggccc
tataaaaagcgaagcgcgcggcgggcgggagtcgctgcgcgctgccttcgccccgtgccccgctccgc
cgccgcctcgcgccgcccgccccggctctgactgaccgcgttactcccacaggtgagcgggcgggacg
gcccttctcctccgggctgtaattagcggcaggaaggaaatgggcggggagggccttcgtgcgtcgcc
gcgccgccgtccccttctccctctccagcctcggggctgtccgcggggggacggctgccttcgggggg
gacggggcagggcggggttcggcttctggcgtgtgaccggcggctctagagcctctgctaaccatgtt
catgccttcttctttttcctacagctcctgggcaacgtgctggttattgtgctgtctcatcattttgg
caaagaattgca SEQ ID NO 18: FHV US-9 polyadenylation signal (55 bp)
caataaacatagcatacgttatgacatggtctaccgcgtcttatatggggacgac SEQ ID NO 19: HSV TK polyadenylation signal (370 bp)
gatccataattgattgacgggagatgggggaggctaactgaaacacggaaggagacaataccggaagg
aacccgcgctatgacggcaataaaaagacagaataaaacgcacgggtgttgggtcgtttgttcataaa
cgcggggttcggtcccagggctggcactctgtcgataccccaccgagaccccattggggccaatacgc
ccgcgtttcttccttttccccaccccaccccccaagttcgggtgaaggcccagggctcgcagccaacg
tcggggcggcaggccctgccatagccactggccccgtgggttagggacggggtcccccatggggaatg
gtttatggttcgtgggggttattattttga SEQ ID NO 20: SV40 polyadenylation signal (199 bp)
agcttcagacatgataagatacattgatgagtttggacaaaccacaactagaatgcagtgaaaaaaat
gctttatttgtgaaatttgtgatgctattgctttatttgtaaccattataagctgcaataaacaagtt
aacaacaacaattgcattcattttatgtttcaggttcagggggaggtgtgggaggttttttcg SEQ ID NO 21: 484-1050-2641-10859(mCMV IEpro-VP2-SV40pA/ILTV/HVT UL54.5 region
(15,252 bp) (HVT/IBDV/ILTV/NDV 670-14 Virus)
ggcgcgccactggagaacggcatgaccgcaaaaggcgttgtagagatcgatcccacgaactctcaggc
gatcgtgtcagtcgccataaacagcgacgatcgtctccaggatctgaacggttttcttctcaacgatc
atcagtatatgaggaactgaacctgatatttagccgagggaaacgcaggttaaaaaccctatcaagcg
attgcgattttcgcgtatctagtaaaaatagatgggcttcggtactagccttcgccgccaactctgaa
tatgcccttcgtggacctcatataacatggcattgtttgttggatgcggggccggaattaagaagaac
attcgaaatacgagcaaaaatttcggccctggcatgtgctgcgcgagaatcggtacttcggggagaaa
gttttatcggagctttgggtagtgcagaggaaactctatcttggttgaaaatgcatgcgaccctgcac
ttgattctggttaaccacgatccaatttttaagacggctggcgcggtcctagataacctccgcttaaa
actagccccaatattgatgtgcagatataacacagaaaaacgatcaatggaagacatgctacggcggt
catctcccgaagacatcaccgattccctaacaatgtgcctgattatgttatcgcgcattcgtcgtacc
atgcgcaccgcaggaaataaatatagctatatgatagatccaatgaatcgtatgtctaattacactcc
aggcgaatgtatgacaggtatattgcgatatattgacgaacatgctagaaggtgtcctgatcacatat
gtaatttgtatatcacatgtacacttatgccgatgtatgtgcacgggcgatatttctattgtaattca
tttttttgttagtaaactaccacaggctgtccggaaatctaagttaatgaataaagtagatggttaat
actcattgcttagaattggactacttttaattctctttaatgttcgtattaaataaaaacatctttaa
taaacttcagcctcttcgcttattgtagaaattgagtattcaaaatcatgttcaaagccgtcttcgga
gagtgtactcgccacggtggttggaacatcactatgtctacacgtcaaatttaagcacgtcaggtctg
tcgaggacaagaaatggttaactagtgtttcaattattcttataaacgttaagcattgtaagcccccc
ggccgtccgcagcaacaatttactagtatgccgtgggctccgggactatcacggatgtccaattcgca
catgcatataatttttctagggtctctcatttcgagaaatcttcggggatccatcagcaatgcgggct
gtagtcccgattcccgtttcaaatgaaggtgctccaacacggtcttcaaagcaaccggcataccagca
aacacagactgcaactccccgctgcaatgattggttataaacagtaatctgtcttctggaagtatatt
tcgcccgacaatccacggcgcccccaaagttaaaaaccatccatgtgtatttgcgtcttctctgttaa
aagaatattgactggcattttcccgttgaccgccagatatccaaagtacagcacgatgttgcacggac
gactttgcagtcaccagccttcctttccacccccccaccaacaaaatgtttatcgtaggacccatatc
cgtaataaggatgggtctggcagcaaccccataggcgcctcggcgtggtagttctcgaggccttaagc
ttaaggatcccccaactccgcccgttttatgactagaaccaatagtttttaatgccaaatgcactgaa
atcccctaatttgcaaagccaaacgcccccctatgtgagtaatacggggactttttacccaatttccca
cgcggaaagcccccctaatacactcatatggcatatgaatcagcacggtcatgcactctaatggcggcc
catagggactttccacatagggggcgttcaccatttcccagcataggggtggtgactcaatggccttt
acccaagtacattgggtcaatgggaggtaagccaatgggtttttcccattactggcaagcacactgag
tcaaatgggactttccactgggttttgcccaagtacattgggtcaatgggaggtgagccaatgggaaa
aacccattgctgccaagtacactgactcaatagggactttccaatgggtttttccattgttggcaagc
atataaggtcaatgtgggtgagtcaatagggactttccattgtattctgcccagtacataaggtcaat
agggggtgaatcaacaggaaagtcccattggagccaagtacactgcgtcaatagggactttccattgg
gttttgcccagtacataaggtcaataggggatgagtcaatgggaaaaacccattggagccaagtacac
tgactcaatagggactttccattgggttttgcccagtacataaggtcaatagggggtgagtcaacagg
aaagttccattggagccaagtacattgagtcaatagggactttccaatgggttttgcccagtacataa
ggtcaatgggaggtaagccaatgggtttttcccattactggcacgtatactgagtcattagggacttt
ccaatgggttttgcccagtacataaggtcaataggggtgaatcaacaggaaagtcccattggagccaa
gtacactgagtcaatagggactttccattgggttttgcccagtacaaaaggtcaatagggggtgagtc
aatgggtttttcccattattggcacgtacataaggtcaataggggtgagtcattgggtttttccagcc
aatttaattaaaacgccatgtactttcccaccattgacgtcaatgggctattgaaactaatgcaacgt
gacctttaaacggtactttcccatagctgattaatgggaaagtaccgttctcgagccaatacacgtca
atgggaagtgaaagggcagccaaaacgtaacaccgccccggttttcccctggaaattccatattggca
cgcattctattggctgagctgcgttctacgtgggtataagaggcgcgaccagcgtcggtaccgtcgca

```
gtcttcggtctgaccaccgtagaacgcagagctcctcgctgcaggcggccgctctagaactcgtcgat
cgcagcgatgacaaacctgcaagatcaaacccaacagattgttccgttcatacggagccttctgatgc
caacaaccggaccggcgtccattccggacgacaccctggagaagcacactctcaggtcagagacctcg
acctacaatttgactgtggggacacagggtcagggctaattgtcttttccctggattccctggctc
aattgtgggtgctcactacacactgcagagcaatgggaactacaagttcgatcagatgctcctgactg
cccagaacctaccggccagctacaactactgcagactagtgagtcggagtctcacagtgaggtcaagc
acactccctggtggcgtttatgcactaaacggcaccataaacgccgtgaccttccaaggaagcctgag
tgaactgacagatgttagctacaatggggttgatgtctgcaacagccaacatcaacgacaaaattggga
atgtcctggtagggggaagggggtcactgtcctcagcctacccacatcatatgatcttgggtatgtgagg
cttggtgaccccattcccgctataggggcttgacccaaaaatggtagctacatgcgacagcagtgacag
gcccagagtctacaccataactgcagccgatgattaccaattctcatcacagtaccaaccaggtgggg
taacaatcacactgttctcagccaacattgatgctatcacaagcctcagcattggggggagagctcgtg
tttcaaacaagcgtccaaggccttgtactgggcgccaccatctaccttataggctttgatgggactgc
ggtaatcaccagagctgtggccgcagataatgggctgacggccggcaccgacaatcttatgccattca
atcttgtcattccaaccaatgagataacccagccaatcacatccatcaaactggagatagtgacctcc
aaaagtggtggtcaggcagggatcagatgtcatggtcggcaagtgggagcctagcagtgacgatcca
tggtggcaactatccaggggccctccgtcccgtcacactagtagcctacgaaagagtggcaacaggat
ccgtcgttacggtcgctggggtgagtaacttcgagctgattccaaatcctgaactagcaaagaacctg
gttacagaatacggccgatttgacccaggagccatgaactacacaaaattgatactgagtgagagggga
ccgtcttggcatcaagaccgtctggccaacaagggagtacactgattttcgtgagtacttcatggagg
tggccgacctcaactctcccctgaagattgcaggagcatttggcttcaaagacataatccgggctata
aggaggtagatccagacatgataagatacattgatgagtttgacaaaccacaactagaatgcagtga
aaaaaatgcttatttgtgaaatttgtgatgctattgcttatttgtaaccattataagctgcaataa
acaagttaacaacaacaattgcattcattttatgtttcaggttcaggggaggtgtgggaggttttt
cggatcctctagagtcgacggcagagtcgcagacgcccctattgacgtcaaaattgtagaggtgaag
ttttcaaacgatggcgaagtaacggcgacttgcgtttccaccgtcaaatctccctatagggtagaaac
taattggaaagtagacctcgtagatgtaatggatgaaatttctgggaacagtcccgccgggttttta
acagtaatgagaaatggcagaaacagctgtactacagagtaaccgatggaagaacatcggtccagcta
atgtgcctgtcgtgcacgagccattctccggaaccttactgtcttttcgacacgtctcttatagcgag
ggaaaagatatcgcgccagagttatacttacctctgatccgcaaacggcatactgcacaataactc
tgccgtccggcgttgttccgagattcgaatggagccttaataatgtttcactgccggaatatttgacg
gccacgaccgttgtttcgcataccgctggccaaagtacagtgtggaagagcagcgcgagagcaggcga
ggcgtggatttctggccggggaggcaatatatacgaatgcaccgtcctcatctcagacggcactcgcg
ttactacgcgaaaggagaggtgcttaacaaacacatggattgcggtggaaacggtgctgctcaggcg
cagctgtattcactcttttctggacttgtgtcaggattatgcgggagcatatctgctttgtacgcaac
gctatgaccgccatttattttttgaggaatgcttttttggactatcgtactgcttcttccttcgctag
ccagagcaccgccgccgtcacgtacgactacattttaggccgtcgcgcgctcgacgcgctaaccatac
cggcggttggcccgtataacagatacctcactagggtatcaagaggctgcgacgttgtcgagctcaac
ccgatttctaacgtggacgacatgatatcggcggccaaagaaaaagagaaggggggcccttttcgaggc
ctccgtcgtctggttctacgtgattaagggcgacgacggcgaggacaagtactgtccaatctatagaa
aagagtacagggaatgtggcgacgtacaactgctatctgaatgcgccgttcaatctgcacagatgtgg
gcagtggactatgttcctagcacccttgtatcgcgaaatggcgcgggactgactatattctcccccac
tgctgcgctctctggccaatacttgctgaccctgaaaatcgggagatttgcgcaaacagctctgtaa
ctctagaagttaacgatcgctgtttaaagatcgggtcgcagcttaacttttttaccgtcgaaatgctgg
acaacagaacagtatcagactggatttcaaggcgaacacctttatccgatcgcagacaccaatacacg
acacgcggacgacgtatatcggggatacgaagatattctgcagcgctggaataatttgctgaggaaaa
agaatcctagcgcgcccagaccctcgtccagatagcgtcccgcaagaaattcccgctgtaaccaagaaa
gcggaagggcgcaccccggacgcagaaagcagcgaaaagaaggcccctccagaagactcggaggacga
catgcaggcagaggcttctggagaaaatcctgccgccctccccgaagacgacgaagtccccgaggaca
ccgagcacgatgatccaaactcggatcctgactattacaatgacatgcccgccgtgatcccggtggag
gagactactaaaagttctaatgccgtctccatgcccatattcgcggcgttcgtagcctgcgcggtcgc
gctcgtggggctactggttggagcatcgtaaaatgcgcgcgtagctaatcgagcctagaataggtgg
tttcttcctacatgccacgcctcacgctcataatataaatcacatggaatagcataccaatgcctatt
cattgggacgttcgaaaagcatggcatcgctacttggaactctggctctccttgccgcgacgctcgca
cccttcggcgcgatgggaatcgtgatcactggaaatcacgtctccgccaggattgacgacgatccat
cgtgatcgtcgcgcctcgccccgaagctacaattcaactgcagctattttttcatgcctggccagagac
cccacaaaccctactcaggaaccgtccgcgtcgcgtttcggtctgatataacaaaccagtgctaccag
gaacttagcgaggagcgctttgaaaattgcactcatcgatcgtcttctgtttttgtcggctgtaaagt
gaccgagtacacgttctccgcctcgaacagactaaccggacctccacacccgtttaagctcactatac
gaaatcctcgtccgaacgacagcgggatgttctacgtaattgttcggctagacgacaccaaagaaccc
attgacgtcttcgcgatccaactatcggtgtatcaattcgcgaacaccgccgcgactcgcggactcta
ttccaaggcttcgtgtcgcaccttcggattacctaccgtccaacttgaggcctatctcaggaccgagg
aaagttggcgcaactggcaagcgtacgttgccacggaggccacgacgaccagcgccgaggcgacaacc
ccgacgcccgtcactgcaaccagcgcctccgaacttgaagcggaacgcttttacctttccctggctaga
aaatggcgtggatcattacgaaccgacaccccgcaaacgaaaattcaaacgttactgtccgtctcggga
caatgagccctacgctaattggggtaaccgtggctgccgtcgtgagcgcaacgatcggcctcgtcatt
gtaatttccatcgtcaccagaaacatgtgcaccccgcaccgaaaattagacacggtctcgcaagacga
cgaagaacgttcccaaactagaagggaatcgcgaaatttggacccatggttgcgtgcgaaataaaca
aggggggtgaccaggatagtgaacttgtgaactggttgcaactggttaacccgtctgcgctaagctcg
cccgactcaataaaaatgtgattaagtctgaatgtggctctccaatcattcgattctctaatctccc
aatcctctcaaaaggggcagtatcggacacggactgggaggggcgtacacgatagttatatggtacag
cagaggcctctgaacacttaggaggagaattcagccgggagagccctgttgagtaggcttgggagc
atattgcaggatgaacatgttagtgatagtctcgcctcttgtcttgcgcgcctaactttttgcgacgc
gacacgtcctcttttggaaggcactcaggctgtcctcggggaagatgatcccagaaacgttccggaa
gggactgtaatcaaatggacaaaagtcctgcggaacgcgtgcaagatgaaggcggccgatgtctgctc
ttcgcctaactattgctttcatgatttaatttacgacggaggaaagaaagactgcccgcccgcgggac
ccctgtctgcaaacctggtaattttactaaagcgcggcgaaagcttcccgggttaattaaggcccctcg
aggatacatccaaagaggttgagtattctctctacacttcttgttaaatggaaagtgcatttgcttgt
tcttacaatcggcccgagtctcgttcacagcgcctcgttcacacttaaaccacaaatagtctacaggc
```

```
tatatgggagccagactgaaactcacatatgactaatattcggggggtgttagtcacgtgtagcccatt
gtgtgcatataacgatgttggacgcgtccttattcgcggtgtacttgatactatggcagcgagcatgg
gatattcatcctcgtcatcgttaacatctctacgggttcagaatgtttggcatgtcgtcgatcctttg
cccatcgttgcaaattacaagtccgatcgccatgaccgcgataagcctgtaccatgtggcattagggt
gacatctcgatcatacattataagaccaacgtgcgagtcttccaaagacctgcacgccttcttcttcg
gattgtcaacgggttcttcagaatctatgcccatatctggcgttgagaccattgtgcgtttaatgaac
aataaagcggcatgccatgaaaggagggctgcagatctccattttctcacgccactatcctggacgc
tgtagacgataattataccatgaatatagagggggtatgtttccactgccactgtgatgataagtttt
ctccagattgttggatatctgcattttctgctgccgaacaaacttcatcgctatgcaaagagatgcgt
gtgtacacgcgccggtggagtatacgggaaactaaatgttcatagaggtctttgggctatatgttatt
aaataaaataattgaccagtgaacaatttgtttaatgttagtttattcaatgcattggttgcaaatat
tcattacttctccaatcccaggtcattctttagcgagatgatgttatgacattgctgtgaaaattact
acaggatatattttttaagatgcaggagtaacaatgtgcatagtaggcgtagttatcgcagacgtgcaa
cgcttcgcatttgagttaccgaagtgcccaacagtgctgcggttatggtttatgcgcacagaatccat
gcatgtcctaattgaaccatccgattttctcttttaatcgcgatcgatgtttgggcaactgcgttattt
cagatctaaaaaatttacccttttatgaccatcacatctctctggctcatacccgcttggataagata
tcatgtagattccgccctaagaaatgcaaactaacattattgtcggttccatatacacttccatcttg
tccttcgaaaataacaaactcgcgcaatagaccgtccgtacatgcatggccgatgtgtgtcaacatca
ttggtctgctagatcccgatgggacgaatcgtacagtcgtcgctccagcattggcaaaaatccccaga
taccctccatgcgggcaaatctaaattgcgaccccgaagagactgcaccaaagtcttatcgacgcacgc
tgatttttttgaacagcgggagcccattatcttcagtggagcgtagacgggcgaggctaattatgtga
catagcaacactgcatgtatgttttttataaatcaataagagtacataatttattacgtatcatttccg
tttgtaatatactgtatacatcatccacactattagtcagcatcagcgcgcgggcgcacgttacaata
gcagcgtgcccgttatctatattgtccgatatttacacataacatttcatcgacatgattaaatacct
aagtactgcacacagatgtttaatgtatatcgtcatataaatttatatcgctaggacagacccaaacga
cctttatcccaaacagtcagatcctcttctcaagtgtcgattttctgtttatggaatatgcataccctgg
cccagaaattgcacgcacgagcgtagtgaatgcgtcattggttttacattttaaaggctaaatgcacaa
attcttttagacgacagcacatcgttaaatagcatctctagcgttcttatgaatgctaagcattggagt
cctcctggtcggccacaataacagctgagtatcataccctgagctccgggggttgtcgcacatagcgga
ttcgtataaacataggattttccgcgaatccatcagttgcaaaaatctgttaggctccatcaacaacg
ctggatttacttcagatccacgcgtaaagtaatggtgctcgaataccgttttagagttgtcggcatt
tcaaggaacaaagaattcatttcttcattgcaacgacgcgccagaaatcccaagacctctttgggtag
tatgttcttgcctataaaacacggcgttccaagtgccaggaaccacgcatgtgttactgttggggcgt
attcagaaataaagcgggtttatgcggcttttgaagctcggatatccaaagtatcgcttgctgatga
acgagcgatgtagctgttacaaaacctccttccatcctccagtcaacataatatttatcggcctacc
tatgtccgtaataagtattggtcgggcaattattccgtatgaggtcttgcaggaataagctcttaggg
acagccagcttggatatggtgcgaaacagaccttctcggcttcagaatgtcgctccgcagtctcttcg
tgtcggtgcatcttagatccaccatcaatgtgtgcagcattgactcccgcccgtcgaatattcctttt
gttacgatgcagtaatgagcacgatcatgggcggggcgatgacgttctatttgcatgtctgcgaacaa
tttgcgtcagtcatacagctatggagtgggccatttctggccgtcaacttaaaaacgcgaaccgcaga
catatgtatttgcatgcaaagacgtatcttcgtatttctgggcatcttcaaatgctctggccaatatg
gcaatgaatttggattcgtttgacgccgatggtatgcagtgcaaatgtgccaatagcccacatccgaa
aaagttatttgtcatacaagcaggtgttaagtagcaatcaataaaggcaccagacgcctcatggcat
cataatgaatagctccttctccccactggaaccactgacaaaatctgcgagtatattccgcaaaccac
attttatttctcatagaaactaccctaaatccttttaacgggaagaagaatcctagatagtgcttgaa
gtcatgactgttactgctgcaataacactgtatattatttataaattccgtttgtctaggtatctgat
gtaggcattccgatcccttttactattgcgtcttcacgaccaaatgggaatgcgccaaaatccccacac
ctcatcaccctggaggcagattgtgtattattaatatccgccgattgaagcacaaaacggtacggtac
tgttcctaattctggtatagattctatggtcaaaagtctgcatatccccgacattgccatgagatcac
acagtccaagtagcatgtttattgagtcactcagactgtcaacgtccctcgccgcaccaccaatcgaa
aataaagtatctcacgcaagttatagctccgcattttctatcgctagcagcaatcgcgacgcaaacat
aaaggccatgttgggatttgaactctctgggggggcttgttatcttctgcaccgtcgcagtcgcagttt
tccgaaatttatgtctaatatattttccggccgtgctccaatcggccgaaaagaatctgcgtattacc
agactcattgacgggccgataaagaccataaaacaaaattcctgtgcactccctcctccagttttgcc
atcgtccaagtcccgtaactttttttgcgtttcgaggagcaagcgttcgttatccctacccacacttg
ttttccaccgttttcttattataagcggttgtatcgccaacgcgtcaccgcaggttgtcacatacagt
gatggcatacttgaacgtgcaacaacgcgctcgctttgcaaatctaagtcattgaccatcaaatcgcg
ttgagaggatagccaggcatctttttttcctagtatggtgacggtgcagccaccccaactcagttcttg
taaaaaaagctattggcgggaatttatgttctgaggtgcattctatatttatgagtccatcaaatgcc
attaaccagattcgtatttttttcgctcgacccggcatcactatggatacaataccttttctatggcca
tttcagctctcgaaccaaccacacggacaattgactaacataagtatgatctttatcacagtcgcacc
catctgagttatatttatggcatccgagcgctcttactgtacggtcggatacacccatggtttttcct
ttatatagtcgggttatagtctgtcgggtttggcggtagcacggagtagtttgattttttaagaatcga
aaaccggcttggagagaccacctgcgaatatttgtccgtatactctacacgtgagtgttgtccacttcc
taggtatattcatctgttcggataccttcaattgctgttcaggcataaccttaaagcatatgttatgt
tgtacatcaaaacttggtgagttatgttcgattgccgcgcataaagaatcgtacatgagcgtttctgc
taacatactatctatattctcacacgcccctgcatatactgttcctattccaaattcacgttttgccc
catccggctatctgctcccaaaaagttgtaaatataggtgccgctgggtgcgaaattttcatcagttgta
ttcctgataaactgaatcactttacataatttttgccacatatctggcgtgcagccatagtatcgaacc
cgtgggctcggagacgacagtgcgtacaatgggtatttttaccttttcccaacaaaataatggtataca
agttaggtccgtacctagaccttaatgttttccaattcttctgaatcactgcactctcgtaggggagta
acggtaataatttcgtctctgagcccgttttgcgttgaaaactaatcacattagataatgtgcaatc
ggtttcttttatccggatacatctaagtattatgacatcggtggtcattgtttccatcaacgaccatc
ttttacgatcgccatactactcatggacgttgtcggtgttgaaaaatcaccagaattgcaacggatc
tctgggtaccatgctgctgatggaattggcggttttaattgttgtttcagtctattattgctatcttt
ggcggggttgaataatgtgggggggagagtgattgcaggaatccgaatgggtcaataaaacgaccgtgc
tccgttctgccggcgccgatccgattgaagctatatacttcgcttctctccccacttttccaatttga
tccggaaataaaacggcccggacaacagtatcgtacgatccggatccggatcctgcttgcctacaga
agaatcaacatctcgccccaatattctggtcaaaactggctcgctcatggcaacgcggacgtttcccc
```

```
cggtggccagtctaatggttaatgttcttttcggcaatcttatacatcagcggttgcgtgaatact
ggtcacagttcagtcatttactacacaccagcaatacgacgacggacagtaccgtcccgacgaacgcg
acgcccaaaattgctatcgcgaccgcgtccgaggcgatgtcgtacgggcggtgcggggttggatcctc
ggcaaagagatcctcgtaattcggcgtgggagcggagggtaaagacgcgggtggggatctccctccg
gaccgcgcgccgggcgcggttcgaaaatgcttccgcctcgtcagtgtcaacgccaagtattcggcg
gggctgggggccggaatatctcccgcgacttcttctatcggcgcggaattggagtcgcggtcgtggcg
cgcttctagcgtcgtcaacggaagtccattttcggggtctcccggtgggcgttcagcgtccatcgtcg
tatatgctctaacacacgtctcgctatattaaaaaaaagaagagtatcggtcagtgtcgagtgtcgcc
gacaatgtcgcgagttctcggcgatttaattttttggaactgctccctatgaatcccgtaactgtagcg
cccgcgcagaaagccgccatcagaccaactacgtgtctgttcgatgtttgcccgccgatcgctttacc
gattaaggttccggcgagaaatgacatgctcgatccaagaacaaagtttttcgcggtaaacaacaaca
tagttaccgtgcgagatggagaaaccacatctcccgaattagtagaggaaagcccgcgctgtcggttt
ggggacatatcgatctttttgtgtttttcctaggacccttttgccagatcgtacaaagtcgcgtctt
atgagcggacgttcttactgcagctcggtaggagtggggcagggttagatttcgtcggcgtttcggcc
cccgtatgcgccgcgccaccctcttcgccgagctcttatgcgcggtgggggtgagcgcttccggagt
tgcgatctccgatctcgagccgcagccggcggtgtctctttcagtggagcgttagcgccatcatgtg
gttcgtggcggtggaaaggctattatgtgttaggggagagaccacgtgatcggcatgcaaatgagcaa
ggcgaacgcgtcagcgttcgcactgcgaaccaataatatatatattatactattggcttaggtgcga
acgtccggctagtccaatagcggggtcgcgtttcgtaccacgtgttatagaccgccctaaactcgcac
tcggggggtccggccgcgcccagacagggcggagacgtgccacaggggctttaaaacaccgcttcgggc
accgttcatctcggcgcgcc
```

SEQ ID NO 22: 1322-48.1 hCMV IEpro-F-IE(term)/HVT US2 region (12,692 bp)
(HVT/IBDV/ILTV/NDV 670-14 Virus)

```
ctcgcgcgtttcggtgatgacggtgaaaacctctgacacatgcagctcccggagacggtcacagcttg
tctgtaagcggatgccgggagcagacaagcccgtcagggcgcgtcagggtcgcgtgcgggggtgtcggg
gctggcttaactatgcggcatcagagcagattgtactgagagtgcaccatatcgacgctctcccttat
gcgactcctgcattaggaagcagcccagtagtaggttgaggccgttgagcaccgccgccgcaaggaat
ggtgcatgcaaggagatggcgcccaacagtcccccggccacggggcctgccaccatacccacgccgaa
acaagcgctcatgagcccgaagtggcgagcccgatcttcccatccggtgatgtcggcgatataggcgc
cagcaaccgcacctgtggcgccggtgatgccggccacgatgcgtccggcgtagaggatctggctagcg
atgaccctgctgattggttcgctgaccattccggggtgcggaacggcgttaccagaaactcagaagg
ttcgtccaaccaaaccgactctgacggcagtttacgagagagatgatagggtctgcttcagtaagcca
gatgctacacaattaggcttgtacatattgtcgttagaacgcggctacaattaatacataaccttatg
tatcatacacatacgatttaggtgacactatagaatacaagctagcttgggctgcaggtcgactctag
aggatcgttaattaacgatccccgggcgagctcgaattccagactaaatgccccggcccaatttgtca
agtgtgcagtcacggaggcgtcgaccgtgtccccggcattaaacaggaaagcgttaaagttttttgaat
gttaggtcacaggtacaaacataaatgtttgtacaaacaggtaacaggtacaaacataaatgccccgg
cataaatgtcccttacggcggatcgaaacgacattaggcatactcgggtaccatttttgcattccgatc
agcacggatgaaattaggcaggaatgcggtttatattatgcggcattggacaaacgatatggcattga
ttggcagtttatgaatgtcttcatgttgggcgtaaacggattcctattggttcagaagacaacgacga
tatatttagagagaaaaagctacccagcataggataaacacacattgagcattgagagacataggtat
cggtatggatgggaaaactacacacgtgaacaccaaacgacttatactcgagcggtgatactactg
agcaagaatgcactgcatctgagccactgaatgaagactgtgatgaaaatgtgaccatcgatggaatt
ggagaagaatatgcgcagttcttcatgtccccgcaatgggtcccaaatctacatcgcttgagcgagga
taccaaaaaggtataccgatgtatggtttccaacagactcaattattttccctattatgaggcgttca
ggcggtctttgtttgatatgtatatgctaggtcggttggggcgtcgacttaagcgatctgactgggag
actattatgcatctgtcaccaacgcaaagtcggcgtctacatagaacttttaagatttgtggagcgtag
aattatcccatctaacagttatatacgcacatcgggccacgttccgccttcgagggcacttccgacag
atacgaatttaaagatggatgaataattaaattggaaagagtaactacattaatcgagcgtcatgacg
gcgtcccgtgaaaatgggaattttctactcgaaacaccgtgacattttgacagacctggaatttgttatt
ctgatatatagtgggtgtgtctggccggcaacatacataatgtgcatgcgaaaccactttttcagtgt
acgctgacattgtgcaacacggaggggtagcatctacatacaatatatgttgattaatgattggagaa
aaaactatgcagctcgccgatcatatggctaactcgccttcgtctatatggcggaccccgcgggaaaa
atcgacgtaccatctgatttacaacaccagtaatgaacatgtcgcatccctgcccagatctgtgcgcc
cattgcgcgggatcgttgtgaatgccgccgaaacacttcaggtcggtatgagagcgggaggccgcca
tcagcaggagtttggcgagaggtgtttgataagaatgatgacagccttccgtgaccacgagcctactgc
gacatttaatgctgcaaatcccattagaaaatggtcgagacagttctacagaataatgaagagcccc
cgcggaccgcatgctgaaatgggtaatcgccttatgaacattatgtactggtgttgcttgggacacga
ggacaatgctcgatatggcagttgtacgagacgaatcaggccattttaagtttattagatgaagtggt
tatcggcacaacaaatccctttttgcaccctcgagcaatactggaagccattatgcaccgcaatcgcca
acaaggggacctcatcgcttgttgaggatgccaaagtggccgagtacctggttagcatgcgcaaattg
atataacataggcacgctctgatgttacagaccacaataccgcatacattttattgtaaggttgttaat
aaaggtttattctatgtaagactacaatacttttcgacattgcttgtatacatattaaatactttctca
agttcctattacataaaatgggatctatcattacattcgttaagagtctggataattttactgtttgc
cagcttcgatcttggaacgtactgtggatagtgccttacttggaatcgtgaaaatttgaaacgtccat
tatttggatatcttccggttgtcccatatcccgccctggtaccgctcggataccttgcccgtatggat
tcgtattgacagtcgcgcaatcgggaccaacaacgcgtgggtccacactcattcggaaattttccga
tgattctgaatatttattgccgctcgttacgagtcgttggacatatctgaatacatttcttcttctg
aaggatcgctgcacatttgatctatacattggccaggatgttcaagtctcagatgttgcattctggca
cagcacaactttatggcatttccgatgtaatcgtccggcagcctggggggagttctatattcgcatat
tgggatggtaaggacaatagcagatctcgcaacctccagggaggctataataacgttttaaaggatg
gatttctcataaaaatctgtcgcaaattacactgagaatatccttttactagcgccgattgagacatc
gtcgtccaattttctaaatggaaagaaaaacaaggcgggcaaagagtgttccaaacattttcattttcgg
cgaatctctcaaatcccatggcgtgcaattgattgcaaaattggcacttccgttcacgtttgtatctc
caaactctaagacacttttaattgaaaaactacgttctagtgtgaaagaaacctataggcagaccat
agaactatttgacaccacatatctttttgtatgtcaaactgaccatgatcgtatgttgctgaatgcac
tagggcaattcgctcgcgcgactccatacattgaataattccacacgtcagctcatcggttagcaagg
tccagtagttgaagtcatttattttttccccgcggctggccaaatctacctctgggaatatccaagttg
```

-continued

```
tcgaatatgatcgcaccggctctggtcatggtgaaggaactgtagcataaagacgcaggtatcatagg
ggtaatatttttttattcactcacatactaaaagtaacgcatattagcaccatgtatgggctatcaat
tgacatttgcgtagcactacatcacgattatgtacaacataatgggacaacatatggcaagtagatgc
aatttcctcacactagtttgggtttatctactattgaatttccccctatctgtgatacacttgggagcc
tctacaagcatattgccatcatgtacgtttttatctactgtcttaacgcccatggggaacggaggcgtc
gtcgtcatgtattggacggcaacataggcagcaacacaaattgcgtttaggtggggtgcatgtggact
cgataccaagcccctgcagctggggaacgtctggtggagagccgataatttgatatacgcacgccata
ttactgtcgttgaagtacgccttatcttctatgttttcaaatttaggttcccaagtggacgtgagaag
tgtttgtatctcacatggaatggcccaaggcattccagcccaggtgcctggtactttaatggcaaaca
aacgtatttggtagaggtattgattctattgcagttctgcagatatctgcagccccgagtatccacagg
ctatacgatacgttatcggaggcaagcttcgcgccaggtcaattccctggcattatgcccagtacatg
accttatgggactttcctacttggcagtacatctacgtattagtcatcgctattaccatggtgatgcg
gttttggcagtacatcaatgggcgtggatagcggtttgactcacggggatttccaagtctccacccca
ttgacgtcaatgggagtttgttttggcaccaaaatcaacgggacttttccaaaatgtcgtaacaactcc
gccccattgacgcaaatgggcggtagcgtgtacggtggaggtctatataagcagagctcgtttagtg
aaccgtcagatcgcctggagacgccatccacgctgttttgacctccatagaagacaccggttgcgccg
ccaccatgggccccagaccttctaccaagaacccagtacctatgatgctgactgtccgagtcgcgctg
gtactgagttgcatctgtccggcaaactccattgatggcaggcctcttgcggctgcaggaattgtggt
tacaggagacaaagccgtcaacatatacacctcatcccagacaggatcaatcatagttaagctcctcc
cgaatctgcccaaggataaggaggcatgtgcgaaagccccccttggatgcatacaacaggacattgacc
actttgctcaccccccttggtgactctatccgtaggatacaagagtctgtgactacatctggagggggg
gagacaggggcgccttataggcgccattattggcggtgtggctcttggggttgcaactgccgcacaaa
taacagcggccgcagctctgatacaagccaaacaaaatgctgccaacatcctccgacttaaagagagc
attgccgcaaccaatgaggctgtgcatgaggtcactgacggattatcgcaactagcagtggcagttgg
gaagatgcagcagtttgttaatgaccaatttaataaaacagctcaggaattagactgcatcaaaattg
cacagcaagttggtgtagagctcaacctgtacctaaccgaactgctacagtattcggaccacaaatc
acttcacctgctttaaacaagctgactattcaggcactttacaatctagctggtggaaatatggatta
cttattgactaagttaggtgtagggaacaatcaactcagtcattaatcggtagcggcttaatcaccg
gtaaccctattctatacgactcacagactcaactcttgggtatacaggtaactctaccttcagtcggg
aagctaaataatatgcgtgccacctacttggaaaccttatccgtaagcacaaccaggggatttgcctc
ggcacttgtcccaaaagtggtgacacaggtcggttctgtgatagaagaacttgacacctcatactgta
tagaaactgacttacatttatattgtacaagaatagtaacgttccctatgtccctggtatttattcc
tgcttgagcggcaatacgtcggcctgtatgtactcaaagaccgaaggcgcacttactacaccatacat
gactatcaaaggttcagtcatcgccaactgcaagatgacaacgtgatgtgtaaaccccccgggta
tcatatcgcaaaactatggagaagccgtgtctctaatagataaacaatcatgcaatgtttttatcctta
ggcgggataaacttaaggctcagtggggaattcgatgtaacttatcagaagaatatctcaatacaaga
ttctcaagtaataataacaggcaatcttgatatctcaactgagcttgggaatgtcaacaactcgatca
gtaatgctttgaataagttagaggaaagcaacagaaaactagacaaagtcaatgtcaaactgactagc
acatctgctctcattacctatatcgtgttgactatcatatctcttgttttttggtatacttagcctgat
tctagcatgctacctaatgtacaagcaaaaggcgcaacaaaagaccttattatggctgggaataata
ctctagatcagatgagagccactacaaaaatgtgaggatctctcgaggaattctagatcccacgtcac
tattgtatactctatattatactctatgttatactctgtaatcctactcaataaacgtgtcacgcctg
tgaaaccgtactaagtctcccgtgtcttcttatccaccatcaggtgacatcctcgcccaggctgtcaat
catgccggtatcgattccagtagcaccggccccacgctgacaaccccactcttgcagcgttagcagcgc
ccctcttaacaagccgaccccccaccagcgtcgcggttactaacactcctctccccgacctgcaactag
taagcttgcctccgattctagcattacatagccggtcagtagatcctgccattcggtagcgcaaccgg
ctacatcttcaaacagtctcacaataaatgcatctctcgttcctgccaatccggaaccgggcataccca
ctcccgcctgccgatttaattctcacaattgggcgatgccggcggggcaaaacgaatgtggatttggc
aaaccgacacaggtctgctgtacggactaatatgggcacaccccatcattcttcagatgctccatgc
attgttctatgagaaagatccatagggtggaggcagcgtcacgagatcgcccaggcaatcgatcgcat
tcgtctagtaaagtgacgagagttatcatgcacacaccccatgccacgccttccgaataactggagct
gtggaagatcggaaacgtcttttttgactgccggtctcgtactactttcgcacaggtgtatacccggac
gcgtactatatattttatatcatccaacgtccgaaattacatacgtggcggcgatggaagtagatgtt
gagtcttcgaaagtaagtgcctcgaatatgggtattgtctgtgaaaatatcgaaagcggtacgacggt
tgcagaaccgtcgatgtcgccagatactagtaacaatagcttcgataacgaagacttccgtgggcctg
aatacgatgtggagataaataccagaaaatctgctaatcttgatcgtatggaatcttcgtgccgtgaa
caacgagcggcgtgcgaacttcgaaagtgttcgtgtcctacgtctgccgtgcgcatgcaatacagtat
tctttcatctctcgctccgggttcagagggtcatgtatatatgtactagatacggggacgcggacc
aaaaaaaatgcatagtgaaggcagtcgttggaggaaagaatcccgggagggaagtggatattttaaaa
accatctcacataaatcaattataaaattaatccatgcctataaatggaaaaatgttgtgtgtatggc
aatgcgtgtatatcgttatgatcttttcacatatattgacggagtcggccctatgcccttcaacaga
tgatctatattcaacgtggactactagaggcgctagcatacatacatgaaaggggcatcattcaccga
gacgtaaagacggagaatatattcttggataatcacgaaaatgcagttttgggtgacttcggtgctgc
atgccaactaggagattgtatagatacgccccaatgttacggttgacatcgtgggaactgtggaaacaaatt
cgccggaattatctgcacttgatccgtattgcacaaaaacagatatttggagtgccggattggttcta
tatgagatggcaattaaaaatgtaccattgtttagtaagcaggtgaaaagttcgggatctcagctgag
atccataatacggtgcatgcaagtgcatgaactggagtttccccgcaacgattctaccaacctctgta
aacatttcaaacaatatgcggttcgttgtacgaccgccttataccattcctcgagttataagaaatggg
gggatgccaatgatgttgaatatgtcatttctaaaatgcttacgtttgaccaggagttcagaccttc
tgctaaggaaatattgaatatgcccctatttactaaggcgccgattaacctgcttaatatcacaccct
ctgacagtgtctaacggtatacaggcgggagcgggtcgtggcgtcatcatcaccacttgagaatttat
attttgaattgttgattgataaattaacctgattcattgagaactgaaacgccatattggttcttgg
atatgtctacaacaattagttaaattgctatgttctactgcgagtaacatttgataagttgtaagaga
cgggcgactcatgtcgaagttgacgaataaaagtacaacgtgtttagaatacccagaatccgaat
agtccgcggggggcgtcttctcgcgtgagtaccaaatactgagttgaacttgaaaatgctaaatctgtg
acactctttgtgtgatgattattgtcaccacttcgaagatggcttcgacattcatgatgttctggtgt
ttgtttggaatcgtaatagcgcttgtttcgtccaagtctgacaacaaagaaaatctgaagaattatat
cacggataagtcaaccaatattagaatacccacgccatttttgtatcaacggaaaactcttatccca
caaaacatgtaatctacgatgaaaactgtggcttcgctgtactcaatcctataagtgaccccaaatat
```

```
gtccttttgagccagcttctaatgggaaggcgcaaatatgatgcgacggtcgcgtggtttgttctcgg
taaaatgtgtgccagattaatatatttgcgcgaattttataactgctcgacaaatgagccttttggca
catgttctatgagctctcctggatggtgggacaggcgctacgtctcaaccagtttcatttctcgcgac
gaattacagctggttttgcagcgccgtcccgagaattagatggtttatatacgcgcgtagtagttgt
caacggggacttactacggccgatataatgctttaatgttaaagtggcatgtgccttttcaaagactg
gaatagaagatgatacattatgcaaacccttcattctttgccaatgcaacattgcacaatttaacc
atgattagatcggtaactcttcgagcgcacgaaagccatttaaaggaatgggtggcacggagaggtgg
taacgtccctgcagtgctacttgagtctaccatgtatcatgcatccaatctgcctagaaatttcaggg
atttctacataaagtctccagatgattataagtataatcacctagatgggccatctgtaatgctcatc
actgacagacctagtgaagatttggatgggaggctcgttcaccaaagtgacattttactactacaag
tcctataaaacaggtccggtatgaagagcatcagtcacatacaaagcagtatcctgtaaacaaaatac
aagctataatttttttgatagggttaggctcgttcattggaagcatattcgtagttttggtagtatgg
attatacgcagatattgcaatggagcgcggagtggggaacgccccccagtcctcgccggtatgtgta
taccaggctatgatcacgtgtgaaacttgggcggacctgtatcatatgtacaccgtccctattcgttt
atagccagtacgtgttatctgcacatagaggaacatgtgtcatactgggatcgcatgcatggtatgtg
tgactctaatattattctgtatcataataaaaacacagtgcatggtatatagaggatcgctggtaagc
actacggtagaccaatcggctcagattgcattctttggcatcgataccgttgttaatttatatggcaa
agtcttgttcatgggagatcagtatttggaggaaatactactctggaacgatggaaatactcaaatgga
atcaagctaaccgctgctattctattgcgcatgcaacatattacgccgactgtcctataatcagttct
acggtattcagaggatgccgggacgccgttgtttatactaggccccacagcagaattcgtaatcatgg
tcatagctgtttcctgtgtgaaattgttatccgctcacaattccacacaacatacgagccggaagcat
aaagtgtaaagcctggggtgcctaatgagtgagctaactcacattaattgcgttgcgtcactgcccg
ctttccagtcgggaaacctgtcgtgccagctgcattaatgaatcggccaacgcgcggggagaggcggt
ttgcgtattgggcgctcttccgcttcctcgctcactgactcgctgcgctcggtcgttcggctgcggcg
agcggtatcagctcactcaaaggcggtaatacggttatccacagaatcaggggataacgcaggaaaga
acatgtgagcaaaaggccagcaaaaggccaggaaccgtaaaaaggccgcgttgctggcgtttttccat
aggctccgcccccctgacgagcatcacaaaaatcgacgctcaagtcagaggtggcgaaacccgacagg
actataaagataccaggcgtttccccctggaagctccctcgtgcgctctcctgttccgaccctgccgc
ttaccggatacctgtccgcctttctcccttcgggaagcgtggcgctttctcaatgctcacgctgtagg
tatctcagttcggtgtaggtcgttcgctccaagctgggctgtgcacgaaccccccgttcagcccga
ccgctgcgccttatccggtaactatcgtcttgagtccaacccggtaagacacgacttatcgccactgg
cagcagccactggtaacaggattagcagagcgaggtatgtaggcggtgctacagagttcttgaagtgg
tggcctaactacggctacactagaaggacagtatttggtatctgcgctctgctgaagccagttacctt
cggaaaaagagttggtagctcttgatccggcaaacaaaccaccgctggtagcggtggtttttttgttt
gcaagcagcagattacgcgcagaaaaaaaggatctcaagaagatcctttgatcttttctacggggtct
gacgctcagtggaacgaaaactcacgttaagggattttggtcatgagattatcaaaaaggatcttcac
ctagatcctttaaattaaaaatgaagttttaaatcaatctaaagtatatatgagtaaacttggtctg
acagttaccaatgcttaatcagtgaggcacctatctcagcgatctgtctatttcgttcatccatagtt
gcctgactccccgtcgtgtagataactacgatacgggagggcttaccatctggccccagtgctgcaat
gataccgcgagacccacgctcaccggctccagatttatcagcaataaaccagccagccggaagggccg
agcgcagaagtggtcctgcaactttatccgcctccatccagtctattaattgttgccgggaagctaga
gtaagtagttcgccagttaatagtttgcgcaacgttgttgccattgctacaggcatcgtggtgtcacg
ctcgtcgtttggtatggcttcattcagctccggttcccaacgatcaaggcgagttacatgatccccca
tgttgtgcaaaaaagcggttagctccttcggtcctccgatcgttgtcagaagtaagttggccgcagtg
ttatcactcatggttatggcagcactgcataattctcttactgtcatgccatccgtaagatgcttttc
tgtgactggtgagtactcaaccaagtcattctgagaatagtgtatgcggcgaccgagttgctcttgcc
cggcgtcaatacgggataataccgcgccacatagcagaactttaaaagtgctcatcattggaaaacgt
tcttcggggcgaaaactctcaaggatcttaccgctgttgagatccagttcgatgtaacccactcgtgc
acccaactgatcttcagcatcttttactttcaccagcgtttctgggtgagcaaaaacaggaaggcaaa
atgccgcaaaaaagggaataagggcgacacggaaatgttgaatactcatactcttcctttttcaatat
tattgaagcatttatcaggttattgtctcatgagcggatacatatttgaatgtatttagaaaaataa
acaaataggggttccgcgcacatttccccgaaaagtgccacctgacgtctaagaaaccattattatca
tgacattaacctataaaaataggcgtatcacgaggccctttcgt
```

SEQ ID NO 23: 228509-ILT-435Vec6 (mCMV IEpro-VP2-SV40pA/ILTV/HVT US2 region)
(14113 bp) (HVT/IBDV/ILTV/NDV #2 Virus)

```
gaattccagactaaatgccccggcccaatttgtcaagtgtgcagtcacgcggaggcgtcgaccgtgtccc
cggcattaaacaggaaagcgttaaagttttgaatgttaggtcacaggtacaaacataaatgttgta
caaacaggtaacaggtacaaacataaatgccccggctaaatgtcccttacggcggatcgaaacgaca
ttaggcatactcgggtaccattttgcattccgatcagcacggatgaaattaggcaggaatgcggttta
tattatgcggcattggacaaacgatatggcattgattggcagtttatgaatgtcttcatgttgggcgt
aaacggattcctattggttcagaagacaacgacgatatattagagagaaaaagctacccagcatagg
ataaacacacattgagcattgagagacataggtatcggtatggatgggaaaactacacacgtgaacac
caaacgacttatatactcgagcggtgatactactgagcaagaatgacgtctgagccactgaatg
aagactgtgatgaaaatgtgaccatcgatggaattggagaagaatatgcgcagttcttcatgtccccg
caatgggtcccaaatctacatcgcttgagcgaggataccaaaaaggtataccgatgtatggtttccaa
cagactcaattatttcctattatgaggcgttcaggcggtcttgtttgatatgtatatgctaggtc
ggttggggcgtcgacttaagcgatctgactgggagactattatgcatctgttgccacaacgcaaagtcgg
cgtctacatagaactttaagatttgtggagcgtgaattatcccatctaacagttattatacgcacatc
gggccacgttccgccttcgagggcacttccgacagatacgaatttaaagatggataataattaaatt
ggaaagagtaactacattaatcgagcgtcatgacggcgtcccgtgaaaatgggaattttctactcgaa
acaccgtgacatttgacagacctggaattgttattctgatatatagtgggtgtgtctggccggcaaca
tacataatgtgcatgcgaaaccactttttcagtgtacgctgacattgtgcaacacggagggttagcat
ctacatacaatatatgttgattaatgattggagaaaaaactatgcagctcgccgatcatatggctaac
tcgccttcgtctatatggcggaccccgcgggaaaaatcgacgtaccatctgatttacaacaccagtaa
tgaacatgtcgcatccctgcccagatctgtgcgcccattggcgcggatcgttgtgaatgccgccgaaa
cacttcaggtcggtatgagagccgggaggccgccatcagcaggagttggcgagaggtgtttgataga
atgatgacagccttccgtgaccacgagcctactgcgacatttaatgctgcaaatcccattagaaaaat
ggtcgagacagttctacagaataatgaagagccccgcggacgcatgctgaaatgggtaatcgcctta
```

```
tgaacattatgtactggtgttgcttgggacacgcaggacaatgctcgatatggcagttgtacgagacg
aatcaggccattttaagtttattagatgaagtggttatcggcacaacaaatcccttttgcaccctcga
gcaatactggaagccattatgcaccgcaatcgccaacaaggggacctcatcgcttgttgaggatgcca
aagtggccgagtacctggttagcatgcgcaaattgatataacataggcacgctctgatgttacagacc
acaataccgcatacatttattgtaaggttgttaataaaggtttattctatgtaagactacaatacttt
cgacattgcttgtatacatattaaatactttctcaagttcctattacataaaatgggatctatcatta
cattcgttaagagtctggataattttactgtttgccagcttcgatcttggaacgtactgtggatagtg
ccttacttggaatcgtgaaaatttgaaacgtccattatttggatatcttccggttgtcccatatcccg
ccctggtaccgctcggataccttgcccgtatggattcgtattgacagtcgcgcaatcggggaccaaca
acgcgtgggtccacactcattcggaaattttccgatgattctgaatatttattgccgctcgttacgag
tcgttggacatatctgtaatacatttcttcttctgaaggatcgctgcacatttgatctatacattggc
caggatgttcaagtctcagatgttgcattctggcacagcacaactttatggcatttccgatgtaatcg
tccggcagccctgggggagttctatattcgcatattgggatggtaaggacaatagcagatctcgcaac
ctccagggaggctataataacgttttaaaggatggatttctcataaaaatctgtcgcaaattacact
gagaatatcctttactagcgccgattgagagcatcgtcgtccaattttctaaatggaaagaaaacaag
gcgggcaagagtgttccaaacattttcattttcggcgaatctctcaaatcccatggcgtgcaattgat
tgcaaaattggcacttccgttcacgtttgtatctccaaactctaagacacttttaattgaaaaactac
gttctagtgtggaaagaaacctataggcagaccatagaactattttgacaccacatatcttttttgtatg
tcaaactgaccatgatcgtatgttgctgaatgcactagggcaattcgctcgcgcgactcctacattg
aataattccacacgtcagctcatcggttagcaaggtccagtagttgaagtcatttattttttccccgcg
gctggccaaatctacctctgggaatatccaagttgtcgaatatgatcgcaccggctctggtcatggtg
aaggaactgtagcataaagacgcaggtcatagggtaatattttttactcactcacatactaaaa
gtaacgcatattagcaccatgtatgggctatcaattgacatttgcgtagcactacatcacgattatgt
acaacataatgggacaacatatggcaagtagatgcaatttcctcacactagttgggtttatctactat
tgaattttcccctatctgtgatacacttgggagcctctacaagcatattgccatcatgtacgttttta
tctactgtcttaacgcccatggaacggaggcgtcgtcgtcatgtattggacggcaacataggcagca
acacaaattgcgtttaggtggggtgcatgtggactcgataccaagcccctgcagctggggaacgtctg
gtggagagccgataatttgatatacgcacgccatattactgtcgttgaagtacgccttatcttctatg
ttttcaaatttaggttcccaagtggacgtgagaagtgtttgtatctcacatggaatggcccaaggcat
tccagcccaggtgcctggtacttaatggcaaacaaacgttttggtagaggtattgattctattgcag
ttctgcagatatctgcagccccgagtatccacaggctatacgatacgtttatcggaggcaagctgcggc
cgctctagaactagtggatcccccgggctgcagcccaatgtggaattcgcccttgcacattgttactc
ctgcatcttaaaaatatatcctgtagtaattttcacagcaatgtcataacatcatctcgctaaagaat
gacctgggattggagaagtaatgaatatttgcaaccaatgcattgaataaactaacattaaacgaatt
cactagtggatcccccaactccgcccgttttatgactagaaccaatagttttaatgccaaatgcact
gaaatcccctaatttgcaaagccaaacgcccctatgtgagtaatacgggggactttttacccaatttc
ccacgcggaaagccccctaatacactcatatggcatatgaatcagcacggtcatgcactctaatggcg
gcccatagggactttccacatagggggcgttcaccatttcccagcatagggggtgactcaatggcc
tttacccaagtacattgggtcaatgggaggtaagccaatgggttttttcccattactggcaagcacact
gagtcaaatgggactttccactgggttttgcccaagtacattgggtcaatgggaggtgagccaatggg
aaaaacccattgctgccaagtacactgactcaataggggactttccaatgggttttttccattgttggca
agcatataaggtcaatgtgggtgagtcaataggggactttccattgtattctgcccagtacataaggtc
aataggggtgaatcaacaggaaagtcccattggagccaagtacactgcgtcaataggggactttccat
tgggttttgcccagtacataaggtcaataggggatgagtcaatgggaaaaacccattggagccaagta
cactgactcaataggggactttccattgggttttgcccagtacataaggtcaataggggtgagtcaac
aggaaagttccattggagccaagtacattgagtcaataggggactttccaatgggttttgcccagtaca
taaggtcaatgggaggtaagccaatgggttttttcccatgcacgtatactgagtcattagggac
tttccaatgggttttgcccagtacataaggtcaataggggtgaatcaacaggaaagtcccattggagc
caagtacactgagtcaataggggactttccattgggttttgcccagtacaaaaggtcaataggggtga
gtcaatgggttttttccattattggcacgtacataaggtcaataggggtgagtcattgggttttttcca
gccaatttaattaaaacgcatgtactttcccaccattgacgtcaatgggctattgaaactaatgcaa
cgtgacctttaaacggtactttcccatagctgattaatgggaaagtaccgttctcgagccaatacacg
tcaatgggaagtgaaagggcagccaaaacgtaacaccgcccggttttccctggaaattccatattg
gcacgcattctattggctgagctgcgttctacgtgggtataagaggcgcgaccagcgtcggtaccgtc
gcagtcttcggtctgaccaccgtagaacgcagagctcctcgctgcaggcggccgctctagaactcgtc
gatcgcagcgatgacaaacctgcaagatcaaacccaacagattgttccgttcatacggagccttctga
tgccaacaaccggaccggcgtccattccggacgacacccctggagaagcacactctcaggtcagagacc
tcgacctacaatttgactgtggggacacagggtcagggctaattgtcttttttccctggattccctgg
ctcaattgtgggtgctcactacacactgcagagcaatgggaactacaagttcgatcagatgctcctga
ctgcccagaacctaccggccagctacaactactgcagactagtgagtcggagtctcacagtgaggtca
agcacactccctggtggcgtttatgcactaaacggcaccataaacgccgtgaccttccaaggaagcct
gagtgaactgacagatgttagctacaatgggttgatgtctgcaacagccaacatcaacgacaaaattg
ggaatgtcctggtaggggaaggggtcactgtcctcagcctacccacatcatatgatcttgggtatgtg
aggcttggtgacccccattcccgctataggcttgacccaaaaatggtagctacatgcgacagcagtga
caggcccagagtctacaccataactgcagccgatgattaccaattctcatcacagtaccaaccaggtg
gggtaacaatcacactgttctcagccaacattgatgctatcacaagcctcagcattgggggagagctc
gtgtttcaaacaagcgtccaaggccttgtactgggcgccaccatctacctttataggctttgatgggac
tgcggtaatcaccagagctgtggccgcagataatgggctgacggccggcaccgacaatcttatgccat
tcaatcttgtcattccaaccaatgagataacccagccaatcaatccatcaaactccattggagatagtgacc
tccaaaagtggtggtcaggcagggggatcagatgtcatggtcggcaagtgggagcctagcagtgacgat
ccatggtggcaactatccaggggccctccgtcccgtcacactagtagcctacgaaagagtggcaacag
gatccgtcgttacggtcgctggggtgagtaacttcgagctgattccaaatcctgaactagcaaagaac
ctggttacagaatacgccgatttgacccaggagccatgaactacacaaaattgatactgagtgagag
ggaccgtcttggcatcaagaccgtctggccaacaagggagtacactgattttcgtgagtacttcatgg
aggtggccgacctcaactctcccctgaagattgcaggagcatttggcttcaaagacataatccgggct
ataaggaggtaagcttcagacatgataagatacattgatgagtttggacaaaccacaactagaatgca
gtgaaaaaatgctttatttgtgaaatttgtgatgctattgctttatttgtaaccattataagctgca
ataaacaagttaacaacaacaattgcattcattttatgtttcaggttcaggggggaggtgtgggaggtt
ttttcggatcctctagagtcgacggcagagtcgcagacgcccctattggacgtcaaaattgtagaggt
```

```
gaagttttcaaacgatggcgaagtaacggcgacttgcgtttccaccgtcaaatctccctatagggtag
aaactaattggaaagtagacctcgtagatgtaatggatgaaatttctgggaacagtcccgccggggtt
tttaacagtaatgagaaatggcagaaacagctgtactacagagtaaccgatggaagaacatcggtcca
gctaatgtgcctgtcgtgcacgagccattctccggaaccttactgtcttttcgacacgtctcttatag
cgagggaaaaagatatcgcgccagagttatactttacctctgatccgcaaacggcatactgcacaata
actctgccgtccggcgttgttccgagattcgaatggagccttaataatgtttcactgccggaatattt
gacggccacgaccgttgtttcgcataccgctggccaaagtacagtgtggaagagcagcgcgagagcag
gcgaggcgtggatttctggccggggaggcaatatatacgaatgcaccgtcctcatctcagacggcact
cgcgttactacgcgaaaggagaggtgcttaacaaacacatggattgcggtggaaaacggtgctgctca
ggcgcagctgtattcactcttttctggacttgtgtcaggattatgcgggagcatatctgctttgtacg
caacgctatggaccgccatttattttgaggaatgcttttggactatcgtactgcttcttccttcg
ctagccagagcaccgccgcgtcacgtacgactacatttaggccgtcgcgcgctcgacgcgctaacc
ataccggcggttggcccgtataacagatacctcactagggtatcaagaggctgcgacgttgtcgagct
caacccgatttctaacgtggacgacatgatatcggcggccaaagaaaaagagaagggggcccttcg
aggcctccgtcgtctggttctacgtgattaagggcgacgacggcgaggacaagtactgtccaatctat
agaaaagagtacagggaatgtggcgacgtacaactgctatctgaatgcgccgttcaatctgcacagat
gtgggcagtggactatgttcctagcacccttgtatcgcgaaatggcgcgggactgactatattctccc
ccactgctgcgctctctggccaatacttgctgaccctgaaaatcgggagatttgcgcaaacagctctc
gtaactctagaagttaacgatcgctgtttaaagatcgggtcgcagcttaacttttaccgtcgaaatg
ctggacaacagaacagtatcagactggatttcaaggcgaacacctttatccgatcgcagacaccaata
cacgacacgcggacgacgtatatcgggatacgaagatattctgcagcgctggaataatttgctgagg
aaaaagaatcctagcgcgccagaccctcgtccagatagcgtcccgcaagaaatttcccgctgtaaccaa
gaaagcggaagggcgcaccccggacgcagaaagcagcgaaaagaaggcccctccagaagactcggagg
acgacatgcaggcagaggcttctggagaaaatcctgccgccctccccgaagacgacgaagtccccgag
gacaccgagcacgatgatccaaactcggatcctgactattacaatgacatgcccgccgtgatcccggt
ggaggagactactaaaagttctaatgccgtctccatgcccatattcgcggcgttcgtagcctgcgcgg
tcgcgctcgtggggctactggtttggagcatcgtaaaatgcgcgcgtagctaatcgagcctagaatag
gtggtttcttcctacatgccacgcctcacgctcataatataaatcacatggaatagcataccaatgcc
tattcattgggacgttcgaaaagcatggcatcgctacttggaactctggctctccttgccgcgacgct
cgcaccctccggcgcgatgggaatcgtgatcactggaaatcacgtctccgccaggattgacgacgatc
acatcgtgatcgtcgcgcctcgccccgaagctacaattcaactgcagctattttcatgcctggccag
agaccccacaaaccctactcaggaaccgtccgcgtcgcgtttcggtctgatataacaaaccagtgcta
ccaggaacttagcgaggagcgctttgaaaattgcactcatcgatcgtcttctgtttttgtcggctgta
aagtgaccgagtacacgttctccgcctcgaacagactaaccggacctccacacccgtttaagctcact
atacgaaatcctcgtccgaacgacagcgggatgttctacgtaattgttcggctagacgacaccaaaga
acccattgacgtcttcgcgatccaactatcggtgtatcaattcgcgaacaccgccgcgactcgcggac
tctattccaaggcttcgtgtcgcaccttcggattacctaccgtccaacttgaggcctatctcaggacc
gaggaaagttggcgcaactggcaagcgtacgttgccacggaggccacgacgaccagcgccgaggcgac
aacccccgacgcccgtcactgcaaccagcgcctccgaacttgaagcggaacactttaccttttccctggc
tagaaaatggcgtggatcattacgaaccgacacccgcaaacgaaaattcaaacgttactgtccgtctc
gggacaatgagccctacgctaattggggtaaccgtggctgccgtcgtgagcgcaacgatcggcctcgt
cattgtaatttccatcgtcaccagaaacatgtgcaccccgcaccgaaaattagacacggtctcgcaag
acgacgaagaacgttcccaaactagaagggaatcgcgaaaatttggacccatggttgcgtgcgaaata
aacaaggggcgtgaccaggatagtgaacttgtggaactggttgcgattgttaacccgtctgcgctaag
ctcgcccgactcaataaaaatgtgattaagtctgaatgtggctctccaatcatttcgattctctaatc
tcccaatcctctcaaaaggggcagtatcggacacggactgggaggggcgtacacgatagttatatggt
acagcagaggcctctgaacacttaggaggagaattcagccgggaggaaacccctgttgagtaggcttgg
gagcatattgcaggatgaacatgttagtgatagttctcgcctcttgtcttcgcgcgcctaacttttgcg
acgcgacacgtcctcttttttggaaggcactcaggctgtcctcggggaagatgatcccagaaacgttcc
ggaagggactgtaatcaaatggacaaaagtcctgcggaacgcgtgcaagatgaaggcggccgatgtct
gctcttcgcctaactattgctttcatgatttaatttacgacggagggaaagaaagactgcccgcccgcg
ggaccctgtctgcaaacctggtaattttactaaagcgcggcgaagcttagcttgcctccgattctag
cattacatagccggtcagtagatcctgccattcggtagcgcaaccggctacatcttcaaacagtctca
cgataaatgcatctctcgttcctgccaatccggaaccgggcataccactcccgcctgccgatttaatt
ctcacaattgggcgatgccggcgggcaaacgaatgtggatttggcaaaccgacacaggtctgctgt
acggactaatatgggcacacccacatcattcttcagatgctccatgcattgttctatgagaaagatcc
ataggtggaggcagcgtcacgagatcgcccaggcaatcgatcgcattcgtctagtaaagtgacgaga
gttatcatgcacacacccatgcccacgccttccgaataactggagctgtggaagatcggaaacgtctt
tttgactgccggtctcgtactacttttcgcacaggtgtataccccggacgcgtactatatattttatatc
atccaacgtccgaaattacatacgtggcggcgatggaagtagatgttgagtcttcgaaagtaagtgcc
tcgaatatgggtattgtctgtgaaaatatcgaaagcggtacgacggttgcagaaccgtcgatgtcgcc
agatactagtaacaatagcttcgataacgaagacttccgtgggcctgaatacgatgtggagataaata
ccagaaaatctgctaatcttgatcgtatggaatcttcgtgccgtgaacaacgagcggcgtgcgaactt
cgaaagtgttcgtgtcctacgtctgccgtgcgcatgcaatacagtattcttcatctctcgctccggg
ttcagagggtcatgtatatatatgtactagatacggggacgcggaccaaaaaaaatgcatagtgaagg
cagtcgttggaggaaagaatcccgggagggaagtggatattttaaaaaccatctcacataaatcaatt
ataaaattaatccatgcctataaatggaaaaatgttgtgtgtatggcaatgcgtgtatatcgttatga
tcttttcacatatattgacggagtcggccctatgccccttcaacagatgatctatattcaacgtggac
tactagaggcgctagcatacatacatgaaaggggcatcattcaccgagacgtaaagacggagatata
ttcttggataatcacgaaaatgcagttttgggtgacttcggtgctgcatgccaactaggagattgtat
agatacgcccaatgttacggttggagcggaactgtggaaacaaattcgccggaattatctgcacttg
atccgtattgcacaaaaacagatatttggagtgccggattggttctatatgagatggcaattaaaaat
gtaccattgtttagtaagcaggtgaaaagttcgggatctcagctgagatccataatacggtgcatgca
agtcatgaactggagtttccccgcaacgattctaccaacctctgtaaacatttcaaacaatatgcgg
ttcgtgtacgaccgccttataccattcctcgagttataagaaatgggggatgccaatggatgttgaa
tatgtcatttctaaaatgcttacgtttgaccaggagttcagaccttctgctaaggaaatattgaatat
gcccctatttactaaggcgccgattaacctgcttaatatcacaccctctgacagtgtctaacggtata
caggcgggagcgggtcgtggcgtcatcatcaccacttgagaatttatatttttgaattgttgattgata
aattaacctgattcattgagaactgaaacgccatattggtttcttggatatgtctacaacaattagtt
```

-continued aaattgctatgttctactgcgagtaacatttgataagttgtaagagacgggcgactcatgtcgaagtt
gacgaatataaagtacataacgtgtttagaatacccagaatccgaatagtccgcgggggcgtcttctc
gcgtgagtaccaaatactgagttgaacttgaaaatgctaaatctgtgacactctttgtgtgatgatta
ttgtcaccacttcgaagatggcttcgacattcatgatgttctggtgtttgtttggaatcgtaatagcg
cttgtttcgtccaagtctgacaacaaagaaaatctgaagaattatatcacggataagtcaaccaatat
tagaatacccacgccatttatttgtatcaacggaaaactcttatcccacaaaacatgtaatctacgatg
aaaactgtggcttcgctgtactcaatcctataagtgaccccaaatatgtccttttgagccagcttcta
atgggaaggcgcaaatatgatgcgacggtcgcgtggtttgttctcggtaaaatgtgtgccagattaat
atatttgcgcgaattttataactgctcgacaaatgagcctttggcacatgttctatgagctctcctg
gatggtgggacaggcgctacgtctcaaccagtttcatttctcgcgacgaattacagctggtttttgca
gcgccgtcccgagaattagatggtttatatacgcgcgtagtagttgtcaacggggactttactacggc
cgatataatgtttaatgttaaagtggcatgtgccttttcaaagactggaatagaagatgatacattat
gcaaaccctttcatttctttgccaatgcaacattgcacaatttaaccatgattagatcggtaactctt
cgagcgcacgaaagccatttaaaggaatgggtggcacggagaggtggtaacgtccctgcagtgctact
tgagtctaccatgtatcatgcatccaatctgcctagaaatttcagggattctacataaagtctccag
atgattataagtataatcacctagatgggccatctgtaatgctcatcactgacagacctagtgaagat
ttggatggggaggctcgttcaccaaagtgacattttttactactacaagtcctataaaacaggtccggta
tgaagagcatcagtcacatacaaagcagtatcctgtaaacaaaatacaagctataattttttgatag
ggttaggctcgttcattggaagcatattcgtagtttttggtagtatggattatacgcagatattgcaat
ggagcgcggagtgggggaacgccccccagtcctcgccggtatgtgtataccaggctatgatcacgtgt
gaaacttgggcggacctgtatcatatgtacaccgtccctattcgtttatagccagtacgtgttatctg
cacatagaggaacatgtgtcatctgggatcgcatgcatggtatgtgtgactctaatattattctgta
tcataaaaaacacagtgcatggtatatagaggatcgctggtaagcactacggtagaccaatcggct
cagattgcattctttggcatcgataccgttgttaatttatatggcaaagtcttgttcatgggagatca
gtatttggaggaaatatactctggaacgatggaaatactcaaatggaatcaagctaaccgctgctatt
ctattgcgcatgcaacatattacgccgactgtcctataatcagttctacggtattcagaggatgccgg
gacgccgttgtttatactaggccccacagcagaattc SEQ ID NO 24: 1333-85.66 (ILTV/Chicken β-actin pro-VP2-FHV US9pA/HVT US2 region) (13064 bp)
gaattcc

```
acacaaattgcgtttaggtggggtgcatgtggactcgataccaagccctgcagctggggaacgtctg
gtggagagccgataatttgatatacgcacgccatattactgtcgttgaagtacgccttatcttctatg
ttttcaaatttaggttcccaagtggacgtgagaagtgtttgtatctcacatggaatggcccaaggcat
tccagcccaggtgcctggtactttaatggcaaacaaacgttttggtagaggtattgattctattgcag
ttctgcagatatctgcagccccgagtatccacaggctatacgatacgttatcggaggcaagcttaatt
aagtaccgagctcgaattggcgcgcccgacggcagagtcgcagacgccctattggacgtcaaaattg
tagaggtgaagttttcaaacgatggcgaagtaacggcgacttgcgtttccaccgtcaaatctccctat
agggtagaaactaattggaaagtagacctcgtagatgtaatggatgaaatttctgggaacagtcccgc
cggggttttttaacagtaatgagaaatggcagaaacagctgtactacagagtaaccgatggaagaacat
cggtccagctaatgtgcctgtcgtgcacgagccattctccggaaccttactgtcttttcgacacgtct
cttatagcgagggaaaaagatatcgcgccagagttatacttacctctgatccgcaaacggcatactg
cacaataactctgccgtccggcgttgttccgagattcgaatggagccttaataatgtttcactgccgg
aatatttgacggccacgaccgttgtttcgcataccgctggccaaagtacagtgtggaagagcagcgcg
agagcaggcgaggcgtggatttctggccggggaggcaatatatacgaatgcaccgtcctcatctcaga
cggcactcgcgttactacgcgaaaggagaggtgcttaacaaacacatggattgcggtggaaaacggtg
ctgctcaggcgcagctgtattcactcttttctggacttgtgtcaggattatgcgggagcatatctgct
ttgtacgcaacgctatggaccgccatttattttttgaggaatgcttttttggactatcgtactgcttct
tccttcgctagccagagcaccgccgccgtcacgtacgactacattttaggccgtcgcgcgcttcgacgc
gctaaccataccggcggttggcccgtataacagataccctcactaggggtatcaagaggctgcgacgttg
tcgagctcaacccgatttctaacgtggacgacatgatatcggcggccaaagaaaaagagaagggggggc
cctttcgaggcctccgtcgtctggttctacgtgattaagggcgacgacggcgaggacaagtactgtcc
aatctatagaaaagagtacagggaatgtggcgacgtacaactgtatctgaatgcgccgttcaatctg
cacagatgtgggcagtggactatgttcctagcacccttgtatcgcgaaatggcgcgggactgactata
ttctcccccactgctgcgctctctggccaatacttgctgaccctgaaaatcgggagatttgcgcaaac
agctctcgtaactctagaagttaacgatcgctgtttaaagatcgggtcgcagcttaacttttttaccgt
cgaaatgctggacaacagaacagtatcagactggatttcaaagtcgaacaccttttatccgatcgcagac
accaatacacgacacgcggacgacgtatatcgggatacgaagatattctgcagcgctggaataattt
gctgaggaaaaagaatcctagcgcgccagaccctcgtccagatagcgtcccgcaagaaattcccgctg
taaccaagaaagcggaagggcgcacccccgacgcagaaagcagcgaaaagaaggcccctccagaagac
tcggaggacgacatgcaggcagaggcttctggagaaaaatcctgccgccctccccgaagacgacgaagt
ccccgaggacaccgagcacgatgatccaaactcggatcctgactattacaatgacatgcccgccgtga
tcccggtggaggagactactaaaagttctaatgccgtctccatgcccatattcgcggcgttcgtagcc
tgcgcggtcgcgctcgtggggctactggtttggagcatcgtaaaatgcgcgcgtagctaatcgagcct
agaataggtggtttcttcctacatgccacgcctcacgctcataatataaatcacatggaatagcatac
caatgcctattcattgggacgttcgaaaagcatggcatcgctacttggaactctggctctccttgccg
cgacgctcgcacccttcggcgcgatgggaatcgtgatcactggaaatcacgtctccgccaggattgac
gacgatcacatcgtgatcgtcgcgcctcgccccgaagctacaattcaactgcagctattttcatgcc
tggccagagaccccacaaaccctactcaggaaccgtccgcgtcgcgtttcggtctgatataacaaacc
agtgctaccaggaacttagcgaggagcgctttgaaaattgcactcatcgatcgtcttctgtttttgtc
ggctgtaaagtgaccgagtacacgttctccgcctcgaacagataaccggacctccacacccgtttaa
gctcactatacgaaatcctcgtccgaacgacagcgggatgttctacgtaattgttcggctagacgaca
ccaaagaacccattgacgtcttcgcgatccaactatcggtgtatcaattcgcgaacaccgccgcgact
cgcggactctattccaaggcttcgtgtcgcaccttcggattacctaccgtccaacttgaggcctatct
caggaccgaggaaagttggcgcaactggcaagcgtacgttgccacggaggccacgacgaccagcgccg
aggcgacaaccccgacgcccgtcactgcaaccagcgcctccgaacttgaagcggaacactttacctt
ccctggctagaaaatggcgtggatcattacgaaccgacacccgcaaacgaaaattcaaacgttactgt
ccgtctcgggacaatgagccctacgctaattgggtaacgtggctgccgtcgtgagcgcaacgatcg
gcctcgtcattgtaatttccatcgtcaccagaaacatgtgcaccccgcaccgaaaattagacacggtc
tcgcaagacgacgaagaacgttcccaaactagaagggaatcgcgaaaatttggacccatggttgcgtg
cgaaatcaaaggggggctgaccaggatagtgaacttgtggaactggttgcgattgttaacccgtctg
cgctaagctcgcccgactcaataaaaatgtgattaagtctgaatgtggctctccaatcattctgattc
tctaatctcccaatcctctcaaaaggggcagtatcggacacggactgggaggggcgtacacgatagtt
atatggtacagcagaggcctctgaacacttaggaggagaattcagccggggagagcccctgttgagta
ggcttgggagcatattgcaggatgaacatgttagtgatagttctcgcctcttgtcttgcgcgcctaac
ttttgcgacgcgacacgtcctctttttggaaggcactcaggcgtgtcctcgggggaagatgatcccagaa
acgttccggaagggactgtaatcaaatggacaaaagtcctgcggaacgcgtgcaagatgaaggcggcc
gatgtctgctcttcgcctaactattgctttcatgatttaatttacgacggaggaaagaaagactgccc
gcccgcgggacccctgtctgcaaacctggtaatttttactaaagcgcggcgggcgcgccggatcagatc
tccatggtcgaggtgagccccacgttctgcttcactctccccatctccccccctccccaccccaat
tttgtatttatttatttttttaattattttgtgcagcgatggggcgggggggggggnnncgcgcgcca
ggcggggcggggcgggcgaggggcgggcggggcgaggcggagaggtcggcggcagccaatcagag
cggcgcgctccgaaagtttcctttatggcgaggcggcggcggcggcggccctataaaaagcgaagcg
cgcggcgggcgggagtcgctgcgcgctgccttcgccccgtgccccgctccgccgccgcctcgcgccgc
ccgccccggctctgactgaccgcgttactcccacaggtgagcgggcgggacggcccttctcctccggg
ctgtaattagcggcaggaaggaaatgggcgggagggccttcgtgcgtcgccgccgccgcgtcccctt
ctccctctccagcctcggggctgtccgcggggggacggctgccttcgggggggacggggcagggcggg
gttcggcttctggcgtgtgaccggcggctctagagcctctgctaaccatgttcatgccttcttctttt
tcctacagctcctgggcaacgtgctggttattgtgctgtctcatcattttggcaaagaattgcagatc
tggatctatgacaaacctgcaagatcaaacccaacagattgttccgttcatacggagccttctgatgc
caacaaccggaccggcgtccattccggacgacaccctggagaagcacactctcaggtcagagacctcg
acctacaatttgactgtgggggacacagggtcagggctaattgtcttttttccctggattccctggctc
aattgtgggtgctcactacacactgcagagcaatgggaactacaagttcgatcagatgctcctgactg
cccagaacctaccggccagctacaactactgcagactagtgagtcggagtctcacagtgaggtcaagc
acactccctggtggcgtttatgcactaaacggcaccataaacgcctgaccttccaaggaagcctgag
tgaactgacagatgttagctacaatggggttgatgtctgcaacagccaacatcaacgacaaagttggga
atgtcctggtaggggaaggggtcactgtcctcagcctacccacatcatatgatcttgggtatgtgagg
cttggtgaccccattcccgctatagggcttgacccaaaaatggtagctacatgcgacagcagtgacag
gcccagagtctacaccataactgcagccgatgattaccaattctcatcacagtaccaaccaggtgggg
taacaatcacactgttctcagccaacattgatgctatcacaagcctcagcattggggagagctcgtg
```

```
tttcaaacaagcgtccaaggccttgtactgggcgccaccatctaccttataggctttgatgggactgc
ggtaatcaccagagctgtggccgcagataatgggctgacggccggcaccgacaatcttatgccattca
atcttgtcattccaaccaatgagataaaccagccgatcacatccatcaaactggagatagtgacctcc
aaaagtggtggtcaggcaggggatcagatgtcatggtcggcaagtgggagcctagcagtgacgatcca
tggtggcaactatccaggggccctccgtcccgtcacactagtagcctacgaaaagagtggcaacaggat
ccgtcgttacggtcgctggggtgagtaacttcgagctgatcccaaatcctgaactagcaaagaacctg
gttacagaatacggccgatttgacccaggagccatgaactacacaaaattgatactgagtgagaggga
ccgtcttggcatcaagaccgtctggccaacaagggagtacactgattttcgtgagtacttcatggagg
tggccgacctcaactctcccctgaagattgcaggagcattttggcttcaaagacataatccgggctata
aggaggtaagatccgatctctcgattaattaacaataaacatagcatacgttatgacatggtctaccg
cgtcttatatggggacgacaagcttgcctccgattctagcattacatagccggtcagtagatcctgcc
attcggtagcgcaaccggctacatcttcaaacagtctcacgataaatgcatctctcgttcctgccaat
ccggaacccgggcataccactcccgcctgccgatttaattctcacaattgggcgatgccggcggggcaa
aacgaatgtggatttggcaaaccgacacaggtctgctgtactaatatgggcacaccccacatcat
tcttcagatgctccatgcattgttctatgagaaagatccataggtggaggcagcgtcacgagatcgc
ccaggcaatcgatcgcattcgtctagtaaagtgacgagagttatcatgcacacacccatgcccacgcc
ttccgaataactggagctgtggaagatcggaaacgtcttttttgactgccggtctcgtactacttcgc
acaggtgtatacccggacgcgtactatatattttatatcatccaacgtccgaaattacatacgtggcg
gcgatggaagtagatgttgagtcttcgaaagtaagtgcctcgaatatgggtattgtctgtgaaaatat
cgaaagcggtacgacggttgcagaaccgtcgatgtcgccagatactagtaacaatagcttcgataacg
aagacttccgtgggcctgaatacgatgtggagataaataccagaaaatctgctaatcttgatcgtatg
gaatcttcgtgccgtgaacaacgagcggcgtgcgaacttcgaaagtgttcgtgtcctacgtctgccgt
gcgcatgcaatacagtattctttcatctctcgctccgggttcagagggtcatgtatatatatgtacta
gatacggggacgcggaccaaaaaaatgcatagtgaaggcagtcgttggaggaaagaatcccggagg
gaagtggatattttaaaaaccatctcacataaatcaattataaaattaatccatgcctataaatggaa
aaatgttgtgtgtatatggcaatgcgtgtatatcgttatgatcttttcacatatattgacggagtcggcc
ctatgcccttcaacagatgatctatattcaacgtggactactagaggcgctagcatacatacatgaa
agggcatcattcaccgagacgtaaagacggagaatatattcttggataatcacgaaaatgcagtttt
gggtgacttcggtgctgcatgccaactaggagattgtatagatacgcccaatgttacggttggagcg
gaactgtggaaacaaattcgccggaattatctgcacttgattccgtattgacgaatataaagtacataacgttttag
agtgccggattggttctatatgagatggcaattaaaaatgtaccattgtttagtaagcaggtgaaaag
ttcgggatctcagctgagatccataatacggtgcatgcaagtgcatgaactggagttttccccgcaacg
attctaccaacctctgtaaacatttcaaacaatatgcggttcgtgtacgaccgccttataccattcct
cgagttataagaaatgggggggatgccaatggatgtttgaatatgtcattttctaaaatgcttacgtttga
ccaggagttcagaccttctgctaaggaaatattgaatatgcccctatttactaaggcgccgattaacc
tgcttaatatcacaccctctgacagtgtctaacggtatacaggcgggagcgggtcgtggcgtcatcat
caccacttgagaatttatattttgaattgttgattgataaattaacctgattcattgagaactgaaac
gccatattggtttcttggatatgtctacaacaattagttaaattgctatgttctactgcgagtaacat
ttgataagttgtaagagacgggcgactcatgtcgaagttgacgaatataagtacataacgtgtttag
aatacccagaatccgaatagtccgcggggggcgtcttctcgcgtgagtaccaaatactgagttgaactt
gaaaatgctaaatctgtgacactctttgtgtgatgattattgtcaccacttcgaagatggcttcgaca
ttcatgatgttctggtgtttgtttggaatcgtaatagcgcttgtttcgtccaagtctgacaacaaaga
aaatctgaagaattatatcacggataagtcaaccaatattagaatacccacgccattatttgtatcaa
cggaaaactcttatcccacaaaacatgtaatctacgatgaaaactgtggcttcgctgtactcaatcct
ataagtgaccccaaatatgtcctttttgagccagcttctaatgggaaggcgcaaatatgatgcgacggt
cgcgtggtttgttctcggtaaaatgtgtgccagattaatatattttgcgcgaattttataactgctcga
caaatgagccttttggcacatgtctatgagctctcctggatggtggggacaggcgctacgtctcaacc
agtttcatttctcgcgacgaattacagctggtttttgcagcgccgtcccgagaattagatggtttata
tacgcgcgtagtagttgtcaacggggactttactacggccgatataatgtttaatgttaaagtggcat
gtgccttttcaaagactggaatagaagatgatacattatgcaaaccctttcatttctttgccaatgca
acattgcacaatttaaccatgattagatcggtaactcttcgagcgcagaaagcatttaaaggaatg
ggtggcacggagaggtggtaacgtccctgcagtgctacttgagtctaccatgtatcatgcatccaatc
tgcctagaaatttcagggatttctacataaagtctccagatgattataagtataatcacctagatggg
ccatctgtaatgctcatcactgacagacctagtgaagattggatgggaggctcgttcaccaaagtga
cattttttactactacaagtcctataaaacaggtccggtatgaagagcatcagtcacatacaaagcagt
atcctgtaaacaaaatacaagctataattttttttgatagggttaggctcgttcattggaagcatattc
gtagttttggtagtatggattatacgcagatattgcaatggagcgcggagtggggaacgcccccag
tcctcgccggtatgtgtataccaggctatgatcacgtgtgaaacttgggcggacctgtatcatatgta
caccgtccctattcgtttatagccagtacgtgttatctgcacatagaggaacatgtgcatactggga
tcgcatgcatggtatgtgactctaatattattctgtatcataataaaaacacagtgcatggtatat
agaggatcgctggtaagcactacggtagaccaatcggctcagattgcattctttggcatcgataccgt
tgttaatttatatggcaaagtcttgttcatgggagatcagtatttggaggaaatatactctggaacga
tggaaatactcaaatggaatcaagctaaccgctgctattctattgcgcatgcaacatattacgccgac
tgtcctataatcagttctacggtattcagaggatgccgggacgccgttgtttatactaggccccacag
cagaattc SEQ ID NO 25: 1386-04.4#1 (ILTV/hCMV IEpro-VP2-HSV TKpA

```
ggttggggcgtcgacttaagcgatctgactgggagactattatgcatctgtcaccaacgcaaagtcgg
cgtctacatagaactttaagatttgtggagcgtagaattatcccatctaacagttatatacgcacatc
gggccacgttccgccttcgagggcacttccgacagatacgaatttaaagatggatgaataattaaatt
ggaaagagtaactacattaatcgagcgtcatgacggcgtcccgtgaaaatgggaattttctactcgaa
acaccgtgacatttgacagacctggaattgttattctgatatatagtggtgtgtctggccggcaaca
tacataatgtgcatgcgaaaccacttttttcagtgtacgctgacattgtgcaacacggaggggtagca
ctacatacaatatatgttgattaatgattggagaaaaaactatgcagctcgccgatcatatggctaac
tcgccttcgtctatatggcggaccccgcgggaaaaatcgacgtaccatctgatttacaacaccagtaa
tgaacatgtcgcatccctgcccagatctgtgcgcccattggcgcggatcgttgtgaatgccgccgaaa
cacttcaggtcggtatgagagccgggaggccgccatcagcaggagtttggcgagaggtgtttgataga
atgatgacagccttccgtgaccacgagcctactgcgacatttaatgctgcaaatcccattagaaaaat
ggtcgagacagttctacagaataatgaagagccccgcggacgcatgctgaaatgggtaatcgcctta
tgaacattatgtactggtgttgcttgggacacgcaggacaatgctcgatatggcagttgtacgagacg
aatcaggccattttaagtttattagatgaagtggttatcggcacaacaaatcccttttgcaccctcga
gcaatactggaagccattatgcaccgcaatcgccaacaaggggacctcatcgcttgttgaggatgcca
aagtggccgagtacctggttagcatgcgcaaattgatataacataggcacgctctgatgttacagacc
acaataccgcatacatttattgtaaggttgttaataaaggtttattctatgtaagactacaatacttt
cgacattgcttgtatacatattaaatactttctcaagttcctattacataaaatgggatctatcatta
cattcgttaagagtctggataattttactgtttgccagcttcgatcttggaacgtactgtggatagtg
ccttacttggaatcgtgaaaatttgaaacgtccattatttggatatcttccggttgtcccatatcccg
ccctggtaccgctcggatccttgcccgtatggattcgtattgacagtcgcgcaatcgggaccaaca
acgcgtgggtccacactcattcggaaattttccgatgattcgtaatatttattgccgctcgttacgag
tcgttggacatatctgtaacatttcttcttctgaaggatcgctgcacatttgatctatacattggc
caggatgttcaagtctcagatgttgcattctggcacagcacaactttatggcatttccgatgtaatcg
tccggcagccctgggggagttctatattcgcatattgggatggtaaggacaatagcagatctcgcaac
ctccagggaggctataataacgtttttaaaggatggatttctcataaaaatctgtcgcaaattacact
gagaatatcctttactagcgccgattgagagcatcgtcgtccaattttctaaatggaaagaaaacaag
gcgggcaagagtgttccaaacattttcattttcggcgaatctctcaaatcccatggcgtgcaattgat
tgcaaaattggcacttccgttcacgtttgtatctccaaactctaagacacttttaattgaaaaactac
gttctagtgtggaaagaaacctataggcagaccatagaactatttgacaccacatatcttttttgtatg
tcaaactgaccatgatcgtatgttgctgaatgcactagggcaattcgctcgcgcgactccatacattg
aataattccacacgtcagctcatcggttagcaaggtccagtagttgaagtcatttattttttccccgcg
gctggccaaatctacctctgggaatatccaagttgtcgaatatgatcgcaccggctctggtcatggtg
aaggaactgtagcataaagacgcaggtatcataggggtaatattttttattcactcacatactaaaa
gtaacgcatattagcaccatgtatgggctatcaattgcaatttcgtgcgtagcactacatcacgattatgt
acaacataatgggacaacatatggcaagtagatgcaatttcctcacactagttgggtttatctactat
tgaattttccctatctgtgatacacttgggagcctctacaagcatattgccatcatgtacgttttta
tctactgtcttaacgcccatgggaacggaggcgtcgtcgtcatgtattggacggcaacataggcagca
acacaaattgcgtttaggtggggtgcatgtggactcgataccaagcccctgcagctggggaacgtctg
gtggagagccgataatttgatatacgcacgccatattactgtcgttgaagtacgccttatcttctatg
ttttcaaatttaggttcccaagtggacgtgagaagtgtttgtatctcacatggaatggcccaaggcat
tccagcccaggtgcctggtactttaatggcaaacaaacgttttggtagaggtattgattctattgcag
ttctgcagatatctgcagccccgagtatccacaggctatacgatactgtcggaggcaagcttgtta
attaagtcgacggcagagtcgcagacgcccctattggacgtcaaaattgtagaggtgaagttttcaaa
cgatggcgaagtaacggcgacttgcgtttccaccgtcaaatctccctatagggtagaaactaattgga
aagtagacctcgtagatgtaatggatgaaatttctgggaacagtcccgccggggttttttaacagtaat
gagaaatggcagaaacagctgtactacagagtaaccgatggaagaacatcggtccagctaatgtgcct
gtcgtgcacgagccattctccggaaccttactgtcttttcgacacgtctcttatagcgagggaaaaag
atatcgcgcagagttatactttacctctgatccgcaaacggcatactgcacaataactctgccgtcc
ggcgttgttccgagattcgaatggagccttaataatgtttcactgccggaatatttgacggccacgac
cgttgtttcgcataccgctggccaaagtacagtgtggaagagcagcgcgagacaggcgaggcgtgga
tttctggccgggggaggcaatatatacgaatgcaccgtcctcatctcagacggcactcgcgttactacg
cgaaggagaggtgcttaacaaacacatggattgcggtgaaaacggtgctgctcaggcgcagctgta
ttcactcttttctggacttgtgtcaggattatgcgggagcatatctgctttgtacgcaacgctatgga
ccgccatttattttgaggaatgcttttttggactatcgtactgctttcttccttcgctagccagagca
ccgccgccgtcacgtacgactacattttaggccgtcgcgcgctcgacgcgctaaccataccggcggtt
ggcccgtataacagatacctcactagggtatcaagaggctgcgacgttgtcgagctcaacccgatttc
taacgtggacgacatgatatcggcggccaaagaaaaagaaggggggccctttcgaggcctccgtcg
tctggttctacgtgattaagggcgacgacggcgaggacaagtactgtccaatctatagaaaagagtac
agggaatgtggcgacgtacaactgctatctgaatgcgccgttcaatctgcacagatgtgggcagtgga
ctatgttcctagcacccttgtatcgcgaaatggcgcgggactgactatattctccccactgctgcgc
tctctggccaatacttgctgaccctgaaaatcgggagatttgcgcaaacagctctcgtaactctagaa
gttaacgatcgctgtttaaagatcgggtcgcagcttaacttttttaccgtcgaaatgctggacaacaga
acagtatcagactcggatttcaaggcgaacaccttatccgatcgcagacaccaatacacgacacgcgg
acgacgtatatcggggatacgaagatattctgcagcgctggaataatttgctgaggaaaaagaatcct
agcgcgccagacccctcgtccagatagcgtcccgcaagaaattcccgctgtaaccaagaaagcggaagg
gcgcaccccggacgcagaaagcagcgaaaagaaggcccctccagaagactcggaggacgacatgcagg
cagaggcttctggagaaaatcctgccgccctccccgaagacgacgaagtccccgaggacaccgagcac
gatgatccaaactcggatcctgactattacaatgacatgcccgccgtgatcccggttggaggagactac
taaaagttctaatgccgtctccatgcccatattcgcggcgttcgtagcctcgcgcggtcgcgctcgtgg
ggctactggttttggagcatcgtaaaatgcgcgcgtagctaatcgagcctagaataggtggtttcttcc
tacatgccacgcctcacgctcataatataaatcacatggaatagcataccaatgcctattcattggga
cgttcgaaaagcatggcatcgctacttggaactctggctctccttgccgcgacgctcgcacccttcgg
cgcgatgggaatcgtgatcactggaaatcacgtctccgccaggattgacgacgatcacatcgtgatcg
tcgcgcctcgccccgaagctacaattcaactgcagctattttcatgcctggccagagaccccacaaa
ccctactcaggaaccgtccgcgtcgcgtttcggtctgatataacaaaccagtgctaccaggaacttag
cgaggagcgctttgaaaattgcactcatcgatcgtcttctgtttttgtcggctgtaaagtgaccgagt
acacgttctccgcctcgaacagactaaccggacctccacacccgtttaagctcactatacgaaatcct
cgtccgaacgacagcgggatgttctacgtaattgttcggctagacgacaccaaagaacccattgacgt
```

```
cttcgcgatccaactatcggtgtatcaattcgcgaacaccgccgcgactcgcggactctattccaagg
cttcgtgtcgcaccttcggattacctaccgtccaacttgaggcctatctcaggaccgaggaaagttgg
cgcaactggcaagcgtacgttgccacggaggccacgacgaccagcgccgaggcgacaaccccgacgcc
cgtcactgcaaccagcgcctccgaacttgaagcggaacactttacctttccctggctagaaaatggcg
tggatcattacgaaccgacacccgcaaacgaaaattcaaacgttactgtccgtctcgggacaatgagc
cctacgctaattggggtaaccgtggctgccgtcgtgagcgcaacgatcggcctcgtcattgtaatttc
catcgtcaccagaaacatgtgcaccccgcaccgaaaattagacacggtctcgcaagacgacgaagaac
gttcccaaactagaagggaatcgcgaaaatttggacccatggttgcgtgcgaaataaacaagggggct
gaccaggatagtgaacttgtggaactggttgcgattgttaacccgtctgcgctaagctcgcccgactc
aataaaaatgtgattaagtctgaatgtggctctccaatcattcgattctctaatctcccaatcctct
caaaaggggcagtatcggacacggactgggaggggcgtacacgatagttatatggtacagcagaggcc
tctgaacacttaggaggagaattcagccggggagagccctgttgagtaggcttgggagcatattgca
ggatgaacatgttagtgatagttctcgcctcttgtcttgcgcgcctaacttttgcgacgcgacacgtc
ctcttttggaaggcactcaggctgtcctcggggaagatgatcccagaaacgttccggacgatgctgt
aatcaaatggacaaaagtcctgcggaacgcgtgcaagatgaaggcggccgatgtctgctcttcgccta
actattgctttcatgatttaatttacgacggaggaaagaaagactgcccgcccgcgggacccctgtct
gcaaacctggtaattttactaaagcgcggcgaaagcttaggtcaattccctggcattatgcccagtac
atgacctttatgggactttcctacttggcagtacatctacgtattagtcatcgctattaccatggtgat
gcggttttggcagtacatcaatgggcgtggatagcggtttgactcacggggatttccaagtctccacc
ccattgacgtcaatgggagtttgttttggcaccaaaatcaacgggactttccaaaatgtcgtaacaac
tccgccccattgacgcaaatgggcggtaggcgtgtacggtgggaggtctatataagcagagctcgttt
agtgaaccgtcagatcgcctggagacgccatccacgctgttttgacctccatagaagacaccgggcgc
gccggatctatgacaaacctgcaagatcaaacccaacagattgttccgttcatacggagccttctgat
gccaacaaccggaccggcgtccattccggacgacaccctggagaagcacactctcaggtcagagacct
cgacctacaatttgactgtgggggacacagggtcagggctaattgtcttttttccctggattccctggc
tcaattgtgggtgctcactacacactgcagagcaatgggaactgcaaagttcgatcagatgctcctgac
tgcccagaacctaccggccagctacaactactgcagactagtgagtcggagtctcacagtgaggtcaa
gcacactccctggtggcgtttatgcactaaacggcaccataaacgccgtgaccttccaaggaagcctg
agtgaactgacagatgttagctacaatgggttgatgtctgcaacagccaacatcaacgacaaagttgg
gaatgtcctggtaggggaaggggtcactgtcctcagcctaccccacatcatatgatcttgggtatgtga
ggcttggtgaccccattcccgctatagggcttgacccaaaaatggtagctacatgcgacagcagtgac
aggcccagagtctacaccataactgcagccgatgattaccaattctcatcacagtaccaaccaggtgg
ggtaacaatcacactgttctcagccaacattgatgctatcacaagcctcagcattgggggagagctcg
tgtttcaaacaagcgtccaaggccttgtactgggcgccaccatctaccttataggctttgatgggact
gcggtaatcaccagagctgtggccgcagataatgggctgacggccgcaccgacaatcttatgccatt
caatcttgtcattccaaccaatgagataaccccagccgatcacatccatcaaactggagatagtgacct
ccaaaagtggtggtcaggcaggggatcagatgtcatggtcggcaagtgggagcctagcagtgacgatc
catggtggcaactatccaggggccctccgtcccgtcacactagtagcctacgaaagagtggcaacagg
atccgtcgttacggtcgctggggtgagtaacttcgagctgatcccaaatcctgaactagcaaagaacc
tggttacagaatacggccgatttgacccaggagccatgaactacacaaaattgatactgagtgagagg
gaccgtcttggcatcaagaccgtctggccaacaagggagtacactgattttcgtgagtacttcatgga
ggtggccgacctcaactctcccctgaagattgcaggagcatttggcttcaaagacataatccgggcta
taaggaggtaagatccataattgattgacggggagtggggggagctaactgaaacacggaaggagaca
ataccggaaggaacccgcgctatgacggcaataaaaagacagaataaaacgcacgggtgttgggtcgt
ttgttcataaacgcggggttcggtcccagggctggcactctgtcgataccccaccgagaccccattgg
ggccaatacgcccgcgtttcttcctttcccccaccccacccccccaagttcgggtgaaggcccagggct
cgcagccaacgtcggggcggcaggccctgccatagccactggcccccgtgggttagggacggggtcccc
catggggaatggtttatggttcgtgggggttattattttgaagcttgcctccgattctagcattacat
agccggtcagtagatcctgccattcggtagcgcaaccggctacatcttcaaacagtctcacaataaat
gcatctctcgttcctgccaatccggaaccgggcataccactcccgcctgccgatttaattctcacaat
tgggcgatgccggcggggcaaaacgaatgtggatttggcaaaccgacacaggtctgctgtacggacta
atatgggcacacccacatcattcttcagatgctccatgcattgttctatgagaaagatccatagggtg
gaggcagcgtcacgagatcgcccaggcaatcgatcgcattcgtctagtaaagtgacgagagttatcat
gcacacacccatgcccacgccttccgaataactggagctgtggaagatcggaaacgtcttttttgactg
ccggtctcgtactactttcgcacaggtgtataccggacgcgtactatatattttatatcatccaacg
tccgaaattacatacgtggcggcgatggaagtagatgttgagtcttcgaaagtaagtgcctcgaatat
gggtattgtctgtgaaaatatcgaaagcggtacgacggttgcagaaccgtcgatgtcgccagatacta
gtaacaatagcttcgataacgaagacttccgtgggcctgaatacgatgtggagataaataccagaaaa
tctgctaatcttgatcgtatggaatcttcgtgccgtgaacaacgagcggcgtgcgaacttcgaaagtg
ttcgtgtcctacgtctgccgtgcgcatgcaatacagtattctttcatctctcgctccgggttcagagg
gtcatgtatatatatgtactagatacggggacgcggaccaaaaaaaatgcatagtgaaggcagtcgtt
ggaggaaagaatcccgggagggaagtggatattttaaaaaccatctcacataaatcaattataaaatt
aatccatgcctataaatggaaaaatgttgtgtgtatggcaatgcgtgtatatcgttatgatcttttca
catatattgacggagtcggccctatgcccccttcaacagatgatctatattcaacgtggactactagag
gcgctagcatacatacatgaaagggcatcattcaccgagacgtaaagacggagaatatattcttgga
taatcacgaaaatgcagttttgggtgacttcggtgctgcatgccaactaggagattgtatagatacgc
cccaatgttacggttggagcggaactgtgaaacaaattcgccgaattatctgcacttgatccgtat
tgcacaaaaacagatatttggagtgccggattggttctatatgagatggcaattaaaaatgtaccatt
gtttagtaagcaggtgaaaagttcgggatctcagctgagatccatatacggtgcatgcaagtgcatg
aactggagtttccccgcaacgattctaccaacctctgtaaacatttcaaacaatatgcggttcgtgta
cgaccgccttataccattcctcgagttataagaaatgggggggatgccaatggatgttgaatatgtcat
ttctaaaatgcttacgtttgaccaggagttcagaccttctgctaaggaaatattgaatatgcccctat
ttactaaggcgccgattaacctgcttaatatcacaccctctgacagtgtctaacggtatacaggcggg
agcgggtcgtggcgtcatcatcaccacttggagaatttatatttttgaattgttgattgataaatttaacc
tgattcattgagaactgaaacgccatattggtttcttggatatgtctacaacaattagttaaattgct
atgttctactgcgagtaacatttgataagttgtaagagacgggcgactcatgtcgaagttgacgaata
taaagtacataacgtgtttagaatacccagaatccgaatagtccgcgggggcgtcttctcgcgtgagt
accaaatactgagttgaacttgaaaatgctaaatctgtgacactctttgtgtgatgattattgtcacc
acttcgaagatggcttcgacattcatgatgttctggtgtttgtttggaatcgtaaatagcgcttgtttc
```

```
gtccaagtctgacaacaaagaaaatctgaagaattatatcacgcgataagtcaaccaatattagaatac
ccacgccattatttgtatcaacggaaaactcttatcccacaaaacatgtaatctacgatgaaaactgt
ggcttcgctgtactcaatcctataagtgaccccaaatatgtccttttgagccagcttctaatgggaag
gcgcaaatatgatgcgacggtcgcgtggtttgttctcggtaaaatgtgtgccagattaatatatttgc
gcgaattttataactgctcgacaaatgagcctttggcacatgttctatgagctctcctggatggtgg
gacaggcgctacgtctcaaccagtttcatttctcgcgacgaattacagctggttttttgcagcgccgt
ccgagaattagatggtttatatacgcgcgtagtagttgtcaacggggactttactacggccgatataa
tgtttaatgttaaagtggcatgtgccttttcaaagactggaatagaagatgatacattatgcaaaccc
tttcatttctttgccaatgcaacattgcacaatttaaccatgattagatcggtaactcttcgagcgca
cgaaagccatttaaaggaatgggtggcacggagaggtggtaacgtccctgcagtgctacttgagtcta
ccatgtatcatgcatccaatctgcctagaaatttcagggatttctacataaaagtctccagatgattat
aagtataatcacctagatgggccatctgtaatgctcatcactgacagacctagtgaagatttggatgg
gaggctcgttcaccaaagtgacattttactactacaagtcctataaaacaggtccggtatgaagagc
atcagtcacatacaaagcagtatcctgtaaacaaaatacaagctataatttttttgataggggttaggc
tcgttcattggaagcatattcgtagttttggtagtatggattatacgcagatattgcaatggagcgcg
gagtgggggaacgcccccagtcctcgccggtatgtgtataccaggctatgatcacgtgtgaaacttg
ggcggacctgtatcatatgtacaccgtccctattcgtttatagccagtacgtgttatctgcacataga
ggaacatgtgtcatactgggatgcatgcatggtatgtgtgactctaatattattctgtatcataata
aaaacacagtgcatggtatatagaggatcgctggtaagcactacggtagaccaatcggctcagattgc
attctttggcatcgataccgttgttaatttatatggcaaagtcttgttcatgggagatcagtatttgg
aggaaatatactctggaacgatggaaatactcaaatggaatcaagctaaccgctgctattctattgcg
catgcaacatattacgccgactgtcctataatcagttctacggtattcagaggatgccgggacgccgt
tgtttatactaggccccacagcagaattc
```

SEQ ID NO 26: 654-45:325341_IE-F/1C1 (HVT/IBDV/ILT/NDV #2 virus)
HCMV IEpro-F-IEpA/HVT UL54.5 region (11,017 bp)
```
ggcgcgccactggagaacggcatgaccgcaaaaggcgttgtagagatcgatcccacgaactctcaggc
gatcgtgtcagtcgccataaacagcgacgatcgtctccaggatctgaacggttttcttctcaacgatc
atcagtatatgaggaactgaacctgatatttagccgagggaaacgcaggttaaaaacccctatcaagcg
attgcgattttcgcgtatctagtaaaaatagatgggcttcggtactagccttcgccgccaactctgaa
tatgcccttcgtggacctcatataacatggcattgtttgttggatgcggggccggaattaagaagaac
attcgaaatacgagcaaaaatttcggccctggcatgtgctgcgcgagaatcggtacttcggggagaaa
gttttatcggagctttgggtagtgcagaggaaactctatcttggttgaaaatgcatgcgaccctgcac
ttgattctggttaaccacgatccaatttttaagacggctggcgcggtcctagataacctccgcttaaa
actagcccaatattgatgtgcagatataacacagaaaaacgatcaatggaagacatgctacggcggt
catctcccgaagacatcaccgattccctaacaatgtgcctgattatgttatcgcgcattcgtcgtacc
atgcgcaccgcaggaaataaatatagctatatgatagatccaatgaatcgtatgtctaattacactcc
aggcgaatgtatgacaggtatattgcgatatattgacgaacatgctagaaggtgtcctgatcacatat
gtaatttgtatatcacatgtacacttatgccgatgtatgtgcacgggcgatatttctattgtaattca
tttttttgttagtaaactaccacaggctgtccggaaatctaagttaatgaataaagtagatggttaat
actcattgcttagaattggactactttaattctctttaatgttcgtattaaataaaaacatctttaa
taaacttcagcctcttcgcttattgtagaaattgagtattcaaaatcatgttcaaagccgtcttcgga
gagtgtactcgccacggtggttggaacatcactatgtctacacgtcaaatttaagcacgtcaggtctg
tcgaggacaagaaatggttaactagtgtttcaattattcttataaacgttaagcattgtaagcccccc
ggccgtccgcagcaacaatttactagtatgccgtgggctccgggactatcacggatgtccaattcgca
catgcatataatttttctagggtctctcatttcgagaaatcttcggggatccatcagcaatgcgggct
gtagtcccgattcccgtttcaaatgaaggtgctccaacacggtcttcaaagcaaccggcatacccagca
aacacagactgcaactccccgctgcaatgattggttataaacagtaatctgtcttctggaagtatatt
tcgcccgacaatccacggcgcccccaaagttaaaaaaccatccatgtgtatttgcgtcttctctgttaa
agaatattgactggcattttcccgttgaccgccagatatccaaagtacagcacgatgttgcacggac
gacttttgcagtcaccagccttccttttccaccccccccaccaacaaaatgttttatcgtaggacccatatc
cgtaataaggatgggtctggcagcaacccccataggcgcctcggcgtggtagttctcgaggccttaatt
aagtaccgagctcgaattggcgcgccaggtcaattccctggcattatgcccagtacatgaccttatgg
gactttcctacttggcagtacatctacgtattagtcatcgctattaccatggtgatgcggttttggca
gtacatcaatgggcgtggataggcggtttgactcacggggattccaagtctccaccccattgacgtca
atgggagtttgttttggcaccaaaatcaacgggactttccaaaatgtcgtaacaactccgccccattg
acgcaaatgggcggtaggcgtgtacggtgggaggtctatataagcagagctcgtttagtgaaccgtca
gatcgcctggagacgccatccacgctgttttgacctccatagaagacaccggggcgcgccggatccatg
ggcccagaccttctaccaagaacccagtacctatgatgctgactgtccgagtcgcgctggtactgag
ttgcatctgtccggcaaactccattgatggcaggcctcttgcggctgcaggaattgtggttacaggag
acaaagccgtcaacatatacacctcatcccagacaggatcaatcatagttaagctcctcccgaatctg
cccaaggataaggaggcatgtgcgaaagcccccttggatgcataacaaggacattgaccactttgct
cacccccttggtgactctatccgtaggatacaagagtctgtgactacatctggagggggagacagg
ggcgccttataggcgccattattggcggtgtggctcttgggtgtcaaattgccgcacaaataacagcg
gccgcagctctgatacaagccaaacaaaatgctgccaacatcctccgacttaaagagagcattgccgc
aaccaatgaggctgtgcatgaggtcactgacggattatcgcaactagcagtggcagttgggaagatgc
agcagtttgttaatgaccaatttaataaaacagctcaggaattagactgcatcaaaattgcacagcaa
gttggtgtagagctcaacctgtacctaaccgaattgactacagtattcggaccacaaatcactcacc
tgctttaaacaagctgactattcaggcacttttacaatctagctggtggaaatatgattacttattga
ctaagttaggtgtagggaacaatcaactcagctcattaatcggtagcggcttaatcaccggtaaccct
attctatacgactcacagactcaactcttgggtatacaggtaactctaccttcagtcgggaacctaaa
taatatgcgtgccacctacttggaaaccttatccgtaagcacaaccaggggatttgcctcggcacttg
tcccaaaagtggtgacacaggtcggttctgtgatagaagaacttgacacctcatactgtatagaaact
gacttagatttatttgtacaagaatagtaacgttcctatgtccctggtatttattcctgcttgag
cggcaatacgtcggcctgtatgtactcaaagaccgaaggcgcacttactacaccatacatgactatca
aaggttcagtcatcgccaactgcaagatgacaacatgtagatgtgtaaaccccccgggtatcatatcg
caaaactatggagaagccgtgtctctaatagataaacaatcatgcaatgttttatccttaggcgggat
aactttaaggctcagtggggaattcgatgtaacttatcagaagaatatctcaatacaagattctcaag
taataataacaggcaatcttgatatctcaactgagcttgggaatgtcaacaactcgatcagtaatgct
```

-continued

```
ttgaataagttagaggaaagcaacagaaaactagacaaagtcaatgtcaaactgactagcacatctgc
tctcattacctatatcgttttgactatcatatctcttgtttttggtatacttagcccgattctagcat
gctacctaatgtacaagcaaaaggcgcaacaaaagaccttattatggcttgggaataatactctagat
cagatgagagccactacaaaaatgtgaggatctctcgaggaattctagatcccacgtcactattgtat
actctatattatactctatgttatactctgtaatcctactcaataaacgtgtcacgcctgtgaaaccg
tactaagtctcccgtgtcttcttatcaccatcaggtgacatcctcgcccaggctgtcaatcatgccgg
tatcgattccagtagcaccggcccacgctgacaacccactcttgcagcgttagcagcgccctctta
acaagccgaccccaccagcgtcgcggttactaacactcctctccctcgaggatacatccaaagagg
ttgagtattctctctacacttcttgttaaatggaaagtgcatttgcttgtcttacaatcggcccgag
tctcgttcacagcgcctcgttcacacttaaaccacaaatagtctacaggctatatgggagccagactg
aaactcacatatgactaatattcgggggtgttagtcacgtgtagcccattgtgtgcataatacgatgt
tggacgcgtccttattcgcggtgtacttgatactatggcagcgagcatgggatattcatcctcgtcat
cgttaacatctctacgggttcagaatgtttggcatgtcgtcgatcctttgcccatcgttgcaaattac
aagtccgatcgccatgaccgcgataagcctgtaccatgtggcatttagggtgacatctcgatcatacat
tataagaccaacgtgcgagtcttccaaagacctgcacgccttcttcttcggattgtcaacgggttctt
cagaatctatgcccatatctggcgttgagaccattgtgcgtttaatgaacaataaagcggcatgccat
ggaaggagggctgcagatctccattttctcacgccactatcctggacgctgtagacgataattatac
catgaatatagaggggggtatgtttccactgccactgtgatgataagttttctccagattgttggatat
ctgcattttctgctgccgaacaaacttcatcgctatgcaaagagatgcgtgtgtacacgcgccgttga
gtatacgggaaactaaatgttcatagaggtctttgggctatatgttattaaataaaataattgaccag
tgaacaatttgtttaatgttagtttattcaatgcattggttgcaaatattcattacttctccaatccc
aggtcattcttagcgagatgatgttatgacattgctgtgaaaattactacaggatatatttttaaga
tgcaggagtaacaatgtgcatagtaggcgtagttatcgcagacgtgcaacgcttcgcatttgagttac
cgaagtgcccaacagtgctgcggttatggtttatgcgcacagaatccatgcatgtcctaattgaacca
tccgattttctcttttaatcgcgatcgttgtttgggcaactgcgttatttcagatctaaaaaatttacc
ctttatgaccatcacatctctctggctcatacccccgcttggataagatatcatgtagattccgcccta
agaaatgcaaactaacattattgtcggttccatatacacttccatcttgtccttcgaaaataacaaac
tcgcgcaatagaccgtccgtacatgcatgccgatgtgtgtcaacatcattggtctgctagatcccga
tgggacgaatcgtacagtcgtcgctccagcattggcaaaaatccccagatacccctccatgcggcaaat
ctaaattgcgacccccgaagagactgcaccaaagtcttatcgacgcacgctgattttttttgaacagcgg
gagcccattatcttcagtggagcgtagacgggcgaggctaattatgtgacatagcaacactgcatgta
tgttttataaatcaataagagtacataatttattacgtatcatttccgtttgtaatatactgtatac
atcatccacactattagtcagcactagcgcgcgggcgcacgttacaatagcagcgtgcccgttatcta
tattgtccgatatttacacataacatttcatcgacatgattaaatacctaagtactgcacacagatgt
ttaatgtatatcgtcatataaattatatcgctaggacagacccaaacgacctttatcccaaacagtca
gatcctcttctcaagtgtcgatttctgttatggaatatgcatacctggcccagaaattgcacgcacg
agcgtagtgaatgcgtcattggttttacatttaaaggctaaatgcacaaattctttagacgacagcac
atcgttaaatagcatctctagcgttcttatgaatgctaagcattggagtcctcctggtcggccacaat
aacagctgagtatcatacctgagctccgggggttgtcgcacatagcggattcgtataaacataggatt
ttccgcgaatccatcagttgcaaaaatctgttaggctccatcaacaacgctggatttacttcagatcc
acgcgtaaagtaatggtgctcgaataccgttttttagagttgtcggcatttcaaggaacaaagaattca
tttcttcattgcaacgacgcgccagaaatcccaagacctctttgggtagtatgttcttgcctataaaa
cacggcgttccaagtgccaggaaccacgcatgtgttactgttgggcgtattcagaaataaagcgggg
tttatgcggcttttgaagctcggatatccaaagtatcgcttgctgatgaacgagcgatgtagctgtta
caaaacctcctttccatcctccagtcaacataatattatcggcctacctatgtccgtaataagtatt
ggtcgggcaattattccgtatgaggtcttgcaggaataagctcttagggacagccagcttggatatgg
tgcgaaacagaccttctcggcttcagaatgtcgctccgcagtctcttcgtgtcggtgcatcttagatc
caccatcaatgtgtgcagcattgactcccgcccgtcgaatattccttttgttacgatgcagtaatgag
cacgatcatgggcggggcgatgacgttctatttgcatgtctgcgaacaatttgcgtcagtcatacagc
tatggagtgggccatttctggccgtcaacttaaaaacgcgaaccgcagacatatgtatttgcatgcaa
agacgtatcttcgtatttctgggcatcttcaaatgctctggccaatatggcaatgaattttggattcgt
ttgacgccgatggtatgcagtgcaaatgtgccaatagcccacatccgaaaaagttatttgtcatacaa
gcaggtgttaagtagcaatcacataaaggcaccagacgcctcatggcatcataatgaatagctcctc
tccccactggaaccactgacaaaatctgcgagtatattccgcaaaccacattttattcctcatagaaa
ctaccctaaatccttttaacgggaagaagaatcctagatagtgcttgaagtcatgactgttactgctg
caataacactgtatattatttataaattccgtttgtctaggtatctgatgtaggcattccgatcccctt
tactattgcgtcttcacgaccaaatgggaatgcgccaaaatcccacacctcatcccctggaggcag
attgtgtattattaatatccgccgattgaagcacaaaacggtacggtactgttcctaattctggtata
gattctatggtcaaaagtctgcatatccccgacattgccatgagatcacacagtccaagtagcatgtt
tattgagtcactcagactgtcaacgtccctcgccgcaccaccaatcgaaaataaagtatctacgcaag
ttatagctccgcattttctatcgctagcagcaatcgcgacgcaaaacataaaggccatgttgggattt
gaactctctgggggggcttgttatcttctgcaccgtcgcagtcgcagttttccgaaatttatgtctaat
atattttccggccgtgctccaatcggccgaaaagaatctgcgtattaccagactcattgacgggccga
taaagaccataaaacaaaattcctgtgcactccctcctccagtttgccatcgtccaagtcccgtaac
tttttttgcgtttcgaggagcaagcgttcgttatccctacccacacttgttttccaccgttttcttat
tataagcggttgtatcgccaacgcgtcaccgcaggttgtcacatacagtgatggcatacttgaacgtg
caacaacgcgctcgctttgcaaatctaagtcattgaccatcaaatcgcgttgagaggatagccaggca
tctttttcctagtatggtgacggtgcagccaccccaactcagttcttgtaaaaaaagctattggcgg
gaatttatgttctgaggtgcattctatatttatgagtccatcaaatgccattaaccagattcgtattt
tttcgctcgacccggcatcactatggatacaataccctttctatggcccatttcagctctcgaaccaac
cacacggacaattgactaacataagtatgatctttatcacagtcgcacccatctgagttatatttatg
gcatccgagcgctcttactgtacggtcggatacacccatggttttccttttatatgtcgggttatag
tctgtcgggtttggcggtagcacggagtagtttgattttttaagaatcgaaaccggcttggagagacc
actgtcgaatatttgtccgtatactctacacgtgagtgttgtccattcctaggtatattcatctgttc
ggatacctctcaattgctcgttcaggcataacccttaaagcatatgtttatgttgtacatcaaaacttggtg
agttatgttcgattgccgcgcataaagaatcgtacatgagcgtttctgctaacatactatctatattc
tcacacgcccctgcatatactgttcctattccaaattcacgttttgcccccatcggctatctgctccca
aaaagttgtaatataggtgccgctgggtgcgaaattttcatcagttgtattcctgataaactgaatca
ctttacataattttttgccacatatctgcgtgcagccatagtatcgaacccgtgggctcggagacgaca
```

-continued

```
gtgcgtacaatgggtattttaccttttccccaacaaaataatggtatacaagttaggtccgtacctaga
ccttaatgtttccaattcttctgaatcactgcactctcgtagggagtaacggtaataatttcgtctc
tgagccccgttttgcgttgaaaactaatcacattagataatgtgcaatcggtttctttatccggata
catctaagtattatgacatcggtggtcattgtttccatcaacgaccatcttttacgatcgcccatact
actcatggacgttgtcggtgttgaaaaatcaccagaattgcaacggatctctgggtaccatgctgctg
atggaattggcggttttaattgttgtttcagtctattattgctatctttggcggggttgaataatgtg
ggggagagtgattgcaggaatccgaatgggtcaataaaacgaccgtgctccgttctgccggcgccga
tccgattgaagctatatacttcgcttctctcccccacttttccaatttgatccggaaataaaacggccc
cggacaacagtatcgtacgatccggatccggatcctgcttgcctacagaagaatcaacatctcgcccc
aatattctggtcaaaactggctcgctcatggcaacgcggacgtttccccggtggccagtcttaatgg
ttaatgttcttttcggcaatcttatacatcagcgggtgcgtgaatactggtcacagttcagtcattt
actacacaccagcaatacgacgacggacagtaccgtcccgacgaacgcgacgcccaaaattgctatcg
cgaccgcgtccgaggcgatgtcgtacgggcggtgcgggttggatcctcggcaaagagatcctcgtaa
ttcggcggtgggagcggagggtaaagacgcgggtggggatctccctccggaccgcgcgccgggcgcgg
ttcgaaaatgctttccgcctcgctcagtgtcaacgccaagtattcgggcgggctgggggccggaatat
ctcccgcgacttcttctatcggcgcggaattggagtcgcggtcgtggcgcgcttctagcgtcgtcaac
ggaagtccattttcggggtctcccggtgggcgttcagcgtccatcgtcgtatatgctctaacacacgt
ctcgctatattaaaaaaaagaagagtatcggtcagtgtcgagtgtcgccgacaatgtcgcgagttctc
ggcgatttaattttttggaactgctccctatgaatcccgtaactgtagcgcccgcgcagaaagccgcca
tcagaccaactacgtgtctgttcgatgtttgcccgccgatcgctttaccgattaaggttccggcgaga
aatgacatgctcgatccaagaacaaagtttttcgcggtaaacaacaacatagttaccgtgcgagatgg
agaaaccacatctcccgaattagtagaggaaagcccgcgctgtcggtttggggacatatcgatcttt
ttgtgttttcctaggacccttttgccagatcgtacaaagtcgcgtcttatgagcggacgttcttact
gcagctcggtaggagtggggcagggttagatttcgtcggcgtttcggccccgtatgcgccgcgccac
cctcttcgccgagctctttatgcgcggtgggggtgagcgcttccggagttgcgatctccgatctcgag
ccgcagcccggcggtgtctcttcagtggagcgttagcgccatcatgtggttcgtggcggtggaaagg
ctattatgtgttaggggagagaccacgtgatcggcatgcaaatgagcaaggcgaacgcgtcagcgttc
gcactgcgaaccaataatatatatattatactattggctttaggtgcgaacgtccggctagtccaata
gcggggtcgcgtttcgtaccacgtgttatagaccgccctaaactcgcactcgggggtccggccgcgcc
cagacagggcggagacgtgccacaggggcttaaaacaccgcttcgggcaccgttcatctcggcgcgc
c SEQ ID NO 27: VP2/1C1#8 (HVT/IBDV/ILT/NDV #3 virus)
MCMV IEpro-VP2-SV40pA/HVT UL54.5 region (11,665 bp)
ggcgcgcactggagaacggcatgaccgcaaaaggcgttgtagagatcgatcccacgaactctcaggc
gatcgtgtcagtcgccataaacagcgacgatcgtctccaggatctgaacggttttcttctcaacgatc
atcagtatatgaggaactgaacctgatatttagccgagggaaacgcaggttaaaaacccatcaagcg
attgcgattttcgcgtatctagtaaaaatagatgggcttcggtactagccttcgccgccaactctgaa
tatgccttcgtggacctcatataacatggcattgtttgttggatgcggggccggaattaagaagaac
attcgaaatacgagcaaaaatttcggccctggcatgtgctgcgcgagaatcggtacttcggggagaaa
gttttatcggagctttgggtagtgcagaggaaactctatcttggttgaaaatgcatgcgaccctgcac
ttgattctggttaaccacgatccaattttaagacggctggcgcggtcctagataacctccgcttaaa
actagcccaatattgatgtgcagatataacacagaaaaacgatcaatggaagacatgctacggcggt
catctcccgaagacatcaccgattccctaacaatgtgcctgattatgttatcgcgcattcgtcgtacc
atgcgcaccgcaggaaataaatatagctatatgatagatccaatgaatcgtatgtctaattacactcc
aggcgaatgtatgacaggtatattgcgatatattgacgaacatgctagaaggtgtcctgatcacatat
gtaatttgtatatcacatgtacacttatgccgatgtatgtgcacgaatattatgtctattgtaattca
tttttttgttagtaaactaccacaggctgtccggaaatctaagttaatgaataaagtagatggttaat
actcattgcttagaattggactacttttaattctctttaatgttcgtattaaataaaaacatcttaa
taaacttcagcctcttcgcttattgtagaaattgagtattcaaaatcatgttcaaagccgtcttcgga
gagtgtactcgccacggtggttggaacatcactatgtctacacgtcaaatttaagcacgtcaggtctg
tcgaggacaagaaatggttaactagtgtttcaattattcttataaacgttaagcattgtaagccccc
ggccgtccgcagcaacaatttactagtatgccgtgggctccgggactatcacggatgtccaattcgca
catgcatataatttttctagggtctctcatttcgagaaatcttcggggatccatcagcaatgcgggct
gtagtcccgattcccgtttcaaatgaaggtgctccaacacggtcttcaaagcaaccggcataccagca
aacacagactgcaactcccgctgcaatgattggttataaacagtaatctgtcttctggaagtatatt
tcgcccgacaatccacggcgccccaaagttaaaaaccatccatgtgtatttgcgtcttctctgttaa
aagaatattgactggcattttcccgttgaccgccagatatccaaagtacagcacgatgttgcacggac
gactttgcagtcaccagccttccttttccaccccccccaccaaacaaaatgtttatcgtaggaccccatatc
cgtaataaggatgggtctggcagcaaccccataggcgcctcggcgtggtagttctcgaggccttaagc
ttaaggatccccaactccgcccgttttatgactagaaccaatagtttttaatgccaaatgcactgaa
atcccctaatttgcaaagccaaacgcccctatgtgagtaatacggggactttttacccaatttccca
cgcggaaagcccctaatacactcatatggcatatgaatcagcacggtcatgcactctaatggcggcc
cataggggactttccacataggggcgttcaccattccccagcaggttggtgactcaatggcctt
acccaagtacattgggtcaatgggaggtaagccaatgggttttccattactggcaagcacactgag
tcaaatgggactttccactgggttttgcccaagtacattgggtcaatgggaggtgagccaatgggaaa
aacccattgctgccaagtacactgactcaatagggactttccaatgggttttccattgttggcaagc
atataaggtcaatgtgggtgagtcaataggggactttccattgtattctgcccagtacataaggtcaat
agggggtgaatcaacaggaaagtcccattggagccaagtacactgcgtcaatagggacttttccattgg
gttttgcccagtacataaggtcaatagggatgagtcaatgggaaaaacccattggagccaagtacac
tgactcaatagggactttccattgggttttgcccagtacataaggtcaataggggtgagtcaacagg
aaagttccattggagccaagtacattgagtcaatagggactttccaatgggttttgcccagtacataa
ggtcaatggaggtaagccaatgggttttccattactggcacgtatactgagtcattagggactttt
ccaatggttttgcccagtacataaggtcaatagggtgaatcaacaggaaagtcccattggagccaa
gtacactgagtcaatagggactttccattgggttttgcccagtacaaaaggtcaataggggtgagtc
aatgggttttcccattattggcacgtacataaggtcaataggggtgagtcattgggttttccagcc
aatttaattaaaacgccatgtactttcccaccattgacgtcaatgggctattgaaactaatgcaacgt
gacctttaaacggtactttcccatagctgattaatgggaaagtaccgttctcgagccaatacacgtca
atgggaagtgaaagggcagccaaaacgtaacaccgccccggttttcccctggaaattccatattggca
```

-continued

```
cgcattctattggctgagctgcgttctacgtgggtataagaggcgcgaccagcgtcggtaccgtcgca
gtcttcggtctgaccaccgtagaacgcagagctcctcgctgcaggcggccgctctagaactcgtcgat
cgcagcgatgacaaacctgcaagatcaaacccaacagattgttccgttcatacgagccttctgatgc
caacaaccggaccggcgtccattccggacgacaccctggagaagcacactctcaggtcagagacctcg
acctacaatttgactgtggggacacagggtcagggctaattgtcttttcctggattccctggctc
aattgtgggtgctcactacacactgcagagcaatgggaactacaagttcgatcagatgctcctgactg
cccagaacctaccggccagctacaactactgcagactagtgagtcggagtctcacagtgaggtcaagc
acactccctggtggcgtttatgcactaaacggcaccataaacgccgtgaccttccaaggaagcctgag
tgaactgacagatgttagctacaatgggttgatgtctgcaacagccaacatcaacgacaaaattggga
atgtcctggtaggggaaggggtcactgtcctcagcctacccacatcatatgatcttgggtatgtgagg
cttggtgacccattcccgctataggcttgacccaaaaatggtagctacatgcgacagcagtgacag
gcccagagtctacaccataactgcagccgatgattaccaattctcatcacagtaccaaccaggtgggg
taacaatcacactgttctcagccaacattgatgctatcacaagcctcagcattggggagagctcgtg
tttcaaacaagcgtccaaggccttgtactgggcgccaccatctaccttataggctttgatgggactgc
ggtaatcaccagagctgtggccgcagataatgggctgacggccggcaccgacaatcttatgccattca
atcttgtcattccaaccaatgagataaaccagccaatcacatccatcaaactggagatagtgacctcc
aaaagtggtggtcaggcaggggatcagatgtcatggtcggcaagtgggagcctagcagtgacgatcca
tggtggcaactatccaggggcctccgtcccgtcacactagtagcctacgaaagagtggcaacaggat
ccgtcgttacggtcgctggggtgagtaacttcgagctgattccaaatcctgaactagcaaagaacctg
gttacagaatacggccgatttgacccaggagccatgaactacacaaaattgatactgagtgagaggga
ccgtcttggcatcaagaccgtctggccaacaagggagtacactgattttcgtgagtacttcatggagg
tggccgacctcaactctcccctgaagattgcaggagcatttggcttcaaagacataatccgggctata
aggaggtagatccagacatgataagatacattgatgagtttggacaaaccacaactagaatgcagtga
aaaaaatgctttatttgtgaaatttgtgatgctattgctttatttgtaaccattataagctgcaataa
acaagttaacaacaacaattgcattcattttatgtttcaggttcaggggagagtgtgggaggtttttt
cggatcctctagagctcgaggatacatccaaagagggttgagtattctctctacacttcttgttaaatgg
aaagtgcatttgcttgttcttacaatcggcccgagtctcgttcacagcgcctcgttcacacttaaacc
acaaatagtctacaggctatatgggagccagactgaaactcacatatgactaatattcgggggtgtta
gtcacgtgtagcccattgtgtgcatataacgatgttggacgcgtccttattcgcggtgtacttgatac
tatggcagcgacgcatgggatattcatcctcgtcatcgttaacatctctacgggttcagaatgtttggc
atgtcgtcgatcctttgcccatcgttgcaaattacaagtccgatcgccatgaccgcgataagcctgta
ccatgtggcattagggtgacatctcgatcatacattataagaccaacgtgcgagtcttccaaagacct
gcacgccttcttcttcggattgtcaacgggttcttcagaatctatgcccatatctggcgttgagacca
ttgtgcgtttaatgaacaataaagcggcatgccatggaaaggagggctgcagatctccattttctcac
gccactatcctggacgctgtagacgataattataccatgaatatagagggggtatgtttccactgcca
ctgtgatgataagtttctccagattgttggatatctgcattttctgctgccgaacaaacttcatcgc
tatgcaaagagatgcgtgtgtacacgcgccggtggagtatacgggaaactaaatgttcatagaggtct
ttgggctatatgttattaaataaaataattgaccagtgaacaattgtttaatgttagtttattcaat
gcattggttgcaaatattcattacttctccaatcccaggtcattcttttagcgagatgatgttatgaca
ttgctgtgaaaattactacaggatatattttttaagatgcaggagtaacaatgtgcatagtaggcgtag
ttatcgcagacgtgcaacgcttcgcatttgagttaccgaagtgcccaacagtgctgcggttatggttt
atgcgcacagaatccatgcatgtcctaattgaaccatccgattttcttttaatcgcgatcgatgttt
gggcaactgcgttatttcagatctaaaaaatttaccctttatgaccatcacatctctctggctcatac
cccgcttggataagatatcatgtgagttccgccctaagaaatgcaaactaacattattgtcggttcca
tatacacttccatcttgtccttcgaaaataacaaactcgcgcaatagaccgtccgtacatgcatggcc
gatgtgtgtcaacatcattggtctgctagatcccgatgggacgaatcgtacagtcgtcgctccagcat
tggcaaaaatccccagatacctccatgcggcaaatctaaattgcgaacgacgcgccaagagactgcaccaaa
gtcttatcgacgcacgctgattttttttgaacagcgggagccattatcttcagtggagcgtagacggg
cgaggctaattatgtgacatagcaacactgcatgtatgttttataaatcaataagagtacataattt
attacgtatcatttccgtttgtaatatactgtatacatcatccacactattagtcagcactagcgcgc
gggcgacgttacaatagcagcgtgcccgttatctatattgtccgatatttacacataacatttcatc
gacatgattaaatacctaagtactgcacacagatgtttaatgtatatcgtcataaatttatatcgct
aggacagacccaaacgacctttatcccaaacagtcagatcctcttctcaagtgtcgatttctgttatg
gaatatgcatacccctggcccagaaattgcacgcacgagcgtagtaatgcgtcattggttttacattt
aaaggctaaatgcacaaattctttagacgacagcacatcgttaaatagcatctctagcgttcttatga
atgctaagcattggagtcctcctggtcggccacaataacagctgagtatcataccctgagctccgggg
ttgtcgcacatagcggattcgtataaacataggattttccgcgaatccatcagttgcaaaaatctgtt
aggctccatcaacaacgctggatttacttcagatccacgcgtaaagtaatggtgctcgaataccgttt
ttagagttgtcggcatttcaaggaacaaagaattcatttcttcattgcaacgacgcgccagaaatccc
aagacctctttgggtagtatgttcttgcctataaaacacggcgttccaagtgccaggaaccacgcatg
tgttactgttggggcgtattcagaaataaagcgggggtttatgcggcttttgaagctcggatatccaaa
gtatcgcttgctgatgaacgagcgatgtagctgttacaaaacctcctttccatcctccagtcaacata
atatttatcggcctacctatgtccgtaataagtattggtcgggcaattattccgtatgaggtcttgca
ggaataagctcttagggacagccagcttggatatggtgcgaagacccttctcggcttcagaatgtc
gctccgcagtctcttcgtgtcggtgcatcttagatccaccatcaatgtgtgcagcattgactcccgcc
cgtcgaatattcctttgttacgatgcagtaatgagcacgatcatgggcggggcgatgacgttctatt
tgcatgtctgcgaacaatttgcgtcagtcatacagctatggagtgggccatttctggccgtcaactta
aaaacgcgaaccgcagacatatgtatttgcatgcaaagacgtatcttcgtatttctgggcatcttcaa
atgctctggccaatatgcaatgaatttggattcgtttgacgcgatggtatgcagtgcaaatgtgcc
aatagcccacatccgaaaaagttatttgtcatacaagcaggtgttaagtagcaatcacataaaggcac
cagacgcctcatggcatcataatgaatagctccttctccccactggaaccactgacaaaatctgcgag
tatattccgcaaaccacattttattttctcatagaaactaccctaaatcctttttaacgggaagaagaat
cctagatagtgcttgaagtcatgactgttactgctgcaataacactgtatatttatttataaaattccgt
ttgtctaggtatctgatgtaggcattccgatcccttttactattgcgtcttcacgaccaaatggaatg
cgccaaaatccccacacctcatcaccctggaggcagattgtgtattattaatatccgccgattgaagc
acaaaacggtacggtactgttcctaattctggtatagattctatggtcaaaagtctgcatatccccga
cattgccatgagatcacacagtccaagtagcatgtttattgagtcactcagactgtcaacgtccctcg
ccgcaccaccaatcgaaaataaagtatctacgcaagttatagctccgcattttctatcgctagcagca
atcgcgacgcaaaacataaaggccatgttgggatttgaactctctgggggggcttgttatcttctgcac
```

-continued cgtcgcagtcgcagttttccgaaatttatgtctaatatattttccggccgtgctccaatcggccgaaa
agaatctgcgtattaccagactcattgacgggccgataaagaccataaaacaaaattcctgtgcactc
cctcctccagttttgccatcgtccaagtcccgtaactttttttgcgtttcgaggagcaagcgttcgtt
atccctacccacacttgttttccaccgttttcttattataagcggttgtatcgccaacgcgtcaccgc
aggttgtcacatacagtgatggcatacttgaacgtgcaacaacgcgctcgctttgcaaatctaagtca
ttgaccatcaaatcgcgttgagaggatagccaggcatcttttttcctagtatggtgacggtgcagcca
ccccaactcagttcttgtaaaaaaagctattggcgggaatttatgttctgaggtgcattctatattta
tgagtccatcaaatgccattaaccagattcgtatttttcgctcgacccggcatcactatggatacaa
taccttttctatggcccatttcagctctcgaaccaaccacacggacaattgactaacataagtatgatc
tttatcacagtcgcacccatctgagttatatttatggcatccgagcgctcttactgtacggtcggata
cacccatggttttcctttatatagtcgggttatagtctgtcggtttggcggtagcacggagtagtt
tgattttaagaatcgaaaaccggcttggagagaccactgtcgaatatttgtccgtatactctacacg
tgagtgttgtccattcctaggtatattcatctgttcggataccttcaattgctgttcaggcataacct
taaagcatatgttatgttgtacatcaaaacttggtgagttatgttcgattgccgcgcataaagaatcg
tacatgagcgtttctgctaacatactatctatattctcacacgcccctgcatatactgttcctattcc
aaattcacgttttgccccatcggctatctgctcccaaaaagttgtaatataggtgccgctgggtgcga
aattttcatcagttgtattcctgataaactgaatcactttacataattttttgccacatatctgcgtgc
agccatagtatcgaacccgtgggctcggagacgacagtcgtgcaacaacgctgtattttacctttcccaa
caaaataatggtatacaagttaggtccgtacctagaccttaatgtttccaattcttctgaatcactgc
actctcgtaggggagtaacggtaataaatttcgtctctgagcccgttttgcgttgaaaactaatcaca
ttagataatgtgcaatcggtttctttttatccggatacatctaagtattatgacatcggtggtcattgt
ttccatcaacgaccatcttttacgatcgcccatactactcagtgacgttgtcggtgttgaaaaatcac
cagaattgcaacggatctctgggtaccatgctgctgatggaattggcggttttaattgttgtttcagt
ctattattgctatctttggcggggttgaataatgtgggggggagagtgattgcaggaatccgaatgggt
caataaaacgaccgtgctccgttctgccggcgccgatccgattgaagctatatacttcgcttctctcc
ccacttttccaatttgatccggaaataaaacggcccggacaactatcgtacgatccggatccgga
tcctgcttgcctacagaagaatcaacatctcgccccaatattctggtcaaaactggctcgctcatggc
aacgcggacgtttccccggtggccagtcttaatggttaatgttcttttcggcaatcttatacatcag
cgggttgcgtgaatactggtcacagttcagtcatttactacacaccagcaatacgacgacggacagta
ccgtcccgacgaacgcgacgcccaaaattgctatcgcgaccgcgtccgaggcgatgtcgtacgggcgg
tgcggggttggatcctcggcaaagagatcctcgtaattcggcggtgggagcggagggtaaagacgcgg
gtggggatctccctccggaccgcgcgccgggcgcggttcgaaaatgcttccgcctcgctcagtgtca
acgccaagtattcgggcgggctgggggccggaatatctcccgcgacttcttctatcggcgcggaattg
gagtcgcggtcgtggcgcgcttctagcgtcgtcaacggaagtccattttcggggtctcccggtgggcg
ttcagcgtccatcgtcgtatatgctctaacacacgtctcgctatattaaaaaaaagaagagtatcgt
cagtgtcgagtgtcgccgacaatgtcgcgagttctccggcgatttaatttttggaactgctccctatga
atcccgtaactgtagcgcccgcgcagaaagccgccatcagaccaactacgtgtctgttcgatgtttgc
ccgccgatcgctttaccgattaaggttccggcgagaaatgacatgctcgatccaagaacaaagtttt
cgcggtaaacaacaacatagttaccgtgcgagatggagaaaccacatctcccgaattagtagaggaaa
gcccgcgctgtcggtttggggacatatcgatcttttttgtgtttttcctaggaccccttttgccagatc
gtacaaagtcgcgtcttatgagcggacgttcttactgcagctcggtaggagtggggcagggttagatt
tcgtcggcgtttcggccccgtatgcgccgcgccaccctcttcgccgagctctttatgcgcggtgggg
gtgagcgcttccggagttgcgatctccgatctcgagccgcaacccggcgggtgctctttcagtggagc
gttagcgccatcatgtggttcgtggcggtggaaaggctattatgtgttagggagagaccacgtgatc
ggcatgcaaatgagcaaggcgaacgcgtcagcgttcgcactgcgaaccaataatatatatattatact
attggctttaggtgcgaacgtccggctagtccaatagcggggtcgcgtttcgtaccacgtgttataga
ccgccctaaactcgcactcggggtccggccgcgcccagacagggcggagacgtgccacaggggcttt
aaaacaccgcttcgggcaccgttcatctcggcgcgcc SEQ ID NO 28: 1332-47.A2 (HVT/IBDV/ILT/NDV #3 virus)
ILT/hCMV IEpro-F-IE(term

```
gacattgcttgtatacatattaaatactttctcaagttcctattacataaaatgggatctatcattac
attcgttaagagtctggataattttactgtttgccagcttcgatcttggaacgtactgtggatagtgc
cttacttggaatcgtgaaaatttgaaacgtccattatttggatatcttccggttgtcccatatcccgc
cctggtaccgctcggataccttgcccgtatggattcgtattgacagtcgcgcaatcggggaccaacaa
cgcgtgggtccacactcattcggaaattttccgatgattctgaatatttattgccgctcgttacgagt
cgttggacatatctgtaatacattcttcttctgaaggatcgctgcacatttgatctatacattggcc
aggatgttcaagtctcagatgttgcattctggcacagcacaactttatggcatttccgatgtaatcgt
ccggcagccctgggggagttctatattcgcatattgggatggtaaggacaatagcagatctcgcaacc
tccagggaggctataataacgtttttaaaggatggatttctcataaaaatctgtcgcaaattcactg
agaatatccttactagcgccgattgagagcatcgtcgtccaattttctaaatggaaagaaaacaagg
cgggcaagagtgttccaaacattttcattttcggcgaatctctcaaatcccatggcgtgcaattgatt
gcaaaattggcacttccgttcacgtttgtatctccaaactctaagacacttttaattgaaaaactacg
ttctagtgtggaaagaaacctataggcagaccatagaactatttgacaccacatatctttttgtatgt
caaactgaccatgatcgtatgttgctgaatgcactagggcaattcgctcgcgcgactccatacattga
ataattccacacgtcagctcatcggttagcaaggtccagtagttgaagtcatttattttttccccgcgg
ctggccaaatctacctctgggaatatccaagttgtcgaatatgatcgcaccggctctggtcatggtga
aggaactgtagcataaagacgcaggtatcatagggtaatattttttttattcactcacatactaaaag
taacgcatattagcaccatgtatgggctatcaattgacatttgcgtagcactacatcacgattatgta
caacataatgggacaacatatggcaagtagatgcaatttcctcacactagttgggtttatctactatt
gaattttccccatctgtgatacacttgggagcctctacaagcatattgccatcatgtacgtttttat
ctactgtcttaacgcccatgggaacggaggcgtcgtcgtcatgtattggacggcaacataggcagcaa
cacaaattgcgtttaggtgggtgcatgtggactcgataccaagccccctgcagctggggaacgtctgg
tggagagccgataaatttgatatacgcacgccatattactgtcgttgaagtacgccttatcttctatgt
tttcaaatttaggttcccaagtggacgtgagaagtgtttgtatctcacatggaatggcccaaggcatt
ccagcccaggtgcctggtactttaatggcaaacaaacgttttggtagaggtattgattctattgcagt
tctgcagatatctgcagccccgagtatccacaggctatacgatacgatcggaggcaagcttgttaa
ttaagtcgacggcagagtcgcagacgcccctattggacgtcaaaattgtagaggtgaagttttcaaac
gatggcgaagtaacggcgacttgcgtttccaccgtcaaatctccctatagggtagaaactaattggaa
agtagacctcgtagatgtaatggatgaaatttctgggaacagtcccgccgggtttttaacagtaatg
agaaatggcagaaacagctgtactacagagtaaccgatggaagaacatcggtccagctaatgtgcctg
tcgtgcacgagccattctccggaaccttactgtcttttcgacacgtctcttatagcgagggaaaaaga
tatcgcgccagagttatacttctgatccgcaaacggcatactgcacaataactctgccgtccg
gcgttgttccgagattcgaatggagccttaataatgtttcactgccggaatatttgacggccacgacc
gttgtttcgcataccgctggccaaagtacagtgtggaagagcagcgcgagagcaggcgaggcgtggat
ttctggccggggaggcaatatatacgaatgcaccgtcctcatctcagacggcactcgcgttactacgc
gaaaggagaggtgcttaacaaacacatggattgcggtggaaaacggtgctgctcaggcgcagctgtat
tcactcttttctggacttgtgtcaggattatgcgggagcatatctgctttgtacgcaacgctatggac
cgccatttatttttgaggaatgcttttggactatcgtactgcttcttccttcgctagccagagcac
cgccgcgtcacgtacgactacattttaggccgtcgcgcgctcgacgcgctaaccataccggcggttg
gcccgtataacagataccctcactagggtatcaagaggctgcgacgttgtcgagctcaacccgatttct
aacgtggacgacatgatatcggcggccaaagaaaaagagaaggggggcccttcgaggcctccgtcgt
ctggttctacgtgattaagggcgacgacggcgaggacaagtactgtccaatctatagaaaagagtaca
gggaatgtggcgacgtacaactgtatctgaatgcgccgttcaatctgcacagatgtgggcagtggac
tatgttcctagcaccctgtatcgcgaaatggcgcgggactgactatattctccccactgctgcgct
ctctggccaatacttgctgaccctgaaaatcgggagatttgcgcaaacagctctcgtaactctagaag
ttaacgatcgctgtttaaagatcgggtcgcagcttaacttttaccgtcgaaatgctggacaacagaa
cagtatcagactggatttcaaggcgaacacctttatccgatcgcaataacacgacacgcgga
cgacgtatatcggggatacgaagatattctgcagcgctggaataatttgctgaggaaaaagaatccta
gcgcgccagaccctcgtccagatagcgtcccgcaagaaattcccgctgtaaccaagaaagcggaaggg
cgcacccgacgcagaaagcagcgaaaagaaggcccctccagaagactcggaggacgacatgcaggc
agaggcttctggagaaaatcctgccgccctccccgaagacgaagtccccgaggacgacgagcacg
atgatccaaactcggatcctgactattacaatgacatgcccgccgtgatcccggtggaggagactact
aaaagttctaatgccgtctccatgcccatattcgcggcgttcgtagcctgcgcggtcgcgctcgtggg
gctactggtttggagcatcgtaaaatgcgcgcgtagctaatcgagcctagaataggtggtttcttcct
acatgccacgcctcacgctcataatataaatcacatggaatagcataccaatgcctattcattgggac
gttcgaaaagcatggcatcgctacttggaactctggctctccttgccgcgacgctcgcacccttcggc
gcgatgggaatcgtgatcactggaaatcacgtctccgccaggattgacgacgatcacatcgtgatcgt
cgcgcctcgccccgaagctacaattcaactgcagctattttttcatgcctggccagagaccccacaaac
cctactcaggaaccgtccgcgtcgcgtttcggtctgatataacaaaccagtgctaccaggaacttagc
gaggagcgctttgaaaattgcactcatcgatcgtcttctgttttttgtcggctgtaaagtgaccgagta
cacgttctccgcctcgaacagactaaccggacctccacacccgtttaagctcactatacgaaatcctc
gtccgaacgacagcgggatgttctacgtaattgttcggctagacgacaccaaagaacccattgacgtc
ttcgcgatccaactatcggtgtatcaattcgcgaacaccgccgcgactcgcggactctattccaaggc
ttcgtgtcgcaaccttcggattacctaccgtccaacttgaggcctatctcaggaccgaggaaagttggc
gcaactggcaagcgtacgttgccacggaggccacgacgaccagcgccgaggcgacaaccccgacgcc
gtcactgcaaccagcgcctccgaacttgaagcggaacactttaccttccctggctagaaaatggcgt
ggatcattacgaaccgacacccgcaaacgaaaattcaaacgttactgtccgtctcgggacaatgagcc
ctacgctaattggggtaaccgtggctgccgtcgtgagcgcaacgatcggcctcgtcattgtaatttcc
atcgtcaccagaaacatgtgcaccccgcaccgaaaattagacacggtctcgcaagacgacgaagaacg
ttcccaaactagaagggaatcgcgaaaatttggacccatggttgcgtgcgaaataaacaaggggggctg
accaggatagtgaacttgtggaactggttgcgattgttaacccgtctgcgctaagctcgcccgactca
ataaaaatgtgattaagtctgaatgtggctctccaatcatttcgattctctaatctcccaatcctctc
aaaaggggcagtatcggacacggactgggaggggcgtacacgatagttatatggtacagcagaggcct
ctgaacttaggaggagaattcagccggggagagcccctgttgagtaggctgggagcatattgcag
gatgaacatgttagtgatagttctcgcctcttgtcttgcgcgcctaacttttgcgacgcgacacgtcc
tcttttggaaggcactcaggctgtcctcggggaagatgatcccagaaacgttccggaagggactgta
atcaaatggacaaagtcctgcggaacgcgtgcaagatgaaggcggccgatgtctgctcttcgcctaa
ctattgctttcatgattttaatttacgacggaggaaagaaagactgcccgcccgcgggaccctgtctg
caaacctggtaattttactaaagcgcggcgaaaagcttcgcgcaggtcaattccctggcattatgccc
```

```
agtacatgaccttatgggactttcctacttggcagtacatctacgtattagtcatcgctattaccatg
gtgatgcggttttggcagtacatcaatgggcgtggatagcggtttgactcacggggatttccaagtct
ccacccattgacgtcaatgggagtttgttttggcaccaaaatcaacgggactttccaaaatgtcgta
acaactccgcccattgacgcaaatgggcggtagcgtgtacggtggaggtctatataagcagagctc
gtttagtgaaccgtcagatcgcctggagacgccatccacgctgttttgacctccatagaagacaccgg
ttgcgcgccaccatgggcccagaccttctaccaagaacccagtacctatgatgctgactgtccgag
tcgcgctggtactgagttgcatctgtccggcaaactccattgatggcaggcctcttgcggctgcagga
attgtggttacaggagacaaagccgtcaacatatacacctcatcccagacaggatcaatcatagttaa
gctcctcccgaatctgcccaaggataaggaggcatgtgcgaaagcccccttggatgcatacaacagga
cattgaccactttgctcacccccccttggtgactctatccgtaggatacaagagtctgtgactacatct
ggaggggggagacaggggcgccttataggcgccattattggcggtgtggctcttggggttgcaactgc
cgcacaaataacagcggccgcagctctgatacaagccaaacaaaatgctgccaacatcctccgactta
aagagagcattgccgcaaccaatgaggctgtgcatgaggtcactgacggattatcgcaactagcagtg
gcagttgggaagatgcagcagtttgttaatgaccaatttaataaaacagctcaggaattagactgcat
caaaattgcacagcaagttggtgtagagctcaacctgtacctaaccgaattgactacagtattcggac
cacaaatcacttcacctgctttaaacaagctgactattcaggcactttacaatctagctggtggaaat
atggattacttattgactaagttaggtgtagggaacaatcaactcagctcattaatcggtagcggctt
aatcaccggtaaccctattctatacgactcacagactcaactcttgggtatacaggtaactctacctt
cagtcgggaagctaaataatatgcgtgccacctacttggaaaccttatccgtaagcacaaccagggga
tttgcctcggcacttgtcccaaaagtggtgacacaggtcggttctgtgatagaagaacttgacacctc
atactgtatagaaactgacttacattttatattgtacaagaatagtaacgttcctatgtccctggta
tttattcctgcttgagcggcaaatacgtcggcctgtatgtactcaaagaccgaaggcgcacttactaca
ccatacatgactatcaaaggttcagtcatcgccaactgcaagatgacaacatgtagatgtgtaaaccc
cccgggtatcatatcgcaaaactatggagaagccgtgtctctaatagataaacaatcatgcaatgttt
tatccttaggcgggataactttaaggctcagtggggaattcgatgtaacttatcagaagaatatctca
atacaagattctcaagtaataataacaggcaatcttgatatctcaactgagcttgggaatgtcaacaa
ctcgatcagtaatgctttgaataagttagaggaaagcaacagaaaactagacaaagtcaatgtcaaac
tgactagcacatctgctctcattacctatatcgtgttgactatcatatctcttgttttttggtatactt
agcctgattctagcatgctacctaatgtacaagcaaaaggcgcaacaaaagaccttattatggcttgg
gaataatactctagatcagatgagagccactacaaaaatgtgagatctctcgaggaattctagatcc
cacgtcactattgtatactctatattatactctatgttatactctgtaatcctactcaataaacgtgt
cacgcctgtgaaaccgtactaagtctcccgtgtcttcttatcaccatcaggtgacatcctcgcccagg
ctgtcaatcatgccggtatcgattccagtagcaccggccccacgctgacaacccactcttgcagcgtt
agcagcgcccctcttaacaagccgacccccaccagcgtcgcggttactaacactcctctccccgacct
gcaactagtaagcttgcctccgattctagcattacatagccggtcagtagatcctgccattcggtagc
gcaaccggctacatcttcaaacagtctcacaataaatgcatctctcgttcctgccaatccggaaccgg
gcataccactcccgcctgccgatttaattctcacaattgggcgatgccggcggggcaaaacgaatgtg
gatttggcaaaccgacacaggtctgctgtacggactaatatgggcacacccacatcattcttcagatg
ctccatgcattgttctatgagaaagatccataggtggaggcagcgtcacgagatcgcccaggcaatc
gatcgcattcgtctagtaaagtgacgagagttatcatgcacacacccatgcccacgccttccgaataa
ctggagctgtggaagatcggaaacgtcttttttgactgccggtctcgtactactttcgcacaggtgtat
acccggacgcgtactatatattttatatcatccaacgtccgaaattacatacgtggcggcgatggaag
tagatgttgagtcttcgaaagtaagtgcctcgaatatgggtattgtctgtgaaaatatcgaaagcggt
acgacggttgcagaaccgtcgatgtcgccagatactagtaacaatagcttcgataacgaagacttccg
tgggcctgaatacgatgtggagataaataccagaaaatctgctaatcttgatcgtatggaatcttcgt
gccgtgaacaacgagcggcgtgcgaacttcgaaagtgttcgtgtcctacgtctgccgtgcgcatgcaa
tacagtattctttcatctctcgctccgggttcagagggtcagtgtatatatatgtactagatacgggga
cgcggaccaaaaaaaatgcatagtgaaggcagtcgttggaggaaagaatcccgggagggaagtggata
ttttaaaaaccatctcacataaatcaattataaaattaatccatgcctataaatggaaaaatgttgtg
tgtatggcaatgcgtgtatatcgttatgatcttttcacatatattgacggagtcggccctatgccct
tcaacagatgatctatattcaacgtggactactagagggcgctagcatacatacatgaaaggggcatca
ttcaccgagacgtaaagacggagaatatattcttggataatcacgaaaatgcagttttgggtgacttc
ggtgctgcatgccaactaggagattgtatagatacgcccaatgttacggttggagcggaactgtgga
aacaaattcgccggaattatctgcacttgatccgtattgcacaaaaacagatatttggagtgccggat
tggttctatatgagatggcaattaaaaatgtaccattgtttagtagcaggtgaaaagttcgggatct
cagctgagatccataatacggtgcatgcaagtgcatgaactggagtttccccgcaacgattctaccaa
cctctgtaaacatttcaaacaatatgcggttcgtgtacgaccgccttataccattcctcgagttataa
gaaatgggggggatgccaatggatgttgaatatgtcatttctaaaatgcttacgtttgaccaggagttc
agacctctgctaaggaaatattgaatatgcccctatttactaaggcgccgattaacctgcttaatat
cacaccctctgacagtgtctaacggtatacaggcgggagcgggtcgtggcgtcatcatcaccacttga
gaatttatattttgaattgttgattgataaattaacctgattcattgagaactgaaacgccatattgg
tttcttggatatgtctacaacaattagttaaattgctatgttctactgcgagtaacatttgataagtt
gtaagagacgggcgactcatgtcgaagttgacgaatataaagtacataacgtgtttagaatacccaga
atccgaatagtccgcggggcgtcttctcgcgtgagtaccaaatactgagttgaacttgaaaatgcta
aatctgtgacactctttgtgtgatgattattgtcaccacttcgaagatggcttcgacattcatgatgt
tctggtgtttgtttggaatcgtaatagcgcttgtttcgtccaagtctgacaacaaagaaaatctgaag
aattatatcacggataagtcaaccaatattagaataccacgccattatttgtatcaacggaaaactc
ttatcccacaaaacatgtaatctacgatgaaaactgtggcttcgctgtactcaatcctataagtgacc
ccaaatatgtccttttgagccagcttctaatgggaaggcgcaaatatgatgcgacggtcgcgtggttt
gttctcggtaaaatgtgtgccagattaatatatttgcgcgaattttataactgctcgacaaatgagcc
ttttggcacatgttctatgagctctcctggatggtgggacaggcgctacgtctcaaccagtttcattt
ctcgcgacgaattacagctggttttttgcagcgccgtcccgagaattagatggtttatatacgcgcgta
gtagttgtcaacggggactttactacggccgatataatgtttaatgttaaagtggcatgtgccttttc
aaagactggaatagaagatgatacattatgcaaaccctttcatttctttgccaatgcaacattgcaca
atttaaccatgattagatcggtaacttctcgagcgcacgaaagccatttaaaggaatgggtggcacgg
agaggtggtaacgtccctgcagtgctacttgagtctaccatgtatcatgcatccaatctgcctagaaa
tttcagggatttctacataaagtctccagatgattataagtataatcacctagatgggccatctgtaa
tgctcatcactgacagacctagtgaagatttggatgggaggctcgttcaccaaagtgacattttact
actacaagtcctataaaacaggtccggtatgaagagcatcagtcacatacaaagcagtatcctgtaaa
```

```
caaaatacaagctataattttttttgatagggttaggctcgttcattggaagcatattcgtagttttgg
tagtatggattatacgcagatattgcaatggagcgcggagtgggggaacgcccccagtcctcgccgg
tatgtgtataccaggctatgatcacgtgtgaaacttgggcggacctgtatcatatgtacaccgtccct
attcgtttatagccagtacgtgttatctgcacatagaggaacatgtgtcatactgggatcgcatgcat
ggtatgtgtgactctaatattattctgtatcataataaaaaacagtgcatggtatatagaggatcgc
tggtaagcactacggtagaccaatcggctcagattgcattctttggcatcgataccgttgttaattta
tatggcaaagtcttgttcatgggagatcagtatttggaggaaatatactctggaacgatggaaatact
caaatgaatcaagctaaccgctgctattctattgcgcatgcaacatattacgccgactgtcctataa
tcagttctacggtattcagaggatgccgggacgccgttgtttatactaggccccacagcag
```

SEQ ID NO 29: 1332-23.7 (HVT/IBDV/ILT/NDV #4 virus)
ILT/HVT UL54.5 region (12,248 bp)

```
ggcgcgccactggagaacggcatgaccgcaaaaggcgttgtagagatcgatcccacgaactctcaggc
gatcgtgtcagtcgccataaacagcgacgatcgtctccaggatctgaacggttttcttctcaacgatc
atcagtatatgaggaactgaacctgatatttagccgagggaaacgcaggttaaaaaccctatcaagcg
attgcgattttcgcgtatctagtaaaaatagatgggcttcggtactagccttcgccgccaactctgaa
tatgcccttcgtggacctcatataacatggcattgtttgttggatgcggggccggaattaagaagaac
attcgaaatacgagcaaaaatttcggccctggcatgtgctgcgcgagaatcggtacttcggggagaaa
gttttatcggagctttgggtagtgcagaggaaactctatcttggttgaaaatgcatgcgaccctgcac
ttgattctggttaaccacgatccaatttttaagacggctggcgcggtcctagataacctccgcttaaa
actagccccaatattgatgtgcagatataacacagaaaaacgatcaatgaagacatgctacggcggt
catctcccgaagacatcaccgattccctaacaatgtgcctgattatgttatcgcgcattcgtcgtacc
atgcgcaccgcaggaaataaatatagctatatgatagatccaatgaatcgtatgtctaattacactcc
aggcgaatgtatgacaggtatattgcgatatattgacgaacatgctagaaggtgtcctgatcacatat
gtaatttgtatatcacatgtacacttatgccgatgtatgtgcacgggcgatatttctattgtaattca
tttttttgttagtaaactaccacaggctgtccggaaatctaagttaatgaataaagtagatggttaat
actcattgcttagaattggactacttttaattctctttaatgttcgtattaaataaaaacatctttaa
taaacttcagcctcttcgcttattgtagaaattgagtattcaaaatcatgttcaaagccgtcttcgga
gagtgtactcgccacggtggttggaacatcactatgtctacacgtcaaatttaagcacgtcaggtctg
tcgaggacaagaaatggttaactagtgtttcaattattcttataaacgttaagcattgtaagccccc
ggccgtccgcagcaacaatttactagtatgccgtgggctccgggactatcacggatgtccaattcgca
catgcatataattttctagggtctctcatttcgagaaatcttcggggatccatcagcaatgcgggct
gtagtcccgattcccgtttcaaatgaaggtgctccaacacggtcttcaaagcaaccggcataccagca
aacacagactgcaactcccgctgcaatgattggttataaacagtaatctgtcttctggaagtatatt
tcgcccgacaatccacggcgccccaaagttaaaaaccatccatgtgtatttgcgtcttctctgttaa
aagaatattgactggcattttcccgttgaccgccagatatccaaagtacagcacgatgttgcacggac
gactttgcagtcaccagccttcctttccacccccccaccaacaaaatgtttatcgtaggacccatatc
cgtaataaggatgggtctggcagcaaccccataggcgcctcggcgtggtagttctcgaggccttaatt
aagtcgacggcagagtcgcagacgccctattggacgtcaaaattgtagaggtgaagttttcaaacga
tggcgaagtaacggcgacttgcgtttccaccgtcaaatctccctataggtagaaactaattggaaag
tagacctcgtagatgtaatggatgaaatttctgggaacagtcccgccgggggtttttaacagtaatgag
aaatggcagaaacagctgtactacagagtaaccgatggaagaacatcggtccagctaatgtgcctgtc
gtgcacgagccattctccggaaccttactgtcttttcgacacgtctcttatagcgagggaaaaagata
tcgcgccagagttatacttacctctgatccgcaaacggcatactgcacaataactctgccgtccggc
gttgttccgagattcgaatggagccttaataatgtttcactgccggaatatttgacggccacgaccgt
tgtttcgcataccgctggccaaagtacagtgtggaagagcagcgcgagagcaggcgaggcgtggattt
ctggccggggaggcaatatatacgaatgcaccgtcctcatctgacgggcactcgcgttactacgcga
aaggagaggtgcttaacaaacacatggattgcggtggaaaacggtgctgctcaggcgcagctgtattc
actctttctggacttgtgtcaggattatgcgggagcatatctgctttgtacgcaacgctatggaccg
ccatttattttttgaggaatgcttttttggactatcgtactgcttcttccttcgctagccagagcaccg
ccgccgtcacgtacgactacattttaggccgtcgcgcgctcgccgctaaccatacccggcggttggc
ccgtataacagatacctcactagggtatcaagaggctgcgacgttgtcgagctcaacccgatttctaa
cgtggacgacatgatatcggcggccaaagaaaaagagaagggggccctttcgaggcctccgtcgtct
ggttctacgtgattaagggcgacgacggcgaggacaagtactgtccaatctatagaaaagagtacagg
gaatgtggcgacgtacaactgctatctgaatgcgccgttcaatctgcacagatgtgggcagtggacta
tgttcctagcacccttgtatcgcgaaatggcgcgggactgactatattctccccactgctgcgctct
ctggccaatacttgctgaccctgaaaatcgggagatttgcgcaaacagctctcgtaactctagaagtt
aacgatcgctgtttaaagatcgggtcgcagcttaacttttttaccgtcgaaatgctggacaacagaaca
gtatcagactggattttcaaggcgaacacctttatccgatcgcagacaccaatacacgacacgcggacg
acgtatatcggggatacgaagatattctgcagcgctggaataatttgctgaggaaaaagaatcctagc
gcgccagaccctcgtccagatagcgtcccgcaagaaattcccgctgtaaccaagaaagcggaagggcg
cacccggacgcagaaagcagcgaaaagaaggcccctccagaagactcggaggacgacatgcaggcag
aggcttctggagaaaatcctgccgcctccccgaagacgacgaagtcccgaggacaccgagcacgat
gatccaaactcggatcctgactattcaatgacatgcccgccctgatcccggtggaggagactactaa
aagttctaatgccgtctccatgcccatattcgcggcgttcgtagcctcgcggtcgcgctcgtgggc
tactggtttggagcatcgtaaaatgcgcgcgtagctaatcgagcctagaataggtggtttcttcctac
atgccacgcctcacgctcataatataaatcacatggaatagcataccaatgcctattcattgggacgt
tcgaaaagcatggcatcgctacttggaactctggctctccttgccgcgacgctcgcaccttcggcgc
gatgggaatcgtgatcactggaaatcacgtctccgccaggattgacgacgatcacatcgtgatcgtcg
cgcctcgccccgaagctacaattcaactgcagctatttttcatgcctggccagagacccacaaaccc
tactcaggaaccgtccgcgtcgcgtttcggtctgatataacaaaccagtgctaccaggaacttagcga
ggagcgctttgaaaattgcactcatcgatcgtcttctgttttttgtcggctgtaaagtgaccgagtaca
cgttctccgcctcgaacagactaaccggacctccacaccgtttaagctcactatacgaaatcctcgt
ccgaacgacacgggatgttctacgtaattgttcggctagacgacaccaaagaacccattgacgtctt
cgcgatccaactatcggtgtatcaattcgcgaacaccgccgcgactcgcggactctattccaaggctt
cgtgtcgcaccttcggattacctaccgtccaacttgaggcctatctcaggaccgaggaaagttggcgc
aactggcaagcgtacgttgccacggagggcacgacgaccagcgccgaggcgacaaccccgacgcccgt
cactgcaaccagcgcctccgaacttgaagcggaacactttacctttccctggctagaaaatggcgtgg
atcattacgaaccgacaccgcaaacgaaaattcaaacgttactgtccgtctcgggacaatgagccct
```

-continued

```
acgctaattggggtaaccgtggctgccgtcgtgagcgcaacgatcggcctcgtcattgtaatttccat
cgtcaccagaaacatgtgcaccccgcaccgaaaattagacacggtctcgcaagacgacgaagaacgtt
cccaaactagaagggaatcgcgaaaatttggacccatggttgcgtgcgaaataaacaaggggctgac
caggatagtgaacttgtggaactggttgcgattgttaacccgtctgcgctaagctcgcccgactcaat
aaaaatgtgattaagtctgaatgtggctctccaatcattttcgattctctaatctcccaatcctctcaa
aaggggcagtatcggacacggactgggaggggcgtacacgatagttatatggtacagcagaggcctct
gaacacttaggaggagaattcagccggggagagcccctgttgagtaggcttgggagcatattgcagga
tgaacatgttagtgatagttctcgcctcttgtcttgcgcgcctaactttttgcgacgcgacacgtcctc
tttttggaaggcactcaggctgtcctcggggaagatgatcccagaaacgttccggaagggactgtaat
caaatggacaaaagtcctgcggaacgcgtgcaagatgaaggcggccgatgtctgctcttcgcctaact
attgctttcatgatttaatttacgacggaggaaagaaagactgcccgcccgcgggaccctgtctgca
aacctggtaattttactaaagcgcggcgaaagcttcccgggttaattaaggccctcgaggatacatcc
aaagaggttgagtattctctctacacttcttgttaaatggaaagtgcatttgcttgttcttacaatcg
gcccgagtctcgttcacagcgcctcgttcacacttaaaccacaaatagtctacaggctatatgggagc
cagactgaaactcacatatgactaatattcggggtgttagtcacgtgtagcccattgtgtgcatata
acgatgttggacgcgtcctattcgcggtgtacttgatactatggcagcgagcatgggatattcatcc
tcgtcatcgttaacatctctacgggttcagaatgtttggcatgtcgtcgatcctttgcccatcgttgc
aaattacaagtccgatcgccatgaccgcgataagcctgtaccatgtggcattagggtgacatctcgat
catacattataagaccaacgtgcgagtcttccaaagacctgcacgccttcttcttcggattgtcaacg
ggttcttcagaatctatgcccatatctggcgttgagaccattgtgcgtttaatgaacaataaagcggc
atgccatggaaggagggctgcagatctccattttctcacgccactatcctggacgctgtagacgata
attataccatgaatatagaggggtattgtttccactgccactgtgatgataagttttctccagattgt
tggatatctgcattttctgctgccgaacaaacttcatcgctatgcaaagagatgcgtgtgtacacgcg
ccgttgagtatacgggaaactaaatgttcatagaggtctttgggctatatgttattaaataaaataat
tgaccagtgaacaatttgtttaatgttagtttattcaatgcattggttgcaaatattcattacttctc
caatcccaggtcattctttagcgagatgatgttatgacattgctgtgaaaattactacaggatatatt
tttaagatgcaggagtaacaatgtgcatagtaggcgtagttatcgcagacgtgcaacgcttcgcattt
gagttaccgaagtgcccaacagtgctgcggttatggtttatgcgcacagaatccatgcatgtcctaat
tgaaccatccgattttttcttttaatcgcgatcgttgtttgggcaactgcgttatttcagatctaaaaa
atttacccttttatgaccatcacatctctctggctcataccccgcttggataagatatcatgtagattc
cgccctaagaaatgcaaactaacattattgtcggttccatatacacttccatcttgtccttcgaaaat
aacaaactcgcgcaatagaccgtccgtacatgcatggccgatgtgtgtcaacatcattggtctgctag
atcccgatgggacgaatcgtacagtcgtcgctccagcattggcaaaaatccccagatacccctccatgc
ggcaaatctaaattgcgaccccgaagagactgcaccaaagtcttatcgacgcacgctgattttttttga
acagcgggagcccattatcttcagtggagcgtagacgggcgaggctaattatgtgacatagcaacact
gcatgtatgttttataaatcaataagagtacataatttattacgtatcatttccgtttgtaatatac
tgtatacatcatccacactattagtcagcactagcgcgcgggcgcacgttacaatagcagcgtgcccg
ttatctatattgtccgatatttacacataacatttcatcgacatgattaaatacctaagtactgcaca
cagatgtttaatgtatatcgtcatataaattatatcgctaggacagaccccaaacgacctttatcccaa
acagtcagatcctcttctcaagtgtcgatttctgttatggaatatgcatacccctggcccagaaattgc
acgcacgagcgtagtgaatgcgtcattggttttacattaaaggctaaatgcacaaattctttagacg
acagcacatcgttaaatagcatctctagcgttcttatgaatgctaagcattggagtcctcctggtcgg
ccacaataacagctgagtatcatacctgagctccggggttgtcgcacatagcggattcgtataaaca
taggattttccgcgaatccatcagttgcaaaaatctgttaggctccatcaacaacgctggatttactt
cagatccacgcgtaaagtaatggtgctcgaatccgttttagagttgtcggcatttcaaggaacaaa
gaattcatttcttcattgcaacgacgcgccagaaatcccaagacctctttgggtagtatgttcttgcc
tataaaacacggcgttccaagtgccaggaaccacgcatgtgttactgttggggcgtattcagaaataa
agcggggtttatgcggcttttgaagctcggatatccaaagtatcgcttgctgatgaacgagcgatgta
gctgttacaaaacctcctttccatcctccagtcaacataatatttatcggcctacctatgtccgtaat
aagtattggtcgggcaattattccgtatgaggtcttgcaggaataagctcttagggacagccagcttg
gatatggtgcgaaacagaccttctcggcttcagaatgtcgctccgcagtctcttcgtgtcggtgcatc
ttagatccaccatcaatgtgtgcagcattgactcccgcccgtcgaatattccttttgttacgatgcag
taatgagcacgatcatgggcggggcgatgacgttctattttgcatgtctgcgaacaatttgcgtcagtc
atacagctatggagtgggccatttctggccgtcaacttaaaaacgcgaaccgcagacatatgtatttg
catgcaaagacgtatcttcgtatttctggggcatcttcaaatgctctggccaatatggcaatgaatttg
gattcgtttgacgccgatggtatgcagtgcaaatgtgccaatagcccacatccgaaaaagttatttgt
catacaagcaggtgttaagtagcaatcacataaaggcaccagacgcctcatggcatcataatgaatag
ctccttctccccactggaaccactgacaaaatctgcgagtatattccgcaaaccacattttatttctc
atagaaactaccctaaatccttttaacgggaagaagaatcctagatagtgcttgaagtcatgactgtt
actgctgcaataacactgtatattatttataaattccgtttgtctaggtatctgatgtaggcattccg
atcccttctactattgcgtcttcacgaccaaatgggaatgcgccaaaatcccccacacctcatcacctg
gaggcagattgtgtattattaatatccgccgattgaagcacaaaacggtacggtactgttcctaattc
tggtatagattctatggtcaaaagtctgcatatccccgacattgccatgagatcacacagtccaagta
gcatgtttattgagtcactcagactgtcaacgtccctcgccgcaccaccaatcgaaaataaagtatct
acgcaagttatagctccgcatttttctatcgctagcagcaatcgcgacgcaaaacataaaggccatgtt
gggatttgaactctctggggggcttgttatcttctgcaccgtcgcagtcgcagttttccgaaatttat
gtctaatatattttccggccgtgctccaatcggccgaaaagaatctgcgtattaccagactcattgac
gggccgataaagaccataaaacaaaattcctgtgcactccctcctccagttttgccatcgtccaagtc
ccgtaactttttttgcgtttcgaggagcaagcttcgttatccctacccacacttgttttccaccgtt
ttcttattataagcggttgtatcgccaacgcgtcaccgcaggttgtcacatacagtgatggcatactt
gaacgtgcaacaacgcgctcgctttgcaaatctaagtcattgaccatcaaatcgcgttgagaggatag
ccaggcatctttttttcctagtatggtgacggtgcagccaccccaactcagttcttgtaaaaaagcta
ttggcgggaatttatgtctgaggtgcattctatatttatgagtccatcaaatgccatttaaccagatt
cgtattttttcgctcgacccggcatcactatggatacaatacctttctatggcccatttcagctctcg
aaccaaccacacggacaattgactaacataagtatgatctttatcacagtcgcacccatctgagttat
atttatggcatccgagcgctcttactgtacggtcggatacacccatggttttttccttttatatagtcgg
gttatagtctgtcgggtttggcggtagcacggagtagtttgattttaagaatcgaaaaccggcttgg
agagaccactgtcgaatatttgtccgtatactctacacgtgagtgttgtccattcctaggtatattca
tctgttcggataccttcaattgctgttcaggcataaccttaaagcatatgttatgttgtacatcaaaa
``` cttggtgagttatgttcgattgccgcgcataaagaatcgtacatgagcgtttctgctaacatactatc
tatattctcacacgccctgcatatactgttcctattccaaattcacgttttgcccatcggctatct
gctcccaaaaagttgtaatataggtgccgctgggtgcgaaattttcatcagttgtattcctgataaac
tgaatcactttacataatttttgccacatatctgcgtgcagccatagtatcgaacccgtgggctcgga
gacgacagtgcgtacaatgggtattttacctttccccaacaaaataatggtatacaagttaggtccgt
acctagaccttaatgtttccaattcttctgaatcactgcactctcgtaggggagtaacggtaataatt
tcgtctctgagccccgttttgcgttgaaaactaatcacattagataatgtgcaatcggtttcttttat
ccggatacatctaagtattatgacatcggtggtcattgtttccatcaacgaccatcttttacgatcgc
ccatactactcatggacgttgtcggtgttgaaaaatcaccagaattgcaacggatctctgggtaccat
gctgctgatggaattggcggttttaattgttgtttcagtctattattgctatctttggcggggttgaa
taatgtggggggagagtgattgcaggaatccgaatgggtcaataaaacgaccgtgctccgttctgccg
gcgccgatccgattgaagctatatacttcgcttctctccccacttttccaatttgatccggaaataaa
acggccccggacaacagtatcgtacgatccggatccgatcctgcttgcctacagaagaatcaacatc
tcgccccaatattctggtcaaaactggctcgctcatggcaacgcggacgtttccccccggtggccagtc
ttaatggttaatgttcttttcggcaatcttatacatcagcgggttgcgtgaatactggtcacagttca
gtcatttactacacaccagcaatacgacgacggacagtaccgtcccgacgaacgcgacgcccaaaatt
gctatcgcgaccgcgtccgaggcgatgtcgtacgggcggtgcggggttggatcctcggcaaagagatc
ctcgtaattcggcggtgggagcggagggtaaagacgcgggtgggatctccctccggaccgcgcgccg
ggcgcggttcgaaaatgctttccgcctcgctcagtgtcaacgccaagtattcgggcgggctgggggcc
ggaatatctcccgcgacttcttctatcggcgcggaattggagtcgcggtcgtggcgcgcttctagcgt
cgtcaacggaagtccattttcggggtctcccggtgggcgttcagcgtccatcgtcgtatatgctctaa
cacacgtctcgctatattaaaaaaaagaagagtatcggtcagtgtcgagtgtcgccgacaatgtcgcg
agttctcggcgatttaattttttggaactgctccctatgaatcccgtaactgtagcgcccgcgcagaaa
gccgccatcagaccaactacgtgtctgttcgatgtttgcccgccgatcgctttaccgattaaggttcc
ggcgagaaatgacatgctcgatccaagaacaaagttttttcgcggtaaacaacaacatagttaccgtgc
gagatggagaaaccacatctcccgaattagtagaggaaagcccgtcgtcggtttggggacatatcg
atcttttttgtgttttttcctaggaccccttttgccagatcgtacaaagtcgcgtcttatgagcggacgt
tcttact

```
caaactgaccatgatcgtatgttgctgaatgcactagggcaattcgctcgcgcgactccatacattga
ataattccacacgtcagctcatcggttagcaaggtccagtagttgaagtcatttattttccccgcgg
ctggccaaatctacctctgggaatatccaagttgtcgaatatgatcgcaccggctctggtcatggtga
aggaactgtagcataaagacgcaggtatcatagggtaatattttttattcactcacatactaaaag
taacgcatattagcaccatgtatgggctatcaattgacatttgcgtagcactacatcacgattatgta
caacataatgggacaacatatggcaagtagatgcaatttcctcacactagttgggtttatctactatt
gaattttcccctatctgtgatacacttgggagcctctacaagcatattgccatcatgtacgtttttat
ctactgtcttaacgcccatgggaacggaggcgtcgtcgtcatgtattggacggcaacataggcagcaa
cacaaattgcgtttaggtggggtgcatgtggactcgataccaagcccctgcagctggggaacgtctgg
tggagagccgataaatttgatatacgcacgccatattactgtcgttgaagtacgccttatcttctatgt
tttcaaatttaggttcccaagtggacgtgagaagtgtttgtatctcacatggaatggcccaaggcatt
ccagcccaggtgcctggtactttaatggcaaacaaacgttttggtagaggtattgattctattgcagt
tctgcagatatctgcagccccgagtatccacaggctatacgatacgttatcggaggcaagctgcggcc
gctctagaactagtggatccccccgggctgcagcccaatgtggaattcgccctttgcacattgttactcc
tgcatcttaaaaatatatcctgtagtaattttcacagcaatgtcataacatcatctcgctaaagaatg
acctgggattggagaagtaatgaatatttgcaaccaatgcattgaataaactaacattaaacgaattc
actagtggatcccccaactccgcccgttttatgactagaaccaatagttttaatgccaaatgcactg
aaatcccctaatttgcaaagccaaacgcccccctatgtgagtaatacgggactttttacccaatttcc
caagcggaaagcccctaatacactcatatggcatatgaatcagcacggtcatgcactctaatggcgg
cccatagggactttccacataggggcgttcaccatttccagcataggggtggtgactcaatggcct
ttacccaagtacattgggtcaatgggaggtaagccaatgggttttcccattactggcaagcacactg
agtcaaatggacttttccactgggttttgcccaagtacattgggtcaatgggaggtgatcaatggga
aaaacccattgctgccaagtacactgactcaataggactttccaatgggttttttccattgttggcaa
gcatataaggtcaatgtgggtgagtcaataggactttccattgtattctgcccagtacataaggtca
ataggggtgaatcaacaggaaagtcccattggagccaagtacactgcgtcaataggggactttccatt
gggttttgcccagtacataaggtcaataggggatgagtcaatgggaaaaacccattggagccaagtac
actgactcaataggggactttccattgggttttgcccagtacataaggtcaataggggtgagtcaaca
ggaaagtcccattggagccaagtacattgagtcaataggggactttccaatgggttttgcccagtacat
aaggtcaatgggaggtaagccaatgggttttttcccattactggcacgtatactgagtcattagggact
ttccaatgggttttgcccagtacataaggtcaatagggggtgaatcaacaggaaagtcccattggagcc
aagtacactgagtcaataggggactttccattgggttttgcccagtacaaaaggtcaataggggtgag
tcaatgggttttttcccattattggcacgtacataaggtcaataggggtgagtcattgggttttttccag
ccaatttaattaaaacgccatgtactttcccaccattgacgtcaatgggctattgaaactaatgcaac
gtgaccttaaacggtactttcccatagctgattaatgggaaagtaccgttctcgagccaatacacgt
caatgggaagtgaaagggcagccaaaacgtaaacaccgcccccggttttcccctggaaattccatattgg
cacgcattctattggctgagctgcgttctacgtgggtataagaggcgcgaccagcgtcggtaccgtcg
cagtcttcggtctgaccaccgtagaacgcagagctcctcgctgcaggcggccgctctagaactcgtcg
atcgcagcgatgacaaacctgcaagatcaaacccaacagattgttccgttcatacggagccttctgat
gccaacaaccggaccggcgtccattccggacgacaccctggagaagcacactctcaggtcagagacct
cgacctacaatttgactgtggggggacacagggtcagggctaattgtcttttttccctggattccctggc
tcaattgtgggtgctcactacacactgcagagcaatgggaactacaagttcgatcagatgctcctgac
tgcccagaacctaccggccagctacaactactgcagactagtgagtcggagtctcacagtgaggtcaa
gcacactccctggtggcgtttatgcactaaacggcaccataaagccgtgaccttccaaggaagcctg
agtgaactgacagatgttagctacaatgggttgatgtctgcaacagccaacatcaacgacaaaattgg
gaatgtcctggtaggggaaggggtcactgtcctcagcctacccacatcatatgatcttgggtatgtga
ggcttggtgaccccattcccgctatagggcttgacccaaaaatggtagctacatgcgacagcagtgac
aggccagagtctacaccataactgcagccgatgattaccaattctcatcacagtaccaaccaggtgg
ggtaacaatcacactgttctcagccaacattgatgctatcacaagcctcagcattggggggagagctcg
tgtttcaaacaagcgtccaaggccttgtactgggcgccaccatctacctttataggctttgatgggact
gcggtaatcaccagagctgtagccgcagataatgggctgacggccggcaccgacaatcttatgccatt
caatcttgtcattccaaccaatgagataaaccagccaatcacatccatcaaactctggagatagtgacct
ccaaaagtggtggtcaggcaggggatcagatgtcatggtcggcaagtgggagcctagcagtgacgatc
catggtggcaactatccagggccctccgtcccgtcacactagtagcctacgaaagagtggcaacagg
atccgtcgttacggtcgctgggtgagtaacttcgagctgattccaaatcctgaactagcaaagaacc
tggttacagaatacggccgatttgacccaggagccatgaactacacaaaattgatactgagtgagagg
gaccgtcttggcatcaagaccgtctggccaacaagggagtacactgattttcgtgagtacttcatgga
ggtgccgacctcaactctcccctgaagattgcaggagcatttggcttcaaagacataatccgggcta
taggaggtaagcttgatctagagcggccgcggggatccagacatgataagatacattgatgagtttg
gacaaaccacaactagaatgcagtgaaaaaaatgcttttatttgtgaaattttgtgatgctattgcttta
tttgtaaccattataagctgcaataaacaagttaacaacaacaattgcattcatttttatgtttcaggt
tcaggggggaggtgtgggaggttttttcggatcctctagagtcgacaattatttcatttaataacatat
agcccaaagacctctatgaacatttagtttcccgtatactcaacggcgcgtgtacacaagggcgaa
ttccacagtggatatcaagcttaattaagtaccgagctcgaattggcgcgccaggtcaatccctggc
attatgcccagtacatgaccttatgggactttcctacttggcagtactctacgtattagtcatcgct
attaccatggtgatgcggttttggcagtacatcaatgggcgtggatagcggtttgactcacgggatt
tccaagtctccaccccattgacgtcaatgggagtttgttttggcaccaaaatcaacgggactttccaa
aatgtcgtaacaactccgcccattgacgcaaatgggcggtaggcgtgtacggtggaggtctatata
agcagagctcgtttagtgaaccgtcagatcgcctggagacgccatccacgctgttttgacctccatag
aagacaccgggcgcgccggatccatgggcccagaccttctaccaagaacccagtacctacctatgctg
actgtccgagtcgcgctggtactgagttgcatctgtccggcaaactccattgatgcaggcctcttgc
ggctgcaggaattgtggttacaggagacaaagccgtcaacatatacctcatcccagacaggatcaa
tcatagttaagctcctcccgaatctgcccaaggataaggaggcatgtgcgaaagcccccttggatgca
tacaacaggacattgaccactttgctcaccccccttggtgactctatccgtaggatacaagagtctgt
gactacatctggaggggggagacagggggcgccttataggcgccattattggcggtgtggctcttgggg
ttgcaactgccgcacaaataacagcggccgcagctctgatacaagccaaacaaaatgctgccaacatc
ctccgacttaaagagagcattgccgcaaccaatgaggctgtgcatgaggtcactgacggattatcgca
actagcagtggcagttgggaagatgcagcagtttgttaatgaccaatttaataaaacagctcaggaat
tagactgcatcaaaattgcacagcaagttggtgtagagctcaacctgtacctaaccgaattgactaca
gtattcggaccacacaaatcacttcacctgcttttaaacaagctgactattcaggcactttacaatctagc
```

```
tggtggaaatatggattacttattgactaagttaggtgtagggaacaatcaactcagctcattaatcg
gtagcggcttaatcaccggtaaccctattctatacgactcacagactcaactcttgggtatacaggta
actctaccttcagtcgggaacctaaataatatgcgtgccacctcttggaaaccttatccgtaagcac
aaccaggggatttgcctcggcacttgtcccaaaagtggtgacacaggtcggttctgtgatagaagaac
ttgacacctcatactgtatagaaactgacttagatttatattgtacaagaatgtaacgttccctatg
tcccctggtatttattcctgcttgagcggcaatacgtcggcctgtatgtactcaaagaccgaaggcgc
acttactacaccatacatgactatcaaaggttcagtcatcgccaactgcaagatgacaacatgtagat
gtgtaaacccccgggtatcatatcgcaaaactatggagaagccgtgtctctaatagataaacaatca
tgcaatgttttatccttaggcgggataactttaaggctcagtggggaattcgatgtaacttatcagaa
gaatatctcaatacaagattctcaagtaataataacaggcaatcttgatatctcaactgagcttggga
atgtcaacaactcgatcagtaatgctttgaataagttagaggaaagcaacagaaaactagacaaagtc
aatgtcaaactgactagcacatctgctctcattacctatatcgttttgactatcatatctcttgtttt
tggtatacttagcccgattctagcatgctacctaatgtacaagcaaaaggcgcaacaaaagaccttat
tatggcttgggaataatactctagatcagatgagagccactacaaaaatgtgaggatctctcgaggaa
ttctagatcccacgtcactattgtatactctatattatactctatgttatactctgtaatcctactca
ataaacgtgtcacgcctgtgaaaccgtactaagtctcccgtgtcttcttatcaccatcaggtgacatc
ctcgcccaggctgtcaatcatgccggtatcgattccagtagcaccggccccacgctgacaacccactc
ttgcagcgttagcagcgcccctcttaacaagcgaccccccaccagctgcggttactaacactcctc
tccccgacctgcaactagtgcggccgcagcttgcctccgattctagcattacatagccggtcagtaga
tcctgccattcggtagcgcaaccggctacatcttcaaacagtctcacgtaaatgcatctctcgttcc
tgccaatccggaaccgggcataccactcccgcctgccgatttaattctcacaattgggcgatgccggc
ggggcaaaacgaatgtggatttggcaaaccgacacaggtctgctgtacggactaatatgggcacaccc
acatcattcttcagatgctccatgcattgttctatgagaaagatccataggtggaggcagcgtcacg
agatcgcccaggcaatcgatcgcattcgtctagtaaagtgacgagagttatcatgcacacacccatgc
ccacgccttccgaataactggagctgtggaagatcggaaacgtctttttgactgccggtctcgtacta
ctttcgcacaggtgtataccggacgcgtactatatattttatatcatccaacgtcccgaaattacat
acgtggcggcgatgaagtagatgttgagtcttcgaaagtaagtgcctcgaatatgggtattgtctgt
gaaaatatcgaaagcggtacgacggttgcagaaccgtcgatgtcgccagatactagtaacaatagctt
cgataacgaagacttccgtgggcctgaatacgatgtggagataaataccagaaatctgctaatcttg
atcgtatggaatcttcgtgccgtgaacaacgagcggcgtgcgaacttcgaaagtgttcgtgtcctacg
tctgccgtgcgcatgcaatacagtattctttcatctctcgctccgggttcagagggtcatgtatatat
atgtactagatacggggacgcggaccaaaaaaaatgcatagtgaaggcagtcgttggaggaaagaatc
ccgggagggaagtggatattttaaaaaccatctcacataaatcaattataaaattaatccatgcctat
aaatggaaaaatgttgtgtgtatggcaatgcgtgtatatcgttatgatctttttcacatatattgacgg
agtcggccctatgcccccttcaacagatgatctatattcaacgtggactactagaggcgctagcataca
tacatgaaaggggcatcattcaccgagacgtaaagacggagaatatattcttggataatcacgaaaat
gcagttttgggtgacttcggtgctgcatgccaactaggagattgtatagatacgcccaatgttacgg
ttggagcggaactgtggaaacaaattcgccggaattatctgcacttgatccgtattgcacaaaaacag
atatttggagtgccggattggttctatatgagatggcaattaaaaatgtaccattgtttagtaagcag
gtgaaaagttcgggatctcagctgagatccataatacggtgcatgcaagtgcatgaactggagtttcc
ccgcaacgattctaccaacctctgtaaacatttcaaacaatatgcggttcgtgtacgaccgcctata
ccattcctcgagttataagaaatgggggatgccaatggatgttgaatatgtcattctaaaatgctt
acgtttgaccaggagttcagaccttctgctaaggaaatattgaatatgcccctattactaaggcgcc
gattaacctgcttaatatcacaccctctgacagtgtctaacggtatacaggcgggagcgggtcgtggc
gtcatcatcaccacttgagaatttatattttgaattgttgattgataaattaacctgattcattgaga
actgaaacgccatattggtttcttggatatgtctacaacaattagttaaattgctatgttctactgcg
agtacatttgataagttgtaagagacgggcgactcatgtcgaagtttgacgaatataaagtacataac
gtgtttagaatacccagaatccgaatagtccgcggggcgtcttctcgcgtgagtaccaaatactgag
ttgaacttgaaaatgctaaatctgtgacactctttgtgtgatgattattgtcaccacttcgaagatgg
cttcgacattcatgatgttctggtgtttgtttggaatcgtaatagcgcttgtttcgtccaagtctgac
aacaaagaaaatctgaagaattatatcacggataagtcaaccaatattagaatacccacgccattatt
tgtatcaacggaaaactcttatcccacaaaacatgtaatctacgatgaaaactgtggcttcgctgtac
tcaatcctataagtgaccccaaatatgtccttttgagccagcttctaatgggaaggcgcaaatatgat
gcgacggtcgcgtggtttgttctcggtaaaatgtgtgccagattaatatatttgcgcgaattttataa
ctgctcgacaaatgagccttttggcacatgttctatgagctctcctggatggtgggacaggcgctacg
tctcaaccagtttcatttctcgcgacgaattacagctggttttttgcagcgccgtcccgagaattagat
ggtttatatacgcgcgtagtagttgtcaacggggactttactacggccgatataatgtttaatgttaa
agtggcatgtgcctttcaaagactggaatagaagatgatacattatgcaaacccttcattcttttg
ccaatgcaacattgcacaatttaaccatgattagatcggtaactcttcgagcgcacaaagccattta
aaggaatgggtggcacggagaggtggtaacgtccctgcagtgctacttgagtctaccatgtatcatgc
atccaatctgcctagaaatttcagggatttctacataaagtctccagatgattataagtataatcacc
tagatggccatctgtaatgctcatcactgacagacctagtgaagatttggatgggaggctcgttcac
caaagtgacatttttactactacaagtcctataaaacaggtccggtatgaagagcatcagtcacatac
aaagcagtatcctgtaaacaaaatacaagctataatttttttgatagggttaggctcgttcattggaa
gcatattcgtagttttggtagtatggattatacgcagatattgcaatggagcgcggagtggggaacg
cccccagtcctcgccggtatgtgtataccaggctatgatcacgtgtgaaactgggcggacctgtat
catatgtacaccgtccctattcgtttatagccagtacgtgttatctgcacatagaggaacatgtgtca
tactgggatcgcatgcatggtatgtgtgactctaatattattctgtatcataataaaaacacagtgca
tggtatatagaggatcgctggtaagcactacggtagaccaatccgctcagattgcattctttggcatc
gataccgttgttaatttatatggcaaagtcttgttcatgggagatcagtatttggaggaaatatactc
tggaacgatggaaatactcaaatgaatcaagctaaccgctgctattctattgcgcatgcaacatatt
acgccgactgtcctataatcagttctacggtattcagaggatgccgggacgccgttgtttatactagg
ccccacagcaga
```

SEQ ID NO 31: 1332-29.4 (HVT/IBDV/ILT/NDV #5 virus)
ILT/hCMV IEpro-F-IEpA(term)/HVT UL54.5 region (14,598 bp)

```
cgcgccactggagaacggcatgaccgcaaaaggcgttgtagagatcgatcccacgaactctcaggcga
tcgtgtcagtcgccataaacagcgacgatcgtctccaggatctgaacggttttcttctcaacgatcat
cagtatatgaggaactgaacctgatatttagccgagggaaacgcaggttaaaaacccctatcaagcgat
```

-continued

```
tgcgattttcgcgtatctagtaaaaatagatgggcttcggtactagccttcgccgccaactctgaata
tgcccttcgtggacctcatataacatggcattgtttgttggatgcggggccggaattaagaagaacat
tcgaaatacgagcaaaaatttcggccctggcatgtgctgcgcgagaatcggtactcggggagaaagt
tttatcggagctttgggtagtgcagaggaaactctatcttggttgaaaatgcatgcgaccctgcactt
gattctggttaaccacgatccaattttttaagacggctggcgcggtcctagataacctccgcttaaaac
tagcccccaatattgatgtgcagatataacacagaaaaacgatcaatggaagacatgctacggcggtca
tctcccgaagacatcaccgattccctaacaatgtgcctgattatgttatcgcgcattcgtcgtaccat
gcgcaccgcaggaaataaatatagctatatgatagatccaatgaatcgtatgtctaattacactccag
gcgaatgtatgacaggtatattgcgatatattgacgaacatgctagaaggtgtcctgatcacatatgt
aatttgtatatcacatgtacacttatgccgatgtatgtgcacgggcgatatttctattgtaattcatt
tttttgttagtaaactaccacaggctgtccggaaatctaagttaatgaataaagtagatggttaatac
tcattgcttagaattggactacttttaattctctttaatgttcgtattaaataaaaacatctttaata
aacttcagcctcttcgcttattgtagaaattgagtattcaaaatcatgttcaaagccgtcttcggaga
gtgtactcgccacggtggttggaacatcactatgtctacacgtcaaatttaagcacgtcaggtctgtc
gaggacaagaaatggttaactagtgtttcaattattcttataaacgttaagcattgtaagccccccgg
ccgtccgcagcaacaatttactagtatgccgtgggctccgggactatcacggatgtccaattcgcaca
tgcatataattttttctagggtctctcatttcgagaaatcttcggggatccatcagcaatgcgggctgt
agtcccgattcccgtttcaaatgaaggtgctccaacacggtcttcaaagcaaccggcataccagcaaa
cacagactgcaactccccgctgcaatgattggttataaacagtaatctgtcttctgcgaagtatatttc
gcccgacaatccacggcgccccaaagttaaaaaccatccatgtgtatttgcgtcttctctgttaaaa
gaatattgactggcattttcccgttgaccgccagatatccaaagtacagcacgatgttgcacggacga
ctttgcagtcaccagccttcctttccaccccccaccaaaaatgtttatcgtaggacccatatccg
taataaggatgggtctggcagcaaccccataggcgcctcggcgtggtagttctcgaggccttaattaa
gtcgacggcagagtcgcagacgccctattggacgtcaaaattgtagaggtgaagttttcaaacgatg
gcgaagtaacgcgacttgcgtttccaccgtcaaatctccctataggtagaaactaattggaaagta
gacctcgtagatgtaatggatgaaatttctgggaacagtcccgccggggttttaacagtaatgagaa
atggcagaaacagctgtactacagagtaaccgatggaagaacatcggtccagctaatgtgcctgtcgt
gcacgagccattctccggaaccttactgtcttttcgacacgtctcttatagcgagggaaaaagatatc
gcgccagagttatactttacctctgatccgcaaacggcatactgcacaataactctgccgtccggcgt
tgttccgagattcgaatggagccttaataatgtttcactgccggaatatttgacggccacgaccgttg
tttcgcataccgctggccaaagtacagtgtggaagagcagcgcgagagcaggcgaggcgtggatttct
ggccggggaggcaatatatacgaatgcaccgtcctcatctcagacggcactcgcgttactacgcgaaa
ggagaggtgcttaacaaacacatggattgcggtggaaaacggtgctgctcaggcgcagctgtattcac
tcttttctggacttgtgtcaggattatgcgggagcatatctgcttttgtacgcaacgctatggaccgcc
atttattttttgaggaatgcttttggactatcgtactgcttcttccttcgctagccagagcaccgcc
gccgtcacgtacgactacattttaggccgtcgcgcgctcgacgcgctaaccataccggcggttggccc
gtataacagatacctcactagggtatcaagaggctgcgacgttgtcgagctcaacccgatttctaacg
tggacgacatgatatcggcggccaaagaaaaagagaaggggggccctttcgaggcctccgtcgtctgg
ttctacgtgattaagggcgacgacggcgaggacaagtactgtccaatctatagaaaagagtacaggga
atgtggcgacgtacaactgctatctgaatgcgccgttcaatctgcacagatgtgggcagtggactatg
ttcctagcacccttgtatcgcgaaatggcgcgggactgactatattctcccccactgctgcgctctct
ggccaatacttgctgaccctgaaaatcgggagatttgcgcaaacagctctcgtaactctagaagttaa
cgatcgctgtttaaagatcgggtcgcagcttaacttttttaccgtcgaaatgctggacaacagaacagt
atcagactggatttcaaggcgaacacctttatccgatcgcagacaccaatacacgacacgcggacgac
gtatatcggggatacgaagatattctgcagcgctggaataatttgctgaggaaaaagaatcctagcgc
gccagaccctcgtccagatagcgtcccgcaagaaatttcccgctgtaaccaagaaagcggaagggcgca
ccccggacgcagaaagcagcgaaaagaaggccctccagaagactcggaggacgacatgcaggcagag
gcttctggagaaaatcctgccgccctccccgaagacgacgaagtccccgaggacaccgagcacgatga
tccaaactcggatcctgactattacaatgacatgcccgccgtgatcccggtggaggagactactaaaa
gttctaatgccgtctccatgcccatattcgcggcgttcgtagcctgcgcggtcgcgctcgtgggcta
ctggtttggagcatcgtaaaatgcgcgcgtagctaatcgagcctgaaataggtggtttcttcctacat
gccacgcctcacgctcataatataaatcacatggaatagcataccaatgcctattcattgggacgttc
gaaaagcatggcatcgctacttggaactctggctctccttgccgcgacgctcgcacccttcggcgcga
tgggaatcgtgatcactggaaatcacgtctccgccaggattgacgacgatcacatcgtgatcgtcgcg
cctcgccccgaagctacaattcaactgcagctatttttcatgcctggccagagaccccacaaaccta
ctcaggaaccgtccgcgtcgcgtttcggtctgatataacaaaccagtgctaccaggaacttagcgagg
agcgctttgaaaattgcactcatcgatcgtcttctgtttttgtcggctgtaaagtgaccgagtacacg
ttctccgcctcgaacagactaaccggacctccacacccgtttaagctcactatacgaaatcctcgtcc
gaacgacagcgggatgttctacgtaattgttcggctagacgacaccaaagaacccattgacgtcttcg
cgatccaactatcggtgtatcaattcgcgaacaccgccgcgactcgcggactctattccaaggcttcg
tgtcgcaccttcggattacctaccgtccaacttgaggcctatctcaggaccgaggaaagttggcgcaa
ctggcaagcgtacgttgccacggaggccacgacgaccagcgccgaggcgacaaccccgacgcccgtca
ctgcaaccagcgcctccgaacttgaagcggaacactttacctttccctggctagaaaatggcgtggat
cattacgaaccgacacccgcaaacgaaaattcaaacgttactgtccgtctcgggacaatggcccctac
gctaattggggtaaccgtggctgccgtcgtgagcgcaacgatcggcctcgtcattgtaatttccatcg
tcaccagaaacatgtgcaccccgcaccgaaaattagacacggtctcgcaagacgacgaagaacgttcc
caaactagaagggaatcgcgaaaatttggacccatggttgcgtgcgaaataaacaaggggcgtgacca
ggatagtgaacttgtggaactggttgcgattgttaacccgtctgcgctaagctcgcccgactcaataa
aaatgtgattaagtctgaatgtggctctccaatcatttcgattctctaatctcccaatcctctcaaaa
ggggcagtatcggacacggactgggaggggcgtacacgatagttatatggtacagcagaggcctctga
acacttaggaggagaattcagccggggagagcccctgttgagtaggcttgggagcatattgcaggatg
aacatgttagtgatagttctcgcctcttgtcttgcgcgcctaactttttgcgacgcgacacgtcctctt
tttggaaggcactcaggctgtcctcggggaagatgatcccagaaacgttccggaagggactgtaatca
aatggacaaaagtcctgcggaacgcgtgcaagatgaaggcggccgatgtctgctcttcgcctaactat
tgctttcatgatttaatttacgacggaggaaagaaagactgcccgcccgcgggacccctgtctgcaaa
cctggtaatttttactaaagcgcggcgaaagcttcgcgccaggtcaattccctggcattatgcccagta
catgaccttatgggactttcctacttggcagtacatctacgtattagtcatcgctattaccatggtga
tgcggttttggcagtacatcaatgggcgtggatagcggtttgactcacggggatttccaagtctccac
cccattgacgtcaatgggagtttgttttggcaccaaaatcaacgggactttccaaaatgtcgtaacaa
```

```
ctccgccccattgacgcaaatgggcggtagcgtgtacggtgggaggtctatataagcagagctcgttt
agtgaaccgtcagatcgcctggagacgccatccacgctgttttgacctccatagaagacaccggttgc
gccgccaccatgggccccagaccttctaccaagaacccagtacctatgatgctgactgtccgagtcgc
gctggtactgagttgcatctgtccggcaaactccattgatggcaggcctcttgcggctgcaggaattg
tggttacaggagacaaagccgtcaacatatacacctcatcccagacaggatcaatcatagttaagctc
ctcccgaatctgcccaaggataaggaggcatgtgcgaaagccccttggatgcatacaacaggacatt
gaccactttgctcacccccttggtgactctatccgtaggatacaagagtctgtgactacatctggag
ggggagacaggggcgccttataggcgccattattggcggtgtggctcttggggttgcaactgccgca
caaataacagcggccgcagctctgatacaagccaaacaaaatgctgccaacatcctccgacttaaaga
gagcattgccgcaaccaatgaggctgtgcatgaggtcactgacggattatcgcaactagcagtggcag
ttgggaagatgcagcagtttgttaatgaccaatttaataaaacagctcaggaattagactgcatcaaa
attgcacagcaagttggtgtagagctcaacctgtacctaaccgaattgactacagtattcggaccaca
aatcacttcacctgctttaaacaagctgactattcaggcactttacaatctagctggtggaaatatgg
attacttattgactaagttaggtgtagggaacaatcaactcagctcattaatcggtagcggcttaatc
accggtaaccctattctatacgactcacagactcaactcttgggtatacaggtaactctaccttcagt
cgggaagctaaataatatgcgtgccacctacttggaaaccttatccgtaagcacaaccaggggatttg
cctcggcacttgtcccaaaagtggtgacacaggtcggttctgtgatagaagaacttgacacctcatac
tgtatagaaactgacttacattttatattgtacaagaatagtaacgttccctatgtcccctggtattta
ttcctgcttgagcggcaatacgtcggcctgtatgtactcaaagaccgaaggcgcacttactacaccat
acatgactatcaaaggttcagtcatcgccaactgcaagatgacaacatgtagatgtgtaaaacccccg
ggtatcatatcgcaaaactatggagaagccgtgtctctaatagataaacaatcatgcaatgttttatc
cttaggcgggataacttttaaggctcagtggggaattcgatgtaacttatcagaagaatatctcaatac
aagattctcaagtaataataacaggcaatcttgatatctcaactgagcttgggaatgtcaacaactcg
atcagtaatgctttgaataagttagaggaaagcaacagaaaactagacaaagtcaatgtcaaactgac
tagcacatctgctctcattacctatatcgtgttgactatcatatctcttgttttggtatacttagcc
tgattctagcatgctacctaatgtacaagcaaaaggcgcaacaaaagaccttattatggcttgggaat
aatactctagatcagatgagagccactacaaaaatgtgaggatctctcgaggaattctagatcccacg
tcactattgtatactctatattatactctatgttatactctgtaatcctactcaataaacgtgtcacg
cctgtgaaaccgtactaagtctcccgtgtcttcttatccaccatcaggtgacatcctcgcccaggctgt
caatcatgccggtatcgattccagtagcaccggcccacgctgacaaccccactcttgcagcgttagca
gcgcccctcttaacaagccgaccccccaccagcgtcgcggttactaacactcctctcccccgacctgcaa
ctagtaagcttcccgggttaattaaggccctcgaggatacatccaaagaggttgagtattctctctac
acttcttgttaaatggaaagtgcatttgcttgttcttacaatcggcccgagtctcgttcacagcgcct
cgttcacacttaaaccacaaatagtctacaggctatatgggagccagactgaaactcacatatgacta
atattcgggggtgttagtcacgtgtagcccattgtgtgcatataacgatgttggacgcgtccttatc
gcggtgtacttgatactatggcagcgagcatgggatattcatcctcgtcatcgttaacatctctacgg
gttcagaatgtttggcatgtcgtcgatccttttgcccatcgttgcaaattacaagtccgatcgccatga
ccgcgataagcctgtaccatgtggcattagggtgacatctcgatcatacattataagaccaacgtgcg
agtcttccaaagacctgcacgccttcttcttcggattgtcaacgggttcttcagaatctatgcccata
tctggcgttgagaccattgtgcgtttaatgaacaataaagcggcatgccatggaaaggaggggctgcag
atctccattttctcacgccactatcctggacgctgtagacgataattataccatgaatatagaggggg
tatgtttccactgccactgtgatgataagttttctccagattgttggatatctgcattttctgctgcc
gaacaaacttcatcgctatgcaaagagatgcgtgtgtacacgcgccgttgagtatacgggaaactaaa
tgttcatagaggtctttgggctatatgttattaaataaaataattgaccagtgaacaatttgtttaat
gttagtttattcaatgcattggttgcaaatattcattacttctccaatcccaggtcattctttagcga
gatgatgttatgacattgctgtgaaaattactacaggatatattttaagatgcaggagtaacaatgt
gcatagtaggcgtagttatcgcaacgcgtgcaacgcttcgcattttgagttaccgaagtgcccaacagtg
ctgcggttatggttatgcgcacagaatccatgcatgtcctaattgaaccatccgatttttcttttaa
tcgcgatcgttgtttgggcaactgcgttatttcagatctaaaaaatttacccttttatgaccatcacat
ctctctggctcatacccgcttggataagatatcatgtagattccgccctaagaaatgcaaactaaca
ttattgtcggttccatatacacttccatcttgtccttcgaaaataacaaactcgcgcaatagaccgtc
cgtacatgcatggccgatgtgtgtcaacatcattggtctgctagatcccgatgggacgaatcgtacag
tcgtcgctccagcattggcaaaaatccccagatacctccatgcggcaaatctaaattgcgaccccga
agagactgcaccaaagtcttatcgacgcacgctgattttttgaacagcgggagccattatcttcag
tggagcgtagacgggcgaggctaattatgtgacatagcaacactgcatgtatgtttttataaatcaat
aagagtacataattttattacgtatcatttccgtttgtaatatactgtatacatcatccacactattag
tcagcactagcgcgcgggcgcacgttacaatagcagcgtgcccgttatctatattgtccgatatttac
acataacatttcatcgacatgattaaatacctaagtactgcacacagatgtttaatgtatatcgtcat
ataaattatatcgctaggacagacccaaacgacctttatcccaaacagtcagatcctcttctcaagtg
tcgatttctgttatggaatatgcataccctggcccagaaattgcacgcacgagcgtagtgaatgcgtc
attggttttacatttaaaggctaaatgcacaaattctttagacgacagcacatcgttaaatagcatct
ctagcgttcttatgaatgctaagcattggagtcctcctggtcggccacaataacagctgagtatcata
ccctgagctccggggttgtcgcacatagcggattcgtataaacataggattttccgcgaatccatcag
ttgcaaaaatctgttaggctccatcaacaacgctggatttacttcagatccacgcgtaaagtaatggt
gctcgaataccgttttttagagttgtcggcatttcaaggaacaaagaattcatttcttcattgcaacga
cgcgccagaaatcccaagacctctttgggtagtatgttcttgcctataaaacacggcgttccaagtgc
caggaaccacgcatgtgttactgttggggcgtattcagaaataaagcggggtttatgcggcttttgaa
gctcggatatccaaagtatcgctgctgatgaacgagcgatgtagctgttacaaaacctcctttccat
cctccagtcaacataatatttatcggctacctatgtccgtaataagtattggtcgggcaattattcc
gtatgaggtcttgcaggaataagctcttagggacagccagcttggatatggtgcgaaacagaccttct
cggcttcagaatgtcgctccgcagtctcttcgtgtcggtgcatcttagatccaccatcaatgtgtgca
gcattgactcccgcccgtcgaatattccttttgttacgatgcagtaatgagcacgatcatgggcgggg
cgatgacgttctatttgcatgtctgcgaacaatttgcgtcagtcatcacagctatggagtgggccattt
ctggccgtcaacttaaaaacgcgaaccgcagacatatgttcatgcaaagacgtatcttcgtatt
tctgggcatcttcaaatgctctggccaatatggcaatgaatttggattcgtttgacgccgatggtatg
cagtgcaaatgtgccaatagcccacatccgaaaaagttatttgtcatacaagcaggtgttaagtagca
atcacataaaggcaccagacgcctcatggcatcataatgaatagctccttctccccactggaaccact
gacaaaatctgcgagtatattccgcaaaccacattttatttctcatagaaactaccctaaatcctttt
aacgggaagaagaatcctagatagtgcttgaagtcatgactgttactgctgcaataacactgtatatt
```

```
atttataaattccgtttgtctaggtatctgatgtaggcattccgatcccttactattgcgtcttcac
gaccaaatgggaatgcgccaaaatccccacacctcatcaccctggaggcagattgtgtattattaata
tccgccgattgaagcacaaaacggtacggtactgttcctaattctggtatagattctatggtcaaaag
tctgcatatccccgacattgccatgagatcacacagtccaagtagcatgtttattgagtcactcagac
tgtcaacgtccctcgccgcaccaccaatcgaaaataaagtatctacgcaagttatagctccgcatttt
ctatcgctagcagcaatcgcgacgcaaaacataaaggccatgttgggatttgaactctctgggggggct
tgttatcttctgcaccgtcgcagtcgcagttttccgaaatttatgtctaatatattttccggccgtgc
tccaatcggccgaaaagaatctgcgtattaccagactcattgacgggccgataaagaccataaaacaa
aattcctgtgcactccctcctccagttttgccatcgtccaagtcccgtaacttttttttgcgtttcgag
gagcaagcgttcgttatccctacccacacttgttttccaccgttttcttattataagcggttgtatcg
ccaacgcgtcaccgcaggttgtcacatacagtgatggcatacttgaacgtgcaacaacgcgctcgctt
tgcaaatctaagtcattgaccatcaaatcgcgttgagaggatagccaggcatctttttttcctagtatg
gtgacggtgcagccaccccaactcagttcttgtaaaaaaagctattggcgggaatttatgttctgagg
tgcattctatatttatgagtccatcaaatgccattaaccagattcgtattttttcgctcgacccggca
tcactatggatacaatacctttctatggcccatttcagctctcgaaccaaccacacggacaattgact
aacataagtatgatctttatcacagtcgcacccatctgagttatatttatggcatccgagcgctctta
ctgtacggtcggatacacccatggttttcctttatatagtcgggttatagtctgtcgggtttggcgg
tagcacggagtagtttgattttaagaatcgaaaacggcttggagagaccactgtcgaatatttgtc
cgtatactctacacgtgagtgttgtccattcctaggtatattcatctgttcggataccttcaattgct
gttcaggcataaccttaaagcatatgttatgttgtacatcaaaacttggtgagttatgttcgattgcc
gcgcataaagaatcgtacatgagcgtttctgctaacatactatctatattctcacacgccctgcata
tactgttcctattccaaattcacgttttgccccatcggctatctgctccaaaaagttgtaatatagg
tgccgctgggtgcgaaatttttcatcagttgtattcctgataaactgaatcactttacataatttttgc
cacatatctgcgtgcagccatagtatcgaacccgtgggctcggagacgacagtgcgtacaatgggtat
tttacctttccccaacaaaataatggtatacaagttaggtccgtacctagacttaatgtttccaatt
cttctgaatcactgcactctcgtagggagtaacggtaataattttcgtctctgagcccccgttttgcgt
tgaaaactaatcacattagataatgtgcaatcggtttcttttatccggatacatctaagtattatgac
atcggtggtcattgtttccatcaacgaccatcttttacgatcgcccatactactcatggacgttgtcg
gtgttgaaaaatcaccagaattgcaacggatctctgggtaccatgctgctgatggaattggcggtttt
aattgttgtttcagtctattattgctatctttggcggggttgaataatgtgggggggagagtgattgca
ggaatccgaatgggtcaataaaacgaccgtgctccgttctgccggcgccgatccgattgaagctatat
acttcgcttctctccccacttttccaatttgatccggaaataaaacggcccggacaacagtatcgta
cgatccggatccggatcctgcttgcctacagaagaatcaacatctcgccccaatattctggtcaaaac
tggctcgctcatggcaacgcggacgtttccccccggtggccagtcttaatggttaatgttcttttcggc
aatcttatacatcagcgggttgcgtgaatactggtcacagttcagtcatttactacacaccagcaata
cgacgacggacagtaccgtcccgacgaacgcgacgcccaaaattgctatcgcgaccgcgtccgaggcg
atgtcgtacgggcggtgcggggttggatcctcggcaaagagatcctcgtaattcggcggtgggagcgg
agggtaaagacgcgggtggggatctccctccggaccgcgcgccgggcgcggttcgaaaatgctttccg
cctcgctcagtgtcaacgccaagtattcgggcgggctggggggccgaatatctcccgcgacttcttct
atcggcgcggaattggagtcgcggtcgtggcgcgcttctagcgtcgtcaacggaagtccattttcggg
gtctcccggtgggcgttcagcgtccatcgtcgtatatgctctaacacacgtctcgctatattaaaaaa
aagaagagtatcggtcagtgtcgagtgtcgccgacaatgtcgcgagttctcggcgatttaattttttg

```
gtcgagacagttctacagaataatgaagagccccgcggacgcatgctgaaatgggtaatcgccttat
gaacattatgtactggtgttgcttgggacacgcaggacaatgctcgatatggcagttgtacgagacga
atcaggccattttaagtttattagatgaagtggttatcggcacaacaaatccctttgcaccctcgag
caatactggaagccattatgcaccgcaatcgccaacaagggacctcatcgcttgttgaggatgccaa
agtggccgagtacctggttagcatgcgcaaattgatataacataggcacgctctgatgttacagacca
caataccgcatacatttattgtaaggttgttaataaaggtttattctatgtaagactacaatactttc
gacattgcttgtatacatattaaatactttctcaagttcctattacataaaatgggatctatcattac
attcgttaagagtctggataattttactgtttgccagcttcgatcttggaacgtactgtggatagtgc
cttacttggaatcgtgaaaatttgaaacgtccattatttggatatcttccggttgtcccatatcccgc
cctggtaccgctcggatccttgcccgtatggattcgtattgacagtcgcgcaatcggggaccaacaa
cgcgtgggtccacactcattcggaaattttccgatgattctgaatatttattgccgctcgttacgagt
cgttggacatatctgtaatacatttcttcttctgaaggatcgctgcacatttgatctatacattggcc
aggatgttcaagtctcagatgttgcattctggcacagcacaactttatggcatttccgatgtaatcgt
ccggcagccctgggggagttctatattcgcatattgggatggtaaggacaatagcagatctcgcaacc
tccagggaggctataataacgttttaaaggatggattctcataaaaatctgtcgcaaattacactg
agaatatcctttactagcgccgattgagagcatcgtcgtccaattttctaaatgaaagaaaacaagg
cgggcaagagtgttccaaacattttcattttcggcgaatctctcaaatcccatggcgtgcaattgatt
gcaaaattggcacttccgttcacgtttgtatctccaaactctaagacacttttaattgaaaaactacg
ttctagtgtggaaagaaacctataggcagaccatagaactatttgacaccacatatcttttgtatgt
caaactgaccatgatcgtatgttgctgaatgcactagggcaattcgctcgcgcgactccatacattga
ataattccacacgtcagctcatcggttagcaaggtccagtagttgaagtcatttattttccccgcgg
ctggccaaatctacctctgggaatatccaagttgtcgaatatgatcgcaccggctctggtcatggtga
aggaactgtagcataaagacgcaggtatcataggggtaatatttttttattcactcacatactaaaag
taacgcatattagcaccatgtatgggctatcaattgacatttgcgtagcactacatcacgattatgta
caacataatgggacaacatggcaagtagatgcaatttcctcacactagttgggtttatctactatt
gaattttcccctatctgtgatacacttgggagcctctacaagcatattgccatcatgtacgtttttat
ctactgtcttaacgcccatgggaacggaggcgtcgtcgtcatgtattggacggcaacataggcagcaa
cacaaattgcgtttaggtggggtgcatgtggactcgataccaagcccctgcagctggggaacgtctgg
tggagagccgataatttgatatacgcacgccatattactgtcgttgaagtacgccttatcttctatgt
tttcaaatttaggttcccaagtggacgtgagaagtgtttgtatctcacatggaatgggcccaaggcatt
ccagcccaggtgcctggtactttaatggcaaacaaacgttttggtagaggtattgattctattgcagt
tctgcagatatctgcagccccgagtatccacaggctatacgatacgttatcggaggcaagctgcggcc
gctctagaactagtggatccccgggctgcagcccaatgtggaattcgcccttgcacattgttactcc
tgcatcttaaaaatatatcctgtagtaattttcacagcaatgtcataacatcatctcgctaaagaatg
acctgggattggagaagtaatgaatatttgcaaccaatgcattgaataaactaacattaaacgaattc
actagtggatccccaactccgcccgttttatgactagaaccaatagttttaatgccaaatgcactg
aaatcccctaatttgcaaagccaaacgcccctatgtgagtaatacgggacttttacccaattcc
caagcggaaagcccctaatacactcatatgcatatgaatgcacgcatgcactctaatggcgg
cccataggggacttccacatagggggcgttcaccatttcccagcataggggtggtgactcaatggcct
ttacccaagtacattgggtcaatggggaggtaagccaatgggttttccccattactggcaagcacactg
agtcaaatgggactttccactgggttttgcccaagtacattgggtcaatggggaggtgagccaatggga
aaaacccattgctgccaagtacactgactcaatagggactttccaatgggttttccattgttggcaa
gcatataaggtcaatgtgggtgagtcaataggggactttccattgtattctgcccagtacataaggtca
ataggggggtgaatcaacaggaaagtcccattggagccaagtacactgcgtcaataggggactttccatt
gggttttgcccagtacataaggtcaataggggatgagtcaatgggaaaaacccattggagccaagtac
actgactcaataggggactttccattgggttttgcccagtacataaggtcaataggggtgagtcaaca
ggaaagtcccattggagccaagtacattgagtcaataggggactttccaatgggttttgcccagtacat
aaggtcaatgggaggtaagccaatgggtttttcccattactggcacgtatactgagtcattagggact
ttccaatgggttttgcccagtacataaggtcaataggggtgaatcaacaggaaagtcccattggagcc
aagtacactgagtcaataggggactttccattgggttttgcccagtacaaaaggtcaataggggtgag
tcaatgggttttccccattattggcacgtacataaggtcaataggggtgagtcattgggttttcccag
ccaatttaattaaaacgccatgtactttcccaccattgacgtcaatgggctattgaaactaatgcaac
gtgacctttaaacggtactttcccatagctgattaatgggaaagtaccgttctcgagccaatacacgt
caatgggaagtgaaagggcagccaaaacgtaacaccgccccggttttccctggaaattccatattgg
cacgcattctattggctgagctgcgttctacgtgggtataagaggcgcgaccagcgtcggtaccgtcg
cagtcttcggtctgaccaccgtagaacgcagagctcctcgctgcaggcggccgctctagaactcgtcg
atcgcagcgatgacaaacctgcaagatcaaacccaacagattgttccgttcatacggagccttctgat
gccaacaaccggaccggcgtccattccggacgacaccctggagaagcacactctcaggtcagagacct
cgacctacaatttgactgtggggacacagggtcagggctaattgtcttttttccctggattccctggc
tcaattgtgggtgctcactacacactgcagagcaatgggaactaaggttcgatcagatgctcctgac
tgcccagaacctaccggccagctacaactactgcagactagtgagtcggagtctcacagtcgaggtcaa
gcacactccctggtggcgtttatgcactaaacggcaccataaacgccgtgaccttccaaggaagcctg
agtgaactgacagatgttagctacaatgggttgatgtctgcaacagccaacatcaacgacaaaattgg
gaatgtcctggtaggggaaggggtcactgtcctcagcctaccacatcatatgatcttgggtatgtga
ggcttggtgaccccattcccgctatagggcttgacccaaaaatggtagctacatgcgacagcagtgac
aggcccagagtctacaccataactgcagccgatgattaccaattctcatcacagtaccaaccaggtgg
ggtaacaatcacactgttctcagccaacattgatgctatcacaagcctcagcattggggagagctcg
tgtttcaaacaagcgtccaaggccttgtactgggcgccaccatctacctttataggctttgatgggact
gcggtaatcaccagagctgtagccgcagataatgggctgacggccggcaccgacaatcttatgccatt
caatcttgtcattccaaccaatgagataaacccagccaatcacatccatcaaactggagatagtgacct
ccaaaagtggtggtcaggcaggggatcagatgtcatggtcggcaagtgggagcctagcagtgacgatc
catggtggcaactatccaggggccctccgtcccgtcacactagtagcctacgaaagagtggcaacagg
atccgtcgttacggtcgctggggtgagtaacttcgagctgattccaaatcctgaactagcaaagaacc
tggttacagaatacggccgatttgacccaggagccatgaactacacaaaattgatactgagtgagagg
```

```
gaccgtcttggcatcaagaccgtctggccaacaagggagtacactgattttcgtgagtacttcatgga
ggtggccgacctcaactctcccctgaagattgcaggagcatttggcttcaaagacataatccgggcta
taaggaggtaagcttgatctagagcggccgcggggatccagacatgataagatacattgatgagtttg
gacaaaccacaactagaatgcagtgaaaaaaatgctttatttgtgaaatttgtgatgctattgcttta
tttgtaaccattataagctgcaataaacaagttaacaacaacaattgcattcattttatgtttcaggt
tcaggggaggtgtggaggttttttcggatcctctagagtcgacaattattttatttaataacatat
agcccaaagacctctatgaacatttagtttcccgtatactcaacggcgcgtgtacacacaagggcgaa
ttccacagtggatatcaagcttagcttgcctccgattctagcattacatagccggtcagtagatcctg
ccattcggtagcgcaaccggctacatcttcaaacagtctcacgataaatgcatctctcgttcctgcca
atccggaaccgggcataccactcccgcctgccgatttaattctcacaattgggcgatgccggcgggc
aaaacgaatgtggatttggcaaaccgacacaggtctgctgtacggactaatatgggcacacccacatc
attcttcagatgctccatgcattgttctatgagaaagatccatagggtggaggcagcgtcacgagatc
gcccaggcaatcgatcgcattcgtctagtaaagtgacgagagttatcatgcacacacccatgcccacg
ccttccgaataactggagctgtggaagatcggaaacgtctttttgactgccggtctcgtactactttc
gcacaggtgtatacccggacgcgtactatatatttttatatcatccaacgtccgaaattacatacgtgg
cggcgatggaagtagatgttgagtcttcgaaagtaagtgcctcgaatatgggtattgtctgtgaaaat
atcgaaagcggtacgacggttgcagaaccgtcgatgtcgccagatactagtaacaatagcttcgataa
cgaagacttccgtgggcctgaatacgatgtggagataaataccagaaaatctgctaatcttgatcgta
tggaatcttcgtgccgtgaacaacgagcggcgtgcgaacttcgaaagtgttcgtgtcctacgtctgcc
gtgcgcatgcaatacagtattctttcatctctcgctccgggttcagagggtcatgtatatatatgtac
tagatacggggacgcggaccaaaaaaaatgcatagtgaaggcagtcgttggaggaaagaatcccggga
gggaagtggatattttaaaaaccatctcacataaatcaattataaaattaatccatgcctataaatgg
aaaaatgttgtgtgtatggcaatgcgtgtatatcgttatgatcttttcacatatattgacggagtcgg
ccctatgcccttcaacagatgatctatattcaacgtggactactagaggcgctagcatacatacatg
aaaggggcatcattcaccgagacgtaaagacggagaatatattcttggataatcacgaaaatgcagtt
ttgggtgacttcggtgctgcatgccaactaggagattgtatagatacgcccaatgttacggttggag
cggaactgtggaaacaaattcgccggaattatctgcacttgatccgtattgcacaaaaacagatattt
ggagtgccggattggttctatatgagatggcaattaaaaatgtaccattgtttagtaagcaggtgaaa
agttcgggatctcagctgagatccataatacggtgcatgcaagtgcatgaactggagtttccccgcaa
cgattctaccaacctctgtaaacatttcaaacaatatgcggttcgtgtacgaccgccttataccattc
ctcgagttataagaaatgggggatgccaatggatgttgaatatgtcatttctaaaatgcttacgttt
gaccaggagttcagaccttctgctaaggaaatattgaatatgcccctatttactaaggcgccgattaa
cctgcttaatatcacaccctctgacagtgtctaacggtatacaggcgggagcgggtcgtggcgtcatc
atcaccacttgagaatttatattttgaattgttgattgataaattaacctgattcattgagaactgaa
acgccatattggtttcttggatatgtctacaacaattagttaaattgctatgttctactgcgagtaac
atttgataagttgtaagagacgggcgactcatgtcgaagttgacgaatataaagtacataacgtgttt
agaatacccagaatccgaatagtccgcggggcgtcttctcgcgtgagtaccaaatactgagttgaac
ttgaaaatgctaaatctgtgacactctttgtgtgatgattattgtcaccacttcgaagatggcttcga
cattcatgatgttctggtgtttgtttggaatcgtaatagcgcttgtttcgtccaagtctgacaacaaa
gaaaatctgaagaattatatcacggataagtcaaccaatattagaatacccacgccattatttgtatc
aacgaaaactcttatcccacaaaacatgtaatctacgatgaaaactgtggcttcgctgtactcaatc
ctataagtgaccccaaatatgtccttttgagccagcttctaatgggaaggcgcaaatatgatgcgacg
gtcgcgtggtttgttctcggtaaaatgtgtgccagattaatatatttgcgcgaattttataactgctc
gacaaatgagccttttggcacatgttctatgagctctcctggatggtgggacaggcgctacgtctcaa
ccagtttcatttctcgcgacgaattacagctggttttttgcagcgccgtcccgagaattagatggttta
tatacgcgcgtagtagttgtcaacggggactttactacggccgatataatgtttaatgttaaagtggc
atgtgccttttcaaagactggaatagaagatgatacattatgcaaacccttcatttctttgccaatg
caacattgcacaatttaaccatgattagatcggtaactcttcgagcgcacgaaagccatttaaaggaa
tgggtggcacgagaggtggtaacgtccctgcagtgctacttgagtctaccatgtatcatgcatccaa
tctgcctagaaatttcagggatttctacataaagtctccagatgattataagtataatcacctagatg
ggccatctgtaatgctcatcactgacagacctagtgaagatttggatgggaggctcgttcaccaaagt
gacatttttactactacaagtcctataaaacaggtccggtatgaagagcatcagtcacatacaaagca
gtatcctgtaaacaaaatacaagctataatttttttgataggggttaggctcgttcattggaagcatat
tcgtagtttttggtagtatggattatacgcagatattgcaatggagcgcggagtggggggaacgccccc
agtcctcgccggtatgtgtataccaggctatgatcacgtgtgaaacttgggcggacctgtatcatatg
tacaccgtccctattcgtttatagccagtacgtgttatctgcacatagaggaacatgtgtcatactgg
gatcgcatgcatggtatgtgtgactctaatattattctgtatcataataaaaacacagtgcatggtat
```

-continued

```
atagaggatcgctggtaagcactacggtagaccaatcggctcagattgcattctttggcatcgatacc
gttgttaatttatatggcaaagtcttgttcatgggagatcagtatttggaggaaatatactctggaac
gatggaaatactcaaatggaatcaagctaaccgctgctattctattgcgcatgcaacatattacgccg
actgtcctataatcagttctacggtattcagaggatgccgggacgccgttgtttatactaggccccac
agcag
```

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A recombinant herpesvirus of turkeys (rHVT) that comprises at least three heterologous nucleotide sequences;
   wherein the first heterologous nucleotide sequence is comprised by a first heterologous nucleic acid or a second heterologous nucleic acid, the second heterologous nucleotide sequence is comprised by the first heterologous nucleic acid or the second heterologous nucleic acid, and the third heterologous nucleotide sequence is comprised by the first heterologous nucleic acid or the second heterologous nucleic acid;
   wherein the first heterologous nucleic acid is located in a first nonessential site in the rHVT genome, and the second heterologous nucleic acid is located in a second nonessential site in the rHVT genome;
   wherein the first nonessential site and the second nonessential site are either the same or different;
   wherein the first heterologous nucleotide sequence comprises a coding sequence for an Infectious Bursal Disease Virus viral protein 2 (IBDV VP2), the second heterologous nucleotide sequence comprises a coding sequence for an Infectious Laryngotracheitis Virus glycoprotein D (ILTV gD) and a coding sequence for an Infectious Laryngotracheitis Virus glycoprotein I (ILTV gI), and the third heterologous nucleotide sequence comprises a coding sequence for a Newcastle Disease Virus fusion protein (NDV F);
   wherein when the first nonessential site and the second nonessential site are two different sites, the two different sites are the US2 site and the UL54.5 site; and
   wherein when the first nonessential site and the second nonessential site are the same site, the site is selected from the group consisting of the US2 site and the UL54.5 site.

2. The rHVT of claim 1,
   wherein the first nonessential site and the second nonessential site are two different sites, and the two different sites are the US2 site and the UL54.5 site.

3. The rHVT of claim 2, wherein the first heterologous nucleic acid comprises a coding sequence for IBDV VP2, and a coding sequence for ILTV gD, and a coding sequence for ILTV gI; and wherein the second heterologous nucleic acid comprises a coding sequence for NDV F.

4. The rHVT of claim 3, wherein the first heterologous nucleic acid comprises the nucleotide sequence of SEQ ID NO: 23, and wherein the second heterologous nucleic acid comprises the nucleotide sequence of SEQ ID NO: 26; or the first heterologous nucleic acid comprises the nucleotide sequence of SEQ ID NO: 21, and the second heterologous nucleic acid comprises the nucleotide sequence of SEQ ID NO: 22.

5. The rHVT of claim 2, wherein the first heterologous nucleic acid comprises a coding sequence for ILTV gD, a coding sequence for ILTV gI, and a coding sequence for NDV F; and wherein the second heterologous nucleic acid comprises a coding sequence for IBDV VP2.

6. The rHVT of claim 5, wherein the first heterologous nucleic acid comprises the nucleotide sequence of SEQ ID NO: 28 and the second heterologous nucleic acid comprises the nucleotide sequence of SEQ ID NO: 27; or the first heterologous nucleic acid comprises the nucleotide sequence of SEQ ID NO: 31 and the second heterologous nucleic acid comprises the nucleotide sequence of SEQ ID NO: 32.

7. The rHVT of claim 2, wherein the first heterologous nucleic acid comprises a coding sequence for IBDV VP2 and a coding sequence for NDV F; and wherein the second heterologous nucleic acid comprises a coding sequence for ILTV gD and a coding sequence for ILTV gI.

8. The rHVT of claim 7, wherein the first heterologous nucleic acid comprises the nucleotide sequence of SEQ ID NO: 30 and the second heterologous nucleic acid comprises the nucleotide sequence of SEQ ID NO: 29.

9. The rHVT of claim 3, wherein the coding sequence of the IBDV VP2 is operatively under the control of a murine cytomegalovirus immediate early 1 gene (mCMV-IE1) promoter; the coding sequence of the ILTV gD is operatively under the control of an endogenous ILTV gD promoter; the coding sequence of the ILTV gI is operatively under the control of an endogenous ILTV gI promoter; and the coding sequence of the NDV F is operatively under the control of a human cytomegalovirus immediate early 1 gene (hCMV-IE1) promoter.

10. An immunogenic composition comprising the rHVT of claim 3.

11. A vaccine comprising the immunogenic composition of claim 10.

12. A method for aiding in the protection of a chicken against a virus selected from the group consisting of NDV, ILTV, IBDV, MDV, and any combination thereof comprising administering the vaccine of claim 11, to the chicken.

13. An immunogenic composition comprising the rHVT of claim 5.

14. A vaccine comprising the immunogenic composition of claim 13.

15. A method for aiding in the protection of a chicken against a virus selected from the group consisting of NDV, ILTV, IBDV, MDV, and any combination thereof comprising administering the vaccine of claim 14, to the chicken.

16. An immunogenic composition comprising the rHVT of claim 7.

17. A vaccine comprising the immunogenic composition of claim 16.

18. A method for aiding in the protection of a chicken against a virus selected from the group consisting of NDV, ILTV, IBDV, MDV, and any combination thereof comprising administering the vaccine of claim 17, to the chicken.

19. The rHVT of claim 5, wherein the coding sequence of the IBDV VP2 is operatively under the control of a murine cytomegalovirus immediate early 1 gene (mCMV-IE1) promoter; the coding sequence of the ILTV gD is operatively under the control of an endogenous ILTV gD promoter; the coding sequence of the ILTV gI is operatively under the control of an endogenous ILTV gI promoter; and the coding sequence of the NDV F is operatively under the control of a human cytomegalovirus immediate early 1 gene (hCMV-IE1) promoter.

20. The rHVT of claim 7, wherein the coding sequence of the IBDV VP2 is operatively under the control of a murine cytomegalovirus immediate early 1 gene (mCMV-IE1) promoter; the coding sequence of the ILTV gD is operatively under the control of an endogenous ILTV gD promoter; the coding sequence of the ILTV gI is operatively under the control of an endogenous ILTV gI promoter; and the coding sequence of the NDV F is operatively under the control of a human cytomegalovirus immediate early 1 gene (hCMV-IE1) promoter.

* * * * *

SEQUENCE LISTING

```
<160> NUMBER OF SEQ ID NOS: 32

<210> SEQ ID NO 1
<211> LENGTH: 1134
<212> TYPE: DNA
<213> ORGANISM: Infectious Laryngotracheitis virus

<400> SEQUENCE: 1
atggaccgcc atttattttt gaggaatgct ttttggacta tcgtactgct ttcttccttc     60
gctagccaga gcaccgccgc cgtcacgtac gactacattt taggccgtcg cgcgctcgac    120
gcgctaacca taccggcggt tggcccgtat aacagatacc tcactagggt atcaagaggc    180
tgcgacgttg tcgagctcaa cccgatttct aacgtggacg acatgatatc ggcggccaaa    240
gaaaaagaga agggggccc tttcgaggcc tccgtcgtct ggttctacgt gattaagggc    300
gacgacggcg aggacaagta ctgtccaatc tatagaaaag agtacaggga atgtggcgac    360
gtacaactgc tatctgaatg cgccgttcaa tctgcacaga tgtgggcagt ggactatgtt    420
cctagcaccc ttgtatcgcg aaatggcgcg ggactgacta tattctcccc cactgctgcg    480
ctctctggcc aatacttgct gaccctgaaa atcgggagat ttgcgcaaac agctctcgta    540
actctagaag ttaacgatcg ctgtttaaag atcgggtcgc agcttaactt tttaccgtcg    600
aaatgctgga caacagaaca gtatcagact ggatttcaag gcgaacacct ttatccgatc    660
gcagacacca atacacgaca cgcggacgac gtatatcggg gatacgaaga tattctgcag    720
cgctggaata atttgctgag gaaaaagaat cctagcgcgc cagaccctcg tccagatagc    780
gtcccgcaag aaattcccgc tgtaaccaag aaagcggaag ggcgcacccc ggacgcagaa    840
agcagcgaaa agaaggcccc tccagaagac tcggaggacg acatgcaggc agaggcttct    900
ggagaaaatc ctgccgccct ccccgaagac gacgaagtcc ccgaggacac cgagcacgat    960
gatccaaact cggatcctga ctattacaat gacatgcccg ccgtgatccc ggtggaggag   1020
actactaaaa gttctaatgc cgtctccatg cccatattcg cggcgttcgt agcctgcgcg   1080
gtcgcgctcg tggggctact ggtttggagc atcgtaaaat gcgcgcgtag ctaa         1134

<210> SEQ ID NO 2
<211> LENGTH: 377
<212> TYPE: PRT
<213> ORGANISM: Infectious Laryngotracheitis virus

<400> SEQUENCE: 2
```

Met Asp Arg His Leu Phe Leu Arg Asn Ala Phe Trp Thr Ile Val Leu
1               5                   10                  15

Leu Ser Ser Phe Ala Ser Gln Ser Thr Ala Ala Val Thr Tyr Asp Tyr
            20                  25                  30

Ile Leu Gly Arg Arg Ala Leu Asp Ala Leu Thr Ile Pro Ala Val Gly
        35                  40                  45

Pro Tyr Asn Arg Tyr Leu Thr Arg Val Ser Arg Gly Cys Asp Val Val
    50                  55                  60

Glu Leu Asn Pro Ile Ser Asn Val Asp Asp Met Ile Ser Ala Ala Lys
65                  70                  75                  80

Glu Lys Glu Lys Gly Gly Pro Phe Glu Ala Ser Val Val Trp Phe Tyr
                85                  90                  95

Val Ile Lys Gly Asp Asp Gly Glu Asp Lys Tyr Cys Pro Ile Tyr Arg
            100                 105                 110

Lys Glu Tyr Arg Glu Cys Gly Asp Val Gln Leu Leu Ser Glu Cys Ala
        115                 120                 125

Val Gln Ser Ala Gln Met Trp Ala Val Asp Tyr Val Pro Ser Thr Leu
    130                 135                 140

Val Ser Arg Asn Gly Ala Gly Leu Thr Ile Phe Ser Pro Thr Ala Ala
145                 150                 155                 160

Leu Ser Gly Gln Tyr Leu Leu Thr Leu Lys Ile Gly Arg Phe Ala Gln
                165                 170                 175

Thr Ala Leu Val Thr Leu Glu Val Asn Asp Arg Cys Leu Lys Ile Gly
            180                 185                 190

Ser Gln Leu Asn Phe Leu Pro Ser Lys Cys Trp Thr Thr Glu Gln Tyr
        195                 200                 205

Gln Thr Gly Phe Gln Gly Glu His Leu Tyr Pro Ile Ala Asp Thr Asn
    210                 215                 220

Thr Arg His Ala Asp Asp Val Tyr Arg Gly Tyr Glu Asp Ile Leu Gln
225                 230                 235                 240

Arg Trp Asn Asn Leu Leu Arg Lys Lys Asn Pro Ser Ala Pro Asp Pro
                245                 250                 255

Arg Pro Asp Ser Val Pro Gln Glu Ile Pro Ala Val Thr Lys Lys Ala
            260                 265                 270

Glu Gly Arg Thr Pro Asp Ala Glu Ser Ser Glu Lys Lys Ala Pro Pro
        275                 280                 285

Glu Asp Ser Glu Asp Asp Met Gln Ala Glu Ala Ser Gly Glu Asn Pro
    290                 295                 300

Ala Ala Leu Pro Glu Asp Asp Glu Val Pro Glu Asp Thr Glu His Asp
305                 310                 315                 320

Asp Pro Asn Ser Asp Pro Asp Tyr Tyr Asn Asp Met Pro Ala Val Ile
                325                 330                 335

Pro Val Glu Glu Thr Thr Lys Ser Ser Asn Ala Val Ser Met Pro Ile
            340                 345                 350

Phe Ala Ala Phe Val Ala Cys Ala Val Ala Leu Val Gly Leu Leu Val
        355                 360                 365

Trp Ser Ile Val Lys Cys Ala Arg Ser
        370                 375

<210> SEQ ID NO 3
<211> LENGTH: 1089
<212> TYPE: DNA
<213> ORGANISM: Infectious Laryngotracheitis virus

<400> SEQUENCE: 3

```
atggcatcgc tacttggaac tctggctctc cttgccgcga cgctcgcacc cttcggcgcg    60
atgggaatcg tgatcactgg aaatcacgtc tccgccagga ttgacgacga tcacatcgtg   120
atcgtcgcgc ctcgccccga agctacaatt caactgcagc tattttcat gcctggccag    180 agacccaca aaccctactc aggaaccgtc cgcgtcgcgt ttcggtctga tataacaaac    240
cagtgctacc aggaacttag cgaggagcgc tttgaaaatt gcactcatcg atcgtcttct    300
gtttttgtcg gctgtaaagt gaccgagtac acgttctccg cctcgaacag actaaccgga    360
cctccacacc cgtttaagct cactatacga aatcctcgtc cgaacgacag cgggatgttc    420
tacgtaattg ttcggctaga cgacaccaaa gaacccattg acgtcttcgc gatccaacta    480
tcggtgtatc aattcgcgaa caccgccgcg actcgcggac tctattccaa ggcttcgtgt    540
cgcaccttcg gattacctac cgtccaactt gaggcctatc tcaggaccga ggaaagttgg    600
cgcaactggc aagcgtacgt tgccacggag gccacgacga ccagcgccga ggcgacaacc    660
ccgacgcccg tcactgcaac cagcgcctcc gaacttgaag cggaacactt tacctttccc    720
tggctagaaa atggcgtgga tcattacgaa ccgacacccg caaacgaaaa ttcaaacgtt    780
actgtccgtc tcgggacaat gagccctacg ctaattgggg taaccgtggc tgccgtcgtg    840
agcgcaacga tcggcctcgt cattgtaatt tccatcgtca ccagaaacat gtgcaccccg    900
caccgaaaat tagacacggt ctcgcaagac gacgaagaac gttcccaaac tagaagggaa    960
tcgcgaaaat ttggacccat ggttgcgtgc gaaataaaca agggggctga ccaggatagt   1020
gaacttgtgg aactggttgc gattgttaac ccgtctgcgc taagctcgcc cgactcaata   1080
aaaatgtga                                                           1089
```

<210> SEQ ID NO 4
<211> LENGTH: 362
<212> TYPE: PRT
<213> ORGANISM: Infectious Laryngotracheitis virus

<400> SEQUENCE: 4

```
Met Ala Ser Leu Leu Gly Thr Leu Ala Leu Leu Ala Ala Thr Leu Ala
1               5                   10                  15

Pro Phe Gly Ala Met Gly Ile Val Ile Thr Gly Asn His Val Ser Ala
                20                  25                  30

Arg Ile Asp Asp Asp His Ile Val Ile Ala Pro Arg Pro Glu Ala
            35                  40                  45

Thr Ile Gln Leu Gln Leu Phe Phe Met Pro Gly Gln Arg Pro His Lys
        50                  55                  60

Pro Tyr Ser Gly Thr Val Arg Val Ala Phe Arg Ser Asp Ile Thr Asn
65                  70                  75                  80

Gln Cys Tyr Gln Glu Leu Ser Glu Glu Arg Phe Glu Asn Cys Thr His
                85                  90                  95

Arg Ser Ser Val Phe Val Gly Cys Lys Val Thr Glu Tyr Thr Phe
            100                 105                 110

Ser Ala Ser Asn Arg Leu Thr Gly Pro Pro His Pro Phe Lys Leu Thr
        115                 120                 125

Ile Arg Asn Pro Arg Pro Asn Asp Ser Gly Met Phe Tyr Val Ile Val
    130                 135                 140

Arg Leu Asp Asp Thr Lys Glu Pro Ile Asp Val Phe Ala Ile Gln Leu
145                 150                 155                 160

Ser Val Tyr Gln Phe Ala Asn Thr Ala Ala Thr Arg Gly Leu Tyr Ser
                165                 170                 175
```

```
Lys Ala Ser Cys Arg Thr Phe Gly Leu Pro Thr Val Gln Leu Glu Ala
            180                 185                 190

Tyr Leu Arg Thr Glu Glu Ser Trp Arg Asn Trp Gln Ala Tyr Val Ala
            195                 200                 205

Thr Glu Ala Thr Thr Ser Ala Glu Ala Thr Thr Pro Thr Pro Val
    210                 215                 220

Thr Ala Thr Ser Ala Ser Glu Leu Glu Ala Glu His Phe Thr Phe Pro
225                 230                 235                 240

Trp Leu Glu Asn Gly Val Asp His Tyr Glu Pro Thr Pro Ala Asn Glu
            245                 250                 255

Asn Ser Asn Val Thr Val Arg Leu Gly Thr Met Ser Pro Thr Leu Ile
            260                 265                 270

Gly Val Thr Val Ala Ala Val Val Ser Ala Thr Ile Gly Leu Val Ile
            275                 280                 285

Val Ile Ser Ile Val Thr Arg Asn Met Cys Thr Pro His Arg Lys Leu
            290                 295                 300

Asp Thr Val Ser Gln Asp Asp Glu Glu Arg Ser Gln Thr Arg Arg Glu
305                 310                 315                 320

Ser Arg Lys Phe Gly Pro Met Val Ala Cys Glu Ile Asn Lys Gly Ala
            325                 330                 335

Asp Gln Asp Ser Glu Leu Val Glu Leu Val Ala Ile Val Asn Pro Ser
            340                 345                 350

Ala Leu Ser Ser Pro Asp Ser Ile Lys Met
            355                 360

<210> SEQ ID NO 5
<211> LENGTH: 1362
<212> TYPE: DNA
<213> ORGANISM: Infectious bursal disease virus

<400> SEQUENCE: 5 atgacaaaacc tgcaagatca aacccaacag attgttccgt tcatacggag ccttctgatg      60
ccaacaaccg accggcgtc cattccggac gacaccctgg agaagcacac tctcaggtca      120
gagacctcga cctacaattt gactgtgggg acacagggtc agggctaat tgtctttttc      180 cctggattcc ctggctcaat tgtgggtgct cactacacac tgcagagcaa tgggaactac      240
aagttcgatc agatgctcct gactgcccag aacctaccgg ccagctacaa ctactgcaga      300
ctagtgagtc ggagtctcac agtgaggtca agcacactcc ctggtggcgt ttatgcacta      360
aacggcacca taaacgccgt gaccttccaa ggaagcctga gtgaactgac agatgttagc      420
tacaatgggt tgatgtctgc aacagccaac atcaacgaca aaattgggaa tgtcctggta      480
ggggaagggg tcactgtcct cagcctaccc acatcatatg atcttgggta tgtgaggctt      540
ggtgacccca ttcccgctat agggcttgac ccaaaaatgg tagctacatg cgacagcagt      600
gacaggccca gagtctacac cataactgca gccgatgatt accaattctc atcacagtac      660
caaccaggtg gggtaacaat cacactgttc tcagccaaca ttgatgctat cacaagcctc      720
agcattgggg gagagctcgt gtttcaaaca agcgtccaag gccttgtact gggcgccacc      780
atctacctta taggctttga tgggactgcg gtaatcacca gagctgtggc cgcagataat      840
gggctgacgg ccggcaccga caatcttatg ccattcaatc ttgtcattcc aaccaatgag      900
ataacccagc caatcacatc catcaaactg gagatagtga cctccaaaag tggtggtcag      960 gcagggggatc agatgtcatg gtcggcaagt gggagcctag cagtgacgat ccatggtggc     1020
```

-continued

```
aactatccag gggccctccg tcccgtcaca ctagtagcct acgaaagagt ggcaacagga    1080
tccgtcgtta cggtcgctgg ggtgagtaac ttcgagctga ttccaaatcc tgaactagca    1140
aagaacctgg ttacagaata cggccgattt gacccaggag ccatgaacta cacaaaattg    1200
atactgagtg agagggaccg tcttggcatc aagaccgtct ggccaacaag ggagtacact    1260
gattttcgtg agtacttcat ggaggtggcc gacctcaact ctcccctgaa gattgcagga    1320
gcatttggct tcaaagacat aatccgggct ataaggaggt aa                      1362
```

<210> SEQ ID NO 6
<211> LENGTH: 453
<212> TYPE: PRT
<213> ORGANISM: Infectious bursal disease virus

<400> SEQUENCE: 6

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Ile Gly Gly Glu Leu Val Phe Gln Thr Ser Val Gln Gly Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asp Asn Gly Leu Thr Ala Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320
```

Ala Gly Asp Gln Met Ser Trp Ser Ala Ser Gly Ser Leu Ala Val Thr
            325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
            405                 410                 415

Arg Glu Tyr Thr Asp Phe Arg Glu Tyr Phe Met Glu Val Ala Asp Leu
        420                 425                 430

Asn Ser Pro Leu Lys Ile Ala Gly Ala Phe Gly Phe Lys Asp Ile Ile
    435                 440                 445

Arg Ala Ile Arg Arg
    450

<210> SEQ ID NO 7
<211> LENGTH: 1662
<212> TYPE: DNA
<213> ORGANISM: Newcastle disease virus

<400> SEQUENCE: 7

| | | | | | |
|---|---|---|---|---|---|
| atgggcccca | gaccttctac | caagaaccca | gtacctatga | tgctgactgt | ccgagtcgcg | 60 |
| ctggtactga | gttgcatctg | tccggcaaac | tccattgatg | caggcctct | tgcggctgca | 120 |
| ggaattgtgg | ttacaggaga | caaagccgtc | aacatataca | cctcatccca | gacaggatca | 180 |
| atcatagtta | agctcctccc | gaatctgccc | aaggataagg | aggcatgtgc | gaaagccccc | 240 |
| ttggatgcat | acaacaggac | attgaccact | ttgctcaccc | ccttggtga | ctctatccgt | 300 |
| aggatacaag | agtctgtgac | tacatctgga | gggggagac | aggggcgcct | tataggcgcc | 360 |
| attattggcg | gtgtggctct | tggggttgca | actgccgcac | aaataacagc | ggccgcagct | 420 |
| ctgatacaag | ccaaacaaaa | tgctgccaac | atcctccgac | ttaaagagag | cattgccgca | 480 |
| accaatgagc | tgtgcatga | ggtcactgac | ggattatcgc | aactagcagt | ggcagttggg | 540 |
| aagatgcagc | agtttgttaa | tgaccaattt | aataaaacag | ctcaggaatt | agactgcatc | 600 |
| aaaattgcac | agcaagttgg | tgtagagctc | aacctgtacc | taaccgaatt | gactacagta | 660 |
| ttcggaccac | aaatcacttc | acctgcttta | aacaagctga | ctattcaggc | actttacaat | 720 |
| ctagctggtg | aaatatgga | ttacttattg | actaagttag | gtgtagggaa | caatcaactc | 780 |
| agctcattaa | tcggtagcgg | cttaatcacc | ggtaacccta | ttctatacga | ctcacagact | 840 |
| caactcttgg | gtatacaggt | aactctacct | tcagtcggga | agctaaataa | tatgcgtgcc | 900 |
| acctacttgg | aaaccttatc | cgtaagcaca | accagggat | ttgcctcggc | acttgtccca | 960 |
| aaagtggtga | cacaggtcgg | ttctgtgata | gaagaacttg | acacctcata | ctgtatagaa | 1020 |
| actgacttac | atttatattg | tacaagaata | gtaacgttcc | ctatgtcccc | tggtattat | 1080 |
| tcctgcttga | gcggcaatac | gtcggcctgt | atgtactcaa | agaccgaagg | cgcacttact | 1140 |
| acaccataca | tgactatcaa | aggttcagtc | atcgccaact | gcaagatgac | aacatgtaga | 1200 |
| tgtgtaaacc | ccccgggtat | catatcgcaa | aactatggag | aagccgtgtc | tctaatagat | 1260 |
| aaacaatcat | gcaatgtttt | atccttaggc | gggataactt | taaggctcag | tgggaattc | 1320 |

```
gatgtaactt atcagaagaa tatctcaata caagattctc aagtaataat aacaggcaat    1380
cttgatatct caactgagct tgggaatgtc aacaactcga tcagtaatgc tttgaataag    1440
ttagaggaaa gcaacagaaa actagacaaa gtcaatgtca aactgactag cacatctgct    1500
ctcattacct atatcgtgtt gactatcata tctcttgttt ttggtatact tagcctgatt    1560
ctagcatgct acctaatgta caagcaaaag gcgcaacaaa agaccttatt atggcttggg    1620
aataatactc tagatcagat gagagccact acaaaaatgt ga                      1662
```

<210> SEQ ID NO 8
<211> LENGTH: 553
<212> TYPE: PRT
<213> ORGANISM: Newcastle disease virus

<400> SEQUENCE: 8

```
Met Gly Pro Arg Pro Ser Thr Lys Asn Pro Val Pro Met Met Leu Thr
1               5                   10                  15

Val Arg Val Ala Leu Val Leu Ser Cys Ile Cys Pro Ala Asn Ser Ile
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Leu Pro Lys Asp Lys Glu Ala Cys Ala Lys Ala Pro
65                  70                  75                  80

Leu Asp Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Arg Gln Gly Arg Leu Ile Gly Ala Ile Ile Gly Gly Val Ala Leu Gly
        115                 120                 125

Val Ala Thr Ala Ala Gln Ile Thr Ala Ala Ala Ala Leu Ile Gln Ala
    130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Ala Gln Gln Val Gly Val
        195                 200                 205

Glu Leu Asn Leu Tyr Leu Thr Glu Leu Thr Thr Val Phe Gly Pro Gln
    210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Val Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Lys Leu Asn Asn Met Arg Ala Thr Tyr Leu Glu
    290                 295                 300

Thr Leu Ser Val Ser Thr Thr Arg Gly Phe Ala Ser Ala Leu Val Pro
```

| | | | | | 305 | | | | | 310 | | | | | 315 | | | | | 320 |
|---|---|---|---|---|---|---|---|---|---|---|---|---|---|---|---|---|---|---|---|---|

Lys Val Val Thr Gln Val Gly Ser Val Ile Glu Glu Leu Asp Thr Ser
                          325                      330                   335

Tyr Cys Ile Glu Thr Asp Leu His Leu Tyr Cys Thr Arg Ile Val Thr
           340                   345                350

Phe Pro Met Ser Pro Gly Ile Tyr Ser Cys Leu Ser Gly Asn Thr Ser
        355                   360                365

Ala Cys Met Tyr Ser Lys Thr Glu Gly Ala Leu Thr Thr Pro Tyr Met
370                    375                    380

Thr Ile Lys Gly Ser Val Ile Ala Asn Cys Lys Met Thr Thr Cys Arg
385                    390                  395                400

Cys Val Asn Pro Pro Gly Ile Ile Ser Gln Asn Tyr Gly Glu Ala Val
           405                   410                415

Ser Leu Ile Asp Lys Gln Ser Cys Asn Val Leu Ser Leu Gly Gly Ile
               420                   425                430

Thr Leu Arg Leu Ser Gly Glu Phe Asp Val Thr Tyr Gln Lys Asn Ile
               435                   440                445

Ser Ile Gln Asp Ser Gln Val Ile Ile Thr Gly Asn Leu Asp Ile Ser
        450                   455                460

Thr Glu Leu Gly Asn Val Asn Asn Ser Ile Ser Asn Ala Leu Asn Lys
465                    470                  475                480

Leu Glu Glu Ser Asn Arg Lys Leu Asp Lys Val Asn Val Lys Leu Thr
               485                   490                495

Ser Thr Ser Ala Leu Ile Thr Tyr Ile Val Leu Thr Ile Ile Ser Leu
        500                   505                510

Val Phe Gly Ile Leu Ser Leu Ile Leu Ala Cys Tyr Leu Met Tyr Lys
           515                   520                525

Gln Lys Ala Gln Gln Lys Thr Leu Leu Trp Leu Gly Asn Asn Thr Leu
        530                   535                540

Asp Gln Met Arg Ala Thr Thr Lys Met
545                    550

<210> SEQ ID NO 9
<211> LENGTH: 1698
<212> TYPE: DNA
<213> ORGANISM: Newcastle disease virus

<400> SEQUENCE: 9

```
atggatcgat cccggttggc gccctccagg tgcaggatgg gctccagacc ttctaccaag      60
aacccagcac ctatgatgct gactatccgg gtcgcgctgg tactgagttg catctgtccg     120
gcaaactcca ttgatggcag gcctcttgca gctgcaggaa ttgtggttac aggagacaaa     180
gcagtcaaca tataccctc atcccagaca ggatcaatca tagttaagct cctcccgaat     240
ctgccaaagg ataaggaggc atgtgcgaaa gcccccttgg atgcatacaa caggacattg     300
accactttgc tcaccccct tggtgactct atccgtagga tacaagagtc tgtgactaca     360
tctggagggg ggagacaggg gcgccttata ggcgccatta ttggcggtgt ggctcttggg     420
gttgcaactg ccgcacaaat aacagcggcc gcagctctga tacaagccaa acaaaatgct     480
gccaacatcc tccgacttaa agagagcatt gccgcaacca atgaggctgt gcatgaggtc     540
actgacggat tatcgcaact agcagtggca gttgggaaga tgcagcagtt cgttaatgac     600
caatttaata aaacagctca ggaattagac tgcatcaaaa ttgcacagca agttggtgta     660
gagctcaacc tgtacctaac cgaatcgact acagtattcg gaccacaaat cacttcacct     720
```

-continued

```
gccttaaaca agctgactat tcaggcactt tacaatctag ctggtgggaa tatggattac    780
ttattgacta agttaggtat agggaacaat caactcagct cattaatcgg tagcggctta    840
atcaccggta acctattct atacgactca cagactcaac tcttgggtat acaggtaact    900
ctaccttcag tcgggaacct aaataatatg cgtgccacct acttggaaac cttatccgta    960
agcacaacca ggggatttgc ctcggcactt gtcccaaaag tggtgacacg ggtcggttct   1020
gtgatagaag aacttgacac ctcatactgt atagaaactg acttagattt atattgtaca   1080
agaatagtaa cgttccctat gtcccctggt atttactcct gcttgagcgg caatacatcg   1140
gcctgtatgt actcaaagac cgaaggcgca cttactacac catatatgac tatcaaaggc   1200
tcagtcatcg ctaactgcaa gatgacaaca tgtagatgtg taaaccccc gggtatcata    1260
tcgcaaaact atggagaagc cgtgtctcta atagataaac aatcatgcaa tgttttatcc   1320
ttaggcggga taactttaag gctcagtggg gaattcgatg taacttatca gaagaatatc   1380
tcaatacaag attctcaagt aataataaca ggcaatcttg atatctcaac tgagcttggg   1440
aatgtcaaca actcgatcag taatgccttg aataagttaa aggaaagcaa cagaaaacta   1500
gacaaagtca atgtcaaact gaccagcaca tctgctctca ttacctatat cgttttgact   1560
atcatatctc ttgtttttgg tatacttagc ctgattctag catgctacct aatgtacaag   1620
caaaaggcgc aacaaaagac cttattatgg cttgggaata taccctaga tcagatgaga    1680
gccactacaa aaatgtga                                                  1698
```

<210> SEQ ID NO 10
<211> LENGTH: 565
<212> TYPE: PRT
<213> ORGANISM: Newcastle disease virus

<400> SEQUENCE: 10

```
Met Asp Arg Ser Arg Leu Ala Pro Ser Arg Cys Arg Met Gly Ser Arg
1               5                   10                  15

Pro Ser Thr Lys Asn Pro Ala Pro Met Met Leu Thr Ile Arg Val Ala
            20                  25                  30

Leu Val Leu Ser Cys Ile Cys Pro Ala Asn Ser Ile Asp Gly Arg Pro
        35                  40                  45

Leu Ala Ala Ala Gly Ile Val Val Thr Gly Asp Lys Ala Val Asn Ile
    50                  55                  60

Tyr Thr Ser Ser Gln Thr Gly Ser Ile Ile Val Lys Leu Leu Pro Asn
65                  70                  75                  80

Leu Pro Lys Asp Lys Glu Ala Cys Ala Lys Ala Pro Leu Asp Ala Tyr
                85                  90                  95

Asn Arg Thr Leu Thr Thr Leu Leu Thr Pro Leu Gly Asp Ser Ile Arg
            100                 105                 110

Arg Ile Gln Glu Ser Val Thr Thr Ser Gly Gly Gly Arg Gln Gly Arg
        115                 120                 125

Leu Ile Gly Ala Ile Ile Gly Gly Val Ala Leu Gly Val Ala Thr Ala
    130                 135                 140

Ala Gln Ile Thr Ala Ala Ala Ala Leu Ile Gln Ala Lys Gln Asn Ala
145                 150                 155                 160

Ala Asn Ile Leu Arg Leu Lys Glu Ser Ile Ala Ala Thr Asn Glu Ala
                165                 170                 175

Val His Glu Val Thr Asp Gly Leu Ser Gln Leu Ala Val Ala Val Gly
            180                 185                 190

Lys Met Gln Gln Phe Val Asn Asp Gln Phe Asn Lys Thr Ala Gln Glu
```

```
            195                 200                 205
Leu Asp Cys Ile Lys Ile Ala Gln Gln Val Gly Val Glu Leu Asn Leu
210                 215                 220
Tyr Leu Thr Glu Ser Thr Thr Val Phe Gly Pro Gln Ile Thr Ser Pro
225                 230                 235                 240
Ala Leu Asn Lys Leu Thr Ile Gln Ala Leu Tyr Asn Leu Ala Gly Gly
            245                 250                 255
Asn Met Asp Tyr Leu Leu Thr Lys Leu Gly Ile Gly Asn Asn Gln Leu
            260                 265                 270
Ser Ser Leu Ile Gly Ser Gly Leu Ile Thr Gly Asn Pro Ile Leu Tyr
            275                 280                 285
Asp Ser Gln Thr Gln Leu Leu Gly Ile Gln Val Thr Leu Pro Ser Val
            290                 295                 300
Gly Asn Leu Asn Asn Met Arg Ala Thr Tyr Leu Glu Thr Leu Ser Val
305                 310                 315                 320
Ser Thr Thr Arg Gly Phe Ala Ser Ala Leu Val Pro Lys Val Val Thr
                325                 330                 335
Arg Val Gly Ser Val Ile Glu Glu Leu Asp Thr Ser Tyr Cys Ile Glu
                340                 345                 350
Thr Asp Leu Asp Leu Tyr Cys Thr Arg Ile Val Thr Phe Pro Met Ser
                355                 360                 365
Pro Gly Ile Tyr Ser Cys Leu Ser Gly Asn Thr Ser Ala Cys Met Tyr
370                 375                 380
Ser Lys Thr Glu Gly Ala Leu Thr Thr Pro Tyr Met Thr Ile Lys Gly
385                 390                 395                 400
Ser Val Ile Ala Asn Cys Lys Met Thr Thr Cys Arg Cys Val Asn Pro
                405                 410                 415
Pro Gly Ile Ile Ser Gln Asn Tyr Gly Glu Ala Val Ser Leu Ile Asp
                420                 425                 430
Lys Gln Ser Cys Asn Val Leu Ser Leu Gly Gly Ile Thr Leu Arg Leu
                435                 440                 445
Ser Gly Glu Phe Asp Val Thr Tyr Gln Lys Asn Ile Ser Ile Gln Asp
450                 455                 460
Ser Gln Val Ile Ile Thr Gly Asn Leu Asp Ile Ser Thr Glu Leu Gly
465                 470                 475                 480
Asn Val Asn Asn Ser Ile Ser Asn Ala Leu Asn Lys Leu Glu Glu Ser
                485                 490                 495
Asn Arg Lys Leu Asp Lys Val Asn Val Lys Leu Thr Ser Thr Ser Ala
                500                 505                 510
Leu Ile Thr Tyr Ile Val Leu Thr Ile Ile Ser Leu Val Phe Gly Ile
                515                 520                 525
Leu Ser Leu Ile Leu Ala Cys Tyr Leu Met Tyr Lys Gln Lys Ala Gln
            530                 535                 540
Gln Lys Thr Leu Leu Trp Leu Gly Asn Asn Thr Leu Asp Gln Met Arg
545                 550                 555                 560
Ala Thr Thr Lys Met
                565

<210> SEQ ID NO 11
<211> LENGTH: 527
<212> TYPE: DNA
<213> ORGANISM: Infectious Laryngotracheitis virus

<400> SEQUENCE: 11
```

```
aaacagctgt actacagagt aaccgatgga agaacatcgg tccagctaat gtgcctgtcg      60
tgcacgagcc attctccgga accttactgt cttttcgaca cgtctcttat agcgagggaa     120
aaagatatcg cgccagagtt atactttacc tctgatccgc aaacggcata ctgcacaata     180
actctgccgt ccggcgttgt tccgagattc gaatggagcc ttaataatgt ttcactgccg     240
gaatatttga cggccacgac cgttgtttcg cataccgctg gccaaagtac agtgtggaag     300
agcagcgcga gagcaggcga ggcgtggatt tctggccggg gaggcaatat atacgaatgc     360
accgtcctca tctcagacgg cactcgcgtt actacgcgaa aggagaggtg cttaacaaac     420
acatggattg cggtggaaaa cggtgctgct caggcgcagc tgtattcact ctttttctgga   480 cttgtgtcag gattatgcgg gagcatatct gctttgtacg caacgct                   527

<210> SEQ ID NO 12
<211> LENGTH: 264
<212> TYPE: DNA
<213> ORGANISM: Infectious Laryngotracheitis virus

<400> SEQUENCE: 12
tgactattac aatgacatgc ccgccgtgat cccggtggag gagactacta aaagttctaa      60
tgccgtctcc atgcccatat tcgcggcgtt cgtagcctgc gcggtcgcgc tcgtggggct     120
actggtttgg agcatcgtaa aatgcgcgcg tagctaatcg agcctagaat aggtggtttc     180
ttcctacatg ccacgcctca cgctcataat ataaatcaca tggaatagca taccaatgcc     240
tattcattgg gacgttcgaa aagc                                             264

<210> SEQ ID NO 13
<211> LENGTH: 1391
<212> TYPE: DNA
<213> ORGANISM: Mouse cytomegalovirus 1

<400> SEQUENCE: 13
aactccgccc gttttatgac tagaaccaat agttttaat gccaaatgca ctgaaatccc       60
ctaatttgca aagccaaacg ccccctatgt gagtaatacg gggactttt acccaatttc      120 ccacgcggaa agcccctaa tacactcata tggcatatga atcagcacgg tcatgcactc      180
taatggcggc ccatagggac tttccacata ggggcgttc accatttccc agcatagggg     240
tggtgactca atggcctta cccaagtaca ttgggtcaat gggaggtaag ccaatgggtt     300
tttcccatta ctggcaagca cactgagtca aatgggactt tccactgggt tttgcccaag     360
tacattgggt caatggggagg tgagccaatg ggaaaaaccc attgctgcca agtacactga   420
ctcaataggg actttccaat gggttttttcc attgttggca agcatataag gtcaatgtgg    480
gtgagtcaat agggactttc cattgtattc tgcccagtac ataaggtcaa taggggtga    540 atcaacagga aagtcccatt ggagccaagt acactgcgtc aatagggact tccattggg      600 ttttgcccag tacataaggt caatagggga tgagtcaatg ggaaaaaccc attggagcca     660
agtacactga ctcaataggg actttccatt gggttttgcc cagtacataa ggtcaatagg     720
gggtgagtca acaggaaagt tccattggag ccaagtacat tgagtcaata gggactttcc     780
aatgggtttt gccagtaca taaggtcaat ggaggtaag ccaatgggtt tttcccatta      840
ctggcacgta tactgagtca ttagggactt tccaatgggt tttgcccagt acataaggtc     900
aataggggtg aatcaacagg aaagtcccat tggagccaag tacactgagt caataggggac    960 tttccattgg gttttgccca gtacaaaagg tcaataggg gtgagtcaat gggttttttcc    1020 cattattggc acgtacataa ggtcaatagg ggtgagtcat tgggttttc cagccaattt    1080
```

| | | |
|---|---|---|
| aattaaaacg ccatgtactt tcccaccatt gacgtcaatg ggctattgaa actaatgcaa | 1140 | |
| cgtgaccttt aaacggtact ttcccatagc tgattaatgg gaaagtaccg ttctcgagcc | 1200 | |
| aatacacgtc aatgggaagt gaaagggcag ccaaaacgta acaccgcccc ggttttcccc | 1260 | |
| tggaaattcc atattggcac gcattctatt ggctgagctg cgttctacgt gggtataaga | 1320 | |
| ggcgcgacca gcgtcggtac cgtcgcagtc ttcggtctga ccaccgtaga acgcagagct | 1380 | |
| cctcgctgca g | 1391 | |

<210> SEQ ID NO 14
<211> LENGTH: 301
<212> TYPE: DNA
<213> ORGANISM: Human cytomegalovirus

<400> SEQUENCE: 14

| | | |
|---|---|---|
| ggcagtacat ctacgtatta gtcatcgcta ttaccatggt gatgcggttt tggcagtaca | 60 | |
| tcaatgggcg tggatagcgg tttgactcac ggggatttcc aagtctccac cccattgacg | 120 | |
| tcaatgggag tttgttttgg caccaaaatc aacgggactt tccaaaatgt cgtaacaact | 180 | |
| ccgccccatt gacgcaaatg gcggtaggc gtgtacggtg gaggtctat ataagcagag | 240 | |
| ctcgtttagt gaaccgtcag atcgcctgga dacgccatcc acgctgtttt gacctccata | 300 | |
| g | 301 | |

<210> SEQ ID NO 15
<211> LENGTH: 360
<212> TYPE: DNA
<213> ORGANISM: Human cytomegalovirus

<400> SEQUENCE: 15

| | | |
|---|---|---|
| cgcgccaggt caattccctg gcattatgcc cagtacatga ccttatggga ctttcctact | 60 | |
| tggcagtaca tctacgtatt agtcatcgct attaccatgg tgatgcggtt ttggcagtac | 120 | |
| atcaatgggc gtggatagcg gtttgactca cggggatttc caagtctcca ccccattgac | 180 | |
| gtcaatggga gtttgttttg gcaccaaaat caacgggact ttccaaaatg tcgtaacaac | 240 | |
| tccgccccat tgacgcaaat gggcggtagc gtgtacggtg gaggtctat ataagcagag | 300 | |
| ctcgtttagt gaaccgtcag atcgcctgga gacgccatcc acgctgtttt gacctccata | 360 | |

<210> SEQ ID NO 16
<211> LENGTH: 1191
<212> TYPE: DNA
<213> ORGANISM: Human cytomegalovirus

<400> SEQUENCE: 16

| | | |
|---|---|---|
| gtgaataata aaatgtgtgt ttgtccgaaa tacgcgtttg agatttctgt cccgactaaa | 60 | |
| ttcatgtcgc gcgatagtgg tgtttatcgc cgatagagat ggcgatattg gaaaaatcga | 120 | |
| tatttgaaaa tatggcatat tgaaaatgtc gccgatgtga gttctgtgt aactgatatc | 180 | |
| gccatttttc caaaagttga ttttggca tacgcgatat ctggcgatac gcttatatcg | 240 | |
| tttacgggggg atggcgatag acgcctttgg tgacttgggc gattctgtgt gtcgcaaata | 300 | |
| tcgcagtttc gatataggtg acagacgata tgaggctata tcgccgatag aggcgacatc | 360 | |
| aagctggcac atggccaatg catatcgatc tatacattga atcaatattg gccattagcc | 420 | |
| atattattca ttggttatat agcataaatc aatattggct attggccatt gcatacgttg | 480 | |
| tatccatatc ataatatgta catttatatt ggctcatgtc caacattacc gccatgttga | 540 | |

```
cattgattat tgactagtta ttaatagtaa tcaattacgg ggtcattagt tcatagccca      600
tatatggagt tccgcgttac ataacttacg gtaaatggcc cgcctggctg accgcccaac      660 gaccccgcc cattgacgtc aataatgacg tatgttccca tagtaacgcc aatagggact      720
ttccattgac gtcaatgggt ggagtattta cggtaaactg cccacttggc agtacatcaa      780
gtgtatcata tgccaagtac gccccctatt gacgtcaatg acggtaaatg gcccgcctgg      840
cattatgccc agtacatgac cttatgggac tttcctactt ggcagtacat ctacgtatta      900
gtcatcgcta ttaccatggt gatgcggttt tggcagtaca tcaatgggcg tggatagcgg      960
tttgactcac ggggatttcc aagtctccac cccattgacg tcaatgggag tttgttttgg      1020
caccaaaatc aacgggactt tccaaaatgt cgtaacaact ccgccccatt gacgcaaatg      1080
ggcggtaggc gtgtacggtg ggaggtctat ataagcagag ctcgtttagt gaaccgtcag      1140
atcgcctgga gacgccatcc acgctgtttt gacctccata aagacaccg g                1191

<210> SEQ ID NO 17
<211> LENGTH: 692
<212> TYPE: DNA
<213> ORGANISM: Gallus gallus
<220> FEATURE:
<221> NAME/KEY: misc_feature
<222> LOCATION: (141)..(143)
<223> OTHER INFORMATION: n is a, c, g, or t

<400> SEQUENCE: 17
cgcgccggat cagatctcca tggtcgaggt gagccccacg ttctgcttca ctctccccat      60 ctccccccc tccccacccc caattttgta tttatttatt ttttaattat tttgtgcagc      120 gatggggcg ggggggggg nnncgcgcgc caggcggggc gggcgggc gagggcggg          180 gcggggcgag gcggagaggt gcggcggcag ccaatcagag cggcgcgctc cgaaagtttc      240
cttttatggc gaggcggcgg cggcggcggc cctataaaaa gcgaagcgcg cggcgggcgg      300
gagtcgctgc gcgctgcctt cgccccgtgc ccgctccgc cgccgcctcg cgccgcccgc      360
cccggctctg actgaccgcg ttactcccac aggtgagcgg gcgggacggc ccttctcctc      420
cgggctgtaa ttagcggcag gaaggaaatg ggcggggagg gccttcgtgc gtcgccgcgc      480
cgccgtcccc ttctccctct ccagcctcgg ggctgtccgc gggggacgg ctgccttcgg      540 gggggacggg gcagggcggg gttcggcttc tggcgtgtga ccggcggctc tagagcctct      600
gctaaccatg ttcatgcctt cttctttttc ctacagctcc tgggcaacgt gctggttatt      660
gtgctgtctc atcattttgg caaagaattg ca                                    692

<210> SEQ ID NO 18
<211> LENGTH: 55
<212> TYPE: DNA
<213> ORGANISM: Feline herpesvirus 1

<400> SEQUENCE: 18
caataaacat agcatacgtt atgacatggt ctaccgcgtc ttatatgggg acgac           55

<210> SEQ ID NO 19
<211> LENGTH: 370
<212> TYPE: DNA
<213> ORGANISM: herpes simplex virus

<400> SEQUENCE: 19
gatccataat tgattgacgg gagatggggg aggctaactg aaacacggaa ggagacaata      60
ccggaaggaa cccgcgctat gacggcaata aaaagacaga ataaaacgca cgggtgttgg      120
```

```
gtcgtttgtt cataaacgcg gggttcggtc ccagggctgg cactctgtcg atacccacc    180 gagacccat tggggccaat acgcccgcgt ttcttccttt tccccacccc acccccaag    240 ttcgggtgaa ggcccagggc tcgcagccaa cgtcggggcg gcaggccctg ccatagccac   300
tggccccgtg ggttagggac ggggtccccc atggggaatg gtttatggtt cgtggggtt    360 attattttga                                                          370
```

<210> SEQ ID NO 20
<211> LENGTH: 199
<212> TYPE: DNA
<213> ORGANISM: Simian virus 40

<400> SEQUENCE: 20

```
agcttcagac atgataagat acattgatga gtttggacaa accacaacta gaatgcagtg    60
aaaaaaatgc tttatttgtg aaatttgtga tgctattgct ttatttgtaa ccattataag   120
ctgcaataaa caagttaaca acaacaattg cattcatttt atgtttcagg ttcaggggga   180
ggtgtgggag gttttttcg                                                199
```

<210> SEQ ID NO 21
<211> LENGTH: 15252
<212> TYPE: DNA
<213> ORGANISM: Artificial Sequence
<220> FEATURE:
<223> OTHER INFORMATION: Expression cassette

<400> SEQUENCE: 21

```
ggcgcgccac tggagaacgg catgaccgca aaggcgttg tagagatcga tcccacgaac    60
tctcaggcga tcgtgtcagt cgccataaac agcgacgatc gtctccagga tctgaacggt   120
tttcttctca acgatcatca gtatatgagg aactgaacct gatatttagc cgagggaaac   180
gcaggttaaa aaccctatca agcgattgcg atttcgcgt atctagtaaa aatagatggg    240
cttcggtact agccttcgcc gccaactctg aatatgccct tcgtggacct catataacat   300
ggcattgttt gttggatgcg gggccggaat taagaagaac attcgaaata cgagcaaaaa   360 tttcggcct ggcatgtgct gcgcgagaat cggtacttcg gggagaaagt tttatcggag    420
ctttgggtag tgcagaggaa actctatctt ggttgaaaat gcatgcgacc ctgcacttga   480
ttctggttaa ccacgatcca attttaaga cggctgcgc ggtcctagat aacctccgct     540
taaaactagc cccaatattg atgtgcagat ataacacaga aaaacgatca atggaagaca   600
tgctacggcg gtcatctccc gaagacatca ccgattccct aacaatgtgc ctgattatgt   660
tatcgcgcat tcgtcgtacc atgcgcaccg caggaaataa atatagctat atgatagatc   720
caatgaatcg tatgtctaat tacactccag gcgaatgtat gacaggtata ttgcgatata   780
ttgacgaaca tgctagaagg tgtcctgatc acatatgtaa tttgtatatc acatgtacac   840
ttatgccgat gtatgtgcac gggcgatatt tctattgtaa ttcattttt tgttagtaaa    900 ctaccacagg ctgtccggaa atctaagtta atgaataaag tagatggtta atactcattg   960
cttagaattg gactactttt aattctcttt aatgttcgta ttaaataaaa acatctttaa  1020
taaacttcag cctcttcgct tattgtagaa attgagtatt caaaatcatg ttcaaagccg  1080
tcttcggaga gtgtactcgc cacggtggtt ggaacatcac tatgtctaca cgtcaaattt  1140
aagcacgtca ggtctgtcga ggacaagaaa tggttaacta gtgtttcaat tattcttata  1200
aacgttaagc attgtaagcc ccccggccgt ccgcagcaac aatttactag tatgccgtgg  1260
```

```
gctccgggac tatcacggat gtccaattcg cacatgcata taatttttct agggtctctc    1320
atttcgagaa atcttcgggg atccatcagc aatgcgggct gtagtcccga ttcccgtttc    1380
aaatgaaggt gctccaacac ggtcttcaaa gcaaccggca taccagcaaa cacagactgc    1440
aactccccgc tgcaatgatt ggttataaac agtaatctgt cttctggaag tatatttcgc    1500
ccgacaatcc acggcgcccc caaagttaaa aaccatccat gtgtatttgc gtcttctctg    1560
ttaaaagaat attgactggc attttcccgt tgaccgccag atatccaaag tacagcacga    1620
tgttgcacgg acgactttgc agtcaccagc cttccttttcc acccccccac caacaaaatg    1680
tttatcgtag gacccatatc cgtaataagg atgggtctgg cagcaacccc ataggcgcct    1740
cggcgtggta gttctcgagg ccttaagctt aaggatcccc caactccgcc cgttttatga    1800
ctagaaccaa tagttttaa tgccaaatgc actgaaatcc cctaatttgc aaagccaaac    1860 gcccctatg tgagtaatac ggggactttt tacccaattt cccacgcgga aagcccccta    1920
atacactcat atggcatatg aatcagcacg gtcatgcact ctaatggcgg cccataggga    1980 cttccacat agggggcgtt caccatttcc cagcataggg gtggtgactc aatggccttt    2040
acccaagtac attgggtcaa tgggaggtaa gccaatgggt ttttcccatt actggcaagc    2100
acactgagtc aaatgggact ttccactggg ttttgcccaa gtacattggg tcaatgggag    2160
gtgagccaat gggaaaaacc cattgctgcc aagtacactg actcaatagg gactttccaa    2220
tgggtttttc cattgttggc aagcatataa ggtcaatgtg ggtgagtcaa tagggacttt    2280
ccattgtatt ctgcccagta cataaggtca atagggggtg aatcaacagg aaagtcccat    2340
tggagccaag tacactgcgt caatagggac tttccattgg ttttgcccca gtacataagg    2400 tcaataggg atgagtcaat gggaaaaacc cattggagcc aagtacactg actcaatagg    2460
gactttccat tgggttttgc ccagtacata aggtcaatag gggtgagtc aacaggaaag    2520 ttccattgga gccaagtaca ttgagtcaat agggactttc caatgggttt tgcccagtac    2580
ataaggtcaa tgggaggtaa gccaatgggt ttttcccatt actggcacgt atactgagtc    2640
attagggact ttccaatggg ttttgcccag tacataaggt caatagggggt gaatcaacag    2700 gaaagtccca ttggagccaa gtacactgag tcaataggga cttccattg gttttgccc    2760 agtacaaaag gtcaataggg ggtgagtcaa tgggttttc ccattattgg cacgtacata    2820
aggtcaatag gggtgagtca ttgggttttt ccagccaatt taattaaaac gccatgtact    2880
ttcccaccat tgacgtcaat gggctattga aactaatgca acgtgacctt taaacggtac    2940
tttcccatag ctgattaatg ggaaagtacc gttctcgagc caatacacgt caatgggaag    3000 tgaagggca gccaaaacgt aacaccgccc cggttttccc ctggaaattc catattggca    3060
cgcattctat tggctgagct gcgttctacg tgggtataag aggcgcgacc agcgtcggta    3120
ccgtcgcagt cttcggtctg accaccgtag aacgcagagc tcctcgctgc aggcggccgc    3180
tctagaactc gtcgatcgca gcgatgacaa acctgcaaga tcaaacccaa cagattgttc    3240
cgttcatacg gagccttctg atgccaacaa ccggaccggc gtccattccg gacgacaccc    3300
tggagaagca cactctcagg tcagagacct cgacctacaa tttgactgtg ggggacacag    3360
ggtcagggct aattgtcttt ttccctggat tccctggctc aattgtgggt gctcactaca    3420
cactgcagag caatgggaac tacaagttcg atcagatgct cctgactgcc cagaacctac    3480
cggccagcta caactactgc agactagtga gtcggagtct cacagtgagg tcaagcacac    3540
tccctggtgg cgtttatgca ctaaacggca ccataaacgc cgtgaccttc caaggaagcc    3600
tgagtgaact gacagatgtt agctacaatg ggttgatgtc tgcaacagcc aacatcaacg    3660
```

```
acaaaattgg gaatgtcctg gtaggggaag gggtcactgt cctcagccta cccacatcat   3720
atgatcttgg gtatgtgagg cttggtgacc ccattcccgc tatagggctt gacccaaaaa   3780
tggtagctac atgcgacagc agtgacaggc ccagagtcta caccataact gcagccgatg   3840
attaccaatt ctcatcacag taccaaccag gtggggtaac aatcacactg ttctcagcca   3900
acattgatgc tatcacaagc ctcagcattg ggggagagct cgtgtttcaa acaagcgtcc   3960
aaggccttgt actgggcgcc accatctacc ttataggctt tgatgggact gcggtaatca   4020
ccagagctgt ggccgcagat aatgggctga cggccggcac cgacaatctt atgccattca   4080
atcttgtcat tccaaccaat gagataaccc agccaatcac atccatcaaa ctggagatag   4140
tgacctccaa aagtggtggt caggcagggg atcagatgtc atggtcggca agtgggagcc   4200
tagcagtgac gatccatggt ggcaactatc caggggccct ccgtcccgtc acactagtag   4260
cctacgaaag agtggcaaca ggatccgtcg ttacggtcgc tggggtgagt aacttcgagc   4320
tgattccaaa tcctgaacta gcaaagaacc tggttacaga atacggccga tttgacccag   4380
gagccatgaa ctacacaaaa ttgatactga gtgagaggga ccgtcttggc atcaagaccg   4440
tctggccaac aagggagtac actgattttc gtgagtactt catggaggtg ccgaccctca   4500
actctcccct gaagattgca ggagcatttg gcttcaaaga cataatccgg gctataagga   4560
ggtagatcca gacatgataa gatacattga tgagtttgga caaaccacaa ctagaatgca   4620
gtgaaaaaaa tgctttattt gtgaaatttg tgatgctatt gctttatttg taaccattat   4680
aagctgcaat aaacaagtta acaacaacaa ttgcattcat tttatgtttc aggttcaggg   4740
ggaggtgtgg gaggtttttt cggatcctct agagtcgacg gcagagtcgc agacgcccct   4800
attggacgtc aaaattgtag aggtgaagtt ttcaaacgat ggcgaagtaa cggcgacttg   4860
cgtttccacc gtcaaatctc cctataggt agaaactaat tggaaagtag acctcgtaga   4920
tgtaatggat gaaatttctg gaacagtcc cgccggggtt tttaacagta atgagaaatg   4980
gcagaaacag ctgtactaca gagtaaccga tggaagaaca tcggtccagc taatgtgcct   5040
gtcgtgcacg agccattctc cggaaccttaa ctgtcttttc gacacgtctc ttatagcgag   5100
ggaaaaagat atcgcgccag agttatactt tacctctgat ccgcaaacgg catactgcac   5160
aataactctg ccgtccggcg ttgttccgag attcgaatgg agccttaata atgtttcact   5220
gccggaatat ttgacggcca cgaccgttgt ttcgcatacc gctggccaaa gtacagtgtg   5280
gaagagcagc gcgagagcag gcgaggcgtg gatttctggc cggggaggca atatatacga   5340
atgcaccgtc ctcatctcag acggcactcg cgttactacg cgaaaggaga ggtgcttaac   5400
aaacacatgg attgcggtgg aaaacggtgc tgctcaggcg cagctgtatt cactcttttc   5460
tggacttgtg tcaggattat gcgggagcat atctgctttg tacgcaacgc tatgaccgc    5520
catttatttt tgaggaatgc ttttttggact atcgtactgc tttcttcctt cgctagccag   5580
agcaccgccg ccgtcacgta cgactacatt ttaggccgtc gcgcgctcga cgcgctaacc   5640
ataccggcgg ttggcccgta taacagatac ctcactaggg tatcaagagg ctgcgacgtt   5700
gtcgagctca acccgatttc taacgtggac gacatgatat cggcggccaa agaaaaagag   5760
aaggggggcc ctttcgaggc ctccgtcgtc tggttctacg tgattaaggg cgacgacggc   5820
gaggacaagt actgtccaat ctatagaaaa gagtacaggg aatgtggcga cgtacaactg   5880
ctatctgaat gcgccgttca atctgcacag atgtgggcag tggactatgt tcctagcacc   5940
cttgtatcgc gaaatggcgc gggactgact atattctccc ccactgctgc gctctctggc   6000
```

```
caatacttgc tgaccctgaa aatcgggaga tttgcgcaaa cagctctcgt aactctagaa      6060
gttaacgatc gctgttttaaa gatcgggtcg cagcttaact ttttaccgtc gaaatgctgg     6120
acaacagaac agtatcagac tggatttcaa ggcgaacacc tttatccgat cgcagacacc     6180
aatacacgac acgcggacga cgtatatcgg ggatacgaag atattctgca gcgctggaat     6240
aatttgctga ggaaaaagaa tcctagcgcg ccagacccct gtccagatag cgtcccgcaa     6300
gaaattcccg ctgtaaccaa gaaagcggaa gggcgcaccc cggacgcaga aagcagcgaa     6360
aagaaggccc ctccagaaga ctcggaggac gacatgcagg cagaggcttc tggagaaaat     6420
cctgccgccc tccccgaaga cgacgaagtc cccgaggaca ccgagcacga tgatccaaac     6480
tcggatcctg actattacaa tgacatgccc gccgtgatcc cggtggagga gactactaaa     6540
agttctaatg ccgtctccat gcccatattc gcggcgttcg tagcctgcgc ggtcgcgctc     6600
gtggggctac tggtttggag catcgtaaaa tgcgcgcgta gctaatcgag cctagaatag     6660
gtggtttctt cctacatgcc acgcctcacg ctcataatat aaatcacatg aatagcata     6720 ccaatgccta ttcattggga cgttcgaaaa gcatggcatc gctacttgga actctggctc     6780
tccttgccgc gacgctcgca cccttcggcg cgatgggaat cgtgatcact ggaaatcacg     6840
tctccgccag gattgacgac gatcacatcg tgatcgtcgc gcctcgcccc gaagctacaa     6900
ttcaactgca gctattttc atgcctggcc agagacccca caaaccctac tcaggaaccg     6960
tccgcgtcgc gtttcggtct gatataacaa accagtgcta ccaggaactt agcgaggagc     7020
gctttgaaaa ttgcactcat cgatcgtctt ctgtttttgt cggctgtaaa gtgaccgagt     7080
acacgttctc cgcctcgaac agactaaccg gacctccaca cccgtttaag ctcactatac     7140
gaaatcctcg tccgaacgac agcgggatgt tctacgtaat tgttcggcta gacgacacca     7200
aagaacccat tgacgtcttc gcgatccaac tatcggtgta tcaattcgcg aacaccgccg     7260
cgactcgcgg actctattcc aaggcttcgt gtcgcacctt cggattacct accgtccaac     7320
ttgaggccta tctcaggacc gaggaaagtt ggcgcaactg gcaagcgtac gttgccacgg     7380
aggccacgac gaccagcgcc gaggcgacaa ccccgacgcc cgtcactgca accagcgcct     7440
ccgaacttga agcggaacac tttacctttc cctggctaga aaatggcgtg gatcattacg     7500
aaccgacacc cgcaaacgaa aattcaaacg ttactgtccg tctcgggaca atgagcccta     7560
cgctaattgg ggtaaccgtg gctgccgtcg tgagcgcaac gatcggcctc gtcattgtaa     7620
tttccatcgt caccagaaac atgtgcaccc cgcaccgaaa attagacacg gtctcgcaag     7680
acgacgaaga acgttcccaa actagaaggg aatcgcgaaa atttggaccc atggttgcgt     7740
gcgaaataaa caagggggct gaccaggata gtgaacttgt ggaactggtt gcgattgtta     7800
acccgtctgc gctaagctcg cccgactcaa taaaaatgtg attaagtctg aatgtggctc     7860
tccaatcatt tcgattctct aatctcccaa tcctctcaaa aggggcagta tcggacacgg     7920
actgggaggg gcgtacacga tagttatatg gtacagcaga ggcctctgaa cacttaggag     7980
gagaattcag ccggggagag cccctgttga gtaggcttgg gagcatattg caggatgaac     8040
atgttagtga tagttctcgc ctcttgtctt gcgcgcctaa cttttgcgac gcgacacgtc     8100 ctcttttttgg aaggcactca ggctgtcctc ggggaagatg atcccagaaa cgttccggaa     8160
gggactgtaa tcaaatggac aaaagtcctg cggaacgcgt gcaagatgaa ggcggccgat     8220
gtctgctctt cgcctaacta ttgctttcat gatttaattt acgacggagg aaagaaagac     8280
tgcccgcccg cgggacccct gtctgcaaac ctggtaattt tactaaagcg cggcgaaagc     8340
ttcccgggtt aattaaggcc ctcgaggata catccaaaga ggttgagtat tctctctaca     8400
```

```
cttcttgtta aatggaaagt gcatttgctt gttcttacaa tcggcccgag tctcgttcac   8460
agcgcctcgt tcacacttaa accacaaata gtctacaggc tatatgggag ccagactgaa   8520
actcacatat gactaatatt cggggtgtt agtcacgtgt agcccattgt gtgcatataa    8580
cgatgttgga cgcgtcctta ttcgcggtgt acttgatact atggcagcga gcatgggata   8640
ttcatcctcg tcatcgttaa catctctacg ggttcagaat gtttggcatg tcgtcgatcc   8700
tttgcccatc gttgcaaatt acaagtccga tcgccatgac cgcgataagc ctgtaccatg   8760
tggcattagg gtgacatctc gatcatacat tataagacca acgtgcgagt cttccaaaga   8820
cctgcacgcc ttcttcttcg gattgtcaac gggttcttca gaatctatgc ccatatctgg   8880
cgttgagacc attgtgcgtt aatgaacaa taaagcggca tgccatggaa aggagggctg    8940
cagatctcca ttttctcacg ccactatcct ggacgctgta gacgataatt ataccatgaa   9000
tatagagggg gtatgtttcc actgccactg tgatgataag ttttctccag attgttggat   9060
atctgcattt tctgctgccg aacaaacttc atcgctatgc aaagagatgc gtgtgtacac   9120
gcgccggtgg agtatacggg aaactaaatg ttcatagagg tctttgggct atatgttatt   9180
aaataaaata attgaccagt gaacaatttg tttaatgtta gtttattcaa tgcattggtt   9240
gcaaatattc attacttctc caatcccagg tcattcttta gcgagatgat gttatgacat   9300
tgctgtgaaa attactacag gatatatttt taagatgcag gagtaacaat gtgcatagta   9360
ggcgtagtta tcgcagacgt gcaacgcttc gcatttgagt taccgaagtg cccaacagtg   9420
ctgcggttat ggtttatgcg cacagaatcc atgcatgtcc taattgaacc atccgatttt   9480
tcttttaatc gcgatcgatg tttgggcaac tgcgttattt cagatctaaa aaatttaccc   9540
tttatgacca tcacatctct ctggctcata ccccgcttgg ataagatatc atgtagattc   9600
cgccctaaga aatgcaaact aacattattg tcggttccat atacacttcc atcttgtcct   9660
tcgaaaataa caaactcgcg caatagaccg tccgtacatg catggccgat gtgtgtcaac   9720
atcattggtc tgctagatcc cgatgggacg aatcgtacag tcgtcgctcc agcattggca   9780
aaaatcccca gataccctcc atgcggcaaa tctaaattgc gaccccgaag agactgcacc   9840
aaagtcttat cgacgcacgc tgattttttt gaacagcggg agcccattat cttcagtgga   9900
gcgtagacgg gcgaggctaa ttatgtgaca tagcaacact gcatgtatgt ttttataaat   9960
caataagagt acataattta ttacgtatca tttccgtttg taatatactg tatacatcat   10020
ccacactatt agtcagcact agcgcgcggg cgcacgttac aatagcagcg tgcccgttat   10080
ctatattgtc cgatatttac acataacatt tcatcgacat gattaaatac ctaagtactg   10140
cacacagatg tttaatgtat atcgtcatat aaattatatc gctaggacag acccaaacga   10200
cctttatccc aaacagtcag atcctcttct caagtgtcga tttctgttat ggaatatgca   10260
taccctggcc cagaaattgc acgcacgagc gtagtgaatg cgtcattggt tttacattta   10320
aaggctaaat gcacaaattc tttagacgac agcacatcgt taaatagcat ctctagcgtt   10380
cttatgaatg ctaagcattg gagtcctcct ggtcggccac aataacagct gagtatcata   10440
ccctgagctc cggggttgtc gcacatagcg gattcgtata acataggat  tttccgcgaa   10500 tccatcagtt gcaaaaatct gttaggctcc atcaacaacg ctggatttac ttcagatcca   10560
cgcgtaaagt aatggtgctc gaataccgtt tttagagttg tcggcatttc aaggaacaaa   10620
gaattcattt cttcattgca acgacgcgcc agaaatccca agacctcttt gggtagtatg   10680
ttcttgccta taaaacacgg cgttccaagt gccaggaacc acgcatgtgt tactgttggg   10740
```

```
gcgtattcag aaataaagcg gggtttatgc ggcttttgaa gctcggatat ccaaagtatc   10800
gcttgctgat gaacgagcga tgtagctgtt acaaaacctc ctttccatcc tccagtcaac   10860
ataatattta tcggcctacc tatgtccgta ataagtattg gtcgggcaat tattccgtat   10920
gaggtcttgc aggaataagc tcttagggac agccagcttg gatatggtgc gaaacagacc   10980
ttctcggctt cagaatgtcg ctccgcagtc tcttcgtgtc ggtgcatctt agatccacca   11040
tcaatgtgtg cagcattgac tcccgcccgt cgaatattcc ttttgttacg atgcagtaat   11100
gagcacgatc atgggcgggg cgatgacgtt ctatttgcat gtctgcgaac aatttgcgtc   11160
agtcatacag ctatggagtg ggccatttct ggccgtcaac ttaaaaacgc gaaccgcaga   11220
catatgtatt tgcatgcaaa gacgtatctt cgtatttctg ggcatcttca aatgctctgg   11280
ccaatatggc aatgaatttg gattcgtttg acgccgatgg tatgcagtgc aaatgtgcca   11340
atagcccaca tccgaaaaag ttatttgtca tacaagcagg tgttaagtag caatcacata   11400
aaggcaccag acgcctcatg gcatcataat gaatagctcc ttctccccac tggaaccact   11460
gacaaaatct gcgagtatat tccgcaaacc acatttt att tctcatagaa actaccctaa   11520
atccttttaa cgggaagaag aatcctagat agtgcttgaa gtcatgactg ttactgctgc   11580
aataacactg tatattattt ataaattccg tttgtctagg tatctgatgt aggcattccg   11640
atccctttac tattgcgtct tcacgaccaa atgggaatgc gccaaaatcc ccacacctca   11700
tcaccctgga ggcagattgt gtattattaa tatccgccga ttgaagcaca aaacggtacg   11760
gtactgttcc taattctggt atagattcta tggtcaaaag tctgcatatc cccgacattg   11820
ccatgagatc acacagtcca agtagcatgt ttattgagtc actcagactg tcaacgtccc   11880
tcgccgcacc accaatcgaa aataaagtat ctacgcaagt tatagctccg cattttctat   11940
cgctagcagc aatcgcgacg caaaacataa aggccatgtt gggatttgaa ctctctgggg   12000
ggcttgttat cttctgcacc gtcgcagtcg cagttttccg aaatttatgt ctaatatatt   12060
ttccggccgt gctccaatcg gccgaaaaga atctgcgtat taccagactc attgacgggc   12120
cgataaagac cataaaacaa aattcctgtg cactccctcc tccagttttg ccatcgtcca   12180
agtcccgtaa cttttttttgc gtttcgagga gcaagcgttc gttatcccta cccacacttg   12240
ttttccaccg ttttcttatt ataagcggtt gtatcgccaa cgcgtcaccg caggttgtca   12300
catacagtga tggcatactt gaacgtgcaa caacgcgctc gctttgcaaa tctaagtcat   12360
tgaccatcaa atcgcgttga gaggatagcc aggcatcttt tttcctagta tggtgacggt   12420
gcagccaccc caactcagtt cttgtaaaaa aagctattgg cgggaattta tgttctgagg   12480
tgcattctat atttatgagt ccatcaaatg ccattaacca gattcgtatt ttttcgctcg   12540
acccggcatc actatggata caataccttt ctatggccca tttcagctct cgaaccaacc   12600
acacggacaa ttgactaaca taagtatgat ctttatcaca gtcgcaccca tctgagttat   12660
atttatggca tccgagcgct cttactgtac ggtcggatac acccatggtt tttcctttat   12720
atagtcgggt tatagtctgt cgggtttggc ggtagcacgg agtagtttga ttttttaagaa  12780 tcgaaaaccg gcttggagag accactgtcg aatatttgtc cgtatactct acacgtgagt   12840
gttgtccatt cctaggtata ttcatctgtt cggataccct caattgctgt tcaggcataa   12900
ccttaaagca tatgttatgt tgtacatcaa aacttggtga gttatgttcg attgccgcgc   12960
ataaagaatc gtacatgagc gtttctgcta acatactatc tatattctca cacgcccctg   13020
catatactgt tcctattcca aattcacgtt ttgccccatc ggctatctgc tcccaaaaag   13080
ttgtaatata ggtgccgctg ggtgcgaaat tttcatcagt tgtattcctg ataaactgaa   13140
```

-continued

```
tcactttaca taattttttgc cacatatctg cgtgcagcca tagtatcgaa cccgtgggct    13200
cggagacgac agtgcgtaca atgggtattt tacctttccc caacaaaata atggtataca    13260
agttaggtcc gtacctagac cttaatgttt ccaattcttc tgaatcactg cactctcgta    13320
ggggagtaac ggtaataatt tcgtctctga gccccgtttt gcgttgaaaa ctaatcacat    13380
tagataatgt gcaatcggtt tcttttatcc ggatacatct aagtattatg acatcggtgg    13440
tcattgtttc catcaacgac catctttac gatcgcccat actactcatg acgttgtcg    13500 gtgttgaaaa atcaccagaa ttgcaacgga tctctgggta ccatgctgct gatggaattg    13560
gcggttttaa ttgttgtttc agtctattat tgctatcttt ggcggggttg aataatgtgg    13620
ggggagagtg attgcaggaa tccgaatggg tcaataaaac gaccgtgctc cgttctgccg    13680
gcgccgatcc gattgaagct atatacttcg cttctctccc cacttttcca atttgatccg    13740
gaaataaaac ggccccggac aacagtatcg tacgatccgg atccggatcc tgcttgccta    13800
cagaagaatc aacatctcgc cccaatattc tggtcaaaac tggctcgctc atggcaacgc    13860
ggacgtttcc cccggtggcc agtcttaatg gttaatgttc ttttcggcaa tcttatacat    13920 cagcggggttg cgtgaatact ggtcacagtt cagtcattta ctacacacca gcaatacgac    13980
gacggacagt accgtcccga cgaacgcgac gcccaaaatt gctatcgcga ccgcgtccga    14040
ggcgatgtcg tacgggcggt gcggggttgg atcctcggca aagagatcct cgtaattcgg    14100
cggtgggagc ggagggtaaa gacgcgggtg gggatctccc tccggaccgc gcgccgggcg    14160
cggttcgaaa atgctttccg cctcgctcag tgtcaacgcc aagtattcgg gcgggctggg    14220
ggccggaata tctcccgcga cttcttctat cggcgcggaa ttggagtcgc ggtcgtggcg    14280
cgcttctagc gtcgtcaacg gaagtccatt ttcggggtct cccggtgggc gttcagcgtc    14340
catcgtcgta tatgctctaa cacacgtctc gctatattaa aaaaaagaag agtatcggtc    14400
agtgtcgagt gtcgccgaca atgtcgcgag ttctcggcga tttaatttttt ggaactgctc    14460 cctatgaatc ccgtaactgt agcgcccgcg cagaaagccg ccatcagacc aactacgtgt    14520
ctgttcgatg tttgcccgcc gatcgcttta ccgattaagg ttccggcgag aaatgacatg    14580
ctcgatccaa gaacaaagtt tttcgcgta aacaacaaca tagttaccgt gcgagatgga    14640
gaaaccacat ctcccgaatt agtagaggaa agcccgcgct gtcggtttgg ggacatatcg    14700
atcttttttg tgttttttcct aggacccttt tgccagatcg tacaaagtcg cgtcttatga    14760
gcggacgttc ttactgcagc tcggtaggag tggggcaggg ttagatttcg tcggcgtttc    14820
ggcccccgta tgccgcgcgc caccctcttc gccgagctct ttatgcgcgg tgggggtgag    14880
cgcttccgga gttgcgatct ccgatctcga gccgcagccc ggcggtgtct ctttcagtgg    14940
agcgttagcg ccatcatgtg gttcgtggcg gtggaaaggc tattatgtgt taggggagag    15000
accacgtgat cggcatgcaa atgagcaagg cgaacgcgtc agcgttcgca ctgcgaacca    15060
ataatatata tattatacta ttggctttag gtgcgaacgt ccggctagtc caatagcggg    15120
gtcgcgtttc gtaccacgtg ttatagaccg ccctaaactc gcactcgggg gtccggccgc    15180
gcccagacag ggcggagacg tgccacaggg gctttaaaac accgcttcgg gcaccgttca    15240
tctcggcgcg cc                                                        15252
```

<210> SEQ ID NO 22
<211> LENGTH: 12692
<212> TYPE: DNA
<213> ORGANISM: Artificial Sequence
<220> FEATURE:

<223> OTHER INFORMATION: Expression cassette

<400> SEQUENCE: 22

```
ctcgcgcgtt tcggtgatga cggtgaaaac ctctgacaca tgcagctccc ggagacggtc      60
acagcttgtc tgtaagcgga tgccgggagc agacaagccc gtcagggcgc gtcagcgggt     120
gttggcgggt gtcggggctg gcttaactat gcggcatcag agcagattgt actgagagtg     180
caccatatcg acgctctccc ttatgcgact cctgcattag gaagcagccc agtagtaggt     240
tgaggccgtt gagcaccgcc gccgcaagga atggtgcatg caaggagatg gcgcccaaca     300
gtcccccggc cacggggcct gccaccatac ccacgccgaa acaagcgctc atgagcccga     360
agtggcgagc ccgatcttcc ccatcggtga tgtcggcgat ataggcgcca gcaaccgcac     420
ctgtggcgcc ggtgatgccg gccacgatgc gtccggcgta gaggatctgg ctagcgatga     480
ccctgctgat tggttcgctg accatttccg gggtgcggaa cggcgttacc agaaactcag     540
aaggttcgtc caaccaaacc gactctgacg gcagtttacg agagagatga tagggtctgc     600
ttcagtaagc cagatgctac acaattaggc ttgtacatat tgtcgttaga acgcggctac     660
aattaataca taaccttatg tatcatacac atacgattta ggtgacacta tagaatacaa     720
gctagcttgg gctgcaggtc gactctagag gatcgttaat taacgatccc gggcgagct     780
cgaattccag actaaatgcc ccggcccaat ttgtcaagtg tgcagtcacg gaggcgtcga     840
ccgtgtcccc ggcattaaac aggaaagcgt taaagttttt gaatgttagg tcacaggtac     900
aaacataaat gtttgtacaa acaggtaaca ggtacaaaca taaatgcccc ggcataaatg     960
tcccttacgg cggatcgaaa cgacattagg catactcggg taccattttg cattccgatc    1020
agcacggatg aaattaggca ggaatgcggt ttatattatg cggcattgga caaacgatat    1080
ggcattgatt ggcagtttat gaatgtcttc atgttgggcg taaacggatt cctattggtt    1140
cagaagacaa cgacgatata tttagagaga aaaagctacc cagcatagga taaacacaca    1200
ttgagcattg agagacatag gtatcggtat ggatgggaaa actacacacg tgaacaccaa    1260
acgacttata tactcgagcg gtgatactac tgagcaagaa tgcactgcat ctgagccact    1320
gaatgaagac tgtgatgaaa atgtgaccat cgatggaatt ggagaagaat atgcgcagtt    1380
cttcatgtcc ccgcaatggg tcccaaatct acatcgcttg agcgaggata ccaaaaaggt    1440
ataccgatgt atggtttcca acagactcaa ttattttccc tattatgagg cgttcaggcg    1500
gtctttgttt gatatgtata tgctaggtcg gttgggggcgt cgacttaagc gatctgactg    1560
ggagactatt atgcatctgt caccaacgca aagtcggcgt ctacatagaa ctttaagatt    1620
tgtggagcgt agaattatcc catctaacag ttatatacgc acatcgggcc acgttccgcc    1680
ttcgagggca cttccgacag atacgaattt aaagatggat gaataattaa attggaaaga    1740
gtaactacat taatcgagcg tcatgacggc gtcccgtgaa aatgggaatt ttctactcga    1800
aacaccgtga catttgacag acctggaatt gttattctga tatatagtgg gtgtgtctgg    1860
ccggcaacat acataatgtg catgcgaaac cactttttca gtgtacgctg acattgtgca    1920
acacggaggg gtagcatcta catacaatat atgttgatta atgattggag aaaaaactat    1980
gcagctcgcc gatcatatgg ctaactcgcc ttcgtctata tggcggaccc cgcgggaaaa    2040
atcgacgtac catctgattt acaacaccag taatgaacat gtcgcatccc tgcccagatc    2100
tgtgcgccca ttggcgcgga tcgttgtgaa tgccgccgaa acacttcagg tcggtatgag    2160
agccgggagg ccgccatcag caggagtttg gcgagaggtg tttgatagaa tgatgacagc    2220
cttccgtgac cacgagccta ctgcgacatt taatgctgca aatcccatta gaaaaatggt    2280
```

```
cgagacagtt ctacagaata atgaagagcc cccgcggacg catgctgaaa tgggtaatcg    2340
ccttatgaac attatgtact ggtgttgctt gggacacgca ggacaatgct cgatatggca    2400
gttgtacgag acgaatcagg ccatttttaag tttattagat gaagtggtta tcggcacaac    2460
aaatcccttt tgcaccctcg agcaaatactg gaagccatta tgcaccgcaa tcgccaacaa    2520
ggggacctca tcgcttgttg aggatgccaa agtggccgag tacctggtta gcatgcgcaa    2580
attgatataa cataggcacg ctctgatgtt acagaccaca ataccgcata catttattgt    2640
aaggttgtta ataaaggttt attctatgta agactacaat actttcgaca ttgcttgtat    2700
acatattaaa tactttctca agttcctatt acataaaatg ggatctatca ttacattcgt    2760
taagagtctg gataatttta ctgtttgcca gcttcgatct tggaacgtac tgtggatagt    2820
gccttacttg gaatcgtgaa aatttgaaac gtccattatt tggatatctt ccggttgtcc    2880
catatcccgc cctggtaccg ctcggatacc ttgcccgtat ggattcgtat tgacagtcgc    2940
gcaatcgggg accaacaacg cgtgggtcca cactcattcg gaaattttcc gatgattctg    3000
aatatttatt gccgctcgtt acgagtcgtt ggacatatct gtaatacatt tcttcttctg    3060
aaggatcgct gcacatttga tctatacatt ggccaggatg ttcaagtctc agatgttgca    3120
ttctggcaca gcacaacttt atggcatttc cgatgtaatc gtccggcagc cctggggggag    3180 ttctatattc gcatattggg atggtaagga caatagcaga tctcgcaacc tccagggagg    3240
ctataataac gttttttaaag gatggatttc tcataaaaat ctgtcgcaaa ttacactgag    3300
aatatccttt actagcgccg attgagagca tcgtcgtcca atttttctaaa tggaaagaaa    3360 acaaggcggg caagagtgtt ccaaacattt tcattttcgg cgaatctctc aaatcccatg    3420
gcgtgcaatt gattgcaaaa ttggcacttc cgttcacgtt tgtatctcca aactctaaga    3480
cacttttaat tgaaaaacta cgttctagtg tggaaagaaa cctataggca gaccatagaa    3540
ctatttgaca ccacatatct ttttgtatgt caaactgacc atgatcgtat gttgctgaat    3600
gcactagggc aattcgctcg cgcgactcca tacattgaat aattccacac gtcagctcat    3660
cggttagcaa ggtccagtag ttgaagtcat ttatttttcc ccgcggctgg ccaaatctac    3720
ctctgggaat atccaagttg tcgaatatga tcgcaccggc tctggtcatg gtgaaggaac    3780
tgtagcataa agacgcaggt atcataggggg taatatttttt ttattcactc acatactaaa    3840
agtaacgcat attagcacca tgtatgggct atcaattgac atttgcgtag cactacatca    3900
cgattatgta caacataatg ggacaacata tggcaagtag atgcaatttc ctcacactag    3960 ttgggttttat ctactattga atttttcccct atctgtgata cacttgggag cctctacaag    4020
catattgcca tcatgtacgt ttttatctac tgtcttaacg cccatgggaa cggaggcgtc    4080
gtcgtcatgt attggacggc aacataggca gcaacacaaa ttgcgtttag gtggggtgca    4140
tgtggactcg ataccaagcc cctgcagctg gggaacgtct ggtggagagc cgataatttg    4200
atatacgcac gccatattac tgtcgttgaa gtacgcctta tcttctatgt tttcaaattt    4260
aggttcccaa gtggacgtga aagtgtttg tatctcacat ggaatggccc aaggcattcc    4320
agcccaggtg cctggtactt taatggcaaa caaacgtttt ggtagaggta ttgattctat    4380
tgcagttctg cagatatctg cagccccgag tatccacagg ctatacgata cgttatcgga    4440
ggcaagcttc gcgccaggtc aattccctgg cattatgccc agtacatgac cttatgggac    4500
tttcctactt ggcagtacat ctacgtatta gtcatcgcta ttaccatggt gatgcggttt    4560
tggcagtaca tcaatgggcg tggatagcgg tttgactcac ggggatttcc aagtctccac    4620
```

```
cccattgacg tcaatgggag tttgttttgg caccaaaatc aacgggactt tccaaaatgt    4680
cgtaacaact ccgccccatt gacgcaaatg ggcggtagcg tgtacggtgg gaggtctata    4740
taagcagagc tcgtttagtg aaccgtcaga tcgcctggag acgccatcca cgctgttttg    4800
acctccatag aagacaccgg ttgcgccgcc accatgggcc ccagaccttc taccaagaac    4860
ccagtaccta tgatgctgac tgtccgagtc gcgctggtac tgagttgcat ctgtccggca    4920
aactccattg atggcaggcc tcttgcggct gcaggaattg tggttacagg agacaaagcc    4980
gtcaacatat acacctcatc ccagacagga tcaatcatag ttaagctcct cccgaatctg    5040
cccaaggata aggaggcatg tgcgaaagcc cccttggatg catacaacag gacattgacc    5100
actttgctca ccccccttgg tgactctatc cgtaggatac aagagtctgt gactacatct    5160
ggaggggggga dacaggggcg cctataggc gccattattg gcggtgtggc tcttggggtt    5220
gcaactgccg cacaaataac agcggccgca gctctgatac aagccaaaca aaatgctgcc    5280
aacatcctcc gacttaaaga gagcattgcc gcaaccaatg aggctgtgca tgaggtcact    5340
gacggattat cgcaactagc agtggcagtt gggaagatgc agcagtttgt taatgaccaa    5400
tttaataaaa cagctcagga attagactgc atcaaaattg cacagcaagt tggtgtagag    5460
ctcaacctgt acctaaccga attgactaca gtattcggac cacaaatcac ttcacctgct    5520
ttaaacaagc tgactattca ggcactttac aatctagctg gtggaaatat ggattactta    5580
ttgactaagt taggtgtagg gaacaatcaa ctcagctcat taatcggtag cggcttaatc    5640
accggtaacc ctattctata cgactcacag actcaactct gggtataca ggtaactcta    5700
ccttcagtcg ggaagctaaa taatatgcgt gccacctact tggaaacctt atccgtaagc    5760
acaaccaggg gatttgcctc ggcacttgtc ccaaaagtgg tgacacaggt cggttctgtg    5820
atagaagaac ttgacacctc atactgtata gaaactgact acatttata ttgtacaaga    5880
atagtaacgt tccctatgtc ccctggtatt tattcctgct tgagcggcaa tacgtcggcc    5940
tgtatgtact caaagaccga aggcgcactt actacaccat acatgactat caaaggttca    6000
gtcatcgcca actgcaagat gacaacatgt agatgtgtaa acccccgggg tatcatatcg    6060
caaaactatg gagaagccgt gtctctaata gataaacaat catgcaatgt ttatccctta    6120
ggcgggataa ctttaaggct cagtgggaa ttcgatgtaa cttatcagaa gaatatctca    6180
atacaagatt ctcaagtaat aataacaggc aatcttgata tctcaactga gcttgggaat    6240
gtcaacaact cgatcagtaa tgctttgaat aagttagagg aaagcaacag aaaactagac    6300
aaagtcaatg tcaaactgac tagcacatct gctctcatta cctatatcgt gttgactatc    6360
atatctcttg ttttttggtat acttagcctg attctagcat gctacctaat gtacaagcaa    6420
aaggcgcaac aaaagacctt attatggctt gggaataata ctctagatca gatgagagcc    6480
actacaaaaa tgtgaggatc tctcgaggaa ttctagatcc cacgtcacta ttgtatactc    6540
tatattatac tctatgttat actctgtaat cctactcaat aaacgtgtca cgcctgtgaa    6600
accgtactaa gtctcccgtg tcttcttatc accatcaggt gacatcctcg cccaggctgt    6660
caatcatgcc ggtatcgatt ccagtagcac cggccccacg ctgacaaccc actcttgcag    6720
cgttagcagc gcccctctta acaagccgac ccccaccagc gtcgcggtta ctaacactcc    6780
tctccccgac ctgcaactag taagcttgcc tccgattcta gcattacata gccggtcagt    6840
agatcctgcc attcggtagc gcaaccggct acatcttcaa acagtctcac aataaatgca    6900
tctctcgttc ctgccaatcc ggaaccgggc ataccactcc cgcctgccga tttaattctc    6960
acaattgggc gatgccggcg gggcaaaacg aatgtggatt tggcaaaccg acacaggtct    7020
```

```
gctgtacgga ctaatatggg cacacccaca tcattcttca gatgctccat gcattgttct   7080
atgagaaaga tccatagggt ggaggcagcg tcacgagatc gcccaggcaa tcgatcgcat   7140
tcgtctagta aagtgacgag agttatcatg cacacaccca tgcccacgcc ttccgaataa   7200
ctggagctgt ggaagatcgg aaacgtcttt ttgactgccg gtctcgtact actttcgcac   7260
aggtgtatac ccggacgcgt actatatatt ttatatcatc caacgtccga aattacatac   7320
gtggcggcga tggaagtaga tgttgagtct tcgaaagtaa gtgcctcgaa tatgggtatt   7380
gtctgtgaaa atatcgaaag cggtacgacg gttgcagaac cgtcgatgtc gccagatact   7440
agtaacaata gcttcgataa cgaagacttc cgtgggcctg aatacgatgt ggagataaat   7500
accagaaaat ctgctaatct tgatcgtatg gaatcttcgt gccgtgaaca acgagcggcg   7560
tgcgaacttc gaaagtgttc gtgtcctacg tctgccgtgc gcatgcaata cagtattctt   7620
tcatctctcg ctccgggttc agagggtcat gtatatatat gtactagata cggggacgcg   7680
gaccaaaaaa aatgcatagt gaaggcagtc gttggaggaa agaatcccgg gagggaagtg   7740
gatattttaa aaaccatctc acataaatca attataaaat taatccatgc ctataaatgg   7800
aaaaatgttg tgtgtatggc aatgcgttgta tatcgttatg atcttttcac atatattgac   7860
ggagtcggcc ctatgcccct tcaacagatg atctatattc aacgtggact actagaggcg   7920
ctagcataca tacatgaaag gggcatcatt caccgagacg taaagacgga gaatatattc   7980
ttggataatc acgaaaatgc agttttgggt gacttcggtg ctgcatgcca actaggagat   8040
tgtatagata cgccccaatg ttacggttgg agcggaactg tggaaacaaa ttcgccggaa   8100
ttatctgcac ttgatccgta ttgcacaaaa acagatattt ggagtgccgg attggttcta   8160
tatgagatgg caattaaaaa tgtaccattg tttagtaagc aggtgaaaag ttcgggatct   8220
cagctgagat ccataatacg gtgcatgcaa gtgcatgaac tggagtttcc ccgcaacgat   8280
tctaccaacc tctgtaaaca tttcaaacaa tatgcggttc gtgtacgacc gccttatacc   8340
attcctcgag ttataagaaa tgggggggatg ccaatggatg ttgaatatgt catttctaaa   8400
atgcttacgt ttgaccagga gttcagacct tctgctaagg aaatattgaa tatgcccta   8460 tttactaagg cgccgattaa cctgcttaat atcacaccct ctgacagtgt ctaacggtat   8520
acaggcggga gcgggtcgtg gcgtcatcat caccacttga gaatttatat tttgaattgt   8580
tgattgataa attaacctga ttcattgaga actgaaacgc catattggtt tcttggatat   8640
gtctacaaca attagttaaa ttgctatgtt ctactgcgag taacatttga taagttgtaa   8700
gagacgggcg actcatgtcg aagttgacga atataaagta cataacgtgt ttagaatacc   8760
cagaatccga atagtccgcg ggggcgtctt ctcgcgtgag taccaaatac tgagttgaac   8820
ttgaaaatgc taaatctgtg acactctttg tgtgatgatt attgtcacca cttcgaagat   8880
ggcttcgaca ttcatgatgt tctggtgttt gtttggaatc gtaatagcgc ttgtttcgtc   8940
caagtctgac aacaaagaaa atctgaagaa ttatatcacg gataagtcaa ccaatattag   9000
aatacccacg ccattatttg tatcaacgga aaactcttat cccacaaaac atgtaatcta   9060
cgatgaaaac tgtggcttcg ctgtactcaa tcctataagt gaccccaaat atgtcctttt   9120
gagccagctt ctaatgggaa ggcgcaaata tgatgcgacg gtcgcgtggt ttgttctcgg   9180
taaaatgtgt gccagattaa tatatttgcg cgaattttat aactgctcga caaatgagcc   9240
ttttggcaca tgttctatga gctctcctgg atggtgggac aggcgctacg tctcaaccag   9300
tttcatttct cgcgacgaat tacagctggt ttttgcagcg ccgtcccgag aattagatgg   9360
```

```
tttatatacg cgcgtagtag ttgtcaacgg ggactttact acggccgata taatgtttaa   9420
tgttaaagtg gcatgtgcct tttcaaagac tggaatagaa gatgatacat tatgcaaacc   9480 cttttcatttc tttgccaatg caacattgca caatttaacc atgattagat cggtaactct   9540
tcgagcgcac gaaagccatt taaaggaatg ggtggcacgg agaggtggta acgtccctgc   9600
agtgctactt gagtctacca tgtatcatgc atccaatctg cctagaaatt tcagggattt   9660
ctacataaag tctccagatg attataagta taatcaccta gatgggccat ctgtaatgct   9720
catcactgac agacctagtg aagatttgga tgggaggctc gttcaccaaa gtgacatttt   9780
tactactaca agtcctataa aacaggtccg gtatgaagag catcagtcac atacaaagca   9840
gtatcctgta aacaaaatac aagctataat ttttttgata gggttaggct cgttcattgg   9900
aagcatattc gtagttttgg tagtatggat tatacgcaga tattgcaatg gagcgcggag   9960
tgggggaacg ccccccagtc ctcgccggta tgtgtatacc aggctatgat cacgtgtgaa  10020
acttgggcgg acctgtatca tatgtacacc gtccctattc gtttatagcc agtacgtgtt  10080
atctgcacat agaggaacat gtgtcatact gggatcgcat gcatggtatg tgtgactcta  10140
atattattct gtatcataat aaaaacacag tgcatggtat atagaggatc gctggtaagc  10200
actacggtag accaatcggc tcagattgca ttctttggca tcgataccgt tgttaattta  10260
tatggcaaag tcttgttcat gggagatcag tatttggagg aaatatactc tggaacgatg  10320
gaaatactca aatggaatca agctaaccgc tgctattcta ttgcgcatgc aacatattac  10380
gccgactgtc ctataatcag ttctacggta ttcagaggat gccgggacgc cgttgtttat  10440
actaggcccc acagcagaat tcgtaatcat ggtcatagct gtttcctgtg tgaaattgtt  10500
atccgctcac aattccacac aacatacgag ccggaagcat aaagtgtaaa gcctggggtg  10560
cctaatgagt gagctaactc acattaattg cgttgcgctc actgcccgct ttccagtcgg  10620
gaaacctgtc gtgccagctg cattaatgaa tcggccaacg cgcggggaga ggcggtttgc  10680
gtattgggcg ctcttccgct tcctcgctca ctgactcgct gcgctcggtc gttcggctgc  10740
ggcgagcggt atcagctcac tcaaaggcgg taatacggtt atccacagaa tcaggggata  10800
acgcaggaaa gaacatgtga gcaaaaggcc agcaaaaggc caggaaccgt aaaaaggccg  10860
cgttgctggc gtttttccat aggctccgcc cccctgacga gcatcacaaa aatcgacgct  10920
caagtcagag gtggcgaaac ccgacaggac tataaagata ccaggcgttt ccccctggaa  10980
gctccctcgt gcgctctcct gttccgaccc tgccgcttac cggatacctg tccgcctttc  11040
tcccttcggg aagcgtggcg ctttctcaat gctcacgctg taggtatctc agttcggtgt  11100
aggtcgttcg ctccaagctg ggctgtgtgc acgaaccccc cgttcagccc gaccgctgcg  11160
ccttatccgg taactatcgt cttgagtcca acccggtaag acacgactta tcgccactgg  11220
cagcagccac tggtaacagg attagcagag cgaggtatgt aggcggtgct acagagttct  11280
tgaagtggtg gcctaactac ggctacacta aggacagt atttggtatc tgcgctctgc  11340
tgaagccagt taccttcgga aaaagagttg gtagctcttg atccggcaaa caaaccaccg  11400
ctggtagcgg tggtttttttt gtttgcaagc agcagattac gcgcagaaaa aaaggatctc  11460
aagaagatcc tttgatcttt tctacggggt ctgacgctca gtggaacgaa aactcacgtt  11520
aagggatttt ggtcatgaga ttatcaaaaa ggatcttcac ctagatcctt ttaaattaaa  11580
aatgaagttt taaatcaatc taaagtatat atgagtaaac ttggtctgac agttaccaat  11640
gcttaatcag tgaggcacct atctcagcga tctgtctatt tcgttcatcc atagttgcct  11700
gactccccgt cgtgtagata actacgatac gggagggctt accatctggc cccagtgctg  11760
```

-continued

```
caatgatacc gcgagaccca cgctcaccgg ctccagattt atcagcaata aaccagccag   11820
ccggaagggc cgagcgcaga agtggtcctg caactttatc cgcctccatc cagtctatta   11880
attgttgccg ggaagctaga gtaagtagtt cgccagttaa tagtttgcgc aacgttgttg   11940
ccattgctac aggcatcgtg gtgtcacgct cgtcgtttgg tatggcttca ttcagctccg   12000
gttcccaacg atcaaggcga gttacatgat cccccatgtt gtgcaaaaaa gcggttagct   12060
ccttcggtcc tccgatcgtt gtcagaagta agttggccgc agtgttatca ctcatggtta   12120
tggcagcact gcataattct cttactgtca tgccatccgt aagatgcttt tctgtgactg   12180
gtgagtactc aaccaagtca ttctgagaat agtgtatgcg cgaccgagt tgctcttgcc    12240 cggcgtcaat acgggataat accgcgccac atagcagaac tttaaaagtg ctcatcattg   12300
gaaaacgttc ttcggggcga aaactctcaa ggatcttacc gctgttgaga tccagttcga   12360
tgtaacccac tcgtgcaccc aactgatctt cagcatcttt tactttcacc agcgtttctg   12420
ggtgagcaaa aacaggaagg caaaatgccg caaaaaaggg aataagggcg acacggaaat   12480
gttgaatact catactcttc cttttcaat attattgaag catttatcag ggttattgtc     12540
tcatgagcgg atacatattt gaatgtattt agaaaaataa acaaataggg gttccgcgca   12600
catttccccg aaaagtgcca cctgacgtct aagaaaccat tattatcatg acattaacct   12660
ataaaaatag gcgtatcacg aggccctttc gt                                 12692
```

<210> SEQ ID NO 23
<211> LENGTH: 14113
<212> TYPE: DNA
<213> ORGANISM: Artificial Sequence
<220> FEATURE:
<223> OTHER INFORMATION: Expression cassette

<400> SEQUENCE: 23

```
gaattccaga ctaaatgccc cggcccaatt tgtcaagtgt gcagtcacgg aggcgtcgac     60
cgtgtccccg gcattaaaca ggaaagcgtt aaagttttg aatgttaggt cacaggtaca     120
aacataaatg tttgtacaaa caggtaacag gtacaaacat aaatgccccg gcataaatgt    180
cccttacggc ggatcgaaac gacattaggc atactcgggt accattttgc attccgatca    240
gcacggatga aattaggcag gaatgcggtt tatattatgc ggcattggac aaacgatatg    300
gcattgattg gcagtttatg aatgtcttca tgttgggcgt aaacggattc ctattggttc    360
agaagacaac gacgatatat ttagagagaa aaagctaccc agcataggat aaacacacat    420
tgagcattga gagacatagg tatcggtatg gatgggaaaa ctacacacgt gaacaccaaa    480
cgacttatat actcgagcgg tgatactact gagcaagaat gcactgcatc tgagccactg    540
aatgaagact gtgatgaaaa tgtgaccatc gatggaattg agaagaata tgcgcagttc    600 ttcatgtccc cgcaatgggt cccaaatcta catcgcttga gcgaggatac caaaaaggta   660
taccgatgta tggtttccaa cagactcaat tattttccct attatgaggc gttcaggcgg   720
tctttgtttg atatgtatat gctaggtcgg ttgggcgtc gacttaagcg atctgactgg    780
gagactatta tgcatctgtc accaacgcaa agtcggcgtc tacatagaac tttaagattt    840
gtggagcgta gaattatccc atctaacagt tatatacgca catcgggcca cgttccgcct   900
tcgagggcac ttccgacaga tacgaattta agatggatg aataattaaa ttggaaagag    960
taactacatt aatcgagcgt catgacgcg tcccgtgaaa atgggaattt tctactcgaa    1020
acaccgtgac atttgacaga cctggaattg ttattctgat atatagtggg tgtgtctggc   1080
```

```
cggcaacata cataatgtgc atgcgaaacc actttttcag tgtacgctga cattgtgcaa    1140
cacggagggg tagcatctac atacaatata tgttgattaa tgattggaga aaaaactatg    1200
cagctcgccg atcatatggc taactcgcct tcgtctatat ggcggacccc gcgggaaaaa    1260
tcgacgtacc atctgattta caacaccagt aatgaacatg tcgcatccct gcccagatct    1320
gtgcgcccat tggcgcggat cgttgtgaat gccgccgaaa cacttcaggt cggtatgaga    1380
gccgggaggc cgccatcagc aggagtttgg cgagaggtgt ttgatagaat gatgacagcc    1440
ttccgtgacc acgagcctac tgcgacattt aatgctgcaa atcccattag aaaaatggtc    1500
gagacagttc tacagaataa tgaagagccc ccgcggacgc atgctgaaat gggtaatcgc    1560
cttatgaaca ttatgtactg gtgttgcttg ggacacgcag acaatgctc gatatggcag    1620 ttgtacgaga cgaatcaggc cattttaagt ttattagatg aagtggttat cggcacaaca    1680
aatccctttt gcaccctcga gcaatactgg aagccattat gcaccgcaat cgccaacaag    1740
gggacctcat cgcttgttga ggatgccaaa gtggccgagt acctggttag catgcgcaaa    1800
ttgatataac ataggcacgc tctgatgtta cagaccacaa taccgcatac atttattgta    1860
aggttgttaa taaaggttta ttctatgtaa gactacaata ctttcgacat tgcttgtata    1920
catattaaat actttctcaa gttcctatta cataaaatgg gatctatcat tacattcgtt    1980
aagagtctgg ataattttac tgtttgccag cttcgatctt ggaacgtact gtggatagtg    2040
ccttacttgg aatcgtgaaa atttgaaacg tccattattt ggatatcttc cggttgtccc    2100
atatcccgcc ctggtaccgc tcggatacct tgcccgtatg gattcgtatt gacagtcgcg    2160
caatcgggga ccaacaacgc gtgggtccac actcattcgg aaattttccg atgattctga    2220
atatttattg ccgctcgtta cgagtcgttg gacatatctg taatacattt cttcttctga    2280
aggatcgctg cacatttgat ctatacattg gccaggatgt tcaagtctca gatgttgcat    2340
tctggcacag cacaacttta tggcatttcc gatgtaatcg tccggcagcc ctggggagt    2400 tctatattcg catattggga tggtaaggac aatagcagat ctcgcaacct ccagggaggc    2460
tataataacg ttttttaaagg atggatttct cataaaaatc tgtcgcaaat tacactgaga    2520 atatcctta ctagcgccga ttgagagcat cgtcgtccaa ttttctaaat ggaaagaaaa    2580
caaggcgggc aagagtgttc caaacatttt catttcggc gaatctctca aatcccatgg    2640
cgtgcaattg attgcaaaat tggcacttcc gttcacgttt gtatctccaa actctaagac    2700 actttaatt gaaaaactac gttctagtgt ggaaagaaac ctataggcag accatagaac    2760
tatttgacac cacatatctt tttgtatgtc aaactgacca tgatcgtatg ttgctgaatg    2820
cactagggca attcgctcgc gcgactccat acattgaata attccacacg tcagctcatc    2880
ggttagcaag gtccagtagt tgaagtcatt tatttttccc cgcggctggc caaatctacc    2940
tctgggaata tccaagttgt cgaatatgat cgcaccggct ctggtcatgg tgaaggaact    3000
gtagcataaa gacgcaggta tcatagggga aatatttttt tattcactca catactaaaa    3060
gtaacgcata ttagcaccat gtatgggcta tcaattgaca tttgcgtagc actacatcac    3120
gattatgtac aacataatgg gacaacatat ggcaagtaga tgcaatttcc tcacactagt    3180
tgggtttatc tactattgaa ttttcccta tctgtgatac acttgggagc ctctacaagc    3240
atattgccat catgtacgtt tttatctact gtcttaacgc ccatgggaac ggaggcgtcg    3300
tcgtcatgta ttggacggca acataggcag caacacaaat tgcgtttagg tggggtgcat    3360
gtggactcga taccaagccc ctgcagctgg ggaacgtctg gtggagagcc gataaatttga   3420 tatacgcacg ccatattact gtcgttgaag tacgccttat cttctatgtt ttcaaattta    3480
```

```
ggttcccaag tggacgtgag aagtgtttgt atctcacatg gaatggccca aggcattcca   3540
gcccaggtgc ctggtacttt aatggcaaac aaacgttttg gtagaggtat tgattctatt   3600
gcagttctgc agatatctgc agccccgagt atccacaggc tatacgatac gttatcggag   3660
gcaagctgcg gccgctctag aactagtgga tcccccgggc tgcagcccaa tgtggaattc   3720
gcccttgcac attgttactc ctgcatctta aaatatatc ctgtagtaat tttcacagca    3780
atgtcataac atcatctcgc taaagaatga cctgggattg gagaagtaat gaatatttgc   3840
aaccaatgca ttgaataaac taacattaaa cgaattcact agtggatccc ccaactccgc   3900
ccgttttatg actagaacca atagttttta atgccaaatg cactgaaatc ccctaatttg   3960
caaagccaaa cgcccctat gtgagtaata cggggacttt ttacccaatt tcccacgcgg    4020
aaagccccct aatacactca tatggcatat gaatcagcac ggtcatgcac tctaatggcg   4080
gcccataggg actttccaca tagggggcgt tcaccatttc ccagcatagg ggtggtgact   4140
caatggcctt tacccaagta cattgggtca atggggaggta agccaatggg tttttcccat  4200
tactggcaag cacactgagt caaatgggac tttccactgg gttttgccca agtacattgg   4260
gtcaatggga ggtgagccaa tgggaaaaac ccattgctgc caagtacact gactcaatag   4320
ggactttcca atgggttttt ccattgttgg caagcatata aggtcaatgt gggtgagtca   4380
atagggactt ccattgtat tctgcccagt acataaggtc aataggggggt gaatcaacag   4440
gaaagtccca ttggagccaa gtacactgcg tcaataggga cttccattg ggttttgccc    4500
agtacataag gtcaataggg gatgagtcaa tgggaaaaac ccattggagc caagtacact   4560
gactcaatag ggactttcca ttgggttttg cccagtacat aaggtcaata ggggggtgagt  4620
caacaggaaa gttccattgg agccaagtac attgagtcaa tagggacttt ccaatgggtt   4680
tgcccagta cataaggtca atgggaggta agccaatggg ttttccccat tactggcacg    4740
tatactgagt cattagggac tttccaatgg gttttgccca gtacataagg tcaataggg    4800
tgaatcaaca ggaaagtccc attggagcca agtacactga gtcaataggg actttccatt   4860
gggttttgcc cagtacaaaa ggtcaatagg gggtgagtca atgggttttt cccattattg   4920
gcacgtacat aaggtcaata ggggtgagtc attgggtttt tccagccaat ttaattaaaa   4980
cgccatgtac tttcccacca ttgacgtcaa tgggctattg aaactaatgc aacgtgacct   5040
ttaaacggta cttccccata gctgattaat gggaaagtac cgttctcgag ccaatacacg   5100
tcaatgggaa gtgaaaggcc agccaaaacg taacaccgcc ccggttttcc cctggaaatt   5160
ccatattggc acgcattcta ttggctgagc tgcgttctac gtgggtataa gaggcgcgac   5220
cagcgtcggt accgtcgcag tcttcggtct gaccaccgta gaacgcagag ctcctcgctg   5280
caggcggccg ctctagaact cgtcgatcgc agcgatgaca aacctgcaag atcaaaccca   5340
acagattgtt ccgttcatac ggagccttct gatgccaaca accggaccgg cgtccattcc   5400
ggacgacacc ctggagaagc acactctcag gtcagagacc tcgacctaca atttgactgt   5460
gggggacaca gggtcagggc taattgtctt tttccctgga ttccctggct caattgtggg   5520
tgctcactac acactgcaga gcaatgggaa ctacaagttc gatcagatgc tcctgactgc   5580
ccagaaccta ccgccagct acaactactg cagactagta gtcggagtc tcacagtgag    5640
gtcaagcaca ctccctggtg gcgtttatgc actaaacggc accataaacg ccgtgacctt   5700
ccaaggaagc ctgagtgaac tgacagatgt tagctacaat gggttgatgt ctgcaacagc   5760
caacatcaac gacaaaattg ggaatgtcct ggtaggggaa gggggtcactg tcctcagcct  5820
```

```
acccacatca tatgatcttg ggtatgtgag gcttggtgac cccattcccg ctatagggct    5880
tgacccaaaa atggtagcta catgcgacag cagtgacagg cccagagtct acaccataac    5940
tgcagccgat gattaccaat tctcatcaca gtaccaacca ggtggggtaa caatcacact    6000
gttctcagcc aacattgatg ctatcacaag cctcagcatt gggggagagc tcgtgtttca    6060
aacaagcgtc caaggccttg tactgggcgc caccatctac cttataggct tgatgggac    6120 tgcggtaatc accagagctg tggccgcaga taatgggctg acggccggca ccgacaatct    6180
tatgccattc aatcttgtca ttccaaccaa tgagataacc cagccaatca catccatcaa    6240
actggagata gtgacctcca aaagtggtgg tcaggcaggg gatcagatgt catggtcggc    6300
aagtgggagc ctagcagtga cgatccatgg tggcaactat ccaggggccc tccgtcccgt    6360
cacactagta gcctacgaaa gagtggcaac aggatccgtc gttacggtcg ctggggtgag    6420
taacttcgag ctgattccaa atcctgaact agcaaagaac ctggttacag aatacggccg    6480
atttgaccca ggagccatga actacacaaa attgatactg agtgagaggg accgtcttgg    6540
catcaagacc gtctggccaa caagggagta cactgatttt cgtgagtact tcatggaggt    6600
ggccgacctc aactctcccc tgaagattgc aggagcattt ggcttcaaag acataatccg    6660
ggctataagg aggtaagctt cagacatgat aagatacatt gatgagtttg acaaaccac    6720 aactagaatg cagtgaaaaa aatgctttat ttgtgaaatt tgtgatgcta ttgctttatt    6780
tgtaaccatt ataagctgca ataaacaagt taacaacaac aattgcattc attttatgtt    6840
tcaggttcag ggggaggtgt gggaggtttt ttcggatcct ctagagtcga cggcagagtc    6900
gcagacgccc ctattggacg tcaaaattgt agaggtgaag ttttcaaacg atggcgaagt    6960
aacggcgact tgcgtttcca ccgtcaaatc tccctatagg gtagaaacta attggaaagt    7020
agacctcgta gatgtaatgg atgaaatttc tgggaacagt cccgccgggg tttttaacag    7080
taatgagaaa tggcagaaac agctgtacta cagagtaacc gatggaagaa catcggtcca    7140
gctaatgtgc ctgtcgtgca cgagccattc tccggaacct tactgtcttt tcgacacgtc    7200
tcttatagcg agggaaaaag atatcgcgcc agagttatac tttacctctg atccgcaaac    7260
ggcatactgc acaataactc tgccgtccgg cgttgttccg agattcgaat ggagccttaa    7320
taatgtttca ctgccggaat atttgacggc cacgaccgtt gtttcgcata ccgctggcca    7380
aagtacagtg tggaagagca gcgcgagagc aggcgaggcg tggatttctg ccgggggagg    7440
caatatatac gaatgcaccg tcctcatctc agacggcact cgcgttacta cgcgaaagga    7500
gaggtgctta acaaacacat ggattgcggt ggaaaacggt gctgctcagg cgcagctgta    7560
ttcactcttt tctggacttg tgtcaggatt atgcgggagc atatctgctt tgtacgcaac    7620
gctatgggcc gccatttatt tttgaggaat gcttttttgga ctatcgtact gctttcttcc    7680
ttcgctagcc agagcaccgc cgccgtcacg tacgactaca ttttaggccg tcgcgcgctc    7740
gacgcgctaa ccataccggc ggttggcccg tataacagat acctcactag ggtatcaaga    7800
ggctgcgacg ttgtcgagct caacccgatt tctaacgtgg acgacatgat atcggcggcc    7860
aaagaaaaag agaagggggg ccctttcgag gcctccgtcg tctggttcta cgtgattaag    7920
ggcgacgacg cgaggacaa gtactgtcca atctatagaa aagagtacag ggaatgtggc    7980
gacgtacaac tgctatctga atgcgccgtt caatctgcac agatgtgggc agtggactat    8040
gttcctagca ccccttgtatc gcgaaatggc gcgggactga ctatattctc ccccactgct    8100
gcgctctctg gccaatactt gctgaccctg aaaatcggga gatttgcgca aacagctctc    8160
gtaactctag aagttaacga tcgctgttta aagatcgggt cgcagcttaa cttttttaccg    8220
```

```
tcgaaatgct ggacaacaga acagtatcag actggatttc aaggcgaaca cctttatccg   8280
atcgcagaca ccaatacacg acacgcggac gacgtatatc ggggatacga agatattctg   8340
cagcgctgga ataatttgct gaggaaaaag aatcctagcg cgccagaccc tcgtccagat   8400
agcgtcccgc aagaaattcc cgctgtaacc aagaaagcgg aagggcgcac cccggacgca   8460
gaaagcagcg aaaagaaggc ccctccagaa gactcggagg acgacatgca ggcagaggct   8520
tctggagaaa atcctgccgc cctccccgaa gacgacgaag tccccgagga caccgagcac   8580
gatgatccaa actcggatcc tgactattac aatgacatgc ccgccgtgat cccggtggag   8640
gagactacta aaagttctaa tgccgtctcc atgcccatat tcgcggcgtt cgtagcctgc   8700
gcggtcgcgc tcgtggggct actggtttgg agcatcgtaa aatgcgcgcg tagctaatcg   8760
agcctagaat aggtggtttc ttcctacatg ccacgcctca cgctcataat ataaatcaca   8820
tggaatagca taccaatgcc tattcattgg gacgttcgaa aagcatggca tcgctacttg   8880
gaactctggc tctccttgcc gcgacgctcg caccccttcgg cgcgatggga atcgtgatca   8940
ctggaaatca cgtctccgcc aggattgacg acgatcacat cgtgatcgtc gcgcctcgcc   9000
ccgaagctac aattcaactg cagctatttt tcatgcctgg ccagagaccc cacaaaccct   9060
actcaggaac cgtccgcgtc gcgtttcggt ctgatataac aaaccagtgc taccaggaac   9120
ttagcgagga gcgctttgaa aattgcactc atcgatcgtc ttctgttttt gtcggctgta   9180
aagtgaccga gtacacgttc tccgcctcga acagactaac cggacctcca cacccgttta   9240
agctcactat acgaaatcct cgtccgaacg acagcgggat gttctacgta attgttcggc   9300
tagacgacac caaagaaccc attgacgtct tcgcgatcca actatcggtg tatcaattcg   9360
cgaacaccgc cgcgactcgc ggactctatt ccaaggcttc gtgtcgcacc ttcggattac   9420
ctaccgtcca acttgaggcc tatctcagga ccgaggaaag ttggcgcaac tggcaagcgt   9480
acgttgccac ggaggccacg acgaccagcc ccgaggcgac aaccccgacg cccgtcactg   9540
caaccagcgc ctccgaactt gaagcggaac actttacctt tccctggcta gaaaatggcg   9600
tggatcatta cgaaccgaca cccgcaaacg aaaattcaaa cgttactgtc cgtctcggga   9660
caatgagccc tacgctaatt ggggtaaccg tggctgccgt cgtgagcgca acgatcggcc   9720
tcgtcattgt aatttccatc gtcaccagaa acatgtgcac cccgcaccga aaattagaca   9780
cggtctcgca agacgacgaa gaacgttccc aaactagaag ggaatcgcga aaatttggac   9840
ccatggttgc gtgcgaaata aacaaggggg ctgaccagga tagtgaactt gtggaactgg   9900
ttgcgattgt taacccgtct cgcgctaagct cgcccgactc aataaaaatg tgattaagtc   9960
tgaatgtggc tctccaatca tttcgattct ctaatctccc aatcctctca aaagggcag  10020 tatcggacac ggactgggag gggcgtacac gatagttata tggtacagca gaggcctctg  10080
aacacttagg aggagaattc agccggggag agcccctgtt gagtaggctt gggagcatat  10140
tgcaggatga acatgttagt gatagttctc gcctcttgtc ttgcgcgcct aacttttgcg  10200
acgcgacacg tcctcttttt ggaaggcact caggctgtcc tcggggaaga tgatcccaga  10260
aacgttccgg aagggactgt aatcaaatgg acaaaagtcc tgcggaacgc gtgcaagatg  10320
aaggcggccg atgtctgctc ttcgcctaac tattgctttc atgatttaat ttacgacgga  10380
ggaaagaaag actgcccgcc cgcgggaccc ctgtctgcaa acctggtaat tttactaaag  10440
cgcggcgaag cttagcttgc ctccgattct agcattacat agccggtcag tagatcctgc  10500
cattcggtag cgcaaccggc tacatcttca aacagtctca cgataaatgc atctctcgtt  10560
```

```
cctgccaatc cggaaccggg cataccactc ccgcctgccg atttaattct cacaattggg   10620
cgatgccggc ggggcaaaac gaatgtggat ttggcaaacc gacacaggtc tgctgtacgg   10680
actaatatgg gcacacccac atcattcttc agatgctcca tgcattgttc tatgagaaag   10740
atccataggg tggaggcagc gtcacgagat cgcccaggca atcgatcgca ttcgtctagt   10800
aaagtgacga gagttatcat gcacacaccc atgcccacgc cttccgaata actggagctg   10860
tggaagatcg gaaacgtctt tttgactgcc ggtctcgtac tactttcgca caggtgtata   10920
cccggacgcg tactatatat tttatatcat ccaacgtccg aaattacata cgtggcggcg   10980
atggaagtag atgttgagtc ttcgaaagta agtgcctcga atatgggtat tgtctgtgaa   11040
aatatcgaaa gcggtacgac ggttgcagaa ccgtcgatgt cgccagatac tagtaacaat   11100
agcttcgata acgaagactt ccgtgggcct gaatacgatg tggagataaa taccagaaaa   11160
tctgctaatc ttgatcgtat ggaatcttcg tgccgtgaac aacgagcggc gtgcgaactt   11220
cgaaagtgtt cgtgtcctac gtctgccgtg cgcatgcaat acagtattct ttcatctctc   11280
gctccgggtt cagagggtca tgtatatata tgtactagat acggggacgc ggaccaaaaa   11340
aaatgcatag tgaaggcagt cgttggagga agaatcccg ggagggaagt ggatattta    11400
aaaccatct cacataaatc aattataaaa ttaatccatg cctataaatg gaaaaatgtt    11460
gtgtgtatgg caatgcgtgt atatcgttat gatcttttca catatattga cggagtcggc   11520
cctatgcccc ttcaacagat gatctatatt caacgtggac tactagaggc gctagcatac   11580
atacatgaaa ggggcatcat tcaccgagac gtaaagacgg agaatatatt cttggataat   11640
cacgaaaatg cagttttggg tgacttcggt gctgcatgcc aactaggaga ttgtatagat   11700
acgccccaat gttacggttg gagcggaact gtggaaacaa attcgccgga attatctgca   11760
cttgatccgt attgcacaaa aacagatatt tggagtgccg gattggttct atatgagatg   11820
gcaattaaaa atgtaccatt gtttagtaag caggtgaaaa gttcgggatc tcagctgaga   11880
tccataatac ggtgcatgca agtgcatgaa ctggagtttc cccgcaacga ttctaccaac   11940
ctctgtaaac atttcaaaca atatgcggtt cgtgtacgac cgccttatac cattcctcga   12000
gttataagaa atgggggat gccaatggat gttgaatatg tcatttctaa aatgcttacg    12060
tttgaccagg agttcagacc ttctgctaag gaaatattga atatgcccct atttactaag   12120
gcgccgatta acctgcttaa tatcacaccc tctgacagtg tctaacggta tacaggcggg   12180
agcgggtcgt ggcgtcatca tcaccacttg agaatttata ttttgaattg ttgattgata   12240
aattaacctg attcattgag aactgaaacg ccatattggt ttcttggata tgtctacaac   12300
aattagttaa attgctatgt tctactgcga gtaacatttg ataagttgta agagacgggc   12360
gactcatgtc gaagttgacg aatataaagt acataacgtg tttagaatac ccagaatccg   12420
aatagtccgc gggggcgtct tctcgcgtga gtaccaaata ctgagttgaa cttgaaaatg   12480
ctaaatctgt gacactcttt gtgtgatgat tattgtcacc acttcgaaga tggcttcgac   12540
attcatgatg ttctggtgtt tgtttggaat cgtaatagcg cttgtttcgt ccaagtctga   12600
caacaaagaa aatctgaaga attatatcac ggataagtca accaatatta gaatacccac   12660
gccattattt gtatcaacgg aaaactctta tcccacaaaa catgtaatct acgatgaaaa   12720
ctgtggcttc gctgtactca atcctataag tgaccccaaa tatgtccttt tgagccagct   12780
tctaatggga aggcgcaaat atgatgcgac ggtcgcgtgg tttgttctcg gtaaaatgtg   12840
tgccagatta atatatttgc gcgaatttta taactgctcg acaaatgagc cttttggcac   12900
atgttctatg agctctcctg gatggtggga caggcgctac gtctcaacca gtttcatttc   12960
```

```
tcgcgacgaa ttacagctgg tttttgcagc gccgtcccga gaattagatg gtttatatac   13020
gcgcgtagta gttgtcaacg gggactttac tacggccgat ataatgttta atgttaaagt   13080
ggcatgtgcc ttttcaaaga ctggaataga agatgataca ttatgcaaac cctttcattt   13140
ctttgccaat gcaacattgc acaatttaac catgattaga tcggtaactc ttcgagcgca   13200
cgaaagccat ttaaggaat gggtggcacg gagaggtggt aacgtccctg cagtgctact   13260
tgagtctacc atgtatcatg catccaatct gcctagaaat ttcagggatt tctacataaa   13320
gtctccagat gattataagt ataatcacct agatgggcca tctgtaatgc tcatcactga   13380
cagacctagt gaagatttgg atgggaggct cgttcaccaa agtgacattt ttactactac   13440
aagtcctata aaacaggtcc ggtatgaaga gcatcagtca catacaaagc agtatcctgt   13500
aaacaaaata caagctataa ttttttttgat agggttaggc tcgttcattg gaagcatatt   13560
cgtagttttg gtagtatgga ttatacgcag atattgcaat ggagcgcgga gtgggggaac   13620
gccccccagt cctcgccggt atgtgtatac caggctatga tcacgtgtga aacttgggcg   13680
gacctgtatc atatgtacac cgtccctatt cgtttatagc cagtacgtgt tatctgcaca   13740
tagaggaaca tgtgtcatac tgggatcgca tgcatggtat gtgtgactct aatattattc   13800
tgtatcataa taaaaacaca gtgcatggta tatagaggat cgctggtaag cactacggta   13860
gaccaatcgg ctcagattgc attctttggc atcgataccg ttgttaattt atatggcaaa   13920
gtcttgttca tgggagatca gtatttggag gaaatatact ctggaacgat ggaaatactc   13980
aaatggaatc aagctaaccg ctgctattct attgcgcatg caacatatta cgccgactgt   14040
cctataatca gttctacggt attcagagga tgccgggacg ccgttgttta tactaggccc   14100
cacagcagaa ttc                                                      14113
```

<210> SEQ ID NO 24
<211> LENGTH: 13064
<212> TYPE: DNA
<213> ORGANISM: Artificial Sequence
<220> FEATURE:
<223> OTHER INFORMATION: Expression cassette
<220> FEATURE:
<221> NAME/KEY: misc_feature
<222> LOCATION: (7401)..(7403)
<223> OTHER INFORMATION: n is a, c, g, or t

<400> SEQUENCE: 24

```
gaattccaga ctaaatgccc cggcccaatt tgtcaagtgt gcagtcacgg aggcgtcgac     60
cgtgtccccg gcattaaaca ggaaagcgtt aaagttttttg aatgttaggt cacaggtaca   120
aacataaatg tttgtacaaa caggtaacag gtacaaacat aaatgccccg gcataaatgt    180
cccttacggc ggatcgaaac gacattaggc atactcgggt accattttgc attccgatca    240
gcacggatga aattaggcag gaatgccggtt tatattatgc ggcattggac aaacgatatg    300
gcattgattg gcagtttatg aatgtcttca tgttgggcgt aaacggattc ctattggttc    360
agaagacaac gacgatatat ttagagagaa aaagctaccc agcataggat aaacacacat    420
tgagcattga gagacatagg tatcggtatg gatgggaaaa ctacacacgt gaacaccaaa    480
cgacttatat actcgagcgg tgatactact gagcaagaat gcactgcatc tgagccactg    540
aatgaagact gtgatgaaaa tgtgaccatc gatggaattg agaagaata tgcgcagttc     600 ttcatgtccc cgcaatgggt cccaaatcta catcgcttga gcgaggatac caaaaaggta    660
taccgatgta tggtttccaa cagactcaat tattttccct attatgaggc gttcaggcgg    720
```

```
tctttgtttg atatgtatat gctaggtcgg ttggggcgtc gacttaagcg atctgactgg    780
gagactatta tgcatctgtc accaacgcaa agtcggcgtc tacatagaac tttaagattt    840
gtggagcgta gaattatccc atctaacagt tatatacgca catcgggcca cgttccgcct    900
tcgagggcac ttccgacaga tacgaattta aagatggatg aataattaaa ttggaaagag    960
taactacatt aatcgagcgt catgacggcg tcccgtgaaa atgggaattt tctactcgaa   1020
acaccgtgac atttgacaga cctggaattg ttattctgat atatagtggg tgtgtctggc   1080
cggcaacata cataatgtgc atgcgaaacc acttttttcag tgtacgctga cattgtgcaa  1140
cacggagggg tagcatctac atacaatata tgttgattaa tgattggaga aaaaactatg   1200
cagctcgccg atcatatggc taactcgcct tcgtctatat ggcggacccc gcggaaaaa    1260 tcgacgtacc atctgattta caacaccagt aatgaacatg tcgcatccct gcccagatct   1320
gtgcgcccat tggcgcggat cgttgtgaat gccgccgaaa cacttcaggt cggtatgaga   1380
gccgggaggc cgccatcagc aggagtttgg cgagaggtgt ttgatagaat gatgacagcc   1440
ttccgtgacc acgagcctac tgcgacattt aatgctgcaa atcccattag aaaaatggtc   1500
gagacagttc tacagaataa tgaagagccc ccgcggacgc atgctgaaat gggtaatcgc   1560
cttatgaaca ttatgtactg gtgttgcttg ggacacgcag acaatgctc gatatggcag    1620 ttgtacgaga cgaatcaggc cattttaagt ttattagatg aagtggttat cggcacaaca   1680
aatccctttt gcaccctcga gcaatactgg aagccattat gcaccgcaat cgccaacaag   1740
gggacctcat cgcttgttga ggatgccaaa gtggccgagt acctggttag catgcgcaaa   1800
ttgatataac ataggcacgc tctgatgtta cagaccacaa taccgcatac atttattgta   1860
aggttgttaa taaggtttta ttctatgtaa gactacaata ctttcgacat tgcttgtata   1920
catattaaat actttctcaa gttcctatta cataaaatgg gatctatcat tacattcgtt   1980
aagagtctgg ataattttac tgtttgccag cttcgatctt ggaacgtact gtggatagtg   2040
ccttacttgg aatcgtgaaa atttgaaacg tccattattt ggatatcttc cggttgtccc   2100
atatcccgcc ctggtaccgc tcggatacct tgcccgtatg gattcgtatt gacagtcgcg   2160
caatcgggga ccaacaacgc gtgggtccac actcattcgg aaattttccg atgattctga   2220
atatttattg ccgctcgtta cgagtcgttg gacatatctg taatacattt cttcttctga   2280
aggatcgctg cacatttgat ctatacattg gccaggatgt tcaagtctca gatgttgcat   2340
tctggcacag cacaacttta tggcatttcc gatgtaatcg tccggcagcc ctgggggagt   2400
tctatattcg catattggga tggtaaggac aatagcagat ctcgcaacct ccagggaggc   2460
tataataacg tttttaaagg atggatttct cataaaaatc tgtcgcaaat tacactgaga   2520 atatcctttta ctagcgccga ttgagagcat cgtcgtccaa ttttctaaat ggaaagaaaa  2580
caaggcgggc aagagtgttc caaacatttt cattttcggc gaatctctca aatcccatgg   2640
cgtgcaattg attgcaaaat tggcacttcc gttcacgttt gtatctccaa actctaagac   2700
acttttaatt gaaaaactac gttctagtgt ggaaagaaac ctataggcag accatagaac   2760
tatttgacac cacatatctt tttgtatgtc aaactgacca tgatcgtatg ttgctgaatg   2820
cactagggca attcgctcgc gcgactccat acattgaata attccacacg tcagctcatc   2880
ggttagcaag gtccagtagt tgaagtcatt tattttttccc cgcggctggc caaatctacc   2940
tctgggaata tccaagttgt cgaatatgat cgcaccggct ctggtcatgg tgaaggaact   3000
gtagcataaa gacgcaggta tcatagggt aatatttttt tattcactca catactaaaa    3060
gtaacgcata ttagcaccat gtatgggcta tcaattgaca tttgcgtagc actacatcac   3120
```

```
gattatgtac aacataatgg acaacatat ggcaagtaga tgcaatttcc tcacactagt      3180
tgggtttatc tactattgaa ttttccccta tctgtgatac acttgggagc ctctacaagc      3240
atattgccat catgtacgtt tttatctact gtcttaacgc ccatgggaac ggaggcgtcg      3300
tcgtcatgta ttggacggca acataggcag caacacaaat tgcgtttagg tggggtgcat      3360
gtggactcga taccaagccc ctgcagctgg ggaacgtctg gtggagagcc gataatttga      3420
tatacgcacg ccatattact gtcgttgaag tacgccttat cttctatgtt ttcaaattta      3480
ggttcccaag tggacgtgag aagtgtttgt atctcacatg gaatggccca aggcattcca      3540
gcccaggtgc ctggtacttt aatggcaaac aaacgttttg gtagaggtat tgattctatt      3600
gcagttctgc agatatctgc agccccgagt atccacaggc tatacgatac gttatcggag      3660
gcaagcttaa ttaagtaccg agctcgaatt ggcgcgcccg acggcagagt cgcagacgcc      3720
cctattggac gtcaaaattg tagaggtgaa gttttcaaac gatggcgaag taacggcgac      3780
ttgcgtttcc accgtcaaat ctccctatag ggtagaaact aattggaaag tagacctcgt      3840
agatgtaatg gatgaaattt ctgggaacag tcccgccggg ttttttaaca gtaatgagaa      3900
atggcagaaa cagctgtact acagagtaac cgatggaaga acatcggtcc agctaatgtg      3960
cctgtcgtgc acgagccatt ctccggaacc ttactgtctt ttcgacacgt ctcttatagc      4020
gagggaaaaa gatatcgcgc cagagttata ctttacctct gatccgcaaa cggcatactg      4080
cacaataact ctgccgtccg gcgttgttcc gagattcgaa tggagcctta ataatgtttc      4140
actgccggaa tatttgacgg ccacgaccgt tgtttcgcat accgctggcc aaagtacagt      4200
gtggaagagc agcgcgagag caggcgaggc gtggatttct ggccggggag gcaatatata      4260
cgaatgcacc gtcctcatct cagacggcac tcgcgttact acgcgaaagg agaggtgctt      4320
aacaaacaca tggattgcgg tggaaaacgg tgctgctcag gcgcagctgt attcactctt      4380
ttctggactt gtgtcaggat tatgcgggag catatctgct ttgtacgcaa cgctatggac      4440
cgccatttat ttttgaggaa tgcttttttgg actatcgtac tgctttcttc cttcgctagc      4500
cagagcaccg ccgccgtcac gtacgactac attttaggcc gtcgcgcgct cgacgcgcta      4560
accataccgg cggttggccc gtataacaga tacctcacta gggtatcaag aggctgcgac      4620
gttgtcgagc tcaacccgat ttctaacgtg gacgacatga tatcggcggc caaagaaaaa      4680 gagaagggggg gccctttcga ggcctccgtc gtctggttct acgtgattaa gggcgacgac      4740
ggcgaggaca agtactgtcc aatctataga aaagagtaca gggaatgtgg cgacgtacaa      4800
ctgctatctg aatgcgccgt tcaatctgca cagatgtggg cagtggacta tgttcctagc      4860
acccttgtat cgcgaaatgg cgcgggactg actatattct cccccactgc tgcgctctct      4920
ggccaatact tgctgaccct gaaaatcggg agatttgcgc aaacagctct cgtaactcta      4980
gaagttaacg atcgctgttt aaagatcggg tcgcagctta acttttacc gtcgaaatgc      5040 tggacaacag aacagtatca gactggattt caaggcgaac accttatcc gatcgcagac      5100 accaatacac gacacgcgga cgacgtatat cggggatacg aagatattct gcagcgctgg      5160
aataatttgc tgaggaaaaa gaatcctagc gcgccagacc ctcgtccaga tagcgtcccg      5220
caagaaattc ccgctgtaac caagaaagcg gaagggcgca ccccgacgc agaaagcagc      5280 gaaaagaagg cccctccaga agactcggag gacgacatgc aggcagaggc ttctggagaa      5340
aatcctgccg ccctccccga agacgacgaa gtccccgagg acaccgagca cgatgatcca      5400
aactcggatc ctgactatta caatgacatg ccgccgtgtga tcccggtgga ggagactact      5460
```

```
aaaagttcta atgccgtctc catgcccata ttcgcggcgt tcgtagcctg cgcggtcgcg    5520
ctcgtgggc tactggtttg gagcatcgta aaatgcgcgc gtagctaatc gagcctagaa     5580
taggtggttt cttcctacat gccacgcctc acgctcataa tataaatcac atggaatagc    5640
ataccaatgc ctattcattg ggacgttcga aaagcatggc atcgctactt ggaactctgg    5700
ctctccttgc cgcgacgctc gcacccttcg gcgcgatggg aatcgtgatc actggaaatc    5760
acgtctccgc caggattgac gacgatcaca tcgtgatcgt cgcgcctcgc ccgaagcta    5820
caattcaact gcagctattt ttcatgcctg gccagagacc ccacaaaccc tactcaggaa    5880
ccgtccgcgt cgcgtttcgg tctgatataa caaaccagtg ctaccaggaa cttagcgagg    5940
agcgctttga aaattgcact catcgatcgt cttctgtttt tgtcggctgt aaagtgaccg    6000
agtacacgtt ctccgcctcg aacagactaa ccggacctcc acaccgtttt aagctcacta    6060
tacgaaatcc tcgtccgaac gacagcggga tgttctacgt aattgttcgg ctagacgaca    6120
ccaaagaacc cattgacgtc ttcgcgatcc aactatcggt gtatcaattc gcgaacaccg    6180
ccgcgactcg cggactctat tccaaggctt cgtgtcgcac cttcggatta cctaccgtcc    6240
aacttgaggc ctatctcagg accgaggaaa gttggcgcaa ctggcaagcg tacgttgcca    6300
cggaggccac gacgaccagc gccgaggcga caaccccgac gcccgtcact gcaaccagcg    6360
cctccgaact tgaagcggaa cactttacct ttccctggct agaaaatggc gtggatcatt    6420
acgaaccgac cccgcaaac gaaaattcaa acgttactgt ccgtctcggg acaatgagcc    6480
ctacgctaat tggggtaacc gtggctgccg tcgtgagcgc aacgatcggc ctcgtcattg    6540
taatttccat cgtcaccaga aacatgtgca ccccgcaccg aaaattagac acggtctcgc    6600
aagacgacga agaacgttcc caaactagaa gggaatcgcg aaaatttgga cccatggttg    6660
cgtgcgaaat aaacaagggg gctgaccagg atagtgaact tgtggaactg gttgcgattg    6720
ttaacccgtc tgcgctaagc tcgcccgact caataaaaat gtgattaagt ctgaatgtgg    6780
ctctccaatc atttcgattc tctaatctcc caatcctctc aaaagggca gtatcggaca     6840
cggactggga ggggcgtaca cgatagttat atggtacagc agaggcctct gaacacttag    6900
gaggagaatt cagccgggga gagccccgt tgagtaggct tgggagcata ttgcaggatg     6960
aacatgttag tgatagttct cgcctcttgt cttgcgcgcc taacttttgc gacgcgacac    7020
gtcctctttt tggaaggcac tcaggctgtc ctcggggaag atgatcccag aaacgttccg    7080
gaagggactg taatcaaatg gacaaaagtc ctgcggaacg cgtgcaagat gaaggcggcc    7140
gatgtctgct cttcgcctaa ctattgcttt catgatttaa tttacgacgg aggaaagaaa    7200
gactgcccgc ccgcgggacc cctgtctgca aacctggtaa ttttactaaa gcgcggcggg    7260
cgcgccggat cagatctcca tggtcgaggt gagcccacg ttctgcttca ctctcccat     7320
ctccccccccc tccccacccc caattttgta tttatttatt ttttaattat tttgtgcagc    7380
gatggggcg ggggggggg nnncgcgcgc caggcgggc ggggcgggc gaggggcggg         7440
gcggggcgag gcggagaggt gcggcggcag ccaatcagag cggcgcgctc cgaaagtttc    7500
cttttatggc gaggcggcgg cggcggcggc cctataaaaa gcgaagcgcg cggcgggcgg    7560
gagtcgctgc gcgctgcctt cgcccgtgc ccgctccgc cgccgcctcg cgccgcccgc      7620
cccggctctg actgaccgcg ttactcccac aggtgagcgg gcgggacggc ccttctcctc    7680
cgggctgtaa ttagcggcag gaaggaaatg ggcggggagg ccttcgtgc gtcgccgcgc     7740
cgccgtcccc ttctccctct ccagcctcgg ggctgtccgc gggggacgg ctgccttcgg     7800
gggggacggg gcagggcggg gttcggcttc tggcgtgtga ccggcggctc tagagcctct    7860
```

```
gctaaccatg ttcatgcctt cttcttttc ctacagctcc tgggcaacgt gctggttatt     7920
gtgctgtctc atcattttgg caaagaattg cagatctgga tctatgacaa acctgcaaga     7980
tcaaacccaa cagattgttc cgttcatacg gagccttctg atgccaacaa ccggaccggc     8040
gtccattccg gacgacaccc tggagaagca cactctcagg tcagagacct cgacctacaa     8100
tttgactgtg ggggacacag ggtcagggct aattgtcttt ttccctggat tccctggctc     8160
aattgtgggt gctcactaca cactgcagag caatgggaac tacaagttcg atcagatgct     8220
cctgactgcc cagaacctac cggccagcta caactactgc agactagtga gtcggagtct     8280
cacagtgagg tcaagcacac tccctggtgg cgtttatgca ctaaacggca ccataaacgc     8340
cgtgaccttc caaggaagcc tgagtgaact gacagatgtt agctacaatg ggttgatgtc     8400
tgcaacagcc aacatcaacg acaaagttgg gaatgtcctg gtaggggaag gggtcactgt     8460
cctcagccta cccacatcat atgatcttgg gtatgtgagg cttggtgacc ccattcccgc     8520
tatagggctt gacccaaaaa tggtagctac atgcgacagc agtgacaggc ccagagtcta     8580
caccataact gcagccgatg attaccaatt ctcatcacag taccaaccag gtgggtaac     8640 aatcacactg ttctcagcca acattgatgc tatcacaagc ctcagcattg ggggagagct     8700
cgtgtttcaa acaagcgtcc aaggccttgt actgggcgcc accatctacc ttataggctt     8760
tgatgggact gcggtaatca ccagagctgt ggccgcagat aatgggctga cggccggcac     8820
cgacaatctt atgccattca atcttgtcat tccaaccaat gagataaccc agccgatcac     8880
atccatcaaa ctggagatag tgacctccaa aagtggtggt caggcagggg atcagatgtc     8940
atggtcggca agtgggagcc tagcagtgac gatccatggt ggcaactatc cagggccct     9000 ccgtcccgtc acactagtag cctacgaaag agtggcaaca ggatccgtcg ttacggtcgc     9060
tggggtgagt aacttcgagc tgatcccaaa tcctgaacta gcaaagaacc tggttacaga     9120
atacggccga tttgacccag gagccatgaa ctacacaaaa ttgatactga gtgagaggga     9180
ccgtcttggc atcaagaccg tctggccaac aagggagtac actgatttc gtgagtactt     9240 catggaggtg gccgacctca actctccccct gaagattgca ggagcatttg gcttcaaaga     9300
cataatccgg gctataagga ggtaagatcc gatctctcga ttaattaaca ataaacatag     9360
catacgttat gacatggtct accgcgtctt atatggggac gacaagcttg cctccgattc     9420
tagcattaca tagccggtca gtagatcctg ccattcggta cgcaaccgg ctacatcttc     9480 aaacagtctc acgataaatg catctctcgt tcctgccaat ccggaaccgg gcataccact     9540
cccgcctgcc gatttaattc tcacaattgg gcgatgccgg cggggcaaaa cgaatgtgga     9600
tttggcaaac cgacacaggt ctgctgtacg gactaatatg ggcacaccca catcattctt     9660
cagatgctcc atgcattgtt ctatgagaaa gatcctagg gtggaggcag cgtcacgaga     9720
tcgcccaggc aatcgatcgc attcgtctag taaagtgacg agagttatca tgcacacacc     9780
catgcccacg ccttccgaat aactggagct gtggaagatc ggaaacgtct ttttgactgc     9840
cggtctcgta ctactttcgc acaggtgtat acccggacgc gtactatata ttttatatca     9900
tccaacgtcc gaaattacat acgtggcggc gatggaagta gatgttgagt cttcgaaagt     9960
aagtgcctcg aatatgggta ttgtctgtga aaatatcgaa agcggtacga cggttgcaga    10020
accgtcgatg tcgccagata ctagtaacaa tagcttcgat aacgaagact tccgtgggcc    10080
tgaatacgat gtggagataa ataccagaaa atctgctaat cttgatcgta tggaatcttc    10140
gtgccgtgaa caacgagcgg cgtgcgaact tcgaaagtgt tcgtgtccta cgtctgccgt    10200
```

```
gcgcatgcaa tacagtattc tttcatctct cgctccgggt tcagagggtc atgtatatat   10260
atgtactaga tacggggacg cggaccaaaa aaaatgcata gtgaaggcag tcgttggagg   10320
aaagaatccc gggagggaag tggatatttt aaaaaccatc tcacataaat caattataaa   10380
attaatccat gcctataaat ggaaaaatgt tgtgtgtatg gcaatgcgtg tatatcgtta   10440
tgatcttttc acatatattg acggagtcgg ccctatgccc cttcaacaga tgatctatat   10500
tcaacgtgga ctactagagg cgctagcata catacatgaa aggggcatca ttcaccgaga   10560
cgtaaagacg gagaatatat tcttggataa tcacgaaaat gcagttttgg gtgacttcgg   10620
tgctgcatgc caactaggag attgtataga tacgccccaa tgttacggtt ggagcggaac   10680
tgtggaaaca aattcgccgg aattatctgc acttgatccg tattgcacaa aaacagatat   10740
ttggagtgcc ggattggttc tatatgagat ggcaattaaa aatgtaccat tgtttagtaa   10800
gcaggtgaaa agttcgggat ctcagctgag atccataata cggtgcatgc aagtgcatga   10860
actggagttt ccccgcaacg attctaccaa cctctgtaaa catttcaaac aatatgcgt   10920 tcgtgtacga ccgccttata ccattcctcg agttataaga aatgggggga tgccaatgga   10980
tgttgaatat gtcatttcta aaatgcttac gtttgaccag gagttcagac cttctgctaa   11040
ggaaatattg aatatgcccc tatttactaa ggcgccgatt aacctgctta atatcacacc   11100
ctctgacagt gtctaacggt atacaggcgg gagcgggtcg tggcgtcatc atcaccactt   11160
gagaatttat attttgaatt gttgattgat aaattaacct gattcattga gaactgaaac   11220
gccatattgg tttcttggat atgtctacaa caattagtta aattgctatg ttctactgcg   11280
agtaacattt gataagttgt aagagacggg cgactcatgt cgaagttgac gaatataaag   11340
tacataacgt gtttagaata cccagaatcc gaatagtccg cggggcgtc ttctcgcgtg   11400 agtaccaaat actgagttga acttgaaaat gctaaatctg tgacactctt tgtgtgatga   11460
ttattgtcac cacttcgaag atggcttcga cattcatgat gttctggtgt tgtttggaa   11520 tcgtaatagc gcttgtttcg tccaagtctg acaacaaaga aaatctgaag aattatatca   11580
cggataagtc aaccaatatt agaatacccca cgccattatt tgtatcaacg gaaaactctt   11640
atcccacaaa acatgtaatc tacgatgaaa actgtggctt cgctgtactc aatcctataa   11700
gtgaccccaa atatgtcctt ttgagccagc ttctaatggg aaggcgcaaa tatgatgcga   11760
cggtcgcgtg gtttgttctc ggtaaaatgt gtgccagatt aatatatttg cgcgaatttt   11820
ataactgctc gacaaatgag cctttggga catgttctat gagctctcct ggatggtggg   11880
acaggcgcta cgtctcaacc agtttcattt ctcgcgacga attacagctg gttttttgcag  11940 cgccgtcccg agaattagat ggtttatata cgcgcgtagt agttgtcaac ggggacttta   12000
ctacggccga tataatgttt aatgttaaag tggcatgtgc cttttcaaag actggaatag   12060
aagatgatac attatgcaaa ccctttcatt tctttgccaa tgcaacattg cacaatttaa   12120
ccatgattag atcggtaact cttcgagcgc acgaaagcca tttaaaggaa tgggtggcac   12180
ggagaggtgg taacgtccct gcagtgctac ttgagtctac catgtatcat gcatccaatc   12240
tgcctagaaa tttcagggat ttctacataa agtctccaga tgattataag tataatcacc   12300
tagatgggcc atctgtaatg ctcatcactg acagacctag tgaagatttg gatgggaggc   12360
tcgttcacca aagtgacatt tttactacta caagtcctat aaaacaggtc cggtatgaag   12420
agcatcagtc acatacaaag cagtatcctg taaacaaaat acaagctata attttttgga   12480
tagggttagg ctcgttcatt ggaagcatat tcgtagtttt ggtagtatgg attatacgca   12540
gatattgcaa tggagcgcgg agtgggggaa cgccccccag tcctcgccgg tatgtgtata   12600
```

```
ccaggctatg atcacgtgtg aaacttgggc ggacctgtat catatgtaca ccgtccctat    12660
tcgtttatag ccagtacgtg ttatctgcac atagaggaac atgtgtcata ctgggatcgc    12720
atgcatggta tgtgtgactc taatattatt ctgtatcata ataaaaacac agtgcatggt    12780
atatagagga tcgctggtaa gcactacggt agaccaatcg gctcagattg cattctttgg    12840
catcgatacc gttgttaatt tatatggcaa agtcttgttc atgggagatc agtatttgga    12900
ggaaatatac tctggaacga tggaaatact caaatgaat  caagctaacc gctgctattc    12960
tattgcgcat gcaacatatt acgccgactg tcctataatc agttctacgg tattcagagg    13020
atgccgggac gccgttgttt atactaggcc ccacagcaga attc                     13064

<210> SEQ ID NO 25
<211> LENGTH: 13017
<212> TYPE: DNA
<213> ORGANISM: Artificial Sequence
<220> FEATURE:
<223> OTHER INFORMATION: Expression cassette

<400> SEQUENCE: 25
gaattccaga ctaaatgccc cggcccaatt tgtcaagtgt gcagtcacgg aggcgtcgac      60
cgtgtccccg gcattaaaca ggaaagcgtt aaagttttg aatgttaggt cacaggtaca     120
aacataaatg tttgtacaaa caggtaacag gtacaaacat aaatgccccg gcataaatgt     180
cccttacggc ggatcgaaac gacattaggc atactcgggt accattttgc attccgatca     240
gcacggatga aattaggcag gaatgcggtt tatattatgc ggcattggac aaacgatatg     300
gcattgattg gcagtttatg aatgtcttca tgttgggcgt aaacggattc ctattggttc     360
agaagacaac gacgatatat ttagagagaa aaagctaccc agcataggat aaacacacat     420
tgagcattga gagacatagg tatcggtatg gatgggaaaa ctacacacgt gaacaccaaa     480
cgacttatat actcgagcgg tgatactact gagcaagaat gcactgcatc tgagccactg     540
aatgaagact gtgatgaaaa tgtgaccatc gatggaattg gagaagaata tgcgcagttc     600
ttcatgtccc cgcaatgggt cccaaatcta catcgcttga gcgaggatac caaaaaggta     660
taccgatgta tggtttccaa cagactcaat tatttccct  attatgaggc gttcaggcgg     720
tctttgtttg atatgtatat gctaggtcgg ttgggcgtc  gacttaagcg atctgactgg     780
gagactatta tgcatctgtc accaacgcaa agtcggcgtc tacatagaac tttaagattt     840
gtggagcgta gaattatccc atctaacagt tatatacgca catcgggcca cgttccgcct     900
tcgagggcac ttccgacaga tacgaattta aagatggatg aataattaaa ttggaaagag     960
taactacatt aatcgagcgt catgacggcg tcccgtgaaa atgggaattt tctactcgaa    1020
acaccgtgac atttgacaga cctggaattg ttattctgat atatagtggg tgtgtctggc    1080
cggcaacata cataatgtgc atgcgaaacc actttttcag tgtacgctga cattgtgcaa    1140
cacggagggg tagcatctac atacaatata tgttgattaa tgattggaga aaaaactatg    1200
cagctcgccg atcatatggc taactcgcct tcgtctatat ggcggacccc gcgggaaaaa    1260
tcgacgtacc atctgattta caacaccagt aatgaacatg tcgcatccct gcccagatct    1320
gtgcgcccat tggcgcggat cgttgtgaat gccgccgaaa cacttcaggt cggtatgaga    1380
gccgggaggc cgccatcagc aggagtttgg cgagaggtgt tgatagaat  gatgacagcc    1440 ttccgtgacc acgagcctac tgcgacattt aatgctgcaa atcccattag aaaaatggtc    1500
gagacagttc tacagaataa tgaagagccc ccgcggacgc atgctgaaat gggtaatcgc    1560
```

```
cttatgaaca ttatgtactg gtgttgcttg ggacacgcag acaatgctc gatatggcag      1620 ttgtacgaga cgaatcaggc catttttaagt ttattagatg aagtggttat cggcacaaca    1680
aatccctttt gcaccctcga gcaatactgg aagccattat gcaccgcaat cgccaacaag    1740
gggacctcat cgcttgttga ggatgccaaa gtggccgagt acctggttag catgcgcaaa    1800
ttgatataac ataggcacgc tctgatgtta cagaccacaa taccgcatac atttattgta    1860
aggttgttaa taaaggttta ttctatgtaa gactacaata ctttcgacat tgcttgtata    1920
catattaaat actttctcaa gttcctatta cataaaatgg gatctatcat tacattcgtt    1980
aagagtctgg ataattttac tgtttgccag cttcgatctt ggaacgtact gtggatagtg    2040
ccttacttgg aatcgtgaaa atttgaaacg tccattattt ggatatcttc cggttgtccc    2100
atatcccgcc ctggtaccgc tcggatacct tgcccgtatg gattcgtatt gacagtcgcg    2160
caatcgggga ccaacaacgc gtgggtccac actcattcgg aaattttccg atgattctga    2220
atatttattg ccgctcgtta cgagtcgttg gacatatctg taatacattt cttcttctga    2280
aggatcgctg cacatttgat ctatacattg gccaggatgt tcaagtctca gatgttgcat    2340
tctggcacag cacaacttta tggcatttcc gatgtaatcg tccggcagcc ctggggagt     2400 tctatattcg catattggga tggtaaggac aatagcagat ctcgcaaccct ccagggaggc   2460 tataataacg ttttaaagg atggatttct cataaaaatc tgtcgcaaat tacactgaga    2520
atatccttta ctagcgccga ttgagagcat cgtcgtccaa ttttctaaat ggaaagaaaa    2580
caaggcgggc aagagtgttc caaacatttt catttcggc gaatctctca aatcccatgg    2640
cgtgcaattg attgcaaaat tggcacttcc gttcacgttt gtatctccaa actctaagac    2700
acttttaatt gaaaaactac gttctagtgt ggaagaaac ctataggcag accatagaac    2760
tatttgacac cacatatctt tttgtatgtc aaactgacca tgatcgtatg ttgctgaatg    2820
cactagggca attcgctcgc gcgactccat acattgaata attccacacg tcagctcatc    2880
ggttagcaag gtccagtagt tgaagtcatt tattttccc cgcggctggc caaatctacc     2940
tctgggaata tccaagttgt cgaatatgat cgcaccggct ctggtcatgg tgaaggaact    3000
gtagcataaa gacgcaggta tcatagggt aatattttttt tattcactca catactaaaa   3060
gtaacgcata ttagcaccat gtatgggcta tcaattgaca tttgcgtagc actacatcac    3120
gattatgtac aacataatgg gacaacatat ggcaagtaga tgcaatttcc tcacactagt    3180
tgggtttatc tactattgaa ttttccccta tctgtgatac acttgggagc ctctacaagc    3240
atattgccat catgtacgtt tttatctact gtcttaacgc ccatgggaac ggaggcgtcg    3300
tcgtcatgta ttggacggca acataggcag caacacaaat tgcgtttagg tggggtgcat    3360
gtggactcga taccaagccc ctgcagctgg ggaacgtctg gtggagagcc gataatttga    3420
tatacgcacg ccatattact gtcgttgaag tacgccttat cttctatgtt ttcaaattta    3480
ggttcccaag tggacgtgag aagtgtttgt atctcacatg gaatggccca aggcattcca    3540
gcccaggtgc ctggtacttt aatggcaaac aaacgtttg gtagaggtat tgattctatt     3600
gcagttctgc agatatctgc agccccgagt atccacaggc tatacgatac gttatcggag    3660
gcaagcttgt taattaagtc gacggcagag tcgcagacgc ccctattgga cgtcaaaatt    3720
gtagaggtga agttttcaaa cgatggcgaa gtaacggcga cttgcgtttc caccgtcaaa    3780
tctccctata gggtagaaac taattggaaa gtagacctcg tagatgtaat ggatgaaatt    3840
tctgggaaca gtcccgccgg ggtttttaac agtaatgaga aatggcagaa acagctgtac    3900
tacagagtaa ccgatggaag aacatcggtc cagctaatgt gcctgtcgtg cacgagccat    3960
```

```
tctccggaac cttactgtct tttcgacacg tctcttatag cgagggaaaa agatatcgcg    4020
ccagagttat actttacctc tgatccgcaa acggcatact gcacaataac tctgccgtcc    4080
ggcgttgttc cgagattcga atggagcctt aataatgttt cactgccgga atatttgacg    4140
gccacgaccg ttgtttcgca taccgctggc caaagtacag tgtggaagag cagcgcgaga    4200
gcaggcgagg cgtggatttc tggccgggga ggcaatatat acgaatgcac cgtcctcatc    4260
tcagacggca ctcgcgttac tacgcgaaag gagaggtgct aacaaacac atggattgcg     4320 gtggaaaacg gtgctgctca ggcgcagctg tattcactct tttctggact tgtgtcagga    4380
ttatgcggga gcatatctgc tttgtacgca acgctatgga ccgccattta tttttgagga    4440 atgcttttg gactatcgta ctgctttctt ccttcgctag ccagagcacc gccgccgtca     4500
cgtacgacta cattttaggc cgtcgcgcgc tcgacgcgct aaccataccg gcggttggcc    4560
cgtataacag atacctcact agggtatcaa gaggctgcga cgttgtcgag ctcaacccga    4620
tttctaacgt ggacgacatg atatcggcgg ccaaagaaaa agagaagggg ggcccttttcg   4680 aggcctccgt cgtctggttc tacgtgatta agggcgacga cggcgaggac aagtactgtc    4740
caatctatag aaaagagtac agggaatgtg gcgacgtaca actgctatct gaatgcgccg    4800
ttcaatctgc acagatgtgg gcagtggact atgttcctag caccctgta tcgcgaaatg     4860 gcgcgggact gactatattc tcccccactg ctgcgctctc tggccaatac ttgctgaccc    4920
tgaaaatcgg gagatttgcg caaacagctc tcgtaactct agaagttaac gatcgctgtt    4980
taaagatcgg gtcgcagctt aactttttac cgtcgaaatg ctggacaaca gaacagtatc    5040
agactggatt tcaaggcgaa cacctttatc cgatcgcaga caccaataca cgacacgcgg    5100
acgacgtata tcggggatac gaagatattc tgcagcgctg gaataatttg ctgaggaaaa    5160
agaatcctag cgcgccagac cctcgtccag atagcgtccc gcaagaaatt cccgctgtaa    5220
ccaagaaagc ggaagggcgc accccggacg cagaaagcag cgaaaagaag gcccctccag    5280
aagactcgga ggacgacatg caggcagagg cttctggaga aaatcctgcc gccctccccg    5340
aagacgacga agtccccgag gacaccgagc acgatgatcc aaactcggat cctgactatt    5400
acaatgacat gcccgccgtg atcccggtgg aggagactac taaaagttct aatgccgtct    5460
ccatgcccat attcgcggcg ttcgtagcct gcgcggtcgc gctcgtgggg ctactggttt    5520
ggagcatcgt aaaatgcgcg cgtagctaat cgagcctaga ataggtggtt tcttcctaca    5580
tgccacgcct cacgctcata atataaatca catggaatag cataccaatg cctattcatt    5640
gggacgttcg aaaagcatgg catcgctact tggaactctg gctctccttg ccgcgacgct    5700
cgcacccttc ggcgcgatgg gaatcgtgat cactggaaat cacgtctccg ccaggattga    5760
cgacgatcac atcgtgatcg tcgcgcctcg ccccgaagct acaattcaac tgcagctatt    5820
tttcatgcct ggccagagac cccacaaacc ctactcagga accgtccgcg tcgcgtttcg    5880
gtctgatata acaaaccagt gctaccagga acttagcgag gagcgctttg aaaattgcac    5940
tcatcgatcg tcttctgttt ttgtcggctg taaagtgacc gagtacacgt tctccgcctc    6000
gaacagacta accggacctc cacacccgtt taagctcact atacgaaatc ctcgtccgaa    6060
cgacagcggg atgttctacg taattgttcg gctagacgca accaaagaac ccattgacgt    6120
cttcgcgatc caactatcgg tgtatcaatt cgcgaacacc gccgcgactc gcggactcta    6180
ttccaaggct tcgtgtcgca ccttcggatt acctaccgtc caacttgagg cctatctcag    6240
gaccgaggaa agttggcgca actggcaagc gtacgttgcc acggaggcca cgacgaccag    6300
```

```
cgccgaggcg acaaccccga cgcccgtcac tgcaaccagc gcctccgaac ttgaagcgga    6360
acactttacc tttccctggc tagaaaatgg cgtggatcat tacgaaccga cacccgcaaa    6420
cgaaaattca aacgttactg tccgtctcgg acaatgagc cctacgctaa ttggggtaac     6480
cgtggctgcc gtcgtgagcg caacgatcgg cctcgtcatt gtaatttcca tcgtcaccag    6540
aaacatgtgc accccgcacc gaaaattaga cacggtctcg caagacgacg aagaacgttc    6600
ccaaactaga agggaatcgc gaaaatttgg acccatggtt gcgtgcgaaa taaacaaggg    6660
ggctgaccag gatagtgaac ttgtggaact ggttgcgatt gttaacccgt ctgcgctaag    6720
ctcgcccgac tcaataaaaa tgtgattaag tctgaatgtg gctctccaat catttcgatt    6780
ctctaatctc ccaatcctct caaagggc agtatcggac acggactggg aggggcgtac      6840
acgatagtta tatggtacag cagaggcctc tgaacactta ggaggagaat tcagccgggg    6900
agagcccctg ttgagtaggc ttgggagcat attgcaggat gaacatgtta gtgatagttc    6960
tcgcctcttg tcttgcgcgc taacttttg cgacgcgaca cgtcctcttt ttggaaggca    7020
ctcaggctgt cctcggggaa gatgatccca gaaacgttcc ggaagggact gtaatcaaat    7080
ggacaaaagt cctgcggaac gcgtgcaaga tgaaggcggc cgatgtctgc tcttcgccta    7140
actattgctt tcatgattta atttacgacg gaggaaagaa agactgcccg cccgcgggac    7200
ccctgtctgc aaacctggta attttactaa agcgcggcga agcttaggt caattccctg     7260 gcattatgcc cagtacatga ccttatggga ctttcctact tggcagtaca tctacgtatt    7320
agtcatcgct attaccatgg tgatgcggtt ttggcagtac atcaatgggc gtggatagcg    7380
gtttgactca cggggatttc caagtctcca ccccattgac gtcaatggga gtttgttttg    7440
gcaccaaaat caacgggact ttccaaaatg tcgtaacaac tccgccccat tgacgcaaat    7500
gggcggtagg cgtgtacggt gggaggtcta tataagcaga gctcgtttag tgaaccgtca    7560
gatcgcctgg agacgccatc cacgctgttt tgacctccat agaagacacc gggcgcgccg    7620
gatctatgac aaacctgcaa gatcaaaccc aacagattgt tccgttcata cggagccttc    7680
tgatgccaac aaccggaccg gcgtccattc cggacgacac cctggagaag cacactctca    7740
ggtcagagac ctcgacctac aatttgactg tggggacaca agggtcaggg ctaattgtct    7800
ttttccctgg attccctggc tcaattgtgg gtgctcacta cacactgcag agcaatggga    7860
actacaagtt cgatcagatg ctcctgactg cccagaacct accggccagc tacaactact    7920
gcagactagt gagtcggagt ctcacagtga ggtcaagcac actccctggt ggcgtttatg    7980
cactaaacgg caccataaac gccgtgacct tccaaggaag cctgagtgaa ctgacagatg    8040
ttagctacaa tggggttgatg tctgcaacag ccaacatcaa cgacaaagtt gggaatgtcc    8100
tggtagggga aggggtcact gtcctcagcc tacccacatc atatgatctt gggtatgtga    8160
ggcttggtga ccccattccc gctatagggc ttgacccaaa aatggtagct acatgcgaca    8220
gcagtgacag gccagagtc tacaccataa ctgcagccga tgattaccaa ttctcatcac     8280
agtaccaacc aggtggggta acaatcacac tgttctcagc caacattgat gctatcacaa    8340
gcctcagcat tggggagag ctcgtgtttc aaacaagcgt ccaaggcctt gtactgggcg      8400
ccaccatcta ccttataggc tttgatggga ctgcggtaat caccagagct gtggccgcag    8460
ataatgggct gacggccggc accgacaatc ttatgccatt caatcttgtc attccaacca    8520
atgagataac ccagccgatc acatccatca aactggagat agtgacctcc aaaagtggtg    8580
gtcaggcagg ggatcagatg tcatggtcgg caagtgggag cctagcagtg acgatccatg    8640
gtggcaacta tccagggggcc ctccgtcccg tcacactagt agcctacgaa agagtggcaa    8700
```

```
caggatccgt cgttacggtc gctggggtga gtaacttcga gctgatccca aatcctgaac   8760
tagcaaagaa cctggttaca gaatacggcc gatttgaccc aggagccatg aactacacaa   8820
aattgatact gagtgagagg gaccgtcttg gcatcaagac cgtctggcca acaagggagt   8880
acactgattt tcgtgagtac ttcatggagg tggccgacct caactctccc ctgaagattg   8940
caggagcatt tggcttcaaa gacataatcc gggctataag gaggtaagat ccataattga   9000
ttgacgggag atgggggagg ctaactgaaa cacggaagga gacaataccg gaaggaaccc   9060
gcgctatgac ggcaataaaa agacagaata aaacgcacgg gtgttgggtc gtttgttcat   9120
aaacgcgggg ttcggtccca gggctggcac tctgtcgata ccccaccgag accccattgg   9180
ggccaatacg cccgcgtttc ttccttttcc ccaccccacc cccaagttc gggtgaaggc    9240
ccagggctcg cagccaacgt cggggcggca ggccctgcca tagccactgg ccccgtgggt   9300
tagggacggg gtcccccatg gggaatggtt tatggttcgt gggggttatt attttgaagc   9360
ttgcctccga ttctagcatt acatagccgg tcagtagatc ctgccattcg gtagcgcaac   9420
cggctacatc ttcaaacagt ctcacaataa atgcatctct cgttcctgcc aatccggaac   9480
cgggcatacc actcccgcct gccgatttaa ttctcacaat tgggcgatgc cggcggggca   9540
aaacgaatgt ggatttggca aaccgacaca ggtctgctgt acggactaat atgggcacac   9600
ccacatcatt cttcagatgc tccatgcatt gttctatgag aaagatccat agggtggagg   9660
cagcgtcacg agatcgccca ggcaatcgat cgcattcgtc tagtaaagtg acgagagtta   9720
tcatgcacac acccatgccc acgccttccg aataactgga gctgtggaag atcggaaacg   9780
tcttttttgac tgccggtctc gtactacttt cgcacaggtg tatacccgga cgcgtactat   9840
atattttata tcatccaacg tccgaaatta catacgtggc ggcgatggaa gtagatgttg   9900
agtcttcgaa agtaagtgcc tcgaatatgg gtattgtctg tgaaaatatc gaaagcggta   9960
cgacggttgc agaaccgtcg atgtcgccag atactagtaa caatagcttc gataacgaag  10020
acttccgtgg gcctgaatac gatgtggaga taaataccag aaaatctgct aatcttgatc  10080
gtatggaatc ttcgtgccgt gaacaacgag cggcgtgcga acttcgaaag tgttcgtgtc  10140
ctacgtctgc cgtgcgcatg caatacagta ttcttcatc tctcgctccg ggttcagagg   10200
gtcatgtata tatatgtact agatacgggg acgcggacca aaaaaaatgc atagtgaagg  10260
cagtcgttgg aggaaagaat cccgggaggg aagtggatat tttaaaaacc atctcacata  10320
aatcaattat aaaattaatc catgcctata aatggaaaaa tgttgtgtgt atggcaatgc  10380
gtgtatatcg ttatgatctt ttcacatata ttgacggagt cggccctatg cccttcaac   10440
agatgatcta tattcaacgt ggactactag aggcgctagc atacatacat gaaaggggca  10500
tcattcaccg agacgtaaag acggagaata tattcttgga taatcacgaa aatgcagttt  10560
tgggtgactt cggtgctgca tgccaactag gagattgtat agatacgccc caatgttacg  10620
gttggagcga aactgtggaa acaaattcgc cggaattatc tgcacttgat ccgtattgca  10680
caaaaacaga tatttggagt gccggattgg ttctatatga gatggcaatt aaaaatgtac  10740
cattgtttag taagcaggtg aaagttcgg gatctcagct gagatccata atacggtgca  10800
tgcaagtgca tgaactggag ttccccgca acgattctac caacctctgt aaacatttca  10860
aacaatatgc ggttcgtgta cgaccgcctt ataccattcc tcgagttata agaaatgggg  10920
ggatgccaat ggatgttgaa tatgtcattt ctaaaatgct tacgtttgac caggagttca  10980
gaccttctgc taaggaaata ttgaatatgc ccctatttac taaggcgccg attaacctgc  11040
```

```
ttaatatcac accctctgac agtgtctaac ggtatacagg cgggagcggg tcgtggcgtc   11100
atcatcacca cttgagaatt tatattttga attgttgatt gataaattaa cctgattcat   11160
tgagaactga aacgccatat tggtttcttg gatatgtcta caacaattag ttaaattgct   11220
atgttctact gcgagtaaca tttgataagt tgtaagagac gggcgactca tgtcgaagtt   11280
gacgaatata aagtacataa cgtgtttaga atacccagaa tccgaatagt ccgcggggc    11340 gtcttctcgc gtgagtacca aatactgagt tgaacttgaa aatgctaaat ctgtgacact   11400
ctttgtgtga tgattattgt caccacttcg aagatggctt cgacattcat gatgttctgg   11460
tgtttgtttg gaatcgtaat agcgcttgtt tcgtccaagt ctgacaacaa agaaaatctg   11520
aagaattata tcacggataa gtcaaccaat attagaatac ccacgccatt atttgtatca   11580
acggaaaact cttatcccac aaaacatgta atctacgatg aaaactgtgg cttcgctgta   11640
ctcaatccta taagtgaccc caaatatgtc cttttgagcc agcttctaat gggaaggcgc   11700
aaatatgatg cgacggtcgc gtggtttgtt ctcggtaaaa tgtgtgccag attaatatat   11760
ttgcgcgaat tttataactg ctcgacaaat gagccttttg gcacatgttc tatgagctct   11820
cctggatggt gggacaggcg ctacgtctca accagtttca tttctcgcga cgaattacag   11880
ctggtttttg cagcgccgtc ccgagaatta gatggtttat atacgcgcgt agtagttgtc   11940
aacggggact ttactacggc cgatataatg tttaatgtta aagtggcatg tgccttttca   12000
aagactggaa tagaagatga tacattatgc aaacccttc atttctttgc caatgcaaca    12060
ttgcacaatt taaccatgat tagatcggta actcttcgag cgcacgaaag ccatttaaag   12120
gaatgggtgg cacggagagg tggtaacgtc cctgcagtgc tacttgagtc taccatgtat   12180
catgcatcca atctgcctag aaatttcagg gatttctaca taaagtctcc agatgattat   12240
aagtataatc acctagatgg gccatctgta atgctcatca ctgacagacc tagtgaagat   12300
ttggatggga ggctcgttca ccaaagtgac attttttacta ctacaagtcc tataaaacag   12360
gtccggtatg aagagcatca gtcacataca aagcagtatc ctgtaaacaa aatacaagct   12420
ataatttttt tgatagggtt aggctcgttc attggaagca tattcgtagt tttggtagta   12480
tggattatac gcagatattg caatggagcg cggagtgggg gaacgcccc cagtcctcgc    12540 cggtatgtgt ataccaggct atgatcacgt gtgaaacttg gcggacctg tatcatatgt    12600 acaccgtccc tattcgttta tagccagtac gtgttatctg cacatagagg aacatgtgtc   12660
atactgggat cgcatgcatg gtatgtgtga ctctaatatt attctgtatc ataataaaaa   12720
cacagtgcat ggtatataga ggatcgctgg taagcactac ggtagaccaa tcggctcaga   12780
ttgcattctt tggcatcgat accgttgtta atttatatgg caaagtcttg ttcatgggag   12840
atcagtattt ggaggaaata tactctggaa cgatggaaat actcaaatgg aatcaagcta   12900
accgctgcta ttctattgcg catgcaacat attacgccga ctgtcctata atcagttcta   12960
cggtattcag aggatgccgg gacgccgttg tttatactag gccccacagc agaattc      13017

<210> SEQ ID NO 26
<211> LENGTH: 11017
<212> TYPE: DNA
<213> ORGANISM: Artificial Sequence
<220> FEATURE:
<223> OTHER INFORMATION: Expression cassette

<400> SEQUENCE: 26
ggcgcgccac tggagaacgg catgaccgca aaaggcgttg tagagatcga tcccacgaac     60
tctcaggcga tcgtgtcagt cgccataaac agcgacgatc gtctccagga tctgaacggt    120
```

```
tttcttctca acgatcatca gtatatgagg aactgaacct gatatttagc cgagggaaac    180
gcaggttaaa aacccctatca agcgattgcg attttcgcgt atctagtaaa aatagatggg   240
cttcggtact agccttcgcc gccaactctg aatatgccct tcgtggacct catataacat    300
ggcattgttt gttggatgcg gggccggaat taagaagaac attcgaaata cgagcaaaaa   360
tttcggccct ggcatgtgct gcgcgagaat cggtacttcg gggagaaagt tttatcggag    420
ctttgggtag tgcagaggaa actctatctt ggttgaaaat gcatgcgacc ctgcacttga    480
ttctggttaa ccacgatcca attttttaaga cggctggcgc ggtcctagat aacctccgct   540
taaaactagc cccaatattg atgtgcagat ataacacaga aaaacgatca atggaagaca   600
tgctacggcg gtcatctccc gaagacatca ccgattccct aacaatgtgc ctgattatgt   660
tatcgcgcat tcgtcgtacc atgcgcaccg caggaaataa atatagctat atgatagatc   720
caatgaatcg tatgtctaat tacactccag gcgaatgtat gacaggtata ttgcgatata   780
ttgacgaaca tgctagaagg tgtcctgatc acatatgtaa tttgtatatc acatgtacac   840
ttatgccgat gtatgtgcac gggcgatatt tctattgtaa ttcattttt tgttagtaaa    900 ctaccacagg ctgtccggaa atctaagtta atgaataaag tagatggtta atactcattg    960
cttagaattg gactactttt aattctcttt aatgttcgta ttaaataaaa acatctttaa   1020
taaacttcag cctcttcgct tattgtagaa attgagtatt caaaatcatg ttcaaagccg   1080
tcttcggaga gtgtactcgc cacggtggtt ggaacatcac tatgtctaca cgtcaaattt   1140
aagcacgtca ggtctgtcga ggacaagaaa tggttaacta gtgtttcaat tattcttata   1200
aacgttaagc attgtaagcc ccccggccgt ccgcagcaac aatttactag tatgccgtgg   1260
gctccgggac tatcacggat gtccaattcg cacatgcata taattttttct agggtctctc   1320 atttcgagaa atcttcgggg atccatcagc aatgcgggct gtagtcccga ttcccgtttc   1380 aaaatgaaggt gctccaacac ggtcttcaaa gcaaccggca taccagcaaa cacagactgc   1440
aactccccgc tgcaatgatt ggttataaac agtaatctgt cttctggaag tatatttcgc   1500
ccgacaatcc acggcgcccc caaagttaaa aaccatccat gtgtatttgc gtcttctctg   1560
ttaaaagaat attgactggc attttcccgt tgaccgccag atatccaaag tacagcacga   1620
tgttgcacgg acgactttgc agtcaccagc cttcctttcc acccccccac caacaaaatg   1680
tttatcgtag gacccatatc cgtaataagg atgggtctgg cagcaacccc ataggcgcct   1740
cggcgtggta gttctcgagg ccttaattaa gtaccgagct cgaattggcg cgccaggtca   1800
attccctggc attatgccca gtacatgacc ttatgggact ttcctacttg gcagtacatc    1860
tacgtattag tcatcgctat taccatggtg atgcggtttt ggcagtacat caatgggcgt   1920
ggatagcggt ttgactcacg gggatttcca agtctccacc ccattgacgt caatgggagt   1980
ttgttttggc accaaaatca acgggacttt ccaaaatgtc gtaacaactc cgccccattg   2040
acgcaaatgg gcggtaggcg tgtacggtgg gaggtctata taagcagagc tcgtttagtg   2100
aaccgtcaga tcgcctggag acgccatcca cgctgttttg acctccatag aagacaccgg   2160
gcgcgccgga tccatgggcc ccagaccttc taccaagaac ccagtaccta tgatgctgac   2220
tgtccgagtc gcgctggtac tgagttgcat ctgtccggca aactccattg atggcaggcc   2280
tcttgcggct gcaggaattg tggttacagg agacaaagcc gtcaacatat acacctcatc   2340
ccagacagga tcaatcatag ttaagctcct cccgaatctg cccaaggata aggaggcatg   2400
tgcgaaagcc cccttggatg catacaacag gacattgacc actttgctca cccccccttgg  2460
```

```
tgactctatc cgtaggatac aagagtctgt gactacatct ggagggggga gacaggggcg      2520
ccttataggc gccattattg gcggtgtggc tcttggggtt gcaactgccg cacaaataac      2580
agcggccgca gctctgatac aagccaaaca aaatgctgcc aacatcctcc gacttaaaga      2640
gagcattgcc gcaaccaatg aggctgtgca tgaggtcact gacggattat cgcaactagc      2700
agtggcagtt gggaagatgc agcagtttgt taatgaccaa tttaataaaa cagctcagga      2760
attagactgc atcaaaattg cacagcaagt tggtgtagag ctcaacctgt acctaaccga      2820
attgactaca gtattcggac cacaaatcac ttcacctgct ttaaacaagc tgactattca      2880
ggcactttac aatctagctg gtggaaatat ggattactta ttgactaagt taggtgtagg      2940
gaacaatcaa ctcagctcat taatcggtag cggcttaatc accggtaacc ctattctata      3000
cgactcacag actcaactct tgggtataca ggtaactcta ccttcagtcg ggaacctaaa      3060
taatatgcgt gccacctact tggaaacctt atccgtaagc acaaccaggg gatttgcctc      3120
ggcacttgtc ccaaaagtgg tgacacaggt cggttctgtg atagaagaac ttgacacctc      3180
atactgtata gaaactgact tagatttata ttgtacaaga atagtaacgt tccctatgtc      3240
ccctggtatt tattcctgct tgagcggcaa tacgtcggcc tgtatgtact caaagaccga      3300
aggcgcactt actacaccat acatgactat caaaggttca gtcatcgcca actgcaagat      3360
gacaacatgt agatgtgtaa accccccggg tatcatatcg caaaactatg gagaagccgt      3420
gtctctaata gataaacaat catgcaatgt tttatcctta ggcgggataa ctttaaggct      3480
cagtggggaa ttcgatgtaa cttatcagaa gaatatctca atacaagatt ctcaagtaat      3540
aataacaggc aatcttgata tctcaactga gcttgggaat gtcaacaact cgatcagtaa      3600
tgctttgaat aagttagagg aaagcaacag aaaactagac aaagtcaatg tcaaactgac      3660
tagcacatct gctctcatta cctatatcgt tttgactatc atatctcttg tttttggtat      3720
acttagcccg attctagcat gctacctaat gtacaagcaa aaggcgcaac aaaagacctt      3780
attatgcctt gggaataata ctctagatca gatgagagcc actacaaaaa tgtgaggatc      3840
tctcgaggaa ttctagatcc cacgtcacta ttgtatactc tatattatac tctatgttat      3900
actctgtaat cctactcaat aaacgtgtca cgcctgtgaa accgtactaa gtctcccgtg      3960
tcttcttatc accatcaggt gacatcctcg cccaggctgt caatcatgcc ggtatcgatt      4020
ccagtagcac cggccccacg ctgacaaccc actcttgcag cgttagcagc gcccctctta      4080
acaagccgac ccccaccagc gtcgcggtta ctaacactcc tctcccctcg aggatacatc      4140
caaagaggtt gagtattctc tctacacttc ttgttaaatg gaaagtgcat ttgcttgttc      4200
ttacaatcgg cccgagtctc gttcacagcg cctcgttcac acttaaacca caaatagtct      4260
acaggctata tgggagccag actgaaactc acatatgact aatattcggg ggtgttagtc      4320
acgtgtagcc cattgtgtgc atataacgat gttggacgcg tccttattcg cggtgtactt      4380
gatactatgg cagcgagcat gggatattca tcctcgtcat cgttaacatc tctacgggtt      4440
cagaatgttt ggcatgtcgt cgatcctttg cccatcgttg caaattacaa gtccgatcgc      4500
catgaccgcg ataagcctgt accatgtggc attagggtga catctcgatc atacattata      4560
agaccaacgt gcgagtcttc caaagacctg cacgccttct tcttcggatt gtcaacgggt      4620
tcttcagaat ctatgcccat atctggcgtt gagaccattg tgcgtttaat gaacaataaa      4680
gcggcatgcc atggaaagga gggctgcaga tctccatttt ctcacgccac tatcctggac      4740
gctgtagacg ataattatac catgaatata gagggggtat gttccactg ccactgtgat       4800 gataagtttt ctccagattg ttggatatct gcattttctg ctgccgaaca aacttcatcg      4860
```

```
ctatgcaaag agatgcgtgt gtacacgcgc cgttgagtat acgggaaact aaatgttcat    4920
agaggtcttt gggctatatg ttattaaata aaataattga ccagtgaaca atttgtttaa    4980
tgttagttta ttcaatgcat tggttgcaaa tattcattac ttctccaatc ccaggtcatt    5040
ctttagcgag atgatgttat gacattgctg tgaaaattac tacaggatat attttttaaga   5100
tgcaggagta acaatgtgca tagtaggcgt agttatcgca gacgtgcaac gcttcgcatt    5160
tgagttaccg aagtgcccaa cagtgctgcg gttatggttt atgcgcacag aatccatgca    5220
tgtcctaatt gaaccatccg atttttcttt taatcgcgat cgttgtttgg caactgcgt     5280
tatttcagat ctaaaaaatt tacccttat gaccatcaca tctctctggc tcataccccg     5340
cttggataag atatcatgta gattccgccc taagaaatgc aaactaacat tattgtcggt    5400
tccatataca cttccatctt gtccttcgaa aataacaaac tcgcgcaata gaccgtccgt    5460
acatgcatgg ccgatgtgtg tcaacatcat tggtctgcta gatcccgatg ggacgaatcg    5520
tacagtcgtc gctccagcat tggcaaaaat ccccagatac cctccatgcg gcaaatctaa    5580
attgcgaccc cgaagagact gcaccaaagt cttatcgacg cacgctgatt ttttgaaca    5640
gcgggagccc attatcttca gtggagcgta gacgggcgag gctaattatg tgacatagca    5700
acactgcatg tatgttttta taaatcaata agagtacata atttattacg tatcatttcc    5760
gtttgtaata tactgtatac atcatccaca ctattagtca gcactagcgc gcgggcgcac    5820
gttacaatag cagcgtgccc gttatctata ttgtccgata tttacacata acatttcatc    5880
gacatgatta aatacctaag tactgcacac agatgtttaa tgtatatcgt catataaatt     5940
atatcgctag gacagaccca aacgaccttt atcccaaaca gtcagatcct cttctcaagt    6000
gtcgatttct gttatggaat atgcataccc tggcccagaa attgcacgca cgagcgtagt    6060
gaatgcgtca ttggttttac atttaaaggc taaatgcaca aattctttag acgacagcac    6120
atcgttaaat agcatctcta gcgttcttat gaatgctaag cattggagtc ctcctggtcg    6180
gccacaataa cagctgagta tcatacccctg agctccgggg ttgtcgcaca tagcggattc    6240
gtataaacat aggatttttcc gcgaatccat cagttgcaaa aatctgttag gctccatcaa    6300
caacgctgga tttacttcag atccacgcgt aaagtaatgg tgctcgaata ccgttttttag   6360
agttgtcggc atttcaagga acaaagaatt catttcttca ttgcaacgac gcgccagaaa    6420
tcccaagacc tctttgggta gtatgttctt gcctataaaa cacggcgttc caagtgccag    6480
gaaccacgca tgtgttactg ttggggcgta ttcagaaata aagcggggtt tatgcggctt    6540
ttgaagctcg gatatccaaa gtatcgcttg ctgatgaacg agcgatgtag ctgttacaaa    6600
acctcctttc catcctccag tcaacataat atttatcggc ctacctatgt ccgtaataag    6660
tattggtcgg gcaattattc cgtatgaggt cttgcaggaa taagctctta gggacagcca    6720
gcttggatat ggtgcgaaac agaccttctc ggcttcagaa tgtcgctccg cagtctcttc    6780
gtgtcggtgc atcttagatc caccatcaat gtgtgcagca ttgactcccg cccgtcgaat    6840
attccttttg ttacgatgca gtaatgagca cgatcatggg cggggcgatg acgttctatt    6900
tgcatgtctg cgaacaattt gcgtcagtca tacagctatg gagtgggcca tttctggccg    6960
tcaacttaaa aacgcgaacc gcagacatat gtatttgcat gcaaagacgt atcttcgtat    7020
ttctgggcat cttcaaatgc tctggccaat atggcaatga atttggattc gtttgacgcc    7080
gatggtatgc agtgcaaatg tgccaatagc ccacatccga aaagttatt tgtcatacaa     7140
gcaggtgtta agtagcaatc acataaaggc accagacgcc tcatggcatc ataatgaata    7200
```

```
gctccttctc cccactggaa ccactgacaa atctgcgag tatattccgc aaaccacatt   7260
ttatttctca tagaaactac cctaaatcct tttaacggga agaagaatcc tagatagtgc   7320
ttgaagtcat gactgttact gctgcaataa cactgtatat tatttataaa ttccgtttgt   7380
ctaggtatct gatgtaggca ttccgatccc tttactattg cgtcttcacg accaaatggg   7440
aatgcgccaa aatccccaca cctcatcacc ctggaggcag attgtgtatt attaatatcc   7500
gccgattgaa gcacaaaacg gtacggtact gttcctaatt ctggtataga ttctatggtc   7560
aaaagtctgc atatccccga cattgccatg agatcacaca gtccaagtag catgtttatt   7620
gagtcactca gactgtcaac gtccctcgcc gcaccaccaa tcgaaaataa agtatctacg   7680
caagttatag ctccgcattt tctatcgcta gcagcaatcg cgacgcaaaa cataaaggcc   7740
atgtttgggat ttgaactctc tgggggggctt gttatcttct gcaccgtcgc agtcgcagtt   7800
ttccgaaatt tatgtctaat atattttccg gccgtgctcc aatcggccga aaagaatctg   7860
cgtattacca gactcattga cgggccgata aagaccataa aacaaaattc ctgtgcactc   7920
cctcctccag ttttgccatc gtccaagtcc cgtaactttt tttgcgtttc gaggagcaag   7980
cgttcgttat ccctacccac acttgttttc caccgttttc ttattataag cggttgtatc   8040
gccaacgcgt caccgcaggt tgtcacatac agtgatggca tacttgaacg tgcaacaacg   8100
cgctcgcttt gcaaatctaa gtcattgacc atcaaatcgc gttgagagga tagccaggca   8160
tctttttttcc tagtatggtg acggtgcagc caccccaact cagttcttgt aaaaaaagct   8220
attggcggga atttatgttc tgaggtgcat tctatattta tgagtccatc aaatgccatt   8280
aaccagattc gtatttttc gctcgacccg gcatcactat ggatacaata cctttctatg   8340
gcccatttca gctctcgaac caaccacacg gacaattgac taacataagt atgatcttta   8400
tcacagtcgc acccatctga gttatattta tggcatccga gcgctcttac tgtacggtcg   8460
gatacaccca tggttttcc tttatatagt cgggttatag tctgtcgggt ttggcggtag   8520
cacggagtag tttgatttt aagaatcgaa accggcttg gagagaccac tgtcgaatat   8580
ttgtccgtat actctacacg tgagtgttgt ccattcctag gtatattcat ctgttcggat   8640
accttcaatt gctgttcagg cataaccta aagcatatgt tatgttgtac atcaaaactt   8700
ggtgagttat gttcgattgc cgcgcataaa gaatcgtaca tgagcgtttc tgctaacata   8760
ctatctatat tctcacacgc ccctgcatat actgttccta ttccaaattc acgttttgcc   8820
ccatcggcta tctgctccca aaaagttgta atataggtgc cgctgggtgc gaaatttca    8880
tcagttgtat tcctgataaa ctgaatcact ttacataatt tttgccacat atctgcgtgc   8940
agccatagta tcgaacccgt gggctcggag acgacagtgc gtacaatggg tatttacct    9000
ttccccaaca aaataatggt atacaagtta ggtccgtacc tagaccttaa tgtttccaat   9060
tcttctgaat cactgcactc tcgtagggga gtaacggtaa taatttcgtc tctgagcccc   9120
gttttgcgtt gaaaactaat cacattagat aatgtgcaat cggtttcttt tatccggata   9180
catctaagta ttatgacatc ggtggtcatt gtttccatca acgaccatct tttacgatcg   9240
cccatactac tcatggacgt tgtcggtgtt gaaaaatcac cagaattgca acggatctct   9300
gggtaccatg ctgctgatgg aattggcggt tttaattgtt gtttcagtct attattgcta   9360
tctttggcgg ggttgaataa tgtgggggga gagtgattgc aggaatccga atgggtcaat   9420
aaaacgaccg tgctccgttc tgccggcgcc gatccgattg aagctatata cttcgcttct   9480
ctccccactt ttccaatttg atccggaaat aaaacggccc cggacaacag tatcgtacga   9540
tccggatccg gatcctgctt gcctacagaa gaatcaacat ctcgccccaa tattctggtc   9600
```

```
aaaactggct cgctcatggc aacgcggacg tttcccccgg tggccagtct taatggttaa   9660
tgttcttttc ggcaatctta tacatcagcg ggttgcgtga atactggtca cagttcagtc   9720
atttactaca caccagcaat acgacgacgg acagtaccgt cccgacgaac gcgacgccca   9780
aaattgctat cgcgaccgcg tccgaggcga tgtcgtacgg gcggtgcggg gttggatcct   9840
cggcaaagag atcctcgtaa ttcggcggtg ggagcggagg gtaaagacgc gggtggggat   9900
ctccctccgg accgcgcgcc gggcgcggtt cgaaaatgct ttccgcctcg ctcagtgtca   9960
acgccaagta ttcgggcggg ctgggggccg gaatatctcc cgcgacttct tctatcggcg  10020
cggaattgga gtcgcggtcg tggcgcgctt ctagcgtcgt caacggaagt ccattttcgg  10080
ggtctcccgg tgggcgttca gcgtccatcg tcgtatatgc tctaacacac gtctcgctat  10140
attaaaaaaa agaagagtat cggtcagtgt cgagtgtcgc cgacaatgtc gcagttctc   10200
ggcgatttaa ttttttggaac tgctccctat gaatcccgta actgtagcgc ccgcgcagaa  10260
agccgccatc agaccaacta cgtgtctgtt cgatgtttgc ccgccgatcg ctttaccgat  10320
taaggttccg gcgagaaatg acatgctcga tccaagaaca aagttttttcg cggtaaacaa  10380
caacatagtt accgtgcgag atggagaaac cacatctccc gaattagtag aggaaagccc  10440
gcgctgtcgg tttggggaca tatcgatctt ttttgtgttt ttcctaggac ccttttgcca  10500
gatcgtacaa agtcgcgtct tatgagcgga cgttcttact gcagctcggt aggagtgggg  10560
cagggttaga tttcgtcggc gtttcggccc ccgtatgcgc cgcgccaccc tcttcgccga  10620
gctctttatg cgcggtgggg gtgagcgctt ccggagttgc gatctccgat ctcgagccgc  10680
agcccggcgg tgtctctttc agtggagcgt tagcgccatc atgtggttcg tggcggtgga  10740
aaggctatta tgtgttaggg gagagaccac gtgatcggca tgcaaatgag caaggcgaac  10800
gcgtcagcgt tcgcactgcg aaccaataat atatatatta tactattggc tttaggtgcg  10860
aacgtccggc tagtccaata gcggggtcgc gtttcgtacc acgtgttata gaccgcccta  10920
aactcgcact cggggggtccg gccgcgccca gacagggcgg agacgtgcca caggggcttt  10980
aaaacaccgc ttcgggcacc gttcatctcg gcgcgcc                           11017
```

<210> SEQ ID NO 27
<211> LENGTH: 11665
<212> TYPE: DNA
<213> ORGANISM: Artificial Sequence
<220> FEATURE:
<223> OTHER INFORMATION: Expression cassette

<400> SEQUENCE: 27

```
ggcgcgccac tggagaacgg catgaccgca aaggcgttg tagagatcga tcccacgaac     60
tctcaggcga tcgtgtcagt cgccataaac agcgacgatc gtctccagga tctgaacggt   120
tttcttctca acgatcatca gtatatgagg aactgaacct gatatttagc cgagggaaac   180
gcaggttaaa aaccctatca agcgattgcg attttcgcgt atctagtaaa aatagatggg   240
cttcggtact agccttcgcc gccaactctg aatatgccct tcgtggacct catataacat   300
ggcattgttt gttggatgcg gggccggaat taagaagaac attcgaaata cgagcaaaaa   360
tttcggccct ggcatgtgct gcgcgagaat cggtacttcg gggagaaagt tttatcggag   420
ctttgggtag tgcagaggaa actctatctt ggttgaaaat gcatgcgacc ctgcacttga   480
ttctggttaa ccacgatcca attttttaaga cggctggcgc ggtcctagat aacctccgct   540
taaaactagc cccaatattg atgtgcagat ataacacaga aaaacgatca atggaagaca   600
```

```
tgctacggcg gtcatctccc gaagacatca ccgattccct aacaatgtgc ctgattatgt    660
tatcgcgcat tcgtcgtacc atgcgcaccg caggaaataa atatagctat atgatagatc    720
caatgaatcg tatgtctaat tacactccag gcgaatgtat gacaggtata ttgcgatata    780
ttgacgaaca tgctagaagg tgtcctgatc acatatgtaa tttgtatatc acatgtacac    840
ttatgccgat gtatgtgcac gggcgatatt tctattgtaa ttcattttt  tgttagtaaa    900 ctaccacagg ctgtccggaa atctaagtta atgaataaag tagatggtta atactcattg    960
cttagaattg gactactttt aattctcttt aatgttcgta ttaaataaaa acatctttaa    1020
taaacttcag cctcttcgct tattgtagaa attgagtatt caaaatcatg ttcaaagccg    1080
tcttcggaga gtgtactcgc cacggtggtt ggaacatcac tatgtctaca cgtcaaattt    1140
aagcacgtca ggtctgtcga ggacaagaaa tggttaacta gtgtttcaat tattcttata    1200
aacgttaagc attgtaagcc ccccggccgt ccgcagcaac aatttactag tatgccgtgg    1260
gctccgggac tatcacggat gtccaattcg cacatgcata taattttttct agggtctctc    1320 atttcgagaa atcttcgggg atccatcagc aatgcgggct gtagtcccga ttcccgtttc    1380
aaatgaaggt gctccaacac ggtcttcaaa gcaaccggca taccagcaaa cacagactgc    1440
aactccccgc tgcaatgatt ggttataaac agtaatctgt cttctggaag tatatttcgc    1500
ccgacaatcc acggcgcccc caaagttaaa aaccatccat gtgtatttgc gtcttctctg    1560
ttaaaagaat attgactggc attttcccgt tgaccgccag atatccaaag tacagcacga    1620
tgttgcacgg acgactttgc agtcaccagc cttcctttcc accccccac caacaaaatg    1680 tttatcgtag gacccatatc cgtaataagg atgggtctgg cagcaacccc ataggcgcct    1740
cggcgtggta gttctcgagg ccttaagctt aaggatcccc caactccgcc cgttttatga    1800
ctagaaccaa tagttttaa  tgccaaatgc actgaaatcc cctaatttgc aaagccaaac    1860 gcccctatg  tgagtaatac ggggactttt tacccaattt cccacgcgga aagcccccta    1920
atacactcat atggcatatg aatcagcacg gtcatgcact ctaatggcgg cccatagga    1980 cttccacat  agggggcgtt caccatttcc cagcataggg gtggtgactc aatggccttt    2040
acccaagtac attgggtcaa tgggaggtaa gccaatgggt ttttcccatt actggcaagc    2100
acactgagtc aaatgggact ttccactggg ttttgcccaa gtacattggg tcaatgggag    2160
gtgagccaat gggaaaaacc cattgctgcc aagtacactg actcaatagg gactttccaa    2220 tgggttttc  cattgttggc aagcatataa ggtcaatgtg ggtgagtcaa tagggacttt    2280
ccattgtatt ctgcccagta cataaggtca ataggggtg  aatcaacagg aaagtcccat    2340
tggagccaag tacactgcgt caatagggac tttccattgg gttttgccca gtacataagg    2400
tcaatagggg atgagtcaat gggaaaaacc cattggagcc aagtacactg actcaatagg    2460
gactttccat tgggttttgc ccagtacata aggtcaatag ggggtgagtc aacaggaaag    2520
ttccattgga gccaagtaca ttgagtcaat agggactttc caatgggttt tgcccagtac    2580
ataaggtcaa tgggaggtaa gccaatgggt ttttcccatt actggcacgt atactgagtc    2640
attagggact ttccaatggg ttttgcccag tacataaggt caatagggt  gaatcaacag    2700 gaaagtccca ttggagccaa gtacactgag tcaataggga cttccattg  ggttttgccc    2760 agtacaaaag gtcaataggg ggtgagtcaa tgggttttc  ccattattgg cacgtacata    2820
aggtcaatag gggtgagtca ttgggttttt ccagccaatt taattaaaac gccatgtact    2880
ttcccaccat tgacgtcaat gggctattga aactaatgca acgtgacctt taaacgtac    2940 tttcccatag ctgattaatg ggaaagtacc gttctcgagc caatacacgt caatgggaag    3000
```

```
tgaaagggca gccaaaacgt aacaccgccc cggttttccc ctggaaattc catattggca   3060
cgcattctat tggctgagct gcgttctacg tgggtataag aggcgcgacc agcgtcggta   3120
ccgtcgcagt cttcggtctg accaccgtag aacgcagagc tcctcgctgc aggcggccgc   3180
tctagaactc gtcgatcgca gcgatgacaa acctgcaaga tcaaacccaa cagattgttc   3240
cgttcatacg gagccttctg atgccaacaa ccggaccggc gtccattccg gacgacaccc   3300
tggagaagca cactctcagg tcagagacct cgacctacaa tttgactgtg ggggacacag   3360
ggtcagggct aattgtcttt ttccctggat tccctggctc aattgtgggt gctcactaca   3420
cactgcagag caatgggaac tacaagttcg atcagatgct cctgactgcc agaacctac    3480
cggccagcta caactactgc agactagtga gtcggagtct cacagtgagg tcaagcacac   3540
tccctggtgg cgtttatgca ctaaacggca ccataaacgc cgtgaccttc caaggaagcc   3600
tgagtgaact gacagatgtt agctacaatg ggttgatgtc tgcaacagcc aacatcaacg   3660
acaaaattgg gaatgtcctg gtaggggaag gggtcactgt cctcagccta cccacatcat   3720
atgatcttgg gtatgtgagg cttggtgacc ccattcccgc tatagggctt gacccaaaaa   3780
tggtagctac atgcgacagc agtgacaggc ccagagtcta caccataact gcagccgatg   3840
attaccaatt ctcatcacag taccaaccag gtggggtaac aatcacactg ttctcagcca   3900
acattgatgc tatcacaagc ctcagcattg ggggagagct cgtgtttcaa acaagcgtcc   3960
aaggccttgt actgggcgcc accatctacc ttataggctt tgatgggact gcggtaatca   4020
ccagagctgt ggccgcagat aatgggctga cggccggcac cgacaatctt atgccattca   4080
atcttgtcat tccaaccaat gagataaccc agccaatcac atccatcaaa ctggagatag   4140
tgacctccaa aagtggtggt caggcagggg atcagatgtc atggtcggca agtgggagcc   4200
tagcagtgac gatccatggt ggcaactatc caggggccct ccgtcccgtc acactagtag   4260
cctacgaaag agtggcaaca ggatccgtcg ttacggtcgc tggggtgagt aacttcgagc   4320
tgattccaaa tcctgaacta gcaaagaacc tggttacaga atacggccga tttgacccag   4380
gagccatgaa ctacacaaaa ttgatactga gtgagaggga ccgtcttggc atcaagaccg   4440
tctggccaac aagggagtac actgattttc gtgagtactt catggaggtg gccgacctca   4500
actctcccct gaagattgca ggagcatttg gcttcaaaga cataatccgg gctataagga   4560
ggtagatcca gacatgataa gatacattga tgagtttgga caaaccacaa ctagaatgca   4620
gtgaaaaaaa tgctttattt gtgaaatttg tgatgctatt gctttatttg taaccattat   4680
aagctgcaat aaacaagtta acaacaacaa ttgcattcat tttatgtttc aggttcaggg   4740
ggaggtgtgg gaggtttttt cggatcctct agagtcgagg atacatccaa agaggttgag   4800
tattctctct acacttcttg ttaaatgaaa agtgcatttg cttgttctta caatcggccc   4860
gagtctcgtt cacagcgcct cgttcacact taaaccacaa atagtctaca ggctatatgg   4920
gagccagact gaaactcaca tatgactaat attcggggggt gttagtcacg tgtagcccat   4980
tgtgtgcata taacgatgtt ggacgcgtcc ttattcgcgg tgtacttgat actatggcag   5040
cgagcatggg atattcatcc tcgtcatcgt aacatctct acgggttcag aatgtttggc    5100
atgtcgtcga tcctttgccc atcgttcaa attacaagtc cgatcgccat gaccgcgata   5160
agcctgtacc atgtggcatt agggtgacat ctcgatcata cattataaga ccaacgtgcg   5220
agtcttccaa agacctgcac gccttcttct tcggattgtc aacgggttct tcagaatcta   5280
tgcccatatc tggcgttgag accattgtgc gtttaatgaa caataaagcg gcatgccatg   5340
```

```
gaaaggaggg ctgcagatct ccatttctc acgccactat cctggacgct gtagacgata    5400
attataccat gaatatagag ggggtatgtt tccactgcca ctgtgatgat aagttttctc    5460
cagattgttg gatatctgca ttttctgctg ccgaacaaac ttcatcgcta tgcaaagaga    5520
tgcgtgtgta cacgcgccgg tggagtatac gggaaactaa atgttcatag aggtctttgg    5580
gctatatgtt attaaataaa ataattgacc agtgaacaat ttgtttaatg ttagtttatt    5640
caatgcattg gttgcaaata ttcattactt ctccaatccc aggtcattct ttagcgagat    5700
gatgttatga cattgctgtg aaaattacta caggatatat ttttaagatg caggagtaac    5760
aatgtgcata gtaggcgtag ttatcgcaga cgtgcaacgc ttcgcatttg agttaccgaa    5820
gtgcccaaca gtgctgcggt tatggtttat gcgcacagaa tccatgcatg tcctaattga    5880
accatccgat ttttctttta atcgcgatcg atgtttgggc aactgcgtta tttcagatct    5940
aaaaaattta ccctttatga ccatcacatc tctctggctc ataccccgct tggataagat    6000
atcatgtaga ttccgcccta agaaatgcaa actaacatta ttgtcggttc catatacact    6060
tccatcttgt ccttcgaaaa taacaaactc gcgcaataga ccgtccgtac atgcatggcc    6120
gatgtgtgtc aacatcattg gtctgctaga tcccgatggg acgaatcgta cagtcgtcgc    6180
tccagcattg gcaaaaatcc ccagataccc tccatgcggc aaatctaaat tgcgaccccg    6240
aagagactgc accaaagtct tatcgacgca cgctgatttt tttgaacagc gggagcccat    6300
tatcttcagt ggagcgtaga cgggcgaggc taattatgtg acatagcaac actgcatgta    6360 tgttttata aatcaataag agtacataat ttattacgta tcatttccgt ttgtaatata    6420
ctgtatacat catccacact attagtcagc actagcgcgc gggcgcacgt tacaatagca    6480
gcgtgcccgt tatctatatt gtccgatatt tacacataac atttcatcga catgattaaa    6540
tacctaagta ctgcacacag atgtttaatg tatatcgtca tataaattat atcgctagga    6600
cagacccaaa cgacctttat cccaaacagt cagatcctct tctcaagtgt cgatttctgt    6660
tatgaaatat gcatacccctg gcccagaaat tgcacgcacg agcgtagtga atgcgtcatt    6720
ggttttacat ttaaaggcta atgcacaaa ttctttagac gacagcacat cgttaaatag    6780
catctctagc gttcttatga atgctaagca ttggagtcct cctggtcggc cacaataaca    6840
gctgagtatc atacctgag ctccggggtt gtcgcacata gcggattcgt ataaacatag    6900
gattttccgc gaatccatca gttgcaaaaa tctgttaggc tccatcaaca acgctggatt    6960
tacttcagat ccacgcgtaa agtaatggtg ctcgaatacc gttttagag ttgtcggcat    7020 ttcaaggaac aaagaattca tttcttcatt gcaacgacgc gccagaaatc ccaagacctc    7080
tttgggtagt atgttcttgc ctataaaaca cggcgttcca agtgccagga accacgcatg    7140
tgttactgtt ggggcgtatt cagaaataaa gcggggttta tgcggctttt gaagctcgga    7200
tatccaaagt atcgcttgct gatgaacgag cgatgtagct gttacaaaac ctccttttcca    7260 tcctccagtc aacataatat ttatcggcct acctatgtcc gtaataagta ttggtcgggc    7320
aattattccg tatgaggtct tgcaggaata agctcttagg gacagccagc ttggatatgg    7380
tgcgaaacag accttctcgg cttcagaatg tcgctccgca gtctcttcgt gtcggtgcat    7440
cttagatcca ccatcaatgt gtgcagcatt gactcccgcc cgtcgaatat tccttttgtt    7500
acgatgcagt aatgagcacg atcatggggcg gggcgatgac gttctatttg catgtctgcg    7560
aacaatttgc gtcagtcata cagctatgga gtgggccatt tctggccgtc aacttaaaaa    7620
cgcgaaccgc agacatatgt atttgcatgc aaagacgtat cttcgtattt ctgggcatct    7680
tcaaatgctc tggccaatat ggcaatgaat ttggattcgt ttgacgccga tggtatgcag    7740
```

```
tgcaaatgtg ccaatagccc acatccgaaa aagttatttg tcatacaagc aggtgttaag    7800
tagcaatcac ataaaggcac cagacgcctc atggcatcat aatgaatagc tccttctccc    7860
cactggaacc actgacaaaa tctgcgagta tattccgcaa accacatttt atttctcata    7920
gaaactaccc taaatccttt taacgggaag aagaatccta gatagtgctt gaagtcatga    7980
ctgttactgc tgcaataaca ctgtatatta tttataaatt ccgtttgtct aggtatctga    8040
tgtaggcatt ccgatccctt tactattgcg tcttcacgac caaatgggaa tgcgccaaaa    8100
tccccacacc tcatcaccct ggaggcagat tgtgtattat taatatccgc cgattgaagc    8160
acaaaacggt acgtactgt tcctaattct ggtatagatt ctatggtcaa aagtctgcat    8220
atccccgaca ttgccatgag atcacacagt ccaagtagca tgtttattga gtcactcaga    8280
ctgtcaacgt ccctcgccgc accaccaatc gaaaataaag tatctacgca agttatagct    8340
ccgcattttc tatcgctagc agcaatcgcg acgcaaaaca taaaggccat gttgggattt    8400
gaactctctg gggggcttgt tatcttctgc accgtcgcag tcgcagtttt ccgaaattta    8460
tgtctaatat attttccggc cgtgctccaa tcggccgaaa agaatctgcg tattaccaga    8520
ctcattgacg ggccgataaa gaccataaaa caaaattcct gtgcactccc tcctccagtt    8580
ttgccatcgt ccaagtcccg taactttttt tgcgtttcga ggagcaagcg ttcgttatcc    8640
ctacccacac ttgttttcca ccgttttctt attataagcg gttgtatcgc caacgcgtca    8700
ccgcaggttg tcacatacag tgatggcata cttgaacgtg caacaacgcg ctcgctttgc    8760
aaatctaagt cattgaccat caaatcgcgt tgagaggata gccaggcatc ttttttccta    8820
gtatggtgac ggtgcagcca ccccaactca gttcttgtaa aaaaagctat tggcgggaat    8880
ttatgttctg aggtgcattc tatatttatg agtccatcaa atgccattaa ccagattcgt    8940
attttttcgc tcgacccggc atcactatgg atacaatacc tttctatggc ccatttcagc    9000
tctcgaacca accacacgga caattgacta acataagtat gatctttatc acagtcgcac    9060
ccatctgagt tatatttatg gcatccgagc gctcttactg tacggtcgga tacacccatg    9120 gttttttcctt tatatagtcg ggttatagtc tgtcgggttt ggcggtagca cggagtagtt    9180 tgattttttaa gaatcgaaaa ccggcttgga gagaccactg tcgaatattt gtccgtatac    9240
tctacacgtg agtgttgtcc attcctaggt atattcatct gttcggatac cttcaattgc    9300
tgttcaggca taaccttaaa gcatatgtta tgttgtacat caaaacttgg tgagttatgt    9360
tcgattgccg cgcataaaga atcgtacatg agcgtttctg ctaacatact atctatattc    9420
tcacacgccc ctgcatatac tgttcctatt ccaaattcac gttttgcccc atcggctatc    9480
tgctcccaaa aagttgtaat ataggtgccg ctgggtgcga aatttcatc agttgtattc    9540 ctgataaact gaatcacttt acataatttt tgccacatat ctgcgtgcag ccatagtatc    9600
gaacccgtgg gctcggagac gacagtgcgt acaatgggta ttttacctt ccccaacaaa    9660 ataatggtat acaagttagg tccgtaccta gaccttaatg tttccaattc ttctgaatca    9720
ctgcactctc gtaggggagt aacggtaata atttcgtctc tgagcccgt tttgcgttga    9780 aaactaatca cattagataa tgtgcaatcg gtttctttta tccggataca tctaagtatt    9840
atgacatcgg tggtcattgt ttccatcaac gaccatcttt tacgatcgcc catactactc    9900
atggacgttg tcggtgttga aaaatcacca gaattgcaac ggatctctgg gtaccatgct    9960
gctgatggaa ttgcggtttt taattgttgt ttcagtctat tattgctatc tttggcgggg   10020
ttgaataatg tgggggagga gtgattgcag gaatccgaat gggtcaataa aacgaccgtg   10080
```

```
ctccgttctg ccggcgccga tccgattgaa gctatatact tcgcttctct ccccacttt     10140
ccaatttgat ccggaaataa aacggccccg acaacagta  tcgtacgatc cggatccgga    10200
tcctgcttgc ctacagaaga atcaacatct cgccccaata ttctggtcaa aactggctcg    10260
ctcatggcaa cgcggacgtt tcccccggtg gccagtctta atggttaatg ttcttttcgg    10320
caatcttata catcagcggg ttgcgtgaat actggtcaca gttcagtcat ttactacaca    10380
ccagcaatac gacgacggac agtaccgtcc cgacgaacgc gacgcccaaa attgctatcg    10440
cgaccgcgtc cgaggcgatg tcgtacgggc ggtgcggggt tggatcctcg gcaaagagat    10500
cctcgtaatt cggcggtggg agcggagggt aaagacgcgg gtggggatct ccctccggac    10560
cgcgcgccgg gcgcggttcg aaaatgcttt ccgcctcgct cagtgtcaac gccaagtatt    10620
cgggcgggct gggggccgga atatctcccg cgacttcttc tatcggcgcg gaattggagt    10680
cgcggtcgtg gcgcgcttct agcgtcgtca acggaagtcc attttcgggg tctcccggtg    10740
ggcgttcagc gtccatcgtc gtatatgctc taacacacgt ctcgctatat taaaaaaag    10800
aagagtatcg gtcagtgtcg agtgtcgccg acaatgtcgc gagttctcgg cgatttaatt    10860
tttggaactg ctccctatga atcccgtaac tgtagcgccc gcgcagaaag ccgccatcag    10920
accaactacg tgtctgttcg atgtttgccc gccgatcgct ttaccgatta aggttccggc    10980
gagaaatgac atgctcgatc caagaacaaa gttttcgcg  gtaaacaaca acatagttac    11040
cgtgcgagat ggagaaacca catctcccga attagtagag aaagcccgc  gctgtcggtt    11100
tggggacata tcgatctttt ttgtgttttt cctaggaccc ttttgccaga tcgtacaaag    11160
tcgcgtctta tgagcggacg ttcttactgc agctcggtag gagtggggca gggttagatt    11220
tcgtcggcgt ttcggccccc gtatgcgccg cgccaccctc ttcgccgagc tctttatgcg    11280
cggtgggggt gagcgcttcc ggagttgcga tctccgatct cgagccgcag cccggcggtg    11340
tctctttcag tggagcgtta gcgccatcat gtggttcgtg gcggtggaaa ggctattatg    11400
tgttagggga gagaccacgt gatcggcatg caaatgagca aggcgaacgc gtcagcgttc    11460
gcactgcgaa ccaataatat atatattata ctattggctt taggtgcgaa cgtccggcta    11520
gtccaatagc ggggtcgcgt ttcgtaccac gtgttataga ccgccctaaa ctcgcactcg    11580
ggggtccggc cgcgcccaga cagggcggag acgtgccaca ggggctttaa aacaccgctt    11640
cgggcaccgt tcatctcggc gcgcc                                           11665
```

<210> SEQ ID NO 28
<211> LENGTH: 13253
<212> TYPE: DNA
<213> ORGANISM: Artificial Sequence
<220> FEATURE:
<223> OTHER INFORMATION: Expression cassette

<400> SEQUENCE: 28

```
aattccagac taaatgcccc ggcccaattt gtcaagtgtg cagtcacgga ggcgtcgacc       60
gtgtccccgg cattaaacag gaaagcgtta agttttttga atgttaggtc acaggtacaa     120
acataaatgt ttgtacaaac aggtaacagg tacaaacata aatgccccgg cataaatgtc     180
ccttacggcg gatcgaaacg acattaggca tactcgggta ccattttgca ttccgatcag    240
cacggatgaa attaggcagg aatgcggttt atattatgcg gcattggaca aacgatatgg    300
cattgattgg cagtttatga atgtcttcat gttgggcgta aacggattcc tattggttca    360
gaagacaacg acgatatatt tagagagaaa aagctaccca gcataggata aacacacatt    420
gagcattgag agacataggt atcggtatgg atgggaaaac tacacacgtg aacaccaaac    480
```

-continued

```
gacttatata ctcgagcggt gatactactg agcaagaatg cactgcatct gagccactga    540
atgaagactg tgatgaaaat gtgaccatcg atggaattgg agaagaatat gcgcagttct    600
tcatgtcccc gcaatgggtc ccaaatctac atcgcttgag cgaggatacc aaaaaggtat    660
accgatgtat ggtttccaac agactcaatt attttcccta ttatgaggcg ttcaggcggt    720
ctttgtttga tatgtatatg ctaggtcggt tggggcgtcg acttaagcga tctgactggg    780
agactattat gcatctgtca ccaacgcaaa gtcggcgtct acatagaact ttaagatttg    840
tggagcgtag aattatccca tctaacagtt atatacgcac atcgggccac gttccgcctt    900
cgagggcact tccgacagat acgaatttaa agatggatga ataattaaat tggaaagagt    960
aactacatta atcgagcgtc atgacggcgt cccgtgaaaa tgggaatttt ctactcgaaa   1020
caccgtgaca tttgacagac ctggaattgt tattctgata tatagtgggt gtgtctggcc   1080
ggcaacatac ataatgtgca tgcgaaacca cttttttcagt gtacgctgac attgtgcaac   1140
acggaggggt agcatctaca tacaatatat gttgattaat gattggagaa aaaactatgc   1200
agctcgccga tcatatggct aactcgcctt cgtctatatg gcggaccccg cgggaaaaat   1260
cgacgtacca tctgatttac aacaccagta atgaacatgt cgcatccctg cccagatctg   1320
tgcgcccatt ggcgcggatc gttgtgaatg ccgccgaaac acttcaggtc ggtatgagag   1380 ccggaggcc gccatcagca ggagtttggc gagaggtgtt tgatagaatg atgacagcct    1440
tccgtgacca cgagcctact gcgacattta atgctgcaaa tcccattaga aaaatggtcg   1500
agacagttct acagaataat gaagagcccc cgcggacgca tgctgaaatg ggtaatcgcc   1560
ttatgaacat tatgtactgg tgttgcttgg gacacgcagg acaatgctcg atatggcagt   1620
tgtacgagac gaatcaggcc attttaagtt tattagatga agtggttatc ggcacaacaa   1680 atccctttg caccctcgag caatactgga agccattatg caccgcaatc gccaacaagg   1740
ggacctcatc gcttgttgag gatgccaaag tggccgagta cctggttagc atgcgcaaat   1800
tgatataaca taggcacgct ctgatgttac agaccacaat accgcataca tttattgtaa   1860
ggttgttaat aaaggtttat tctatgtaag actacaatac tttcgacatt gcttgtatac   1920
atattaaata ctttctcaag ttcctattac ataaaatggg atctatcatt acattcgtta   1980
agagtctgga taattttact gtttgccagc ttcgatcttg gaacgtactg tggatagtgc   2040
cttacttgga atcgtgaaaa tttgaaacgt ccattatttg gatatcttcc ggttgtccca   2100
tatcccgccc tggtaccgct cggatacctt gcccgtatgg attcgtattg acagtcgcgc   2160
aatcggggac caacaacgcg tgggtccaca ctcattcgga aattttccga tgattctgaa   2220
tatttattgc cgctcgttac gagtcgttgg acatatctgt aatacatttc ttcttctgaa   2280
ggatcgctgc acatttgatc tatacattgg ccaggatgtt caagtctcag atgttgcatt   2340
ctggcacagc acaactttat ggcatttccg atgtaatcgt ccggcagccc tggggagtt    2400 ctatattcgc atattgggat ggtaaggaca atagcagatc tcgcaacctc cagggaggct   2460
ataataacgt tttttaaagga tggatttctc ataaaaatct gtcgcaaatt acactgagaa   2520
tatcctttac tagcgccgat tgagagcatc gtcgtccaat tttctaaatg gaaagaaaac   2580
aaggcgggca agagtgttcc aaacatttc attttcggcg aatctctcaa atcccatggc    2640
gtgcaattga ttgcaaaatt ggcacttccg ttcacgtttg tatctccaaa ctctaagaca   2700
cttttaattg aaaaactacg ttctagtgtg gaaagaaacc tataggcaga ccatagaact   2760
atttgacacc acatatcttt ttgtatgtca aactgaccat gatcgtatgt tgctgaatgc   2820
```

-continued

```
actagggcaa ttcgctcgcg cgactccata cattgaataa ttccacacgt cagctcatcg    2880
gttagcaagg tccagtagtt gaagtcattt attttcccc gcggctggcc aaatctacct    2940
ctgggaatat ccaagttgtc gaatatgatc gcaccggctc tggtcatggt gaaggaactg    3000
tagcataaag acgcaggtat catagggta atattttttt attcactcac atactaaaag    3060
taacgcatat tagcaccatg tatgggctat caattgacat ttgcgtagca ctacatcacg    3120
attatgtaca acataatggg acaacatatg gcaagtagat gcaatttcct cacactagtt    3180
gggtttatct actattgaat tttcccctat ctgtgataca cttgggagcc tctacaagca    3240
tattgccatc atgtacgttt ttatctactg tcttaacgcc catgggaacg gaggcgtcgt    3300
cgtcatgtat tggacggcaa cataggcagc aacacaaatt gcgtttaggt ggggtgcatg    3360
tggactcgat accaagcccc tgcagctggg aacgtctgg tggagagccg ataatttgat    3420
atacgcacgc catattactg tcgttgaagt acgccttatc ttctatgttt tcaaatttag    3480
gttcccaagt ggacgtgaga agtgtttgta tctcacatgg aatggcccaa ggcattccag    3540
cccaggtgcc tggtacttta atggcaaaca acgttttgg tagaggtatt gattctattg    3600
cagttctgca gatatctgca gccccgagta ccacaggct atacgatacg ttatcggagg    3660
caagcttgtt aattaagtcg acggcagagt cgcagacgcc cctattggac gtcaaaattg    3720
tagaggtgaa gttttcaaac gatggcgaag taacggcgac ttgcgtttcc accgtcaaat    3780
ctccctatag ggtagaaact aattggaaag tagacctcgt agatgtaatg gatgaaattt    3840
ctgggaacag tcccgccggg ttttaaca gtaatgagaa atggcagaaa cagctgtact    3900
acagagtaac cgatggaaga acatcggtcc agctaatgtg cctgtcgtgc acgagccatt    3960
ctccggaacc ttactgtctt ttcgacacgt ctcttatagc gagggaaaaa gatatcgcgc    4020
cagagttata ctttacctct gatccgcaaa cggcatactg cacaataact ctgccgtccg    4080
gcgttgttcc gagattcgaa tggagcctta ataatgtttc actgccggaa tatttgacgg    4140
ccacgaccgt tgtttcgcat accgctggcc aaagtacagt gtggaagagc agcgcgagag    4200
caggcgaggc gtggatttct ggccggggag gcaatatata cgaatgcacc gtcctcatct    4260
cagacggcac tcgcgttact acgcgaaagg agaggtgctt aacaaacaca tggattgcgg    4320
tggaaaacgg tgctgctcag gcgcagctgt attcactctt ttctggactt gtgtcaggat    4380
tatgcgggag catatctgct ttgtacgcaa cgctatggac cgccatttat ttttgaggaa    4440 tgcttttttgg actatcgtac tgctttcttc cttcgctagc cagagcaccg ccgccgtcac    4500
gtacgactac attttaggcc gtcgcgcgct cgacgcgcta accataccgg cggttggccc    4560
gtataacaga tacctcacta gggtatcaag aggctgcgac gttgtcgagc tcaacccgat    4620
ttctaacgtg gacgacatga tatcggcggc caaagaaaaa gagaagggg gcccttttcga    4680 ggcctccgtc gtctggttct acgtgattaa gggcgacgac ggcgaggaca agtactgtcc    4740
aatctataga aaagagtaca gggaatgtgg cgacgtacaa ctgctatctg aatgcgccgt    4800
tcaatctgca cagatgtggg cagtggacta tgttcctagc acccttgtat cgcgaaatgg    4860
cgcgggactg actatattct cccccactgc tgcgctctct ggccaatact tgctgaccct    4920
gaaaatcggg agatttgcgc aaacagctct cgtaactcta gaagttaacg atcgctgttt    4980
aaagatcggg tcgcagctta acttttaccc gtcgaaatgc tggacaacag aacagtatca    5040
gactggattt caaggcgaac acctttatcc gatcgcagac accaatacac gacacgcgga    5100
cgacgtatat cggggatacg aagatattct gcagcgctgg aataatttgc tgaggaaaaa    5160
gaatcctagc gcgccagacc ctcgtccaga tagcgtcccg caagaaattc ccgctgtaac    5220
```

```
caagaaagcg gaagggcgca ccccggacgc agaaagcagc gaaaagaagg cccctccaga    5280
agactcggag gacgacatgc aggcagaggc ttctggagaa aatcctgccg ccctccccga    5340
agacgacgaa gtccccgagg acaccgagca cgatgatcca aactcggatc ctgactatta    5400
caatgacatg cccgccgtga tcccggtgga ggagactact aaaagttcta atgccgtctc    5460
catgcccata ttcgcggcgt tcgtagcctg cgcggtcgcg ctcgtgggc tactggtttg     5520
gagcatcgta aaatgcgcgc gtagctaatc gagcctagaa taggtggttt cttcctacat    5580
gccacgcctc acgctcataa tataaatcac atggaatagc ataccaatgc ctattcattg    5640
ggacgttcga aaagcatggc atcgctactt ggaactctgg ctctccttgc cgcgacgctc    5700
gcacccttcg gcgcgatggg aatcgtgatc actggaaatc acgtctccgc caggattgac    5760
gacgatcaca tcgtgatcgt cgcgcctcgc cccgaagcta caattcaact gcagctattt    5820
ttcatgcctg ccagagacc ccacaaaccc tactcaggaa ccgtccgcgt cgcgtttcgg     5880
tctgatataa caaccagtg ctaccaggaa cttagcgagg agcgctttga aaattgcact    5940
catcgatcgt cttctgtttt tgtcggctgt aaagtgaccg agtacacgtt ctccgcctcg    6000
aacagactaa ccggacctcc acaccgcttt aagctcacta tacgaaatcc tcgtccgaac    6060
gacagcggga tgttctacgt aattgttcgg ctagacgaca ccaaagaacc cattgacgtc    6120
ttcgcgatcc aactatcggt gtatcaattc gcgaacaccg ccgcgactcg cggactctat    6180
tccaaggctt cgtgtcgcac cttcggatta cctaccgtcc aacttgaggc ctatctcagg    6240
accgaggaaa gttggcgcaa ctggcaagcg tacgttgcca cggaggccac gacgaccagc    6300
gccgaggcga caaccccgac gcccgtcact gcaaccagcg cctccgaact tgaagcggaa    6360
cactttacct ttccctggct agaaaatggc gtggatcatt acgaaccgac acccgcaaac    6420
gaaaattcaa acgttactgt ccgtctcggg acaatgagcc ctacgctaat tggggtaacc    6480
gtggctgccg tcgtgagcgc aacgatcggc ctcgtcattg taatttccat cgtcaccaga    6540
aacatgtgca ccccgcaccg aaaattagac acggtctcgc aagacgacga agaacgttcc    6600
caaactagaa gggaatcgcg aaaatttgga cccatggttg cgtgcgaaat aaacaagggg    6660
gctgaccagg atagtgaact tgtggaactg gttgcgattg ttaacccgtc tgcgctaagc    6720
tcgcccgact caataaaaat gtgattaagt ctgaatgtgg ctctccaatc atttcgattc    6780
tctaatctcc caatcctctc aaaaggggca gtatcggaca cggactggga ggggcgtaca    6840
cgatagttat atggtacagc agaggcctct gaacacttag gaggagaatt cagccgggga    6900
gagcccctgt tgagtaggct tgggagcata ttgcaggatg aacatgttag tgatagttct    6960
cgcctcttgt cttgcgcgcc taacttttgc gacgcgacac gtcctctttt tggaaggcac    7020
tcaggctgtc ctcggggaag atgatcccag aaacgttccg gaagggactg taatcaaatg    7080
gacaaaagtc ctgcggaacg cgtgcaagat gaaggcggcc gatgtctgct cttcgcctaa    7140
ctattgcttt catgatttaa tttacgacgg aggaaagaaa gactgcccgc cgcgggaccc    7200
cctgtctgca aacctggtaa ttttactaaa gcgcggcgaa agcttcgcgc caggtcaatt    7260
ccctggcatt atgcccagta catgacctta tgggactttc ctacttggca gtacatctac    7320
gtattagtca tcgctattac catggtgatg cggttttggc agtacatcaa tgggcgtgga    7380
tagcggtttg actcacgggg atttccaagt ctccacccca ttgacgtcaa tgggagtttg    7440
ttttggcacc aaaatcaacg ggactttcca aaatgtcgta acaactccgc cccattgacg    7500
caaatgggcg gtagcgtgta cggtgggagg tctatataag cagagctcgt ttagtgaacc    7560
```

```
gtcagatcgc ctggagacgc catccacgct gttttgacct ccatagaaga caccggttgc    7620
gccgccacca tgggcccag accttctacc aagaacccag tacctatgat gctgactgtc     7680
cgagtcgcgc tggtactgag ttgcatctgt ccggcaaact ccattgatgg caggcctctt    7740
gcggctgcag gaattgtggt tacaggagac aaagccgtca acatatacac ctcatcccag    7800
acaggatcaa tcatagttaa gctcctcccg aatctgccca aggataagga ggcatgtgcg    7860
aaagccccct tggatgcata caacaggaca ttgaccactt tgctcacccc ccttggtgac    7920
tctatccgta ggatacaaga gtctgtgact acatctggag gggggagaca ggggcgcctt    7980
ataggcgcca ttattggcgg tgtggctctt ggggttgcaa ctgccgcaca ataacagcg     8040
gccgcagctc tgatacaagc caaacaaaat gctgccaaca tcctccgact aaagagagc     8100
attgccgcaa ccaatgaggc tgtgcatgag gtcactgacg gattatcgca actagcagtg    8160
gcagttggga agatgcagca gtttgttaat gaccaattta ataaaacagc tcaggaatta    8220
gactgcatca aaattgcaca gcaagttggt gtagagctca acctgtacct aaccgaattg    8280
actacagtat tcggaccaca aatcacttca cctgctttaa acaagctgac tattcaggca    8340
ctttacaatc tagctggtgg aaatatggat tacttattga ctaagttagg tgtagggaac    8400
aatcaactca gctcattaat cggtagcggc ttaatcaccg gtaaccctat tctatacgac    8460
tcacagactc aactcttggg tatacaggta actctaccct cagtcgggaa gctaaataat    8520
atgcgtgcca cctacttgga aaccttatcc gtaagcacaa ccaggggatt tgcctcggca    8580
cttgtcccaa aagtggtgac acaggtcggt tctgtgatag aagaacttga cacctcatac    8640
tgtatagaaa ctgacttaca tttatattgt acaagaatag taacgttccc tatgtcccct    8700
ggtatttatt cctgcttgag cggcaatacg tcggcctgta tgtactcaaa gaccgaaggc    8760
gcacttacta caccatacat gactatcaaa ggttcagtca tcgccaactg caagatgaca    8820
acatgtagat gtgtaaaccc cccgggtatc atatcgcaaa actatggaga agccgtgtct    8880
ctaatagata aacaatcatg caatgttttta tccttaggcg ggataacttt aaggctcagt    8940
ggggaattcg atgtaactta tcagaagaat atctcaatac aagattctca agtaataata    9000
acaggcaatc ttgatatctc aactgagctt gggaatgtca caactcgat cagtaatgct    9060
ttgaataagt tagaggaaag caacagaaaa ctagacaaag tcaatgtcaa actgactagc    9120
acatctgctc tcattaccta tatcgtgttg actatcatat ctcttgtttt tggtatactt    9180
agcctgattc tagcatgcta cctaatgtac aagcaaaagg cgcaacaaaa gaccttatta    9240
tggcttggga ataatactct agatcagatg agagccacta caaaaatgtg aggatctctc    9300
gaggaattct agatcccacg tcactattgt atactctata ttatactcta tgttatactc    9360
tgtaatccta ctcaataaac gtgtcacgcc tgtgaaaccg tactaagtct cccgtgtctt    9420
cttatcacca tcaggtgaca tcctcgccca ggctgtcaat catgccggta tcgattccag    9480
tagcaccggc cccacgctga caacccactc ttgcagcgtt agcagcgccc ctcttaacaa    9540
gccgaccccc accagcgtcg cggttactaa cactcctctc cccgacctgc aactagtaag    9600
cttgcctccg attctagcat tacatagccg gtcagtagat cctgccattc ggtagcgcaa    9660
ccggctacat cttcaaacag tctcacaata aatgcatctc tcgttcctgc aatccggaa     9720
ccgggcatac cactcccgcc tgccgattta attctcacaa ttgggcgatg ccggcggggc    9780
aaaacgaatg tggatttggc aaaccgacac aggtctgctg tacggactaa tatgggcaca    9840
cccacatcat tcttcagatg ctccatgcat tgttctatga gaaagatcca tagggtggag    9900
gcagcgtcac gagatcgccc aggcaatcga tcgcattcgt ctagtaaagt gacgagagtt    9960
```

```
atcatgcaca cacccatgcc cacgccttcc gaataactgg agctgtggaa gatcggaaac   10020 gtcttttga ctgccggtct cgtactactt tcgcacaggt gtatacccgg acgcgtacta   10080
tatattttat atcatccaac gtccgaaatt acatacgtgg cggcgatgga agtagatgtt   10140
gagtcttcga aagtaagtgc ctcgaatatg ggtattgtct gtgaaaatat cgaaagcggt   10200
acgacggttg cagaaccgtc gatgtcgcca gatactagta acaatagctt cgataacgaa   10260
gacttccgtg ggcctgaata cgatgtggag ataaatacca gaaaatctgc taatcttgat   10320
cgtatggaat cttcgtgccg tgaacaacga gcggcgtgcg aacttcgaaa gtgttcgtgt   10380
cctacgtctg ccgtgcgcat gcaatacagt attctttcat ctctcgctcc gggttcagag   10440
ggtcatgtat atatatgtac tagatacggg gacgcggacc aaaaaaaatg catagtgaag   10500
gcagtcgttg gaggaaagaa tcccgggagg gaagtggata ttttaaaaac catctcacat   10560
aaatcaatta taaaattaat ccatgcctat aaatggaaaa atgttgtgtg tatggcaatg   10620
cgtgtatatc gttatgatct tttcacatat attgacggag tcggccctat gccccttcaa   10680
cagatgatct atattcaacg tggactacta gaggcgctag catacataca tgaaagggggc   10740 atcattcacc gagacgtaaa gacggagaat atattcttgg ataatcacga aaatgcagtt   10800
ttgggtgact tcggtgctgc atgccaacta ggagattgta tagatacgcc ccaatgttac   10860
ggttggagcg gaactgtgga aacaaattcg ccggaattat ctgcacttga tccgtattgc   10920
acaaaaacag atatttggag tgccggattg gttctatatg agatggcaat taaaaatgta   10980
ccattgttta gtaagcaggt gaaaagttcg ggatctcagc tgagatccat aatacggtgc   11040
atgcaagtgc atgaactgga gtttccccgc aacgattcta ccaacctctg taaacatttc   11100
aaacaatatg cggttcgtgt acgaccgcct tataccattc ctcgagttat aagaaatggg   11160
gggatgccaa tggatgttga atatgtcatt tctaaaatgc ttacgtttga ccaggagttc   11220
agaccttctg ctaaggaaat attgaatatg cccctattta ctaaggcgcc gattaacctg   11280
cttaatatca caccctctga cagtgtctaa cggtatacag gcgggagcgg tcgtggcgt   11340 catcatcacc acttgagaat ttatatttg aattgttgat tgataaatta acctgattca   11400
ttgagaactg aaacgccata ttggtttctt ggatatgtct acaacaatta gttaaattgc   11460
tatgttctac tgcgagtaac atttgataag ttgtaagaga cgggcgactc atgtcgaagt   11520
tgacgaatat aaagtacata acgtgtttag aatacccaga atccgaatag tccgcggggg   11580
cgtcttctcg cgtgagtacc aaatactgag ttgaacttga aaatgctaaa tctgtgacac   11640
tctttgtgtg atgattattg tcaccacttc gaagatggct tcgacattca tgatgttctg   11700
gtgtttgttt ggaatcgtaa tagcgcttgt ttcgtccaag tctgacaaca aagaaaatct   11760
gaagaattat atcacggata agtcaaccaa tattagaata cccacgccat tatttgtatc   11820
aacggaaaac tcttatccca caaaacatgt aatctacgat gaaaactgtg cttcgctgt   11880 actcaatcct ataagtgacc ccaaatatgt ccttttgagc cagcttctaa tgggaaggcg   11940
caaatatgat gcgacggtcg cgtggtttgt tctcggtaaa atgtgtgcca gattaatata   12000
tttgcgcgaa tttataact gctcgacaaa tgagccttt ggcacatgtt ctatgagctc   12060
tcctggatgg tgggacaggc gctacgtctc aaccagtttc atttctcgcg acgaattaca   12120
gctggttttt gcagcgccgt cccgagaatt agatggttta tacgcgcg tagtagttgt   12180 caacggggac tttactacgg ccgatataat gtttaatgtt aaagtggcat gtgccttttc   12240
aaagactgga atagaagatg atacattatg caaacccttt catttctttg ccaatgcaac   12300
```

| | |
|---|---:|
| attgcacaat ttaaccatga ttagatcggt aactcttcga gcgcacgaaa gccatttaaa | 12360 |
| ggaatgggtg gcacggagag gtggtaacgt ccctgcagtg ctacttgagt ctaccatgta | 12420 |
| tcatgcatcc aatctgccta gaaatttcag ggatttctac ataaagtctc cagatgatta | 12480 |
| taagtataat cacctagatg ggccatctgt aatgctcatc actgacagac ctagtgaaga | 12540 |
| tttggatggg aggctcgttc accaaagtga catttttact actacaagtc ctataaaaca | 12600 |
| ggtccggtat gaagagcatc agtcacatac aaagcagtat cctgtaaaca aaatacaagc | 12660 |
| tataattttt ttgatagggt taggctcgtt cattggaagc atattcgtag ttttggtagt | 12720 |
| atggattata cgcagatatt gcaatggagc gcggagtggg ggaacgcccc ccagtcctcg | 12780 |
| ccggtatgtg tataccaggc tatgatcacg tgtgaaactt gggcggacct gtatcatatg | 12840 |
| tacaccgtcc ctattcgttt atagccagta cgtgttatct gcacatagag gaacatgtgt | 12900 |
| catactggga tcgcatgcat ggtatgtgtg actctaatat tattctgtat cataataaaa | 12960 |
| acacagtgca tggtatatag aggatcgctg gtaagcacta cggtagacca atcggctcag | 13020 |
| attgcattct ttggcatcga taccgttgtt aatttatatg gcaaagtctt gttcatggga | 13080 |
| gatcagtatt tggaggaaat atactctgga acgatggaaa tactcaaatg gaatcaagct | 13140 |
| aaccgctgct attctattgc gcatgcaaca tattacgccg actgtcctat aatcagttct | 13200 |
| acggtattca gaggatgccg ggacgccgtt gtttatacta ggccccacag cag | 13253 |

<210> SEQ ID NO 29
<211> LENGTH: 12248
<212> TYPE: DNA
<213> ORGANISM: Artificial Sequence
<220> FEATURE:
<223> OTHER INFORMATION: Expression cassette

<400> SEQUENCE: 29

| | |
|---|---:|
| ggcgcgccac tggagaacgg catgaccgca aaaggcgttg tagagatcga tcccacgaac | 60 |
| tctcaggcga tcgtgtcagt cgccataaac agcgacgatc gtctccagga tctgaacggt | 120 |
| tttcttctca acgatcatca gtatatgagg aactgaacct gatatttagc cgagggaaac | 180 |
| gcaggttaaa aaccctatca agcgattgcg attttcgcgt atctagtaaa atagatgggg | 240 |
| cttcggtact agccttcgcc gccaactctg aatatgccct tcgtggacct catataacat | 300 |
| ggcattgttt gttggatgcg gggccggaat taagaagaac attcgaaata cgagcaaaaa | 360 |
| tttcggccct ggcatgtgct gcgcgagaat cggtacttcg gggagaaagt tttatcggag | 420 |
| cttttgggtag tgcagaggaa actctatctt ggttgaaaat gcatgcgacc ctgcacttga | 480 |
| ttctggttaa ccacgatcca atttttaaga cggctggcgc ggtcctagat aacctccgct | 540 |
| taaaactagc cccaatattg atgtgcagat ataacacaga aaacgatca atggaagaca | 600 |
| tgctacggcg gtcatctccc gaagacatca ccgattccct aacaatgtgc ctgattatgt | 660 |
| tatcgcgcat tcgtcgtacc atgcgcaccg caggaaataa atatagctat atgatagatc | 720 |
| caatgaatcg tatgtctaat tacactccag gcgaatgtat gacaggtata ttgcgatata | 780 |
| ttgacgaaca tgctagaagg tgtcctgatc acatatgtaa tttgtatatc acatgtacac | 840 |
| ttatgccgat gtatgtgcac gggcgatatt ctattgtaa ttcattttt tgttagtaaa | 900 |
| ctaccacagg ctgtccggaa atctaagtta atgaataaag tagatggtta atactcattg | 960 |
| cttagaattg gactactttt aattctcttt aatgttcgta ttaaataaaa acatctttaa | 1020 |
| taaacttcag cctcttcgct tattgtagaa attgagtatt caaatcatg ttcaaagccg | 1080 |
| tcttcggaga gtgtactcgc cacggtggtt ggaacatcac tatgtctaca cgtcaaattt | 1140 |

```
aagcacgtca ggtctgtcga ggacaagaaa tggttaacta gtgtttcaat tattcttata    1200
aacgttaagc attgtaagcc ccccggccgt ccgcagcaac aatttactag tatgccgtgg    1260
gctccgggac tatcacggat gtccaattcg cacatgcata taattttcct agggtctctc    1320
atttcgagaa atcttcgggg atccatcagc aatgcgggct gtagtcccga ttcccgtttc    1380
aaatgaaggt gctccaacac ggtcttcaaa gcaaccggca taccagcaaa cacagactgc    1440
aactccccgc tgcaatgatt ggttataaac agtaatctgt cttctggaag tatatttcgc    1500
ccgacaatcc acggcgcccc caaagttaaa aaccatccat gtgtatttgc gtcttctctg    1560
ttaaaagaat attgactggc attttcccgt tgaccgccag atatccaaag tacagcacga    1620
tgttgcacgg acgactttgc agtcaccagc cttccttttcc accccccac caacaaaatg    1680 tttatcgtag gacccatatc cgtaataagg atgggtctgg cagcaaccccc ataggcgcct    1740 cggcgtggta gttctcgagg ccttaattaa gtcgacggca gagtcgcaga cgcccctatt    1800
ggacgtcaaa attgtagagg tgaagttttc aaacgatggc gaagtaacgg cgacttgcgt    1860
ttccaccgtc aaatctccct atagggtaga aactaattgg aaagtagacc tcgtagatgt    1920
aatggatgaa atttctggga acagtcccgc cggggttttt aacagtaatg agaaatggca    1980
gaaacagctg tactacagag taaccgatgg aagaacatcg gtccagctaa tgtgcctgtc    2040
gtgcacgagc cattccccgg aaccttactg tcttttcgac acgtctctta tagcgaggga    2100
aaaagatatc gcgccagagt tatactttac ctctgatccg caaacggcat actgcacaat    2160
aactctgccg tccggcgttg ttccgagatt cgaatggagc cttaataatg tttcactgcc    2220
ggaatatttg acggccacga ccgttgtttc gcataccgct ggccaaagta cagtgtggaa    2280
gagcagcgcg agagcaggcg aggcgtggat ttctggccgg ggaggcaata tatacgaatg    2340
caccgtcctc atctcagacg gcactcgcgt tactacgcga aggagaggt gcttaacaaa    2400 cacatggatt gcggtggaaa acggtgctgc tcaggcgcag ctgtattcac tcttttctgg    2460
acttgtgtca ggattatgcg ggagcatatc tgctttgtac gcaacgctat ggaccgccat    2520 ttattttttga ggaatgcttt ttggactatc gtactgcttt cttccttcgc tagccagagc    2580
accgccgccg tcacgtacga ctacatttta ggccgtcgcg cgctcgacgc gctaaccata    2640
ccggcggttg gcccgtataa cagatacctc actagggtat caagaggctg cgacgttgtc    2700
gagctcaacc cgatttctaa cgtggacgac atgatatcgg cggccaaaga aaaagagaag    2760
gggggccctt tcgaggcctc cgtcgtctgg ttctacgtga ttaagggcga cgacggcgag    2820
gacaagtact gtccaatcta tagaaaagag tacagggaat gtggcgacgt acaactgcta    2880
tctgaatgcg ccgttcaatc tgcacagatg tgggcagtgg actatgttcc tagcacccctt    2940 gtatcgcgaa atggcgcggg actgactata ttctccccca ctgctgcgct ctctggccaa    3000
tacttgctga ccctgaaaat cgggagattt gcgcaaacag ctctcgtaac tctagaagtt    3060
aacgatcgct gtttaaagat cgggtcgcag cttaactttt taccgtcgaa atgctggaca    3120
acagaacagt atcagactgg atttcaaggc gaacacctt atccgatcgc agacaccaat    3180
acacgacacg cggacgacgt atatcggga tacgaagata ttctgcagcg ctggaataat    3240
ttgctgagga aaaagaatcc tagcgcgcca gaccctcgtc cagatagcgt cccgcaagaa    3300
attcccgctg taaccaagaa agcggaaggg cgcaccccgg acgcagaaag cagcgaaaag    3360
aaggcccctc cagaagactc ggaggacgac atgcaggcag aggcttctgg agaaaatcct    3420
gccgccctcc ccgaagacga cgaagtcccc gaggacaccg agcacgatga tccaaactcg    3480
```

```
gatcctgact attacaatga catgcccgcc gtgatcccgg tggaggagac tactaaaagt   3540
tctaatgccg tctccatgcc catattcgcg gcgttcgtag cctgcgcggt cgcgctcgtg   3600
gggctactgg tttggagcat cgtaaaatgc gcgcgtagct aatcgagcct agaataggtg   3660
gtttcttcct acatgccacg cctcacgctc ataatataaa tcacatggaa tagcatacca   3720
atgcctattc attgggacgt tcgaaaagca tggcatcgct acttggaact ctggctctcc   3780
ttgccgcgac gctcgcaccc ttcggcgcga tgggaatcgt gatcactgga aatcacgtct   3840
ccgccaggat tgacgacgat cacatcgtga tcgtcgcgcc tcgccccgaa gctacaattc   3900
aactgcagct attttttcatg cctggccaga gaccccacaa accctactca ggaaccgtcc   3960
gcgtcgcgtt tcggtctgat ataacaaacc agtgctacca ggaacttagc gaggagcgct   4020
ttgaaaattg cactcatcga tcgtcttctg tttttgtcgg ctgtaaagtg accgagtaca   4080
cgttctccgc ctcgaacaga ctaaccggac ctccacaccc gtttaagctc actatacgaa   4140
atcctcgtcc gaacgacagc gggatgttct acgtaattgt tcggctagac gacaccaaag   4200
aacccattga cgtcttcgcg atccaactat cggtgtatca attcgcgaac accgccgcga   4260
ctcgcggact ctattccaag gcttcgtgtc gcaccttcgg attacctacc gtccaacttg   4320
aggcctatct caggaccgag gaaagttggc gcaactggca agcgtacgtt gccacggagg   4380
ccacgacgac cagcgccgag gcgacaaccc cgacgcccgt cactgcaacc agcgcctccg   4440
aacttgaagc ggaacacttt acctttccct ggctagaaaa tggcgtggat cattacgaac   4500
cgacacccgc aaacgaaaat tcaaacgtta ctgtccgtct cgggacaatg agccctacgc   4560
taattggggt aaccgtggct gccgtcgtga gcgcaacgat cggcctcgtc attgtaattt   4620
ccatcgtcac cagaaacatg tgcaccccgc accgaaaatt agacacggtc tcgcaagacg   4680
acgaagaacg ttcccaaact agaagggaat cgcgaaaatt tggacccatg gttgcgtgcg   4740
aaataaacaa gggggctgac caggatagtg aacttgtgga actggttgcg attgttaacc   4800
cgtctgcgct aagctcgccc gactcaataa aaatgtgatt aagtctgaat gtggctctcc   4860
aatcatttcg attctctaat ctcccaatcc tctcaaaagg ggcagtatcg gacacggact   4920
gggaggggcg tacacgatag ttatatggta cagcagaggc ctctgaacac ttaggaggag   4980
aattcagccg gggagagccc ctgttgagta ggcttgggag catattgcag gatgaacatg   5040
ttagtgatag ttctcgcctc ttgtcttgcg cgcctaactt ttgcgacgcg acacgtcctc   5100
tttttggaag gcactcaggc tgtcctcggg gaagatgatc ccagaaacgt tccggaaggg   5160
actgtaatca aatggacaaa agtcctgcgg aacgcgtgca agatgaaggc ggccgatgtc   5220
tgctcttcgc ctaactattg ctttcatgat ttaatttacg acggaggaaa gaaagactgc   5280
ccgcccgcgg gacccctgtc tgcaaacctg gtaattttac taaagcgcgg cgaaagcttc   5340
ccgggttaat taaggccctc gaggatacat ccaaagaggt tgagtattct ctctacactt   5400
cttgttaaat ggaaagtgca tttgcttgtt cttacaatcg gcccgagtct cgttcacagc   5460
gcctcgttca cacttaaacc acaaatagtc tacaggctat atgggagcca gactgaaact   5520
cacatatgac taatattcgg gggtgttagt cacgtgtagc ccattgtgtg catataacga   5580
tgttggacgc gtcctattc gcggtgtact tgatactatg gcagcgagca tgggatattc   5640
atcctcgtca tcgttaacat ctctacgggt tcagaatgtt tggcatgtcg tcgatccttt   5700
gcccatcgtt gcaaattaca agtccgatcg ccatgaccgc gataagcctg taccatgtgg   5760
cattagggtg acatctcgat catacattat aagaccaacg tgcgagtctt ccaaagacct   5820
gcacgccttc ttcttcggat tgtcaacggg ttcttcagaa tctatgccca tatctggcgt   5880
```

```
tgagaccatt gtgcgtttaa tgaacaataa agcggcatgc catggaaagg agggctgcag    5940
atctccattt tctcacgcca ctatcctgga cgctgtagac gataattata ccatgaatat    6000 agaggggta tgtttccact gccactgtga tgataagttt tctccagatt gttggatatc     6060
tgcattttct gctgccgaac aaacttcatc gctatgcaaa gagatgcgtg tgtacacgcg    6120
ccgttgagta tacgggaaac taaatgttca tagaggtctt tgggctatat gttattaaat    6180
aaaataattg accagtgaac aatttgttta atgttagttt attcaatgca ttggttgcaa    6240
atattcatta cttctccaat cccaggtcat tctttagcga gatgatgtta tgacattgct    6300
gtgaaaatta ctacaggata tattttaag atgcaggagt aacaatgtgc atagtaggcg     6360
tagttatcgc agacgtgcaa cgcttcgcat ttgagttacc gaagtgccca acagtgctgc    6420
ggttatggtt tatgcgcaca gaatccatgc atgtcctaat tgaaccatcc gattttctt     6480 ttaatcgcga tcgttgtttg ggcaactgcg ttatttcaga tctaaaaaat ttacccttta    6540
tgaccatcac atctctctgg ctcatacccc gcttggataa gatatcatgt agattccgcc    6600
ctaagaaatg caaactaaca ttattgtcgg ttccatatac acttccatct tgtccttcga    6660
aaataacaaa ctcgcgcaat agaccgtccg tacatgcatg gccgatgtgt gtcaacatca    6720
ttggtctgct agatcccgat gggacgaatc gtacagtcgt cgctccagca ttggcaaaaa    6780
tccccagata ccctccatgc ggcaaatcta aattgcgacc ccgaagagac tgcaccaaag    6840
tcttatcgac gcacgctgat tttttgaac agcgggagcc cattatcttc agtggagcgt     6900
agacgggcga ggctaattat gtgacatagc aacactgcat gtatgttttt ataaatcaat    6960
aagagtacat aatttattac gtatcatttc cgtttgtaat atactgtata catcatccac    7020
actattagtc agcactagcg cgcgggcgca cgttacaata gcagcgtgcc cgttatctat    7080
attgtccgat atttacacat aacatttcat cgacatgatt aaatacctaa gtactgcaca    7140
cagatgttta atgtatatcg tcatataaat tatatcgcta ggacagaccc aaacgacctt    7200
tatcccaaac agtcagatcc tcttctcaag tgtcgatttc tgttatggaa tatgcatacc    7260
ctggcccaga aattgcacgc acgagcgtag tgaatgcgtc attggtttta catttaaagg    7320
ctaaatgcac aaattcttta gacgacagca catcgttaaa tagcatctct agcgttctta    7380
tgaatgctaa gcattggagt cctcctggtc ggccacaata acagctgagt atcatccct     7440 gagctccggg gttgtcgcac atagcggatt cgtataaaca taggattttc cgcgaatcca    7500
tcagttgcaa aaatctgtta ggctccatca acaacgctgg atttacttca gatccacgcg    7560
taaagtaatg gtgctcgaat accgttttta gagttgtcgg catttcaagg aacaaagaat    7620
tcatttcttc attgcaacga cgcgccagaa atcccaagac ctctttgggt agtatgttct    7680
tgcctataaa acacggcgtt ccaagtgcca ggaaccacgc atgtgttact gttgggcgt     7740 attcagaaat aaagcggggt ttatgcggct tttgaagctc ggatatccaa agtatcgctt    7800
gctgatgaac gagcgatgta gctgttacaa aacctccttt ccatcctcca gtcaacataa    7860
tatttatcgg cctacctatg tccgtaataa gtattggtcg ggcaattatt ccgtatgagg    7920
tcttgcagga ataagctctt agggacagcc agcttggata tggtgcgaaa cagaccttct    7980
cggcttcaga atgtcgctcc gcagtctctt cgtgtcggtg catcttagat ccaccatcaa    8040
tgtgtgcagc attgactccc gcccgtcgaa tattccttt gttacgatgc agtaatgagc      8100
acgatcatgg gcgggcgat gacgttctat ttgcatgtct gcgaacaatt tgcgtcagtc     8160
atacagctat ggagtgggcc atttctggcc gtcaacttaa aaacgcgaac cgcagacata    8220
```

```
tgtatttgca tgcaaagacg tatcttcgta tttctgggca tcttcaaatg ctctggccaa      8280
tatggcaatg aatttggatt cgtttgacgc cgatggtatg cagtgcaaat gtgccaatag      8340
cccacatccg aaaaagttat tgtcataca agcaggtgtt aagtagcaat cacataaagg       8400
caccagacgc ctcatggcat cataatgaat agctccttct ccccactgga accactgaca      8460
aaatctgcga gtatattccg caaaccacat tttatttctc atagaaacta ccctaaatcc      8520
ttttaacggg aagaagaatc ctagatagtg cttgaagtca tgactgttac tgctgcaata      8580
acactgtata ttatttataa attccgtttg tctaggtatc tgatgtaggc attccgatcc      8640
ctttactatt gcgtcttcac gaccaaatgg gaatgcgcca aaatccccac acctcatcac      8700
cctggaggca gattgtgtat tattaatatc cgccgattga agcacaaaac ggtacggtac      8760
tgttcctaat tctggtatag attctatggt caaaagtctg catatcccg acattgccat       8820 gagatcacac agtccaagta gcatgtttat tgagtcactc agactgtcaa cgtccctcgc      8880
cgcaccacca atcgaaaata aagtatctac gcaagttata gctccgcatt ttctatcgct      8940
agcagcaatc gcgacgcaaa acataaaggc catgttggga tttgaactct ctgggggct      9000 tgttatcttc tgcaccgtcg cagtcgcagt tttccgaaat ttatgtctaa tatattttcc      9060
ggccgtgctc caatcggccg aaaagaatct gcgtattacc agactcattg acgggccgat      9120
aaagaccata aaacaaaatt cctgtgcact ccctcctcca gttttgccat cgtccaagtc      9180
ccgtaacttt ttttgcgttt cgaggagcaa gcgttcgtta tccctaccca cacttgtttt      9240
ccaccgtttt cttattataa gcggttgtat cgccaacgcg tcaccgcagg ttgtcacata      9300
cagtgatggc atacttgaac gtgcaacaac gcgctcgctt tgcaaatcta agtcattgac      9360
catcaaatcg cgttgagagg atagccaggc atcttttttc ctagtatggt gacggtgcag      9420 ccacccccaac tcagttcttg taaaaaaagc tattggcggg aatttatgtt ctgaggtgca     9480
ttctatattt atgagtccat caaatgccat taaccagatt cgtatttttt cgctcgaccc      9540
ggcatcacta tggatacaat acctttctat ggcccatttc agctctcgaa ccaaccacac      9600
ggacaattga ctaacataag tatgatcttt atcacagtcg cacccatctg agttatattt      9660
atggcatccg agcgctctta ctgtacggtc ggatacaccc atggttttc ctttatatag       9720 tcgggttata gtctgtcggg tttggcggta gcacggagta gtttgatttt taagaatcga      9780
aaaccggctt ggagagacca ctgtcgaata tttgtccgta tactctacac gtgagtgttg      9840
tccattccta ggtatattca tctgttcgga taccttcaat tgctgttcag gcataacctt      9900
aaagcatatg ttatgttgta catcaaaact tggtgagtta tgttcgattg ccgcgcataa      9960
agaatcgtac atgagcgttt ctgctaacat actatctata ttctcacacg cccctgcata     10020
tactgttcct attccaaatt cacgttttgc cccatcggct atctgctccc aaaaagttgt     10080
aatataggtg ccgctgggtg cgaaattttc atcagttgta ttcctgataa actgaatcac     10140
tttacataat ttttgccaca tatctgcgtg cagccatagt atcgaacccg tgggctcgga     10200
gacgacagtg cgtacaatgg gtattttacc tttccccaac aaaataatgg tatacaagtt     10260
aggtccgtac ctagacctta atgtttccaa ttcttctgaa tcactgcact ctcgtagggg     10320
agtaacggta ataatttcgt ctctgagccc cgttttgcgt tgaaaactaa tcacattaga     10380
taatgtgcaa tcggtttctt ttatccggat acatctaagt attatgacat cggtggtcat     10440
tgtttccatc aacgaccatc ttttacgatc gcccatacta ctcatggacg ttgtcggtgt     10500
tgaaaaatca ccagaattgc aacggatctc tgggtaccat gctgctgatg gaattggcgg     10560
ttttaattgt tgtttcagtc tattattgct atctttggcg gggttgaata atgtgggggg     10620
```

```
agagtgattg caggaatccg aatgggtcaa taaaacgacc gtgctccgtt ctgccggcgc    10680
cgatccgatt gaagctatat acttcgcttc tctccccact tttccaattt gatccggaaa    10740
taaaacggcc ccggacaaca gtatcgtacg atccggatcc ggatcctgct tgcctacaga    10800
agaatcaaca tctcgcccca atattctggt caaaactggc tcgctcatgg caacgcggac    10860 gtttccccg gtggccagtc ttaatggtta atgttctttt cggcaatctt atacatcagc    10920
gggttgcgtg aatactggtc acagttcagt catttactac acaccagcaa tacgacgacg    10980
gacagtaccg tcccgacgaa cgcgacgccc aaaattgcta tcgcgaccgc gtccgaggcg    11040
atgtcgtacg ggcggtgcgg ggttggatcc tcggcaaaga gatcctcgta attcggcggt    11100
gggagcggag ggtaaagacg cgggtgggga tctccctccg gaccgcgcgc cgggcgcggt    11160
tcgaaaatgc tttccgcctc gctcagtgtc aacgccaagt attcgggcgg ctgggggcc    11220 ggaatatctc ccgcgacttc ttctatcggc gcggaattgg agtcgcggtc gtggcgcgct    11280
tctagcgtcg tcaacggaag tccatttcg gggtctcccg gtgggcgttc agcgtccatc    11340
gtcgtatatg ctctaacaca cgtctcgcta tattaaaaaa aagaagagta cggtcagtg    11400 tcgagtgtcg ccgacaatgt cgcgagttct cggcgattta attttggaa ctgctcccta    11460 tgaatcccgt aactgtagcg cccgcgcaga aagccgccat cagaccaact acgtgtctgt    11520
tcgatgtttg cccgccgatc gctttaccga ttaaggttcc ggcgagaaat gacatgctcg    11580
atccaagaac aaagttttc gcggtaaaca acaacatagt taccgtgcga gatggagaaa    11640
ccacatctcc cgaattagta gaggaaagcc cgcgctgtcg gtttgggac atatcgatct    11700 tttttgtgtt tttcctagga cccttttgcc agatcgtaca aagtcgcgtc ttatgagcgg    11760
acgttcttac tgcagctcgg taggagtggg gcagggttag atttcgtcgg cgtttcggcc    11820
cccgtatgcg ccgcgccacc ctcttcgccg agctctttat gcgcggtggg ggtgagcgct    11880
tccggagttg cgatctccga tctcgagccg cagcccggcg gtgtctcttt cagtggagcg    11940
ttagcgccat catgtggttc gtggcggtgg aaaggctatt atgtgttagg ggagagacca    12000
cgtgatcggc atgcaaatga gcaaggcgaa cgcgtcagcg ttcgcactgc gaaccaataa    12060
tatatatatt atactattgg ctttaggtgc gaacgtccgg ctagtccaat agcggggtcg    12120
cgtttcgtac cacgtgttat agaccgccct aaactcgcac tcggggggtcc ggccgcgccc    12180 agacagggcg gagacgtgcc acaggggctt taaaacaccg cttcgggcac cgttcatctc    12240
ggcgcgcc                                                           12248

<210> SEQ ID NO 30
<211> LENGTH: 13068
<212> TYPE: DNA
<213> ORGANISM: Artificial Sequence
<220> FEATURE:
<223> OTHER INFORMATION: Expression cassette

<400> SEQUENCE: 30
aattccagac taaatgcccc ggcccaattt gtcaagtgtg cagtcacgga ggcgtcgacc       60
gtgtccccgg cattaaacag gaaagcgtta agttttttga atgttaggtc acaggtacaa      120
acataaatgt ttgtacaaac aggtaacagg tacaaacata aatgccccgg cataaatgtc      180
ccttacggcg gatcgaaacg acattaggca tactcgggta ccatttttgca ttccgatcag      240 cacggatgaa attaggcagg aatgcggttt atattatgcg gcattggaca acgatatgg       300 cattgattgg cagtttatga atgtcttcat gttgggcgta aacggattcc tattggttca      360
```

```
gaagacaacg acgatatatt tagagagaaa aagctaccca gcataggata aacacacatt    420
gagcattgag agacataggt atcggtatgg atgggaaaac tacacacgtg aacaccaaac    480
gacttatata ctcgagcggt gatactactg agcaagaatg cactgcatct gagccactga    540
atgaagactg tgatgaaaat gtgaccatcg atggaattgg agaagaatat gcgcagttct    600
tcatgtcccc gcaatgggtc ccaaatctac atcgcttgag cgaggatacc aaaaaggtat    660
accgatgtat ggtttccaac agactcaatt attttcccta ttatgaggcg ttcaggcggt    720 cttgtttga tatgtatatg ctaggtcggt tggggcgtcg acttaagcga tctgactggg    780
agactattat gcatctgtca ccaacgcaaa gtcggcgtct acatagaact ttaagatttg    840
tggagcgtag aattatccca tctaacagtt atatacgcac atcgggccac gttccgcctt    900
cgagggcact tccgacagat acgaatttaa agatggatga ataattaaat tggaaagagt    960
aactacatta atcgagcgtc atgacggcgt cccgtgaaaa tgggaatttt ctactcgaaa    1020
caccgtgaca tttgacagac ctggaattgt tattctgata tatagtgggt gtgtctggcc    1080
ggcaacatac ataatgtgca tgcgaaacca cttttttcagt gtacgctgac attgtgcaac    1140
acggaggggt agcatctaca tacaatatat gttgattaat gattggagaa aaaactatgc    1200
agctcgccga tcatatggct aactcgcctt cgtctatatg gcggaccccg cgggaaaaat    1260
cgacgtacca tctgatttac aacaccagta atgaacatgt cgcatccctg cccagatctg    1320
tgcgcccatt ggcgcggatc gttgtgaatg ccgccgaaac acttcaggtc ggtatgagag    1380
ccgggaggcc gccatcagca ggagtttggc gagaggtgtt tgatagaatg atgacagcct    1440
tccgtgacca cgagcctact gcgacattta atgctgcaaa tcccattaga aaaatggtcg    1500
agacagttct acagaataat gaagagcccc cgcggacgca tgctgaaatg ggtaatcgcc    1560
ttatgaacat tatgtactgg tgttgcttgg gacacgcagg acaatgctcg atatggcagt    1620
tgtacgagac gaatcaggcc attttaagtt tattagatga agtggttatc ggcacaacaa    1680
atcccttttg caccctcgag caatactgga agccattatg caccgcaatc gccaacaagg    1740
ggacctcatc gcttgttgag gatgccaaag tggccgagta cctggttagc atgcgcaaat    1800
tgatataaca taggcacgct ctgatgttac agaccacaat accgcataca tttattgtaa    1860
ggttgttaat aaaggtttat tctatgtaag actacaatac tttcgacatt gcttgtatac    1920
atattaaata ctttctcaag ttcctattac ataaaatggg atctatcatt acattcgtta    1980
agagtctgga taatttact gtttgccagc ttcgatcttg gaacgtactg tggatagtgc    2040
cttacttgga atcgtgaaaa tttgaaacgt ccattatttg gatatcttcc ggttgtccca    2100
tatcccgccc tggtaccgct cggatacctt gcccgtatgg attcgtattg acagtcgcgc    2160
aatcggggac caacaacgcg tgggtccaca ctcattcgga aattttccga tgattctgaa    2220
tatttattgc cgctcgttac gagtcgttgg acatatctgt aatacatttc ttcttctgaa    2280
ggatcgctgc acatttgatc tatacattgg ccaggatgtt caagtctcag atgttgcatt    2340
ctggcacagc acaactttat ggcatttccg atgtaatcgt ccggcagccc tggggagtt    2400 ctatattcgc atattgggat ggtaaggaca atagcagatc tcgcaacctc cagggaggct    2460
ataataacgt ttttaaagga tggatttctc ataaaaatct gtcgcaaatt acactgagaa    2520
tatcctttac tagcgccgat tgagagcatc gtcgtccaat tttctaaatg gaaagaaaac    2580
aaggcgggca agagtgttcc aaacatttc atttcggcg aatctctcaa atcccatggc    2640
gtgcaattga ttgcaaaatt ggcacttccg ttcacgtttg tatctccaaa ctctaagaca    2700
cttttaattg aaaaactacg ttctagtgtg gaaagaaacc tataggcaga ccatagaact    2760
```

```
atttgacacc acatatctttt ttgtatgtca aactgaccat gatcgtatgt tgctgaatgc   2820
actagggcaa ttcgctcgcg cgactccata cattgaataa ttccacacgt cagctcatcg   2880
gttagcaagg tccagtagtt gaagtcattt attttcccc gcggctggcc aaatctacct    2940
ctgggaatat ccaagttgtc gaatatgatc gcaccggctc tggtcatggt gaaggaactg   3000
tagcataaag acgcaggtat catagggta atattttttt attcactcac atactaaaag    3060
taacgcatat tagcaccatg tatgggctat caattgacat ttgcgtagca ctacatcacg   3120
attatgtaca acataatggg acaacatatg gcaagtagat gcaatttcct cacactagtt   3180
gggtttatct actattgaat tttccctat ctgtgataca cttgggagcc tctacaagca    3240
tattgccatc atgtacgttt ttatctactg tcttaacgcc catgggaacg gaggcgtcgt   3300
cgtcatgtat tggacggcaa cataggcagc aacacaaatt gcgtttaggt ggggtgcatg   3360
tggactcgat accaagcccc tgcagctggg gaacgtctgg tggagagccg ataatttgat   3420
atacgcacgc catattactg tcgttgaagt acgccttatc ttctatgttt tcaaatttag   3480
gttcccaagt ggacgtgaga agtgtttgta tctcacatgg aatggcccaa ggcattccag   3540
cccaggtgcc tggtacttta atggcaaaca aacgttttgg tagaggtatt gattctattg   3600
cagttctgca gatatctgca gccccgagta tccacaggct atacgatacg ttatcggagg   3660
caagctgcgg ccgctctaga actagtggat ccccgggct gcagcccaat gtggaattcg    3720
cccttgcaca ttgttactcc tgcatcttaa aaatatatcc tgtagtaatt ttcacagcaa   3780
tgtcataaca tcatctcgct aaagaatgac ctgggattgg agaagtaatg aatatttgca   3840
accaatgcat tgaataaact aacattaaac gaattcacta gtggatcccc caactccgcc   3900
cgttttatga ctagaaccaa tagttttaa tgccaaatgc actgaaatcc cctaatttgc    3960
aaagccaaac gcccctatg tgagtaatac ggggacttt tacccaattt cccaagcgga     4020
aagcccccta atacactcat atggcatatg aatcagcacg gtcatgcact ctaatggcgg   4080
cccataggga cttttccacat agggggcgtt caccatttcc cagcataggg gtggtgactc   4140
aatggccttt acccaagtac attgggtcaa tgggaggtaa gccaatgggt ttttcccatt   4200
actggcaagc acactgagtc aaatgggact ttccactggg ttttgcccaa gtacattggg   4260
tcaatgggag gtgagccaat gggaaaaacc cattgctgcc aagtacactg actcaatagg   4320 gacttttccaa tggttttttc cattgttggc aagcatataa ggtcaatgtg ggtgagtcaa   4380
tagggacttt ccattgtatt ctgcccagta cataaggtca ataggggtg aatcaacagg    4440 aaagtcccat tggagccaag tacactgcgt caataggac ttccattgg gttttgccca     4500 gtacataagg tcaataggg atgagtcaat gggaaaaacc cattggagcc aagtacactg    4560
actcaatagg gactttccat tgggttttgc ccagtacata aggtcaatag ggggtgagtc   4620
aacaggaaag tcccattgga gccaagtaca ttgagtcaat agggactttc caatgggttt   4680
tgcccagtac ataaggtcaa tgggaggtaa gccaatgggt ttttcccatt actggcacgt   4740
atactgagtc attagggact ttccaatggg ttttgcccag tacataaggt caataggggt   4800
gaatcaacag gaaagtccca ttggagccaa gtacactgag tcaataggga ctttccattg   4860
ggttttgccc agtacaaaag gtcaataggg ggtgagtcaa tgggttttt ccattattgg    4920 cacgtacata aggtcaatag gggtgagtca ttgggttttt ccagccaatt taattaaaac   4980
gccatgtact ttcccaccat tgacgtcaat gggctattga aactaatgca acgtgacctt   5040
taaacggtac tttcccatag ctgattaatg ggaaagtacc gttctcgagc caatacacgt   5100
```

-continued

```
caatgggaag tgaaagggca gccaaaacgt aacaccgccc cggttttccc ctggaaattc    5160
catattggca cgcattctat tggctgagct gcgttctacg tgggtataag aggcgcgacc    5220
agcgtcggta ccgtcgcagt cttcggtctg accaccgtag aacgcagagc tcctcgctgc    5280
aggcggccgc tctagaactc gtcgatcgca gcgatgacaa acctgcaaga tcaaacccaa    5340
cagattgttc cgttcatacg gagccttctg atgccaacaa ccggaccggc gtccattccg    5400
gacgacaccc tggagaagca cactctcagg tcagagacct cgacctacaa tttgactgtg    5460
ggggacacag ggtcagggct aattgtcttt ttccctggat tccctggctc aattgtgggt    5520
gctcactaca cactgcagag caatgggaac tacaagttcg atcagatgct cctgactgcc    5580
cagaacctac cggccagcta caactactgc agactagtga gtcggagtct cacagtgagg    5640
tcaagcacac tccctggtgg cgtttatgca ctaaacggca ccataaacgc cgtgaccttc    5700
caaggaagcc tgagtgaact gacagatgtt agctacaatg ggttgatgtc tgcaacagcc    5760
aacatcaacg acaaaattgg gaatgtcctg gtaggggaag gggtcactgt cctcagccta    5820
cccacatcat atgatcttgg gtatgtgagg cttggtgacc ccattcccgc tatagggctt    5880
gacccaaaaa tggtagctac atgcgacagc agtgacaggc ccagagtcta caccataact    5940
gcagccgatg attaccaatt ctcatcacag taccaaccag gtggggtaac aatcacactg    6000
ttctcagcca acattgatgc tatcacaagc ctcagcattg ggggagagct cgtgtttcaa    6060
acaagcgtcc aaggccttgt actgggcgcc accatctacc ttataggctt tgatgggact    6120
gcggtaatca ccagagctgt agccgcagat aatgggctga cggccggcac cgacaatctt    6180
atgccattca atcttgtcat tccaaccaat gagataaccc agccaatcac atccatcaaa    6240
ctggagatag tgacctccaa aagtggtggt caggcagggg atcagatgtc atggtcggca    6300
agtgggagcc tagcagtgac gatccatggt ggcaactatc caggggccct ccgtcccgtc    6360
acactagtag cctacgaaag agtggcaaca ggatccgtcg ttacggtcgc tggggtgagt    6420
aacttcgagc tgattccaaa tcctgaacta gcaaagaacc tggttacaga atacggccga    6480
tttgacccag gagccatgaa ctacacaaaa ttgatactga gtgagaggga ccgtcttggc    6540
atcaagaccg tctggccaac aagggagtac actgattttc gtgagtactt catggaggtg    6600
gccgacctca actctcccct gaagattgca ggagcatttg gcttcaaaga cataatccgg    6660
gctataagga ggtaagcttg atctagagcg gccgcgggga tccagacatg ataagataca    6720
ttgatgagtt tggacaaacc acaactagaa tgcagtgaaa aaaatgcttt atttgtgaaa    6780
tttgtgatgc tattgcttta tttgtaacca ttataagctg caataaacaa gttaacaaca    6840
acaattgcat tcattttatg tttcaggttc agggggaggt gtgggaggtt ttttcggatc    6900
ctctagagtc gacaattatt tcatttaata acatatagcc caaagacctc tatgaacatt    6960
tagtttcccg tatactcaac ggcgcgtgta cacacaaggg cgaattccac agtggatatc    7020
aagcttaatt aagtaccgag ctcgaattgg cgcgccaggt caattccctg gcattatgcc    7080
cagtacatga ccttatggga cttctcctact tggcagtaca tctacgtatt agtcatcgct    7140
attaccatgg tgatgcggtt ttggcagtac atcaatgggc gtggatagcg gtttgactca    7200
cggggatttc caagtctcca ccccattgac gtcaatggga gtttgttttg gcaccaaaat    7260
caacgggact ttccaaaatg tcgtaacaac tccgccccat tgacgcaaat gggcggtagg    7320
cgtgtacggt gggaggtcta tataagcaga gctcgtttag tgaaccgtca gatcgcctgg    7380
agacgccatc cacgctgttt tgacctccat agaagacacc gggcgcgccg gatccatggg    7440
ccccagacct tctaccaaga acccagtacc tatgatgctg actgtccgag tcgcgctggt    7500
```

```
actgagttgc atctgtccgg caaactccat tgatggcagg cctcttgcgg ctgcaggaat    7560
tgtggttaca ggagacaaag ccgtcaacat atacacctca tcccagacag gatcaatcat    7620
agttaagctc ctcccgaatc tgcccaagga taaggaggca tgtgcgaaag ccccccttgga   7680 tgcatacaac aggacattga ccactttgct caccccccctt ggtgactcta tccgtaggat   7740
acaagagtct gtgactacat ctggaggggg gagacagggg cgccttatag gcgccattat    7800
tggcggtgtg gctcttgggg ttgcaactgc cgcacaaata acagcggccg cagctctgat   7860
acaagccaaa caaatgctgc caacatcct ccgacttaaa gagagcattg ccgcaaccaa     7920
tgaggctgtg catgaggtca ctgacggatt atcgcaacta gcagtggcag ttgggaagat   7980
gcagcagttt gttaatgacc aatttaataa aacagctcag gaattagact gcatcaaaat   8040
tgcacagcaa gttggtgtag agctcaacct gtacctaacc gaattgacta cagtattcgg   8100
accacaaatc acttcacctg ctttaaacaa gctgactatt caggcacttt acaatctagc   8160
tggtggaaat atggattact tattgactaa gttaggtgta gggaacaatc aactcagctc   8220
attaatcggt agcggcttaa tcaccggtaa ccctattcta tacgactcac agactcaact   8280
cttgggtata caggtaactc taccttcagt cgggaaccta aataatatgc gtgccaccta   8340
cttggaaacc ttatccgtaa gcacaaccag gggatttgcc tcggcacttg tcccaaaagt    8400
ggtgacacag gtcggttctg tgatagaaga acttgcacc tcatactgta tagaaactga     8460
cttagattta tattgtacaa gaatagtaac gttccctatg tccctggta tttattcctg     8520 cttgagcggc aatacgtcgg cctgtatgta ctcaaagacc gaaggcgcac ttactacacc    8580
atacatgact atcaaaggtt cagtcatcgc caactgcaag atgacaacat gtagatgtgt   8640
aaaccccccg ggtatcatat cgcaaaacta tggagaagcc gtgtctctaa tagataaaca   8700
atcatgcaat gttttatcct taggcgggat aactttaagg ctcagtgggg aattcgatgt   8760
aacttatcag aagaatatct caatacaaga ttctcaagta ataataacag gcaatcttga   8820
tatctcaact gagcttggga atgtcaacaa ctcgatcagt aatgctttga ataagttaga   8880
ggaaagcaac agaaaactag acaaagtcaa tgtcaaactg actagcacat ctgctctcat   8940
tacctatatc gttttgacta tcatatctct tgttttggt atacttagcc cgattctagc    9000
atgctaccta atgtacaagc aaaaggcgca acaaaagacc ttattatggc ttgggaataa   9060
tactctagat cagatgagag ccactacaaa aatgtgagga tctctcgagg aattctagat   9120
cccacgtcac tattgtatac tctatattat actctatgtt atactctgta atcctactca   9180
ataaacgtgt cacgcctgtg aaaccgtact aagtctcccg tgtcttctta tcaccatcag   9240
gtgacatcct cgcccaggct gtcaatcatg ccggtatcga ttccagtagc accggcccca   9300
cgctgacaac ccactcttgc agcgttagca gcgcccctct taacaagccg acccccacca   9360
gcgtcgcggt tactaacact cctctccccg acctgcaact agtgcggccg cagcttgcct   9420
ccgattctag cattacatag ccggtcagta gatcctgcca ttcggtagcg caaccggcta   9480
catcttcaaa cagtctcacg ataaatgcat ctctcgttcc tgccaatccg gaaccgggca   9540
taccactccc gcctgccgat ttaattctca caattgggcg atgccggcgg ggcaaaacga   9600
atgtggattt ggcaaaccga cacaggtctg ctgtacggac taatatgggc acacccacat   9660
cattcttcag atgctccatg cattgttcta tgagaaagat ccataggtg gaggcagcgt    9720 cacgagatcg cccaggcaat cgatcgcatt cgtctagtaa agtgacgaga gttatcatgc   9780
acacacccat gcccacgcct tccgaataac tggagctgtg gaagatcgga aacgtctttt   9840
```

-continued

```
tgactgccgg tctcgtacta ctttcgcaca ggtgtatacc cggacgcgta ctatatattt   9900
tatatcatcc aacgtcccga aattacatac gtggcggcga tggaagtaga tgttgagtct   9960
tcgaaagtaa gtgcctcgaa tatgggtatt gtctgtgaaa atatcgaaag cggtacgacg  10020
gttgcagaac cgtcgatgtc gccagatact agtaacaata gcttcgataa cgaagacttc  10080
cgtgggcctg aatacgatgt ggagataaat accagaaaat ctgctaatct tgatcgtatg  10140
gaatcttcgt gccgtgaaca acgagcggcg tgcgaacttc gaaagtgttc gtgtcctacg  10200
tctgccgtgc gcatgcaata cagtattctt tcatctctcg ctccgggttc agagggtcat  10260
gtatatatat gtactagata cggggacgcg gaccaaaaaa aatgcatagt gaaggcagtc  10320
gttggaggaa agaatcccgg gagggaagtg gatattttaa aaaccatctc acataaatca  10380
attataaaat taatccatgc ctataaatgg aaaaatgttg tgtgtatggc aatgcgtgta  10440
tatcgttatg atcttttcac atatattgac ggagtcggcc ctatgcccct tcaacagatg  10500
atctatattc aacgtggact actagaggcg ctagcataca tacatgaaag gggcatcatt  10560
caccgagacg taaagacgga gaatatattc ttggataatc acgaaaatgc agttttgggt  10620
gacttcggtg ctgcatgcca actaggagat tgtatagata cgccccaatg ttacggttgg  10680
agcggaactg tggaaacaaa ttcgccggaa ttatctgcac ttgatccgta ttgcacaaaa  10740
acagatattt ggagtgccgg attggttcta tatgagatgg caattaaaaa tgtaccattg  10800
tttagtaagc aggtgaaaag ttcgggatct cagctgagat ccataatacg gtgcatgcaa  10860
gtgcatgaac tggagtttcc ccgcaacgat tctaccaacc tctgtaaaca tttcaaacaa  10920
tatgcggttc gtgtacgacc gccttatacc attcctcgag ttataagaaa tgggggggatg  10980 ccaatggatg ttgaatatgt catttctaaa atgcttacgt ttgaccagga gttcagacct  11040
tctgctaagg aaatattgaa tatgccccta tttactaagg cgccgattaa cctgcttaat  11100
atcacaccct ctgacagtgt ctaacggtat acaggcggga gcgggtcgtg gcgtcatcat  11160
caccacttga gaatttatat tttgaattgt tgattgataa attaacctga ttcattgaga  11220
actgaaacgc catattggtt tcttggatat gtctacaaca attagttaaa ttgctatgtt  11280
ctactgcgag taacatttga taagttgtaa gagacgggcg actcatgtcg aagttgacga  11340
atataaagta cataacgtgt ttagaatacc cagaatccga atagtccgcg ggggcgtctt  11400
ctcgcgtgag taccaaatac tgagttgaac ttgaaaatgc taaatctgtg acactctttg  11460
tgtgatgatt attgtcacca cttcgaagat ggcttcgaca ttcatgatgt tctggtgttt  11520
gtttggaatc gtaatagcgc ttgtttcgtc caagtctgac aacaaagaaa atctgaagaa  11580
ttatatcacg gataagtcaa ccaatattag aatacccacg ccattatttg tatcaacgga  11640
aaactcttat cccacaaaac atgtaatcta cgatgaaaac tgtggcttcg ctgtactcaa  11700
tcctataagt gaccccaaat atgtcctttt gagccagctt ctaatgggaa ggcgcaaata  11760
tgatgcgacg gtcgcgtggt ttgttctcgg taaaatgtgt gccagattaa tatatttgcg  11820
cgaattttat aactgctcga caaatgagcc ttttggcaca tgttctatga gctctcctgg  11880
atggtgggac aggcgctacg tctcaaccag tttcatttct cgcgacgaat tacagctggt  11940
ttttgcagcg ccgtcccgag aattagatgg tttatatacg cgcgtagtag ttgtcaacgg  12000
ggactttact acggccgata taatgtttaa tgttaaagtg gcatgtgcct tttcaaagac  12060
tggaatagaa gatgatacat tatgcaaacc ctttcatttc tttgccaatg caacattgca  12120
caatttaacc atgattagat cggtaactct tcgagcgcac gaaagccatt taaaggaatg  12180
ggtggcacgg agaggtggta acgtccctgc agtgctactt gagtctacca tgtatcatgc  12240
```

```
atccaatctg cctagaaatt tcagggattt ctacataaag tctccagatg attataagta    12300
taatcaccta gatgggccat ctgtaatgct catcactgac agacctagtg aagatttgga    12360
tgggaggctc gttcaccaaa gtgacatttt tactactaca agtcctataa aacaggtccg    12420
gtatgaagag catcagtcac atacaaagca gtatcctgta aacaaaatac aagctataat    12480
tttttttgata gggttaggct cgttcattgg aagcatattc gtagttttgg tagtatggat    12540
tatacgcaga tattgcaatg gagcgcggag tgggggaacg cccccagtc ctcgccggta    12600
tgtgtatacc aggctatgat cacgtgtgaa acttgggcgg acctgtatca tatgtacacc    12660
gtccctattc gtttatagcc agtacgtgtt atctgcacat agaggaacat gtgtcatact    12720
gggatcgcat gcatggtatg tgtgactcta atattattct gtatcataat aaaaacacag    12780
tgcatggtat atagaggatc gctggtaagc actacggtag accaatcggc tcagattgca    12840
ttctttggca tcgataccgt tgttaattta tatggcaaag tcttgttcat gggagatcag    12900
tatttggagg aaatatactc tggaacgatg gaaatactca aatggaatca agctaaccgc    12960
tgctattcta ttgcgcatgc aacatattac gccgactgtc ctataatcag ttctacggta    13020
ttcagaggat gccgggacgc cgttgtttat actaggcccc acagcaga              13068
```

<210> SEQ ID NO 31
<211> LENGTH: 14598
<212> TYPE: DNA
<213> ORGANISM: Artificial Sequence
<220> FEATURE:
<223> OTHER INFORMATION: Expression cassette

<400> SEQUENCE: 31

```
cgcgccactg gagaacggca tgaccgcaaa aggcgttgta gagatcgatc ccacgaactc      60
tcaggcgatc gtgtcagtcg ccataaacag cgacgatcgt ctccaggatc tgaacggttt     120
tcttctcaac gatcatcagt atatgaggaa ctgaacctga tatttagccg agggaaacgc     180
aggttaaaaa ccctatcaag cgattgcgat tttcgcgtat ctagtaaaaa tagatgggct     240
tcggtactag ccttcgccgc caactctgaa tatgcccttc gtggacctca tataacatgg     300
cattgtttgt tggatgcggg gccggaatta agaagaacat tcgaaatacg agcaaaaatt     360
tcggccctgg catgtgctgc gcgagaatcg gtacttcggg gagaaagttt tatcggagct     420
ttgggtagtg cagaggaaac tctatcttgg ttgaaaatgc atgcgaccct gcacttgatt     480
ctggttaacc acgatccaat ttttaagacg gctggcgcgg tcctagataa cctccgctta     540
aaactagccc caatattgat gtgcagatat aacacagaaa aacgatcaat ggaagacatg     600
ctacggcggt catctcccga agacatcacc gattccctaa caatgtgcct gattatgtta     660
tcgcgcattc gtcgtaccat gcgcaccgca ggaaataaat atagctatat gatagatcca     720
atgaatcgta tgtctaatta cactccaggc gaatgtatga caggtatatt gcgatatatt     780
gacgaacatg ctagaaggtg tcctgatcac atatgtaatt tgtatatcac atgtacactt     840
atgccgatgt atgtgcacgg gcgatatttc tattgtaatt catttttttg ttagtaaact     900
accacaggct gtccggaaat ctaagttaat gaataaagta gatggttaat actcattgct     960
tagaattgga ctacttttaa ttctcttttaa tgttcgtatt aaataaaaac atctttaata    1020
aacttcagcc tcttcgctta ttgtagaaat tgagtattca aaatcatgtt caaagccgtc    1080
ttcggagagt gtactcgcca cggtggttgg aacatcacta tgtctacacg tcaaatttaa    1140
gcacgtcagg tctgtcgagg acaagaaatg gttaactagt gtttcaatta ttcttataaa    1200
```

```
cgttaagcat tgtaagcccc ccggccgtcc gcagcaacaa tttactagta tgccgtgggc  1260
tccgggacta tcacggatgt ccaattcgca catgcatata attttctag ggtctctcat    1320
ttcgagaaat cttcggggat ccatcagcaa tgcgggctgt agtcccgatt cccgtttcaa   1380
atgaaggtgc tccaacacgg tcttcaaagc aaccggcata ccagcaaaca cagactgcaa   1440
ctccccgctg caatgattgg ttataaacag taatctgtct tctggaagta tatttcgccc   1500
gacaatccac ggcgccccca aagttaaaaa ccatccatgt gtatttgcgt cttctctgtt   1560
aaaagaatat tgactggcat tttcccgttg accgccagat atccaaagta cagcacgatg   1620
ttgcacggac gactttgcag tcaccagcct tcctttccac ccccccacca acaaaatgtt   1680
tatcgtagga cccatatccg taataaggat gggtctggca gcaaccccat aggcgcctcg   1740
gcgtggtagt tctcgaggcc ttaattaagt cgacggcaga gtcgcagacg cccctattgg   1800
acgtcaaaat tgtagaggtg aagttttcaa acgatggcga agtaacggcg acttgcgttt   1860
ccaccgtcaa atctccctat agggtagaaa ctaattggaa agtagacctc gtagatgtaa   1920
tggatgaaat ttctgggaac agtcccgccg gggttttta cagtaatgag aaatggcaga    1980
aacagctgta ctacagagta accgatggaa gaacatcggt ccagctaatg tgcctgtcgt   2040
gcacgagcca ttctccggaa ccttactgtc ttttcgacac gtctcttata gcgagggaaa   2100
aagatatcgc gccagagtta tactttacct ctgatccgca aacggcatac tgcacaataa   2160
ctctgccgtc cggcgttgtt ccgagattcg aatggagcct taataatgtt tcactgccgg   2220
aatatttgac ggccacgacc gttgtttcgc ataccgctgg ccaaagtaca gtgtggaaga   2280
gcagcgcgag agcaggcgag gcgtggattt ctggccgggg aggcaatata tacgaatgca   2340
ccgtcctcat ctcagacggc actcgcgtta ctacgcgaaa ggagaggtgc ttaacaaaca   2400
catgattgc ggtggaaaac ggtgctgctc aggcgcagct gtattcactc ttttctggac    2460
ttgtgtcagg attatgcggg agcatatctg ctttgtacgc aacgctatgg accgccattt   2520
atttttgagg aatgcttttt ggactatcgt actgctttct tccttcgcta gccagagcac   2580
cgccgccgtc acgtacgact acattttagg ccgtcgcgcg ctcgacgcgc taaccatacc   2640
ggcggttggc ccgtataaca gataccctcac tagggtatca agaggctgcg acgttgtcga   2700
gctcaacccg atttctaacg tggacgacat gatatcggcg gccaaagaaa aagagaaggg   2760
gggccctttc gaggcctccg tcgtctggtt ctacgtgatt aagggcgacg acggcgagga   2820
caagtactgt ccaatctata gaaaagagta cagggaatgt ggcgacgtac aactgctatc   2880
tgaatgcgcc gttcaatctg cacagatgtg ggcagtggac tatgttccta gcacccttgt   2940
atcgcgaaat ggcgcgggac tgactatatt ctcccccact gctgcgctct ctggccaata   3000
cttgctgacc ctgaaaatcg ggagatttgc gcaaacagct ctcgtaactc tagaagttaa   3060
cgatcgctgt ttaaagatcg ggtcgcagct taactttta ccgtcgaaat gctggacaac    3120
agaacagtat cagactggat ttcaaggcga cacctttat ccgatcgcag acaccaatac    3180
acgacacgcg gacgacgtat atcggggata cgaagatatt ctgcagcgct ggaataattt   3240
gctgaggaaa aagaatccta gcgcgccaga ccctcgtcca gatagcgtcc cgcaagaaat   3300
tcccgctgta accaagaaag cggaaggcg caccccggac gcagaaagca gcgaaaagaa    3360
ggcccctcca gaagactcgg aggacgacat gcaggcagag gcttctggag aaaatcctgc   3420
cgccctcccc gaagacgacg aagtccccga ggacaccgag cacgatgatc caaactcgga   3480
tcctgactat tacaatgaca tgcccgccgt gatcccggtg gaggagacta ctaaaagttc   3540
taatgccgtc tccatgccca tattcgcggc gttcgtagcc tgcgcggtcg cgctcgtggg   3600
```

```
gctactggtt tggagcatcg taaaatgcgc gcgtagctaa tcgagcctag aataggtggt    3660
ttcttcctac atgccacgcc tcacgctcat aatataaatc acatggaata gcataccaat    3720
gcctattcat tgggacgttc gaaaagcatg gcatcgctac ttggaactct ggctctcctt    3780
gccgcgacgc tcgcacccct cggcgcgatg ggaatcgtga tcactggaaa tcacgtctcc    3840
gccaggattg acgacgatca catcgtgatc gtcgcgcctc gccccgaagc tacaattcaa    3900
ctgcagctat ttttcatgcc tggccagaga ccccacaaac cctactcagg aaccgtccgc    3960
gtcgcgtttc ggtctgatat aacaaaccag tgctaccagg aacttagcga ggagcgcttt    4020
gaaaattgca ctcatcgatc gtcttctgtt tttgtcggct gtaaagtgac cgagtacacg    4080
ttctccgcct cgaacagact aaccggacct ccacacccgt ttaagctcac tatacgaaat    4140
cctcgtccga cgacagcgg gatgttctac gtaattgttc ggctagacga caccaaagaa    4200
cccattgacg tcttcgcgat ccaactatcg gtgtatcaat tcgcgaacac cgccgcgact    4260
cgcggactct attccaaggc ttcgtgtcgc accttcggat tacctaccgt ccaacttgag    4320
gcctatctca ggaccgagga agttggcgc aactggcaag cgtacgttgc cacggaggcc    4380
acgacgacca cgcgccgaggc gacaaccccg acgcccgtca ctgcaaccag cgcctccgaa    4440
cttgaagcgg aacactttac cttccctgg ctagaaaatg gcgtggatca ttacgaaccg    4500
acacccgcaa cgaaaattc aaacgttact gtccgtctcg ggacaatgag ccctacgcta    4560
attggggtaa ccgtggctgc cgtcgtgagc gcaacgatcg gcctcgtcat tgtaatttcc    4620
atcgtcacca gaaacatgtg caccccgcac cgaaaattag acacggtctc gcaagacgac    4680
gaagaacgtt cccaaactag aagggaatcg cgaaaatttg acccatggt tgcgtgcgaa    4740 ataaacaagg gggctgacca ggatagtgaa cttgtggaac tggttgcgat tgttaacccg    4800
tctgcgctaa gctcgcccga ctcaataaaa atgtgattaa gtctgaatgt ggctctccaa    4860
tcatttcgat tctctaatct cccaatcctc tcaaaagggg cagtatcgga cacggactgg    4920
gaggggcgta cacgatagtt atatggtaca gcagaggcct ctgaacactt aggaggagaa    4980
ttcagccggg gagagcccct gttgagtagg cttgggagca tattgcagga tgaacatgtt    5040
agtgatagtt ctcgcctctt gtcttgcgcg cctaactttt gcgacgcgac acgtcctctt    5100
tttggaaggc actcaggctg tcctcgggga agatgatccc agaaacgttc cggaagggac    5160
tgtaatcaaa tggacaaaag tcctgcgaa cgcgtgcaag atgaaggcgg ccgatgtctg    5220
ctcttcgcct aactattgct ttcatgattt aatttacgac ggaggaaaga aagactgccc    5280
gccgcgggga cccctgtctg caaacctggt aattttacta aagcgcggcg aaagcttcgc    5340
gccaggtcaa ttccctggca ttatgcccag tacatgacct tatgggactt tcctacttgg    5400
cagtacatct acgtattagt catcgctatt accatggtga tgcggttttg gcagtacatc    5460
aatgggcgtg gatagcggtt tgactcacgg ggatttccaa gtctccaccc cattgacgtc    5520
aatgggagtt tgttttggca ccaaaatcaa cgggactttc caaatgtcg taacaactcc    5580 gccccattga cgcaaatggg cggtagcgtg tacggtggga ggtctatata agcagagctc    5640
gtttagtgaa ccgtcagatc gcctggagac gccatccacg ctgttttgac ctccatagaa    5700
gacaccggtt gcgccgccac catgggcccc agaccttcta ccaagaaccc agtacctatg    5760
atgctgactg tccgagtcgc gctggtactg agttgcatct gtccggcaaa ctccattgat    5820
ggcaggcctc ttgcggctgc aggaattgtg gttacaggag acaaagccgt caacatatac    5880
acctcatccc agacaggatc aatcatagtt aagctcctcc cgaatctgcc caaggataag    5940
```

```
gaggcatgtg cgaaagcccc cttggatgca tacaacagga cattgaccac tttgctcacc    6000 cccttggtg actctatccg taggatacaa gagtctgtga ctacatctgg aggggggaga     6060
caggggcgcc ttataggcgc cattattggc ggtgtggctc ttggggttgc aactgccgca    6120 caataacag cggccgcagc tctgataaca gccaaacaaa atgctgccaa catcctccga     6180
cttaaagaga gcattgccgc aaccaatgag gctgtgcatg aggtcactga cggattatcg    6240
caactagcag tggcagttgg gaagatgcag cagtttgtta atgaccaatt taataaaaca    6300
gctcaggaat tagactgcat caaaattgca cagcaagttg gtgtagagct caacctgtac    6360
ctaaccgaat tgactacagt attcggacca caaatcactt cacctgcttt aaacaagctg    6420
actattcagg cactttacaa tctagctggt ggaaatatgg attacttatt gactaagtta    6480
ggtgtaggga acaatcaact cagctcatta atcggtagcg gcttaatcac cggtaaccct    6540
attctatacg actcacagac tcaactcttg ggtatacagg taactctacc ttcagtcggg    6600
aagctaaata atatgcgtgc cacctacttg gaaaccttat ccgtaagcac aaccagggga    6660
tttgcctcgg cacttgtccc aaaagtggtg acacaggtcg gttctgtgat agaagaactt    6720
gacacctcat actgtataga aactgactta catttatatt gtacaagaat agtaacgttc    6780
cctatgtccc ctggtattta ttcctgcttg agcggcaata cgtcggcctg tatgtactca    6840
aagaccgaag gcgcacttac tacaccatac atgactatca aaggttcagt catcgccaac    6900
tgcaagatga caacatgtag atgtgtaaac cccccgggta tcatatcgca aaactatgga    6960
gaagccgtgt ctctaataga taaacaatca tgcaatgttt tatccttagg cgggataact    7020
ttaaggctca gtggggaatt cgatgtaact tatcagaaga atatctcaat acaagattct    7080
caagtaataa taacaggcaa tcttgatatc tcaactgagc ttgggaatgt caacaactcg    7140
atcagtaatg ctttgaataa gttagaggaa agcaacagaa actagacaa agtcaatgtc      7200 aaactgacta gcacatctgc tctcattacc tatatcgtgt tgactatcat atctcttgtt    7260
tttggtatac ttagcctgat tctagcatgc tacctaatgt acaagcaaaa ggcgcaacaa    7320
aagaccttat tatggcttgg gaataatact ctagatcaga tgagagccac tacaaaaatg    7380
tgaggatctc tcgaggaatt ctagatccca cgtcactatt gtatactcta tattatactc    7440
tatgttatac tctgtaatcc tactcaataa acgtgtcacg cctgtgaaac cgtactaagt    7500
ctcccgtgtc ttcttatcac catcaggtga catcctcgcc caggctgtca atcatgccgg    7560
tatcgattcc agtagcaccg gccccacgct gacaacccac tcttgcagcg ttagcagcgc    7620
ccctcttaac aagccgaccc ccaccagcgt cgcggttact aacactcctc tccccgacct    7680
gcaactagta agcttcccgg gttaattaag gccctcgagg atacatccaa agaggttgag    7740
tattctctct acacttcttg ttaaatggaa agtgcatttg cttgttctta caatcggccc    7800
gagtctcgtt cacagcgcct cgttcacact taaaccacaa atagtctaca ggctatatgg    7860
gagccagact gaaactcaca tatgactaat attcgggggt gttagtcacg tgtagcccat    7920
tgtgtgcata taacgatgtt ggacgcgtcc ttattcgcgg tgtacttgat actatggcag    7980
cgagcatggg atattcatcc tcgtcatcgt taacatctct acgggttcag aatgtttggc    8040
atgtcgtcga tcctttgccc atcgttgcaa attacaagtc cgatcgccat gaccgcgata    8100
agcctgtacc atgtggcatt agggtgacat ctcgatcata cattataaga ccaacgtgcg    8160
agtcttccaa agacctgcac gccttcttct tcggattgtc aacgggttct tcagaatcta    8220
tgcccatatc tggcgttgag accattgtgc gtttaatgaa caataaagcg gcatgccatg    8280
gaaaggaggg ctgcagatct ccatttctc acgccactat cctggacgct gtagacgata      8340
```

```
attataccat gaatatagag gggtatgtt tccactgcca ctgtgatgat aagttttctc    8400
cagattgttg gatatctgca ttttctgctg ccgaacaaac ttcatcgcta tgcaaagaga    8460
tgcgtgtgta cacgcgccgt tgagtatacg ggaaactaaa tgttcataga ggtctttggg    8520
ctatatgtta ttaaataaaa taattgacca gtgaacaatt tgtttaatgt tagtttattc    8580
aatgcattgg ttgcaaatat tcattacttc tccaatccca ggtcattctt tagcgagatg    8640
atgttatgac attgctgtga aaattactac aggatatatt tttaagatgc aggagtaaca    8700
atgtgcatag taggcgtagt tatcgcagac gtgcaacgct tcgcatttga gttaccgaag    8760
tgcccaacag tgctgcggtt atggtttatg cgcacagaat ccatgcatgt cctaattgaa    8820
ccatccgatt tttctttaa tcgcgatcgt tgtttgggca actgcgttat ttcagatcta    8880
aaaaatttac cctttatgac catcacatct ctctggctca tacccgctt ggataagata    8940 tcatgtagat tccgccctaa gaaatgcaaa ctaacattat tgtcggttcc atatacactt    9000
ccatcttgtc cttcgaaaat aacaaactcg cgcaatagac cgtccgtaca tgcatggccg    9060
atgtgtgtca acatcattgg tctgctagat cccgatggga cgaatcgtac agtcgtcgct    9120
ccagcattgg caaaaatccc cagatacct ccatgcggca atctaaatt gcgaccccga    9180 agagactgca ccaaagtctt atcgacgcac gctgattttt ttgaacagcg ggagcccatt    9240
atcttcagtg gagcgtagac gggcgaggct aattatgtga catagcaaca ctgcatgtat    9300 gttttataa atcaataaga gtacataatt tattacgtat catttccgtt tgtaatatac    9360
tgtatacatc atccacacta ttagtcagca ctagcgcgcg ggcgcacgtt acaatagcag    9420
cgtgcccgtt atctatattg tccgatattt acacataaca tttcatcgac atgattaaat    9480
acctaagtac tgcacacaga tgtttaatgt atatcgtcat ataaattata tcgctaggac    9540
agacccaaac gacctttatc ccaaacagtc agatcctctt ctcaagtgtc gatttctgtt    9600
atggaatatg catacccctgg cccagaaatt gcacgcacga gcgtagtgaa tgcgtcattg    9660
gttttacatt taaaggctaa atgcacaaat tctttagacg acagcacatc gttaaatagc    9720
atctctagcg ttcttatgaa tgctaagcat tggagtcctc ctggtcggcc acaataacag    9780
ctgagtatca taccctgagc tccggggttg tcgcacatag cggattcgta taaacatagg    9840
attttccgcg aatccatcag ttgcaaaaat ctgttaggct ccatcaacaa cgctggattt    9900
acttcagatc cacgcgtaaa gtaatggtgc tcgaataccg ttttagagt tgtcggcatt    9960 tcaaggaaca aagaattcat ttcttcattg caacgacgcg ccagaaatcc caagacctct   10020
ttgggtagta tgttcttgcc tataaaacac ggcgttccaa gtgccaggaa ccacgcatgt   10080
gttactgttg gggcgtattc agaaataaag cggggtttat gcggcttttg aagctcggat   10140
atccaaagta tcgcttgctg atgaacgagc gatgtagctg ttacaaaacc tccttccat   10200 cctccagtca acataatatt tatcggccta cctatgtccg taataagtat tggtcgggca   10260
attattccgt atgaggtctt gcaggaataa gctcttaggg acagccagct tggatatggt   10320
gcgaaacaga ccttctcggc ttcagaatgt cgctccgcag tctcttcgtg tcggtgcatc   10380
ttagatccac catcaatgtg tgcagcattg actcccgccc gtcgaatatt ccttttgtta   10440
cgatgcagta atgagcacga tcatgggcgg ggcgatgacg ttctatttgc atgtctgcga   10500
acaatttgcg tcagtcatac agctatggag tgggccattt ctggccgtca acttaaaaac   10560
gcgaaccgca gacatatgta tttgcatgca aagacgtatc ttcgtatttc tgggcatctt   10620
caaatgctct ggccaatatg gcaatgaatt tggattcgtt tgacgccgat ggtatgcagt   10680
```

```
gcaaatgtgc caatagccca catccgaaaa agttatttgt catacaagca ggtgttaagt    10740
agcaatcaca taaaggcacc agacgcctca tggcatcata atgaatagct ccttctcccc    10800
actggaacca ctgacaaaat ctgcgagtat attccgcaaa ccacatttta tttctcatag    10860
aaactaccct aaatccttttt aacgggaaga agaatcctag atagtgcttg aagtcatgac    10920
tgttactgct gcaataacac tgtatattat ttataaattc cgtttgtcta ggtatctgat    10980
gtaggcattc cgatcccttt actattgcgt cttcacgacc aaatgggaat gcgccaaaat    11040
ccccacacct catcaccctg gaggcagatt gtgtattatt aatatccgcc gattgaagca    11100
caaaacggta cggtactgtt cctaattctg gtatagattc tatggtcaaa agtctgcata    11160
tccccgacat tgccatgaga tcacacagtc caagtagcat gtttattgag tcactcagac    11220
tgtcaacgtc cctcgccgca ccaccaatcg aaaataaagt atctacgcaa gttatagctc    11280 cgcatttttct atcgctagca gcaatcgcga cgcaaaacat aaaggccatg ttgggatttg    11340
aactctctgg ggggcttgtt atcttctgca ccgtcgcagt cgcagttttc cgaaatttat    11400
gtctaatata ttttccggcc gtgctccaat cggccgaaaa gaatctgcgt attaccagac    11460
tcattgacgg gccgataaag accataaaac aaaattcctg tgcactccct cctccagttt    11520
tgccatcgtc caagtcccgt aacttttttt gcgtttcgag gagcaagcgt tcgttatccc    11580
tacccacact tgttttccac cgtttttctta ttataagcgg ttgtatcgcc aacgcgtcac    11640
cgcaggttgt cacatacagt gatggcatac ttgaacgtgc aacaacgcgc tcgctttgca    11700
aatctaagtc attgaccatc aaatcgcgtt gagaggatag ccaggcatct tttttcctag    11760
tatggtgacg gtgcagccac cccaactcag ttccttgtaaa aaaagctatt ggcgggaatt    11820
tatgttctga ggtgcattct atatttatga gtccatcaaa tgccattaac cagattcgta    11880 tttttttcgct cgacccggca tcactatgga tacaatacct ttctatggcc catttcagct    11940
ctcgaaccaa ccacacggac aattgactaa cataagtatg atctttatca cagtcgcacc    12000
catctgagtt atatttatgg catccgagcg ctcttactgt acggtcggat acacccatgg    12060
tttttccttt atatagtcgg gttatagtct gtcgggtttg gcggtagcac ggagtagttt    12120 gattttttaag aatcgaaaac cggcttggag agaccactgt cgaatatttg tccgtatact    12180
ctacacgtga gtgttgtcca ttcctaggta tattcatctg ttcggatacc ttcaattgct    12240
gttcaggcat aaccttaaag catatgttat gttgtacatc aaaacttggt gagttatgtt    12300
cgattgccgc gcataaagaa tcgtacatga gcgtttctgc taacatacta tctatattct    12360
cacacgcccc tgcatatact gttcctattc caaattcacg ttttgcccca tcggctatct    12420
gctcccaaaa agttgtaata taggtgccgc tgggtgcgaa attttcatca gttgtattcc    12480
tgataaactg aatcactttta cataattttt gccacatatc tgcgtgcagc catagtatcg    12540
aacccgtggg ctcggagacg acagtgcgta caatgggtat tttacctttc cccaacaaaa    12600
taatggtata caagttaggt ccgtacctag accttaatgt ttccaattct tctgaatcac    12660
tgcactctcg tagggagta acggtaataa tttcgtctct gagccccgtt ttgcgttgaa    12720
aactaatcac attagataat gtgcaatcgg tttcttttat ccggatacat ctaagtatta    12780
tgacatcggt ggtcattgtt tccatcaacg accatcttttt acgatcgccc atactactca    12840
tggacgttgt cggtgttgaa aaatcaccag aattgcaacg gatctctggg taccatgctg    12900
ctgatggaat tggcggtttt aattgttgtt tcagtctatt attgctatct ttggcggggt    12960
tgaataatgt gggggggagag tgattgcagg aatccgaatg ggtcaataaa acgaccgtgc    13020
tccgttctgc cggcgccgat ccgattgaag ctatatactt cgcttctctc cccactttcc    13080
```

```
caatttgatc cggaaataaa acggccccgg acaacagtat cgtacgatcc ggatccggat    13140
cctgcttgcc tacagaagaa tcaacatctc gccccaatat tctggtcaaa actggctcgc    13200
tcatggcaac gcggacgttt cccccggtgg ccagtcttaa tggttaatgt tcttttcggc    13260
aatcttatac atcagcgggt tgcgtgaata ctggtcacag ttcagtcatt tactacacac    13320
cagcaatacg acgacggaca gtaccgtccc gacgaacgcg acgcccaaaa ttgctatcgc    13380
gaccgcgtcc gaggcgatgt cgtacggcg gtgcggggtt ggatcctcgg caaagagatc    13440
ctcgtaattc ggcggtggga gcggagggta aagacgcggg tggggatctc cctccggacc    13500
gcgcgccggg cgcggttcga aaatgctttc cgcctcgctc agtgtcaacg ccaagtattc    13560
gggcgggctg ggggccggaa tatctcccgc gacttcttct atcggcgcgg aattggagtc    13620
gcggtcgtgg cgcgcttcta gcgtcgtcaa cggaagtcca ttttcggggt ctcccggtgg    13680
gcgttcagcg tccatcgtcg tatatgctct aacacacgtc tcgctatatt aaaaaaaaga    13740
agagtatcgg tcagtgtcga gtgtcgccga caatgtcgcg agttctcggc gatttaatt    13800 ttggaactgc tccctatgaa tcccgtaact gtagcgcccg cgcagaaagc cgccatcaga    13860
ccaactacgt gtctgttcga tgtttgcccg ccgatcgctt taccgattaa ggttccggcg    13920
agaaatgaca tgctcgatcc aagaacaaag ttttcgcgg taaacaacaa catagttacc    13980
gtgcgagatg gagaaaccac atctcccgaa ttagtagagg aaagcccgcg ctgtcggttt    14040
ggggacatat cgatcttttt tgtgtttttc ctaggaccct tttgccagat cgtacaaagt    14100
cgcgtcttat gagcggacgt tcttactgca gctcggtagg agtggggcag ggttagattt    14160
cgtcggcgtt tcggcccccg tatgcgccgc gccaccctct tcgccgagct ctttatgcgc    14220
ggtgggggtg agcgcttccg gagttgcgat ctccgatctc gagccgcagc ccggcggtgt    14280
ctctttcagt ggagcgttag cgccatcatg tggttcgtgg cggtggaaag gctattatgt    14340
gttaggggag agaccacgtg atcggcatgc aaatgagcaa ggcgaacgcg tcagcgttcg    14400
cactgcgaac caataatata tatattatac tattggcttt aggtgcgaac gtccggctag    14460
tccaatagcg gggtcgcgtt tcgtaccacg tgttatagac cgccctaaac tcgcactcgg    14520
gggtccggcc gcgcccagac agggcggaga cgtgccacag gggctttaaa acaccgcttc    14580
gggcaccgtt catctcgg                                                   14598
```

<210> SEQ ID NO 32
<211> LENGTH: 10681
<212> TYPE: DNA
<213> ORGANISM: Artificial Sequence
<220> FEATURE:
<223> OTHER INFORMATION: Expression cassette

<400> SEQUENCE: 32

```
aattccagac taaatgcccc ggcccaattt gtcaagtgtg cagtcacgga ggcgtcgacc      60
gtgtccccgg cattaaacag gaaagcgtta aagtttttga atgttaggtc acaggtacaa     120
acataaatgt ttgtacaaac aggtaacagg tacaaacata aatgccccgg cataaatgtc     180
ccttacggcg gatcgaaacg acattaggca tactcgggta ccattttgca ttccgatcag     240
cacggatgaa attaggcagg aatgcggttt atattatgcg gcattggaca acgatatgg     300 cattgattgg cagtttatga atgtcttcat gttgggcgta aacggattcc tattggttca     360
gaagacaacg acgatatatt tagagagaaa aagctaccca gcataggata aacacacatt     420
gagcattgag agacataggt atcggtatgg atgggaaaac tacacacgtg aacaccaaac     480
```

```
gacttatata ctcgagcggt gatactactg agcaagaatg cactgcatct gagccactga    540
atgaagactg tgatgaaaat gtgaccatcg atggaattgg agaagaatat gcgcagttct    600
tcatgtcccc gcaatgggtc ccaaatctac atcgcttgag cgaggatacc aaaaaggtat    660
accgatgtat ggtttccaac agactcaatt attttcccta ttatgaggcg ttcaggcggt    720
ctttgtttga tatgtatatg ctaggtcggt tggggcgtcg acttaagcga tctgactggg    780
agactattat gcatctgtca ccaacgcaaa gtcggcgtct acatagaact ttaagatttg    840
tggagcgtag aattatccca tctaacagtt atatacgcac atcgggccac gttccgcctt    900
cgagggcact tccgacagat acgaatttaa agatggatga ataattaaat tggaaagagt    960
aactacatta atcgagcgtc atgacggcgt cccgtgaaaa tgggaatttt ctactcgaaa   1020
caccgtgaca tttgacagac ctggaattgt tattctgata tagtgggt gtgtctggcc     1080 ggcaacatac ataatgtgca tgcgaaacca cttttttcagt gtacgctgac attgtgcaac  1140
acggaggggt agcatctaca tacaatatat gttgattaat gattggagaa aaaactatgc   1200
agctcgccga tcatatggct aactcgcctt cgtctatatg gcggacccg cgggaaaaat    1260 cgacgtacca tctgatttac aacaccagta atgaacatgt cgcatccctg cccagatctg   1320
tgcgcccatt ggcgcggatc gttgtgaatg ccgccgaaac acttcaggtc ggtatgagag   1380 ccggaggcc gccatcagca ggagtttggc gagaggtgtt tgatagaatg atgcagcct    1440 tccgtgacca cgagcctact gcgacattta atgctgcaaa tcccattaga aaaatggtcg   1500
agacagttct acagaataat gaagagcccc cgcggacgca tgctgaaatg ggtaatcgcc   1560
ttatgaacat tatgtactgg tgttgcttgg gacacgcagg acaatgctcg atatggcagt   1620
tgtacgagac gaatcaggcc attttaagtt tattagatga agtggttatc ggcacaacaa   1680 atccctttg cacctcgag caatactgga agccattatg caccgcaatc gccaacaagg    1740
ggacctcatc gcttgttgag gatgccaaag tggccgagta cctggttagc atgcgcaaat   1800
tgatataaca taggcacgct ctgatgttac agaccacaat accgcataca tttattgtaa   1860
ggttgttaat aaaggtttat tctatgtaag actacaatac tttcgacatt gcttgtatac   1920
atattaaata ctttctcaag ttcctattac ataaaatggg atctatcatt acattcgtta   1980
agagtctgga taattttact gtttgccagc ttcgatcttg gaacgtactg tggatagtgc   2040
cttacttgga atcgtgaaaa tttgaaacgt ccattatttg gatatcttcc ggttgtccca   2100
tatcccgccc tggtaccgct cggatacctt gcccgtatgg attcgtattg acagtcgcgc   2160
aatcggggac caacaacgcg tgggtccaca ctcattcgga aattttccga tgattctgaa   2220
tatttattgc cgctcgttac gagtcgttgg acatatctgt aatacatttc ttcttctgaa   2280
ggatcgctgc acatttgatc tatacattgg ccaggatgtt caagtctcag atgttgcatt   2340
ctggcacagc acaactttat ggcatttccg atgtaatcgt ccggcagccc tggggagtt   2400 ctatattcgc atattgggat ggtaaggaca atagcagatc tcgcaacctc cagggaggct   2460
ataataacgt ttttaaagga tggatttctc ataaaaatct gtcgcaaatt acactgagaa   2520
tatcctttac tagcgccgat tgagagcatc gtcgtccaat tttctaaatg gaaagaaaac   2580
aaggcgggca agagtgttcc aaacattttc attttcggcg aatctctcaa atcccatggc   2640
gtgcaattga ttgcaaaatt ggcacttccg ttcacgtttg tatctccaaa ctctaagaca   2700
cttttaattg aaaaactacg ttctagtgtg gaaagaaacc tataggcaga ccatagaact   2760
atttgacacc acatatcttt ttgtatgtca aactgaccat gatcgtatgt tgctgaatgc   2820
actagggcaa ttcgctcgcg cgactccata cattgaataa ttccacacgt cagctcatcg   2880
```

```
gttagcaagg tccagtagtt gaagtcattt attttttccc gcggctggcc aaatctacct    2940
ctgggaatat ccaagttgtc gaatatgatc gcaccggctc tggtcatggt gaaggaactg    3000
tagcataaag acgcaggtat catagggta atattttttt attcactcac atactaaaag     3060
taacgcatat tagcaccatg tatgggctat caattgacat ttgcgtagca ctacatcacg    3120
attatgtaca acataatggg acaacatatg gcaagtagat gcaatttcct cacactagtt    3180
gggtttatct actattgaat tttccctat ctgtgataca cttgggagcc tctacaagca     3240
tattgccatc atgtacgttt ttatctactg tcttaacgcc catgggaacg gaggcgtcgt    3300
cgtcatgtat tggacggcaa cataggcagc aacacaaatt gcgtttaggt ggggtgcatg    3360
tggactcgat accaagcccc tgcagctggg gaacgtctgg tggagagccg ataatttgat    3420
atacgcacgc catattactg tcgttgaagt acgccttatc ttctatgttt tcaaatttag    3480
gttcccaagt ggacgtgaga agtgtttgta tctcacatgg aatggcccaa ggcattccag    3540
cccaggtgcc tggtactta atggcaaaca acgttttgg tagaggtatt gattctattg      3600
cagttctgca gatatctgca gccccgagta ccacaggct atacgatacg ttatcggagg     3660
caagctgcgg ccgctctaga actagtggat ccccgggct gcagcccaat gtggaattcg     3720
cccttgcaca ttgttactcc tgcatcttaa aaatatatcc tgtagtaatt ttcacagcaa    3780
tgtcataaca tcatctcgct aaagaatgac ctgggattgg agaagtaatg aatatttgca    3840
accaatgcat tgaataaact aacattaaac gaattcacta gtggatcccc caactccgcc   3900
cgttttatga ctagaaccaa tagtttttaa tgccaaatgc actgaaatcc cctaatttgc    3960
aaagccaaac gcccccatg tgagtaatac ggggactttt acccaatttt cccaagcgga     4020
aagcccccta atacactcat atggcatatg aatcagcacg gtcatgcact ctaatggcgg    4080
cccataggga cttttccacat aggggcgtt caccatttcc cagcataggg gtggtgactc    4140
aatggccttt acccaagtac attgggtcaa tgggaggtaa gccaatgggt ttttcccatt    4200 actgcaagc acactgagtc aaatgggact ttccactggg ttttgcccaa gtacattggg    4260
tcaatgggag gtgagccaat gggaaaaacc cattgctgcc aagtacactg actcaatagg    4320
gactttccaa tgggtttttc cattgttggc aagcatataa ggtcaatgtg ggtgagtcaa    4380
tagggacttt ccattgtatt ctgcccagta cataaggtca ataggggtg aatcaacagg     4440 aaagtcccat tggagccaag tacactgcgt caataggac tttccattgg gttttgccca     4500
gtacataagg tcaataggg atgagtcaat gggaaaaacc cattggagcc aagtacactg    4560
actcaatagg gactttccat tgggttttgc ccagtacata aggtcaatag ggggtgagtc    4620
aacaggaaag tcccattgga gccaagtaca ttgagtcaat agggactttc caatgggttt    4680
tgcccagtac ataaggtcaa tgggaggtaa gccaatgggt ttttcccatt actggcacgt    4740
atactgagtc attagggact ttccaatggg ttttgcccag tacataaggt caataggggt    4800
gaatcaacag gaaagtccca ttggagccaa gtacactgag tcaatagggg ctttccattg    4860
ggttttgccc agtacaaaag gtcaataggg ggtgagtcaa tgggttttc ccattattgg     4920 cacgtacata aggtcaatag ggtgagtca ttgggttttt ccagccaatt taattaaaac     4980
gccatgtact ttcccaccat tgacgtcaat gggctattga aactaatgca acgtgacctt    5040
taaacggtac tttcccatag ctgattaatg ggaaagtacc gttctcgagc caatacacgt    5100
caatgggaag tgaaagggca gccaaaacgt aacaccgccc cggttttccc ctggaaattc    5160
catattggca cgcattctat tggctgagct gcgttctacg tgggtataag aggcgcgacc    5220
```

```
agcgtcggta ccgtcgcagt cttcggtctg accaccgtag aacgcagagc tcctcgctgc    5280
aggcggccgc tctagaactc gtcgatcgca gcgatgacaa acctgcaaga tcaaacccaa    5340
cagattgttc cgttcatacg gagccttctg atgccaacaa ccggaccggc gtccattccg    5400
gacgacaccc tggagaagca cactctcagg tcagagacct cgacctacaa tttgactgtg    5460
ggggacacag ggtcagggct aattgtcttt ttccctggat tccctggctc aattgtgggt    5520
gctcactaca cactgcagag caatgggaac tacaagttcg atcagatgct cctgactgcc    5580
cagaacctac cggccagcta caactactgc agactagtga gtcggagtct cacagtgagg    5640
tcaagcacac tccctggtgg cgtttatgca ctaaacggca ccataaacgc cgtgaccttc    5700
caaggaagcc tgagtgaact gacagatgtt agctacaatg ggttgatgtc tgcaacagcc    5760
aacatcaacg acaaaattgg gaatgtcctg gtagggaagg ggtcactgt cctcagccta    5820 cccacatcat atgatcttgg gtatgtgagg cttggtgacc ccattcccgc tatagggctt    5880
gacccaaaaa tggtagctac atgcgacagc agtgacaggc ccagagtcta caccataact    5940
gcagccgatg attaccaatt ctcatcacag taccaaccag gtggggtaac aatcacactg    6000
ttctcagcca acattgatgc tatcacaagc ctcagcattg ggggagagct cgtgtttcaa    6060
acaagcgtcc aaggccttgt actgggcgcc accatctacc ttataggctt tgatgggact    6120
gcggtaatca ccagagctgt agccgcagat aatgggctga cggccggcac cgacaatctt    6180
atgccattca atcttgtcat tccaaccaat gagataaccc agccaatcac atccatcaaa    6240
ctggagatag tgacctccaa aagtggtggt caggcagggg atcagatgtc atggtcggca    6300
agtgggagcc tagcagtgac gatccatggt ggcaactatc caggggcccct ccgtcccgtc    6360 acactagtag cctacgaaag agtggcaaca ggatccgtcg ttacggtcgc tggggtgagt    6420
aacttcgagc tgattccaaa tcctgaacta gcaaagaacc tggttacaga atacggccga    6480
tttgacccag gagccatgaa ctacacaaaa ttgatactga gtgagaggga ccgtcttggc    6540
atcaagaccg tctggccaac aagggagtac actgattttc gtgagtactt catgagggtg    6600
gccgacctca actctcccct gaagattgca ggagcatttg gcttcaaaga cataatccgg    6660
gctataagga ggtaagcttg atctagagcg gccgcgggga tccagacatg ataagataca    6720
ttgatgagtt tggacaaacc acaactagaa tgcagtgaaa aaaatgcttt atttgtgaaa    6780
tttgtgatgc tattgcttta tttgtaacca ttataagctg caataaacaa gttaacaaca    6840
acaattgcat tcattttatg tttcaggttc agggggaggt gtgggaggtt ttttcggatc    6900
ctctagagtc gacaattatt ttatttaata acatatagcc caaagacctc tatgaacatt    6960
tagtttcccg tatactcaac ggcgcgtgta cacacaaggg cgaattccac agtggatatc    7020
aagcttagct tgcctccgat tctagcatta catagccggt cagtagatcc tgccattcgg    7080
tagcgcaacc ggctacatct tcaaacagtc tcacgataaa tgcatctctc gttcctgcca    7140
atccggaacc gggcatacca ctcccgcctg ccgatttaat tctcacaatt gggcgatgcc    7200 ggcgggcaa acgaatgtg atttggcaa accgacacag gtctgctgta cggactaata    7260
tgggcacacc cacatcattc ttcagatgct ccatgcattg ttctatgaga aagatccata    7320
gggtggaggc agcgtcacga gatcgcccag gcaatcgatc gcattcgtct agtaaagtga    7380
cgagagttat catgcacaca cccatgccca cgccttccga ataactggag ctgtggaaga    7440
tcggaaacgt cttttttgact gccggtctcg tactactttc gcacaggtgt atacccggac    7500
gcgtactata tattttatat catccaacgt ccgaaattac atacgtggcg gcgatggaag    7560
tagatgttga gtcttcgaaa gtaagtgcct cgaatatggg tattgtctgt gaaaatatcg    7620
```

-continued

```
aaagcggtac gacggttgca gaaccgtcga tgtcgccaga tactagtaac aatagcttcg   7680
ataacgaaga cttccgtggg cctgaatacg atgtggagat aaataccaga aaatctgcta   7740
atcttgatcg tatggaatct tcgtgccgtg aacaacgagc ggcgtgcgaa cttcgaaagt   7800
gttcgtgtcc tacgtctgcc gtgcgcatgc aatacagtat tctttcatct ctcgctccgg   7860
gttcagaggg tcatgtatat atatgtacta gatacgggga cgcggaccaa aaaaaatgca   7920
tagtgaaggc agtcgttgga ggaaagaatc ccgggaggga agtggatatt ttaaaaacca   7980
tctcacataa atcaattata aaattaatcc atgcctataa atggaaaaat gttgtgtgta   8040
tggcaatgcg tgtatatcgt tatgatcttt tcacatatat tgacggagtc ggccctatgc   8100
cccttcaaca gatgatctat attcaacgtg gactactaga ggcgctagca tacatacatg   8160
aaagggcat cattcaccga gacgtaaaga cggagaatat attcttggat aatcacgaaa    8220
atgcagtttt gggtgacttc ggtgctgcat gccaactagg agattgtata gatacgcccc   8280
aatgttacgg ttggagcgga actgtggaaa caaattcgcc ggaattatct gcacttgatc   8340
cgtattgcac aaaaacagat atttggagtg ccggattggt tctatatgag atggcaatta   8400
aaaatgtacc attgtttagt aagcaggtga aaagttcggg atctcagctg agatccataa   8460
tacggtgcat gcaagtgcat gaactggagt ttccccgcaa cgattctacc aacctctgta   8520
aacatttcaa acaatatgcg gttcgtgtac gaccgcctta taccattcct cgagttataa   8580
gaaatggggg gatgccaatg gatgttgaat atgtcatttc taaaatgctt acgtttgacc   8640
aggagttcag accttctgct aaggaaatat tgaatatgcc cctatttact aaggcgccga   8700
ttaacctgct taatatcaca ccctctgaca gtgtctaacg gtatacaggc gggagcgggt   8760
cgtggcgtca tcatcaccac ttgagaattt atattttgaa ttgttgattg ataaattaac   8820
ctgattcatt gagaactgaa acgccatatt ggtttcttgg atatgtctac aacaattagt   8880
taaattgcta tgttctactg cgagtaacat ttgataagtt gtaagagacg ggcgactcat   8940
gtcgaagttg acgaatataa agtacataac gtgtttagaa tacccagaat ccgaatagtc   9000
cgcgggggcg tcttctcgcg tgagtaccaa atactgagtt gaacttgaaa atgctaaatc   9060
tgtgacactc tttgtgtgat gattattgtc accacttcga agatggcttc gacattcatg   9120
atgttctggt gtttgtttgg aatcgtaata gcgcttgttt cgtccaagtc tgacaacaaa   9180
gaaaatctga agaattatat cacgataag tcaaccaata ttagaatacc cacgccatta    9240
tttgtatcaa cggaaaactc ttatcccaca aaacatgtaa tctacgatga aaactgtggc   9300
ttcgctgtac tcaatcctat aagtgacccc aaatatgtcc ttttgagcca gcttctaatg   9360
ggaaggcgca aatatgatgc gacggtcgcg tggtttgttc tcggtaaaat gtgtgccaga   9420
ttaatatatt tgcgcgaatt ttataactgc tcgacaaatg agccttttgg cacatgttct   9480
atgagctctc ctggatggtg ggacaggcgc tacgtctcaa ccagtttcat ttctcgcgac   9540
gaattacagc tggttttgc agcgccgtcc cgagaattag atggtttata tacgcgcgta   9600
gtagttgtca acggggactt tactacggcc gatataatgt ttaatgttaa agtggcatgt   9660
gccttttcaa agactggaat agaagatgat acattatgca aaccctttca tttctttgcc   9720
aatgcaacat tgcacaattt aaccatgatt agatcggtaa ctcttcgagc gcacgaaagc   9780
catttaaagg aatgggtggc acggagaggt ggtaacgtcc ctgcagtgct acttgagtct   9840
accatgtatc atgcatccaa tctgcctaga aatttcaggg attttctacat aaagtctcca   9900
gatgattata agtataatca cctagatggg ccatctgtaa tgctcatcac tgacagacct   9960
```

-continued

```
agtgaagatt tggatgggag gctcgttcac caaagtgaca tttttactac tacaagtcct  10020
ataaaacagg tccggtatga agagcatcag tcacatacaa agcagtatcc tgtaaacaaa  10080
atacaagcta taattttttt gatagggtta ggctcgttca ttggaagcat attcgtagtt  10140
ttggtagtat ggattatacg cagatattgc aatggagcgc ggagtggggg aacgcccccc  10200
agtcctcgcc ggtatgtgta taccaggcta tgatcacgtg tgaaacttgg gcggacctgt  10260
atcatatgta caccgtccct attcgtttat agccagtacg tgttatctgc acatagagga  10320
acatgtgtca tactgggatc gcatgcatgg tatgtgtgac tctaatatta ttctgtatca  10380
taataaaaac acagtgcatg gtatatagag gatcgctggt aagcactacg gtagaccaat  10440
cggctcagat tgcattcttt ggcatcgata ccgttgttaa tttatatggc aaagtcttgt  10500
tcatgggaga tcagtatttg gaggaaatat actctggaac gatggaaata ctcaaatgga  10560
atcaagctaa ccgctgctat tctattgcgc atgcaacata ttacgccgac tgtcctataa  10620
tcagttctac ggtattcaga ggatgccggg acgccgttgt ttatactagg ccccacagca  10680
g                                                                  10681
```